(12) United States Patent
Alvaro et al.

(10) Patent No.: US 11,583,527 B2
(45) Date of Patent: Feb. 21, 2023

(54) HYDANTOIN DERIVATIVES USEFUL AS KV3 INHIBITORS

(71) Applicant: AUTIFONY THERAPEUTICS LIMITED, Stevenage (GB)

(72) Inventors: Giuseppe Alvaro, Verona (IT); Paolo Dambruoso, Verona (IT); Simona Tommasi, Verona (IT); Anne Decor, Langenfeld (DE); Charles Large, Verona (IT); Agostino Marasco, Verona (IT)

(73) Assignee: AUTIFONY THERAPEUTICS LIMITED, Stevenage (GB)

( * ) Notice: Subject to any disclaimer, the term of this patent is extended or adjusted under 35 U.S.C. 154(b) by 0 days.

(21) Appl. No.: 17/517,620

(22) Filed: Nov. 2, 2021

(65) Prior Publication Data

US 2022/0054490 A1 Feb. 24, 2022

Related U.S. Application Data

(60) Continuation of application No. 16/985,160, filed on Aug. 4, 2020, now Pat. No. 11,197,859, which is a continuation of application No. 16/285,996, filed on Feb. 26, 2019, now abandoned, which is a continuation of application No. 15/621,400, filed on Jun. 13, 2017, now Pat. No. 10,265,316, which is a division of application No. 15/093,004, filed on Apr. 7, 2016, now abandoned, which is a division of application No. 13/991,486, filed as application No. PCT/GB2011/052414 on Dec. 6, 2011, now Pat. No. 9,346,790.

(30) Foreign Application Priority Data

| Dec. 6, 2010 | (GB) | ................................... 1020607 |
| Dec. 6, 2010 | (WO) | ................. PCT/EP2010/068946 |
| Jun. 7, 2011 | (GB) | ................................... 1109508 |
| Aug. 10, 2011 | (GB) | ................................... 1113757 |

(51) Int. Cl.

| C07D 413/12 | (2006.01) |
| A61K 31/506 | (2006.01) |
| C07D 405/12 | (2006.01) |
| C07D 413/14 | (2006.01) |
| C07D 307/79 | (2006.01) |
| C07D 307/94 | (2006.01) |
| C07D 405/14 | (2006.01) |
| C07D 317/46 | (2006.01) |
| A61K 31/4439 | (2006.01) |

(52) U.S. Cl.
CPC ........ *A61K 31/506* (2013.01); *A61K 31/4439* (2013.01); *C07D 307/79* (2013.01); *C07D 307/94* (2013.01); *C07D 317/46* (2013.01); *C07D 405/12* (2013.01); *C07D 405/14* (2013.01); *C07D 413/12* (2013.01); *C07D 413/14* (2013.01)

(58) Field of Classification Search
CPC ..................................................... C07D 413/12
See application file for complete search history.

(56) References Cited

U.S. PATENT DOCUMENTS

| 3,474,170 A | 10/1969 | Scharpf |
| 4,143,055 A | 3/1979 | Occelli |
| 4,350,701 A | 9/1982 | Rentzea et al. |
| 4,675,403 A | 6/1987 | Abou-Gharbia et al. |
| 4,804,671 A | 2/1989 | Rentzea et al. |
| 5,011,950 A | 4/1991 | Fukuoka et al. |
| 5,362,878 A | 11/1994 | Chang et al. |
| 5,656,634 A | 8/1997 | Chang et al. |
| 5,703,087 A | 12/1997 | Perregaard et al. |

(Continued)

FOREIGN PATENT DOCUMENTS

| DE | 3836175 A1 | 5/1990 |
| EP | 0379174 A3 | 1/1990 |

(Continued)

OTHER PUBLICATIONS

Aroniadou-Andeijaska et al., Mechanisms regulating GABAergic inhibitory transmission in the basolateral amygdala: implications for epilepsy and anxiety disorders, Amino Acids, 32, pp. 305-315, 2007.

Atzori et al., H2 histamine receptor-phosphorylation of Kv3.2 modulates interneuron fast spiking, Nat. Neurosci., 3, pp. 791-798, 2000.

(Continued)

*Primary Examiner* — David K O'Dell
(74) *Attorney, Agent, or Firm* — McDermott Will & Emery LLP

(57) ABSTRACT

The disclosure provides compounds of formula (I):

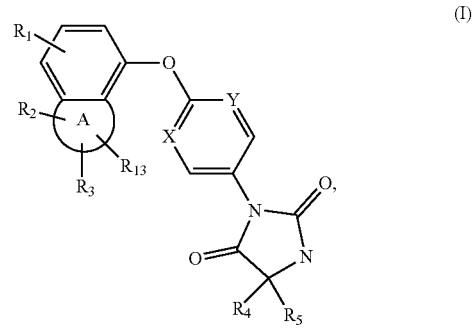

said compounds being inhibitors of Kv3 channels and of use in the prophylaxis or treatment of related disorders.

18 Claims, 7 Drawing Sheets

(56) References Cited

U.S. PATENT DOCUMENTS

| | | |
|---|---|---|
| 9,133,175 B2 | 9/2015 | Alvaro et al. |
| 9,193,704 B2 | 11/2015 | Alvaro et al. |
| 9,346,790 B2 | 5/2016 | Alvaro et al. |
| 9,422,272 B2 | 8/2016 | Alvaro et al. |
| 2003/0008884 A1 | 1/2003 | Gerusz et al. |
| 2003/0149061 A1 | 8/2003 | Nishihara et al. |
| 2005/0009817 A1 | 1/2005 | Savoy et al. |
| 2005/0153968 A1 | 7/2005 | Bi et al. |
| 2007/0004753 A1 | 1/2007 | Sawyers et al. |
| 2007/0254933 A1 | 11/2007 | Jung et al. |
| 2008/0139634 A2 | 6/2008 | Jung et al. |
| 2008/0261961 A1 | 10/2008 | Flynn et al. |
| 2009/0215728 A1 | 8/2009 | Jaehne et al. |
| 2010/0158860 A1 | 6/2010 | Steiner et al. |
| 2010/0172975 A1 | 7/2010 | Sawyers et al. |
| 2010/0210665 A1 | 8/2010 | Sawyers et al. |
| 2011/0003839 A1 | 1/2011 | Jung et al. |
| 2011/0123490 A1 | 5/2011 | Schoenfeld et al. |
| 2012/0190718 A1 | 7/2012 | Jung et al. |
| 2012/0289526 A1 | 11/2012 | Alvaro et al. |
| 2013/0267510 A1 | 10/2013 | Alvaro et al. |
| 2014/0107139 A1 | 4/2014 | Alvaro et al. |
| 2016/0251340 A1 | 9/2016 | Alvaro et al. |
| 2016/0317537 A1 | 11/2016 | Alvaro et al. |

FOREIGN PATENT DOCUMENTS

| | | | |
|---|---|---|---|
| EP | 0368008 A1 | 5/1990 | |
| EP | 0726898 B1 | 12/2000 | |
| EP | 1206935 A1 | 5/2002 | |
| GB | 2216890 A | 10/1989 | |
| JP | 11-279129 A | 10/1999 | |
| JP | 2000-072731 A | 3/2000 | |
| JP | 2000-336071 A | 12/2000 | |
| WO | WO 1991/004027 A1 | 4/1991 | |
| WO | WO 1996/036229 A1 | 11/1996 | |
| WO | WO 1996/036633 A1 | 11/1996 | |
| WO | WO 1997/000612 A1 | 1/1997 | |
| WO | WO 1998/005652 A2 | 2/1998 | |
| WO | WO 1998/023155 A1 | 6/1998 | |
| WO | WO 1998/023156 A1 | 6/1998 | |
| WO | WO 1998/033382 A1 | 8/1998 | |
| WO | WO 2001/076582 A1 | 10/2001 | |
| WO | WO 2003/048134 A1 | 6/2003 | |
| WO | WO 2003/066050 A1 | 8/2003 | |
| WO | WO-2004063191 A1 * | 7/2004 | ........... C07D 213/75 |
| WO | WO 2004/099159 A1 | 11/2004 | |
| WO | WO 2005/000309 A2 | 1/2005 | |
| WO | WO 2005/049040 A1 | 6/2005 | |
| WO | WO 2005/049580 A1 | 6/2005 | |
| WO | WO 2006/071471 A2 | 7/2006 | |
| WO | WO 2006/124118 A1 | 11/2006 | |
| WO | 2007/126765 A2 | 11/2007 | |
| WO | WO 2007/127010 A1 | 11/2007 | |
| WO | WO 2010/072598 A1 | 7/2010 | |
| WO | WO 2011/069951 A1 | 6/2011 | |
| WO | WO 2011/073114 A1 | 6/2011 | |
| WO | WO 2012/076877 A1 | 6/2012 | |
| WO | WO 2012/168710 A1 | 12/2012 | |

OTHER PUBLICATIONS

Australian Patent Office Search Report dated Oct. 8, 2014, issued in connection with Singapore Application No. 201303535-7 (Autifony Therapeutics Limited).
Australian Patent Office Written Opinion dated Oct. 8, 2014, issued in connection with Singapore Application No. 201303535-7 (Autifony Therapeutics Limited).
Ben-Ari, Seizures Beget Seizures: The Quest for GABA as a Key Player, Crit. Rev. Neurobiol., 18, pp. 135-144, 2006.
Benes et al., Circuitry based gene expression profiles in GABA cells of the trisynaptic pathway in schizophrenics versus bi polars, PNAS, 105, pp. 20935-20940, 2008.
Berge et al., Pharmaceutical Salts, J. Pharm, Sci., 66, pp. 1-19, 1977.
Brambilla et al., GABAergic dysfunction in mood disorders, Mol. Psychiatry, 8, pp. 721-737, 2003.
Chang et al., Distribution of Kv3.3 Potassium Channel Subunits in Distinct Neuronal Populations of Mouse Brain, J. Comp. Neurol., 502, pp. 953-972, 2007.
Chow et al., J.Neurosci., K+ Channel Expression Distinguishes Subpopulations of Parvalbumin-and Somatostatin- Containing Neocortical Interneurons, 19, pp. 9332-9345, 1999.
Costall, B. et al., A Primate Model for the Assessment of Anxiolytic Drug Action, Br. J. Pharmac., 1988, 95, pp. 475P, 1988.
Diochot et al., Sea Anemone Peptides with a Specific Blocking Activity against the Fast Inactivating Potassium Channel Kv3.4, J, Biol. Chem., 273, pp. 6744-6749, 1998.
Engel et al., Dynamic Predictions: Oscillations and Synchrony in Top-Down Processing, Nat.Rev.Neurosci., 2, pp. 704-716, 2001.
EP/RO, International Search Report and Written Opinion for related International Application No. PCTEP2010068946 dated Mar. 18, 2011, 11 pgs.
EP/RO, International Search Report and Written Opinion for related International Application No. PCTGB2011052414 dated Feb. 24, 2012, 11 pgs.
EPO/RO—International Search Report and Written Opinion for PCT/GB2012/053045 dated Jan. 25, 2013, 12 pgs.
Espinosa et al., Ablation of Kv3.1 and Kv3.3 Potassium Channels Disrupts Thalamocortical Oscillations In Vitro and In Vivo, J.Neurosci., 28, pp. 5570-5581, 2008.
Espinosa et al., Alcohol Hypersensitivity, Increased Locomotion, and Spontaneous Myoclonus in Mice Lacking the Potassium Channels Kv3.1 and Kv3.3, J.Neurosci., 21, pp. 6657-6665, 2001.
Fisahn, Kainate receptors and rhythmic activity in neuronal networks: hippocampal gamma oscillations as a tool, J. Physiol, 562, pp. 65-72, 2005.
Goldman and Holme, Hearing loss and tinnitus—the hidden healthcare time bomb, Drug Discovery Today, 15, pp. 253-255, 2010.
Harte et al., "Efficacy and relevance of the modulation of Ky3 channels to alleviate cognitive dysfunction in an animal model of schizaphrenia symptomatology", 4th Biennial Schizophrenia International Research Conference (Apr. 2014), Abstract.
Joho et al., Increased y- and Decreased a-Oscillations in a Mouse Deficient for a Potassium Channel Expressed in Fast-Spiking Interneurons, J.Neurophysiol., 82, pp. 1855-1864, 1999.
Jung et al., Age-related changes in the distribution of Kv1 .1 and Kv3.1 in rat cochlear nuclei, Neurol. Res., 27, pp. 436-440, 2005.
Kaczmarek et al., Regulation of the timing of MNTB nemons by short-term and long-term modulation of potassium channels, Hearing Res., 206, pp. 133-145, 2005.
Kasten et al., Differential regulation of action potential firing in adult murine thalamocortical nemons by Kv3.2, Kv1 and SK potassium and N-type calcium channels, J.Physiol., 584, pp. 565-582, 2007.
KIPO, First Examination Report of the Indian Patent Office in IN application 1913/KOLNP/2013 (Jan. 2018).
Lan et al., Impaired Fast-Spiking, Suppressed Cortical Inhibition, and Increased Susceptibility to Seizures in Mice Lacking Kv3.2 K+ Channel Proteins, J.Neurosci., 20, pp. 9071-9085, 2000.
Leger et al., "Two novel KV3 ion channel modulators alleviate cognitive dysfunction and social behaviom deficits of relevance to schizophrenia in an animal model", 4th Biennial Schizophrenia International Research Conference (Apr. 2014), Abstract.
Li et al., Localization of Two High-Threshold Potassium Channel Subunits in the Rat Auditory System, J. Comp, Neurol., 437, pp. 196-218, 2001.
Mabrouk et al., "A novel Kv3 positive modulator augments gamma frequency oscillations in the mammalian neocortex in vitro", 4th Biennial Schizophrenia International Research Conference (Apr. 2014), Abstract.
Marcotte, E.R., "Animal models of schizophrenia: a critical review." Psychiatry Nemosci 2001;26(5):395-410.
Markram et al., Interneurons of the Neocortical Inhibitory System, Nat.Rev.Neurosci., 5, pp. 793-807, 2004.

(56) References Cited

OTHER PUBLICATIONS

Martina et al., Functional and Moleculm Differences between Voltage-Gated K+ Channels of Fast-spiking Interneurons and Pyramidal Neurons of Rat Hippocampus, J.Neurosci., 18, pp. 8111-8125, 1998.

McDonald and Mascagni, Differential Expression of Kv3.1 b and Kv3.2 Potassium Channel Subunits in Interneurons of the Basolateral Amygdala, J.Neurosci., 138, pp. 537-547, 2006.

McMahon et al., Allele-dependent changes of olivocerebellar circuit properties in the absence of the voltage-gated potassium channels Kv3.1 and Kv3.3, Eur. J.Neurosci., 19, pp. 3317-3327, 2004.

Miyamoto, et al., "Pharmacological treatment of schizophrenia: a critical review of the pharmacology and clinical effects of current and future therapeutic agents" Molecular Psychiatry (2012) 17, 1206-1227.

Neill et al., "A novel Kv3 ion channel modulator restores cognitive function in an animal model of cognitive impairment in schizophrenia", European College of Neuropsychopharmacology Conference (Oct. 2013), Abstract.

Pilati et al., Acoustic over-exposure triggers burst firing in dorsal cochlear nucleus fusiform cells, HearinQ Research, 283, pp. 98-106, 2012.

Reynolds et al., Calcium Binding Protein Markers of GABA Deficits in Schizophrenia—Post Mortem Studies and Animal Models, Neurotox. Res., 6, pp. 57-61, 2004.

Rudy and McBain, Kv3 channels: voltage-gated K+ channels designed for high-frequency repetitive firing, Trends in Neurosciences, 24, 517-526, 2001.

Sacco et al., Properties and expression of Kv3 channels is cerebellar Purkinje cells, Mol. Cell. Neurosci., 33, pp. 170-179, 2006.

Schulz and Steimer, Neurobiology of Circadian Systems, CNS Drugs, 23 Suppl 2, pp. 3-13, 2009.

Shield, Evaluation of the social and economic costs of hearing impairment, A report for Hear-It AISBL: www.hear-it.org/multimedia/Hear It Report Oct. 2006.pdf, 2006.

Sidor et al., "Potential anti-manic efficacy of a Kv3 channel modulator in a model of amphetamine-induced hyperactivity and in CLOCK?19 mutant mice", Society for Neuroscience Annual Meeting (Oct. 2012), Abstract.

Song et al., Acoustic environment determines phosphorylation state of the Kv3.1 potassium channel in auditory neurons, Nat Neurosci., 8, pp. 1335-1342, 2005.

Spencer et al., Neural synchrony indexes disordered perception and cognition in schizophrenia, PNAS, 101, pp. 17288-17293, 2004.

Stean TO, et al., Postsynaptic 5-HT1B receptors modulate electroshock-induced generalised seizures in rats, Br J Pharmacol., 144(5):628-35, 2005.

Stmmbos et al., Fragile X Mental Retardation Protein is Required for Rapid Experience-Dependent Regulation of Potassium Channel Kv3.1b, J. Neuroscience, 167, pp. 10263-10271, 2010.

Stmmbos et al., Specific and Rapid Effects of Acoustic Stimulation on the Tonotopic Distribution of Kv3.1b Potassium Channels in the Adult Rat, J. Neuroscience, 167, oo 567-572, 2010.

U.S. Patent Office, Office Action dated Feb. 20, 2015, issued in connection with U.S. Appl. No. 14/361,510 (Alvaro et al).

Von Helm et al., Loss of Kv3.1 Tonotopicity and Alterations in cAMP Response Element-Binding Protein Signaling in Central Auditory Neurons of Hearing Impaired Mice, J. Neurosci., 24, pp. 1936-1940, 2004.

Weiser et al., Differential Expression of Shaw-related K+ Channels in the Rat Central Nervous System, J.Neurosci., 14, pp. 949-972, 1994.

Written Opinion of the International Searching Authority for PCT/GB2011/052414, dated Feb. 24, 2012.

Yeung et al., Modulation of Kv3 Subfamily Potassium Currents by the Sea Anemone Toxin BOS: Significance for CNS and Biophysical Studies, J.Neurosci., 25, pp. 8735-8745, 2005.

Zhang et al., Total synthesis and reassignment of stereochemistry of obyanamide, Tetrahedron, 62(42), pp. 9966-9972, 2006.

* cited by examiner

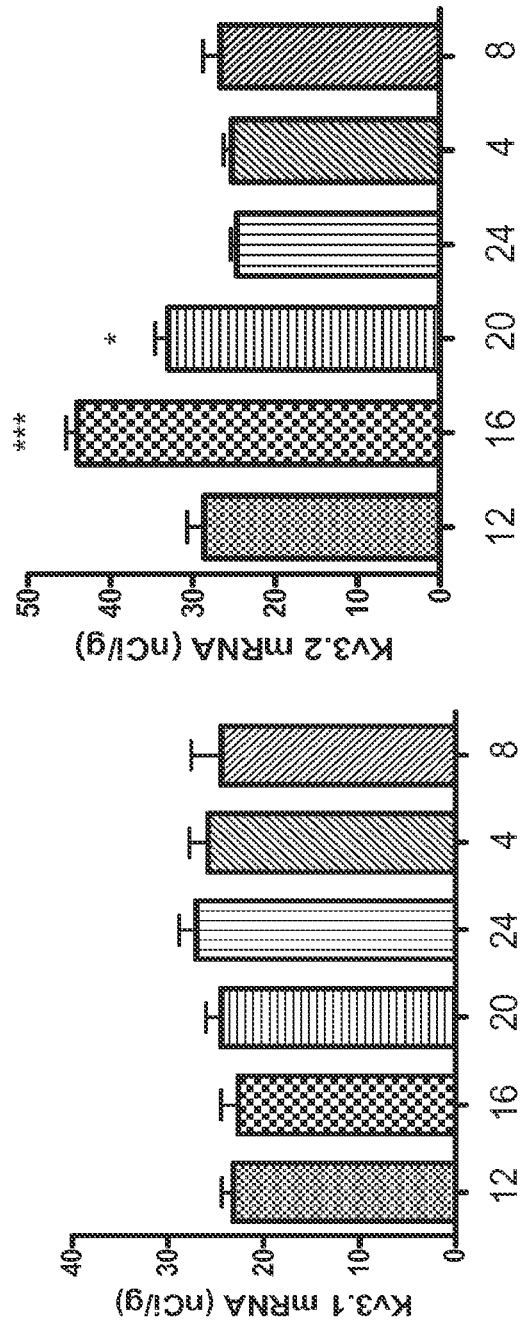

HYDANTOIN DERIVATIVES USEFUL AS KV3 INHIBITORS

RELATED APPLICATIONS

The present application is a continuation of, and claims the benefit of and priority to, U.S. patent application Ser. No. 16/985,160, filed Aug. 4, 2020, now allowed, which is a continuation of U.S. patent application Ser. No. 16/285,996, filed Feb. 26, 2019, which is a continuation of U.S. patent application Ser. No. 15/621,400, filed on Jun. 13, 2017 (now U.S. Pat. No. 10,265,316), which is a divisional of U.S. patent application Ser. No. 15/093,004, filed on Apr. 7, 2016, which is a divisional of U.S. application Ser. No. 13/991,486, filed on Jun. 4, 2013 (now U.S. Pat. No. 9,346,790), which is a U.S. national phase of International Application No. PCT/GB2011/052414, filed on Dec. 6, 2011, which designated the U.S. and claims priority to GB Application No. 1020607.6, filed on Dec. 6, 2010, International Application No. PCT/EP2010/068946, filed on Dec. 6, 2010, GB Application No. 1109508.0, filed on Jun. 7, 2011, and GB Application No. 1113757.7, filed on Aug. 10, 2011. The contents of each of which are hereby incorporated by reference in their entirety.

TECHNICAL FIELD

This disclosure relates to novel compounds, pharmaceutical compositions containing them and their use in therapy, in particular in the prophylaxis or treatment of hearing disorders, including hearing loss and tinnitus, as well as schizophrenia, bipolar disorder, epilepsy and sleep disorders.

BACKGROUND

The Kv3 voltage-gated potassium channel family includes four members, Kv3.1, Kv3.2, Kv3.3, and Kv3.4. Genes for each of these subtypes can generate multiple isoforms by alternative splicing, producing versions with different C-terminal domains. Thirteen isoforms have been identified in mammals to date, but the currents expressed by these variants appear similar (Rudy and McBain, 2001, Trends in Neurosciences 24, 517-526). Kv3 channels are activated by depolarisation of the plasma membrane to voltages more positive than −20 mV; furthermore, the channels deactivate rapidly upon repolarisation of the membrane. These biophysical properties ensure that the channels open towards the peak of the depolarising phase of the neuronal action potential to initiate repolarisation. Rapid termination of the action potential mediated by Kv3 channels allows the neuron to recover more quickly to reach sub-threshold membrane potentials from which further action potentials can be triggered. As a result, the presence of Kv3 channels in certain neurons contributes to their ability to fire at high frequencies (Rudy and McBain, 2001, Trends in Neurosci. 24, 517-526). Kv3.1-3 subtypes are predominant in the CNS, whereas Kv3.4 channels are found predominantly in skeletal muscle and sympathetic neurons (Weiser et al., 1994, J. Neurosci. 14, 949-972). Kv3.1-3 channel subtypes are differentially expressed by sub-classes of interneurons in cortical and hippocampal brain areas (e.g. Chow et al., 1999, J. Neurosci. 19, 9332-9345; Martina et al., 1998, J. Neurosci. 18, 8111-8125; McDonald and Mascagni, 2006, Neurosci. 138, 537-547, Chang et al., 2007, J. Comp. Neurol. 502, 953-972), in the thalamus (e.g. Kasten et al., 2007, J. Physiol. 584, 565-582), cerebellum (e.g. Sacco et al., 2006, Mol. Cell. Neurosci. 33, 170-179), and auditory brain stem nuclei (Li et al., 2001, J. Comp. Neurol. 437, 196-218).

Characterisation of mice in which one or more of the Kv3 subtypes has been deleted shows that the absence of Kv3.1 gives rise to increased locomotor activity, altered electroencephalographic activity, and a fragmented sleep pattern (Joho et al., 1999, J. Neurophysiol. 82, 1855-1864). The deletion of Kv3.2 leads to a reduction in seizure threshold and altered cortical electroencephalographic activity (Lau et al., 2000, J. Neurosci. 20, 9071-9085). Deletion of Kv3.3 is associated with mild ataxia and motor deficits (McMahon et al., 2004, Eur. J. Neurosci. 19, 3317-3327). Double deletion of Kv3.1 and Kv3.3 gives rise to a severe phenotype characterised by spontaneous seizures, ataxia, and an increased sensitivity to the effects of ethanol (Espinosa et al., 2001, J. Neurosci. 21, 6657-6665; Espinosa et al., 2008, J. Neurosci. 28, 5570-5581).

The known pharmacology of Kv3 channels is limited. Tetraethylammonium (TEA) has been shown to inhibit the channels at low millimolar concentrations (Rudy and McBain, 2001, Trends in Neurosci. 24, 517-526), and blood-depressing substance (BDS) toxins from the sea anemone, *Anemonia sulcata* (Diochot et al., 1998, J. Biol. Chem. 273, 6744-6749), have been shown to selectively inhibit Kv3 channels with high affinity (Yeung et al., 2005, J. Neurosci. 25, 8735-8745). In addition to compounds acting directly on Kv3 channels, agonists of receptors that activate protein kinase A (PKA) and protein kinase C (PKC) have been shown to modulate Kv3-mediated currents in specific brain areas, leading to a reduction in the ability of the neurons to fire at high frequency (Atzori et al., 2000, Nat. Neurosci. 3, 791-798; Song et al., 2005, Nat Neurosci. 8, 1335-1342); these studies suggest that PKA and PKC can specifically phosphorylate Kv3 channels in a neuron-specific manner, causing a reduction in Kv3-mediated currents.

Bipolar disorder, schizophrenia, anxiety, and epilepsy are serious disorders of the central nervous system that have been associated with reduced function of inhibitory interneurons and gamma-amino butyric acid (GABA) transmission (Reynolds et al., 2004, Neurotox. Res. 6, 57-61; Benes et al., 2008, PNAS, 105, 20935-20940; Brambilla et al., 2003, Mol. Psychiatry. 8, 721-37, 715; Aroniadou-Anderjaska et al., 2007, Amino Acids 32, 305-315; Ben-Ari, 2006, Crit. Rev. Neurobiol. 18, 135-144). Parvalbumin positive basket cells that express Kv3 channels in the cortex and hippocampus play a key role in generating feedback inhibition within local circuits (Markram et al., 2004, Nat. Rev. Neurosci. 5, 793-807). Given the relative dominance of excitatory synaptic input over inhibitory input to glutamatergic pyramidal neurons in these circuits, fast-firing of interneurons supplying inhibitory input is essential to ensure balanced inhibition. Furthermore, accurate timing of inhibitory input is necessary to sustain network synchronisation, for example, in the generation of gamma frequency field potential oscillations that have been associated with cognitive function (Fisahn et al., 2005, J. Physiol 562, 65-72; Engel et al., 2001, Nat. Rev. Neurosci. 2, 704-716). Notably, a reduction in gamma oscillations has been observed in patients with schizophrenia (Spencer et al., 2004, PNAS 101, 17288-17293). Consequently, positive modulators of Kv3 channels might be expected to enhance the firing capabilities of specific groups of fast-firing neurons in the brain. These effects may be beneficial in disorders associated with abnormal activity of these neuronal groups.

In addition, Kv3.2 channels have been shown to be expressed by neurons of the superchiasmatic nucleus (SCN) the main circadian pacemaker in the CNS (Schulz and Steimer, 2009, CNS Drugs 23 Suppl 2, 3-13).

Hearing loss represents an epidemic that affects approximately 16% of the population in Europe and the US (Goldman and Holme, 2010, Drug Discovery Today 15, 253-255), with a prevalence estimated at 250 million people worldwide (B. Shield, 2006, Evaluation of the social and economic costs of hearing impairment. A report for Hear-It AISBL: www.hear-it.org/multimedia/Hear_It_Report_October_2006.pdf). As life expectancy continues to increase, so too will the number of people suffering from hearing disorders. Furthermore, it is believed that modern lifestyles may exacerbate this burden as the younger generation ages. Hearing conditions, including tinnitus have a profound effect on the quality of life, causing social isolation, depression, work and relationship difficulties, low self-esteem, and prejudice. Voltage-gated ion channels of the Kv3 family are expressed at high levels in auditory brainstem nuclei (Li et al., 2001, J. Comp. Neurol. 437, 196-218) where they permit the fast firing of neurons that transmit auditory information from the cochlear to higher brain regions. Loss of Kv3.1 channel expression in central auditory neurons is observed in hearing impaired mice (von Hehn et al., 2004, J. Neurosci. 24, 1936-1940), and a decline in Kv3.1 expression may be associated with loss of hearing in aged mice (Jung et al. 2005 Neurol. Res. 27, 436-440). Furthermore, pathological plasticity of auditory brainstem networks is likely to contribute to symptoms that are experienced by many people suffering from hearing loss of different types. Recent studies have shown that regulation of Kv3.1 channel function and expression has a major role in controlling auditory neuron excitability (Kaczmarek et al., 2005, Hearing Res. 206, 133-145), suggesting that this mechanism could account for some of the plastic changes that give rise to tinnitus. More specifically, a reduction in Kv3-like potassium currents in neurons of the dorsal cochlear nucleus has now been observed following acoustic trauma in rats, suggesting that reduced Kv3 function could contribute to the pathological process that is triggered by damaging noise (Pilati et al., 2011, Hearing Res., doi: 10.1016/j.hearingres.2011.10.008), and supporting the hypothesis that positive modulation of Kv3 channels in auditory brainstem nuclei could have a therapeutic benefit in patients suffering from noise-induced hearing loss. Finally, Fraglie X syndrome and autism are frequently associated with hypersensitivity to sensory input, including auditory stimuli. Recent findings suggest that the protein coded by the FMR-I gene, whose mutation or absence gives rise to Fragile X syndrome, may directly regulate the expression of Kv3.1 channels in the auditory brainstem nuclei (Strumbos et al., 2010, J. Neuroscience, in press), suggesting that mis-regulation of Kv3.1 channels could give rise to hyperacusis in patients suffering from Fragile X or autism. Consequently, we propose that small molecule modulators of Kv3 channels in auditory brainstem nuclei could have a benefit in the treatment of disorders of hearing, including tinnitus and auditory hyper-acuity associated with Fragile X syndrome and autism.

SUMMARY

The present disclosure provides compounds of formula (I):

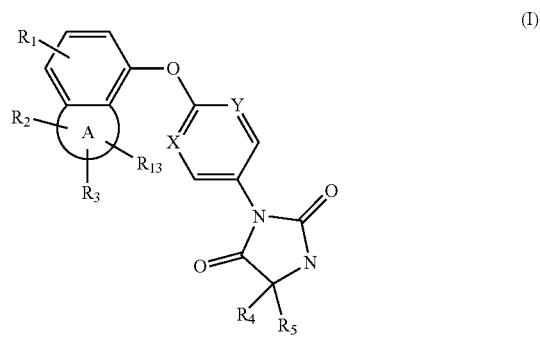

wherein:

$R_1$ is H, or $C_{1-4}$alkyl, halo, halo$C_{1-4}$alkyl, CN, $C_{1-4}$alkoxy, halo$C_{1-4}$alkoxy;

$R_2$ is H, $C_{1-4}$alkyl, $C_{3-4}$ spiro carbocycly, halo$C_{1-4}$alkyl or halo;

$R_3$ is H, $C_{1-4}$alkyl, halo$C_{1-4}$alkyl, halo; or $R_3$ is absent;

$R_{13}$ is H, $C_{1-4}$alkyl, halo$C_{1-4}$alkyl, halo; or $R_{13}$ is absent;

A is a 5 or 6 membered saturated or unsaturated heterocycle, with at least one O atom; which heterocycle is optionally fused with a cyclopropyl group to form a tricycle when considered together with the phenyl;

X is C or N;

Y is C or N;

$R_4$ is $C_{1-4}$ alkyl;

$R_5$ is H, Deuterium, $C_{1-4}$ alkyl;

or $R_4$ and $R_5$ can be fused to form $C_{3-4}$ spiro carbocycly;

wherein $R_2$ and $R_3$ may be attached to the same or a different ring atom; and wherein $R_2$ may be attached to a fused ring atom.

Compounds of formula (I) may be provided in the form of a pharmaceutically acceptable salt and/or solvate. In one embodiment of the disclosure a compound of formula (I) is provided in the form of a pharmaceutically acceptable salt.

The compounds of formula (I) may be used as medicaments, in particular for the prophylaxis or treatment of hearing disorders, including hearing loss and tinnitus, as well as schizophrenia, bipolar disorder, epilepsy and sleep disorders.

Further, there is provided a method for the prophylaxis or treatment of hearing disorders, including hearing loss and tinnitus, as well as schizophrenia, bipolar disorder, epilepsy and sleep disorders by administering to a subject a compound of formula (I).

Compounds of formula (I) may be used in the manufacture of a medicament for the prophylaxis or treatment of hearing disorders, including hearing loss and tinnitus, as well as schizophrenia, bipolar disorder, epilepsy and sleep disorders.

Also provided are pharmaceutical compositions containing a compound of formula (I) and a pharmaceutically acceptable carrier or excipient.

DETAILED DESCRIPTION

The present disclosure provides compounds of formula (I):

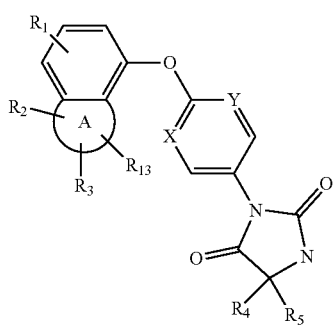

(I)

wherein:
  $R_1$ is H, or $C_{1-4}$alkyl, halo, halo$C_{1-4}$alkyl, CN, $C_{1-4}$alkoxy, halo$C_{1-4}$alkoxy;
  $R_2$ is H, $C_{1-4}$alkyl, $C_{3-4}$ spiro carbocycly, halo$C_{1-4}$alkyl or halo;
  $R_3$ is H, $C_{1-4}$alkyl, halo$C_{1-4}$alkyl, halo;
  $R_{13}$ is H, $C_{1-4}$alkyl, halo$C_{1-4}$alkyl, halo;
  A is a 5 or 6 membered saturated or unsaturated heterocycle, with at least one O atom; which heterocycle is optionally fused with a cyclopropyl group to form a tricycle when considered together with the phenyl;
  X is C or N;
  Y is C or N;
  $R_4$ is $C_{1-4}$ alkyl;
  $R_5$ is H, Deuterium, $C_{1-4}$ alkyl;
  or $R_4$ and $R_5$ can be fused to form $C_{3-4}$ spiro carbocycly;
  wherein $R_2$ and $R_3$ may be attached to the same or a different ring atom; and wherein $R_2$ may be attached to a fused ring atom.

Suitably $R_1$ is H or methyl. In one embodiment of the disclosure $R_1$ is H. In a second embodiment the disclosure $R_1$ is $C_{1-4}$alkyl, in particular $R_1$ is methyl.

Suitably $R_2$ is H, F, methyl, ethyl, isopropyl or a $C_3$ spiro group. In one embodiment of the disclosure $R_2$ is H. In a second embodiment of the disclosure $R_2$ is $C_{1-4}$alkyl, in a particular example of this embodiment $R_2$ is methyl, in a further example of this embodiment $R_2$ is ethyl and in another example of this embodiment $R_2$ is propyl (e.g. isopropyl). In a third embodiment of the disclosure $R_2$ is a $C_3$ spiro group. In a fourth embodiment of the disclosure $R_2$ is a $C_4$ spiro group. In a fifth embodiment of the disclosure $R_2$ is halo, in particular fluoro.

Suitably $R_3$ is H, F, methyl or ethyl. In one embodiment of the disclosure $R_3$ is H. In a second embodiment of the disclosure $R_3$ is $C_{1-4}$ alkyl, in a particular example of this embodiment $R_3$ is methyl, in a further example of this embodiment $R_3$ is ethyl. In a third embodiment of the disclosure $R_3$ is halo, in particular fluoro. The skilled person will appreciate that, depending on the size, presence of heteroatoms and the degree of unsaturation of the A ring, $R_3$ may be absent. Consequently, in another embodiment of the disclosure $R_3$ is absent.

Suitably, $R_3$ may be H, F, methyl or ethyl and $R_2$ may be H, F, methyl, ethyl, isopropyl or $C_{3-4}$ spiro carbocycly. In particular, $R_3$ may be H, F, methyl or ethyl and $R_2$ may be H, F, methyl, ethyl, isopropyl or $C_3$ spiro carbocycly. In certain embodiments $R_3$ is H and $R_2$ is H, methyl, ethyl, isopropyl or $C_{3-4}$ spiro carbocycly. In other embodiments, $R_3$ is methyl or ethyl and $R_2$ is methyl or ethyl, in one example of this embodiment $R_3$ and $R_2$ are both methyl (such as attached to the same ring carbon atom), in a second example of this embodiment $R_3$ and $R_2$ are both ethyl (such as attached to the same ring carbon atom). In further embodiments $R_3$ and $R_2$ are both fluoro (such as attached to the same ring carbon atom).

Suitably $R_{13}$ is may be H, F or methyl. In one embodiment of the disclosure $R_{13}$ is H. In a second embodiment of the disclosure $R_{13}$ is $C_{1-4}$ alkyl, in a particular example of this embodiment $R_{13}$ is methyl. In a third embodiment of the disclosure $R_{13}$ is halo, in particular fluoro. The skilled person will appreciate that, depending on the size, presence of heteroatoms and the degree of unsaturation of the A ring, $R_{13}$ may be absent. Consequently, in another embodiment of the disclosure $R_{13}$ is absent.

In one embodiment of the disclosure A is a 5 membered saturated or unsaturated heterocycle, with at least one O atom; which heterocycle is optionally fused with a cyclopropyl group to form a tricycle when considered together with the phenyl. In a second embodiment of the disclosure A is a 6 membered saturated or unsaturated heterocycle, with at least one O atom; which heterocycle is optionally fused with a cyclopropyl group to form a tricycle when considered together with the phenyl.

In certain embodiments the ring A contains one heteroatom. In other embodiments the ring A contains two heteroatoms (e.g. two oxygen atoms, alternatively one oxygen atom and one nitrogen atom).

Suitably, A is dihydrofuran, isoxazole, dihydropyran, 1,3-dioxolane, 1,3-oxazine or dihydropyran fused with a cyclopropyl group. In one embodiment of the disclosure A is dihydrofuran. In a second embodiment of the disclosure A is dihydropyran. In a third embodiment the disclosure A is dihydrofuran fused with a cyclopropyl group. In a fourth embodiment the disclosure A is dihydropyran fused with a cyclopropyl group. In a fifth embodiment of the disclosure A is dihydrofuran, isoxazole or dihydropyran. In a sixth embodiment of the disclosure A is dihydrofuran, isoxazole or dihydropyran, fused with a cyclopropyl group. In a seventh embodiment of the disclosure A is 1,3-oxazine. In an eighth embodiment of the disclosure A is 1,3-dioxolane.

When A contains a 5 membered heterocycle containing one heteroatom, suitably the oxygen atom is located in the meta position relative to the phenyl ring.

When A contains a 5 membered heterocycle containing one heteroatom, suitably the heterocycle is dihydrofuran.

When A contains a 6 membered heterocycle containing one heteroatom, suitably the oxygen atom is located in the meta position relative to the phenyl ring.

When A contains a 6 membered heterocycle containing one heteroatom, suitably the heterocycle is dihydropyran.

When A is a five membered ring, in particular embodiments of the disclosure one of $R_2$, $R_3$ and $R_{13}$ is H and the others are both methyl, for example one of $R_2$, $R_3$ and $R_{13}$ is H and the others are both methyl attached to the same ring carbon. Alternatively when A is a five membered ring, $R_2$ is a $C_3$ spiro group and $R_3$ and $R_{13}$ are both H.

When A is a five membered ring fused with a cyclopropyl group, suitably $R_2$, $R_3$ and $R_{13}$ are all H.

When A is a six membered ring, in particular embodiments of the disclosure one of $R_2$, $R_3$ and $R_{13}$ is methyl and the others are both H. Alternatively when A is a six membered ring, $R_2$ is a $C_3$ spiro group and $R_3$ and $R_{13}$ are both H.

When A is a five membered ring fused with a cyclopropyl group, suitably $R_2$, $R_3$ and $R_{13}$ are all H.

When A is a six membered ring fused with a cyclopropyl group, suitably $R_2$, $R_3$ and $R_{13}$ are all H.

In one embodiment of the disclosure X is C and Y is C. In a second embodiment of the disclosure X is N and Y is C. In a third embodiment of the disclosure X is N and Y is N.

Suitably, $R_4$ is methyl, ethyl, isopropyl or t-butyl. In one embodiment of the disclosure $R_4$ is methyl. In another embodiment of the disclosure $R_4$ is ethyl. In a further embodiment of the disclosure $R_4$ is propyl, such is isopropyl. In a yet further embodiment of the disclosure $R_4$ is butyl, such as t-butyl. Suitably, $R_5$ is H or methyl. In one embodiment of the disclosure $R_5$ is H. In a second embodiment of the disclosure $R_5$ is $C_{1-4}$alkyl, in particular $R_5$ is methyl.

In one embodiment of the disclosure $R_4$ and $R_5$ together form a $C_3$ spiro carbocycle. In a second embodiment of the disclosure $R_4$ and $R_5$ together form a $C_4$ spiro carbocycle. In a further embodiment of the disclosure $R_4$ is methyl and $R_5$ is methyl. In an embodiment of particular interest, $R_4$ is ethyl and $R_5$ is methyl.

Suitably, $R_4$ and $R_5$ have the stereochemical arrangement:

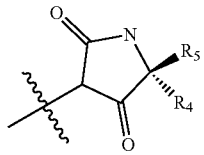

In one embodiment of the disclosure, $R_5$ is H and the $R_4$ substituent is in the S configuration.

In one embodiment of the disclosure $R_4$ is methyl, $R_5$ is methyl, X is N and Y is C, such as where A is dihydrofuran, in particular where A is dihydrofuran and $R_1$ is H, especially where A is dihydrofuran, $R_1$ is H and $R_2$ is a $C_3$ spiro group.

Compounds of formula (I), or any subset thereof including compounds of formula (Ib) and compounds of formula (Ic) may optionally be provided in the form of a pharmaceutically acceptable salt and/or solvate. In one embodiment of the disclosure a compound of formula (I) is provided in the form of a pharmaceutically acceptable salt. In a second embodiment of the disclosure a compound of formula (I) is provided in the form of a pharmaceutically acceptable solvate. In a third embodiment of the disclosure a compound of formula (I) is not in the form of a salt or solvate.

In a further aspect, the disclosure provides a compound of formula (Ib);

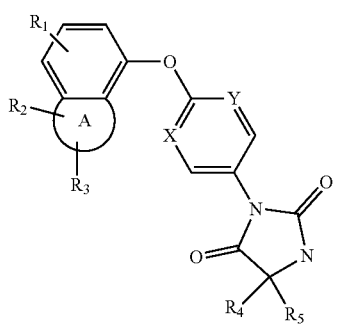

wherein:
$R_1$ is H, or $C_{1-4}$alkyl, halo, halo$C_{1-4}$alkyl, CN, $C_{1-4}$alkoxy, halo$C_{1-4}$alkoxy;
$R_2$ is H, $C_{1-4}$alkyl, $C_{3-4}$ spiro carbocycly, halo$C_{1-4}$alkyl or halo;
$R_3$ is H, $C_{1-4}$alkyl, halo$C_{1-4}$alkyl, halo;
A is a 5 or 6 membered saturated or unsaturated heterocycle, with at least one O atom; which heterocycle is optionally fused with a cyclopropyl group to form a tricycle when considered together with the phenyl;
X is C or N;
Y is C or N;
$R_4$ is $C_{1-4}$ alkyl;
$R_5$ is H, Deuterium, $C_{1-4}$ alkyl;
or $R_4$ and $R_5$ can be fused to form $C_{3-4}$ spiro carbocycly;
wherein $R_2$ and $R_3$ may be attached to the same or a different ring atom; and wherein $R_2$ may be attached to a fused ring atom;
or a pharmaceutically acceptable salt thereof.

Also provided is a compound of formula (Ic)

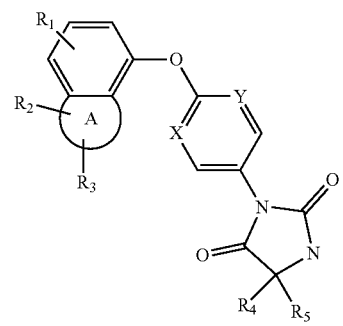

wherein:
$R_1$ is H, or $C_{1-4}$alkyl;
$R_2$ is H, $C_{1-4}$alkyl, $C_{3-4}$ spiro carbocycly, halo$C_{1-4}$alkyl or halo;
$R_3$ is H, $C_{1-4}$alkyl, halo$C_{1-4}$alkyl, halo;
A is a 5 or 6 membered saturated or unsaturated heterocycle, with at least one O atom; which heterocycle is optionally fused with a cyclopropyl group to form a tricycle when considered together with the phenyl;
X is C or N;
Y is C or N;
$R_4$ is $C_{1-4}$ alkyl;
$R_5$ is H, Deuterium, $C_{1-4}$ alkyl;
or $R_4$ and $R_5$ can be fused to form $C_{3-4}$ spiro carbocycly;
wherein $R_2$ and $R_3$ may be attached to the same or a different ring atom;
and wherein $R_2$ may be attached to a fused ring atom;
or a pharmaceutically acceptable salt thereof.

In respect of the compounds of formula (Ib) and (Ic):
In one embodiment of the disclosure $R_1$ is H.
In one embodiment of the disclosure $R_1$ is $C_{1-4}$alkyl. In another embodiment of the disclosure $R_1$ is methyl.
In one embodiment of the disclosure $R_2$ is H.
In one embodiment of the disclosure $R_2$ is $C_{1-4}$alkyl. In another embodiment $R_2$ is methyl. In a further embodiment $R_2$ is ethyl. In a yet further embodiment $R_2$ is propyl.
In one embodiment of the disclosure $R_2$ is a $C_3$ spiro group.
In one embodiment of the disclosure $R_3$ is H.

In one embodiment of the disclosure $R_3$ is $C_{1-4}$ alkyl. In another embodiment of the disclosure $R_3$ is methyl.

In one embodiment of the disclosure A is tetrahydrofuran, isoxazole or tetrahydropyran.

In one embodiment of the disclosure A is tetrahydrofuran, isoxazole or tetrahydropyran, fused with a cyclopropyl group.

In one embodiment of the disclosure X is C and Y is C.

In one embodiment of the disclosure X is N and Y is C.

In one embodiment of the disclosure X is N and Y is N.

In one embodiment of the disclosure $R_4$ is methyl. In another embodiment of the disclosure $R_4$ is ethyl. In a further embodiment of the disclosure $R_4$ is propyl. In a yet further embodiment of the disclosure $R_4$ is butyl.

In one embodiment of the disclosure $R_5$ is H.

In one embodiment of the disclosure $R_5$ is $C_{1-4}$alkyl. In another embodiment of the disclosure $R_5$ is methyl.

In one embodiment of the disclosure $R_4$ and $R_5$ together form a $C_3$ spiro carbocycle.

In one embodiment of the disclosure $R_4$ and $R_5$ together form a $C_4$ spiro carbocycle.

In one embodiment of the disclosure, $R_5$ is H and the $R_4$ substituent is in the S configuration.

In one embodiment of the disclosure $R_4$ is methyl and $R_5$ is methyl.

In one embodiment of the disclosure $R_4$ is methyl, $R_5$ is methyl, X is N and Y is C.

In one embodiment of the disclosure $R_4$ is methyl, $R_5$ is methyl, X is N, Y is C and A is tetrahydrofuran.

In one embodiment of the disclosure $R_4$ is methyl, $R_5$ is methyl, X is N, Y is C, A is tetrahydrofuran and $R_1$ is H.

In one embodiment of the disclosure $R_4$ is methyl, $R_5$ is methyl, X is N, Y is C, A is tetrahydrofuran, $R_1$ is H and $R_2$ is a $C_3$ spiro group.

In one embodiment of the disclosure the compound is selected from the group consisting of:

(5R)-3-[4-(1,3-dihydro-2-benzofuran-4-yloxy)phenyl]-5-methyl-2,4-imidazolidinedione;

(5R)-5-methyl-3-{4-[(3-methyl-1,2-benzisoxazol-4-yl)oxy]phenyl}-2,4-imidazolidinedione;

(5R)-3-{4-[(3,6-dimethyl-1,2-benzisoxazol-4-yl)oxy]phenyl}-5-methyl-2,4-imidazolidinedione;

5,5-dimethyl-3-{4-[(3-methyl-1,2-benzisoxazol-4-yl)oxy]phenyl}-2,4-imidazolidinedione;

(5R)-5-ethyl-3-{6-[(3-ethyl-1,2-benzisoxazol-4-yl)oxy]-3-pyridinyl}-2,4-imidazolidinedione;

(5R)-5-ethyl-3-(6-{[3-(1-methylethyl)-1,2-benzisoxazol-4-yl]oxy}-3-pyridinyl)-2,4-imidazolidinedione;

(5R)-3-{4-[(3,3-dimethyl-2,3-dihydro-1-benzofuran-4-yl)oxy]phenyl}-5-methyl-2,4-imidazolidinedione;

(5R)-3-{6-[(3,3-dimethyl-2,3-dihydro-1-benzofuran-4-yl)oxy]-3-pyridinyl}-5-methyl-2,4-imidazolidinedione;

(5R)-3-{6-[(3,3-dimethyl-2,3-dihydro-1-benzofuran-4-yl)oxy]-3-pyridinyl}-5-ethyl-2,4-imidazolidinedione;

(5R)-3-{2-[(3,3-dimethyl-2,3-dihydro-1-benzofuran-4-yl)oxy]-5-pyrimidinyl}-5-ethyl-2,4-imidazolidinedione;

7-{6-[(3,3-dimethyl-2,3-dihydro-1-benzofuran-4-yl)oxy]-3-pyridinyl}-5,7-diazaspiro[3.4]octane-6,8-dione;

6-{6-[(3,3-dimethyl-2,3-dihydro-1-benzofuran-4-yl)oxy]-3-pyridinyl}-4,6-diazaspiro[2.4]heptane-5,7-dione;

3-{6-[(3,3-dimethyl-2,3-dihydro-1-benzofuran-4-yl)oxy]-3-pyridinyl}-5,5-dimethyl-2,4-imidazolidinedione;

(5R)-3-{2-[(3,3-dimethyl-2,3-dihydro-1-benzofuran-4-yl)oxy]-5-pyrimidinyl}-5-(1,1-dimethylethyl)-2,4-imidazolidinedione;

(5R)-5-ethyl-3-[6-(spiro[1-benzofuran-3,1'-cyclopropan]-4-yloxy)-3-pyridinyl]-2,4-imidazolidinedione;

5,5-dimethyl-3-[6-(spiro[1-benzofuran-3,1'-cyclopropan]-4-yloxy)-3-pyridinyl]-2,4-imidazolidinedione;

(5R)-5-ethyl-5-methyl-3-[6-(spiro[1-benzofuran-3,1'-cyclopropan]-4-yloxy)-3-pyridinyl]-2,4-imidazolidinedione;

(5R)-5-ethyl-3-(6-{[(3S/R)-3-methyl-1,3-dihydro-2-benzofuran-4-yl]oxy}-3-pyridinyl)-2,4-imidazolidinedione (diastereoisomeric mixture);

(5R)-5-ethyl-3-{6-[(3-methyl-1,3-dihydro-2-benzofuran-4-yl)oxy]-3-pyridinyl}-2,4-imidazolidinedione (diastereoisomers 1 and 2);

(5R)-5-ethyl-3-{6-[(3-ethyl-1,3-dihydro-2-benzofuran-4-yl)oxy]-3-pyridinyl}-2,4-imidazolidinedione (diastereoisomeric mixture);

(5R)-5-ethyl-3-{6-[(3-ethyl-1,3-dihydro-2-benzofuran-4-yl)oxy]-3-pyridinyl}-2,4-imidazolidinedione (diastereoisomers 1 and 2);

5,5-dimethyl-3-{6-[(3-methyl-3,4-dihydro-2H-chromen-5-yl)oxy]-3-pyridinyl}-2,4-imidazolidinedione (racemate mixture);

5,5-dimethyl-3-{6-[(3-methyl-3,4-dihydro-2H-chromen-5-yl)oxy]-3-pyridinyl}-2,4-imidazolidinedione (enantiomers 1 and enantiomer 2);

5,5-dimethyl-3-{6-[(1a-methyl-1,1a,2,7b-tetrahydrocyclopropa[c]chromen-7-yl)oxy]-3-pyridinyl}-2,4-imidazolidinedione;

5,5-dimethyl-3-{6-[(1a-methyl-1,1a,2,7b-tetrahydrocyclopropa[c]chromen-7-yl)oxy]-3-pyridinyl}-2,4-imidazolidinedione (enantiomer 1 and enantiomer 2);

(5R)-5-ethyl-5-methyl-3-[6-(1H-spiro[2-benzopyran-4,1'-cyclopropan]-5-yloxy)-3-pyridinyl]-2,4-imidazolidinedione;

3-{2-[(3,3-dimethyl-2,3-dihydro-1-benzofuran-4-yl)oxy]-5-pyrimidinyl}-5,5-dimethyl-2,4-imidazolidinedione;

(5R)-3-{2-[(3,3-dimethyl-2,3-dihydro-1-benzofuran-4-yl)oxy]-5-pyrimidinyl}-5-(1-methylethyl)-2,4-imidazolidinedione;

(5R)-3-{6-[(2,2-dimethyl-2,3-dihydro-1-benzofuran-4-yl)oxy]-3-pyridinyl}-5-ethyl-2,4-imidazolidinedione;

5,5-dimethyl-3-[6-(1H-spiro[2-benzopyran-4,1'-cyclopropan]-5-yloxy)-3-pyridinyl]-2,4-imidazolidinedione;

(5R)-3-[2-(2,3-dihydrospiro[chromene-4,1'-cyclopropan]-5-yloxy)-5-pyrimidinyl]-5-ethyl-5-methyl-2,4-imidazolidinedione;

5,5-dimethyl-3-{6-[(4-methyl-3,4-dihydro-2H-chromen-5-yl)oxy]-3-pyridinyl}-2,4-imidazolidinedione (racemate mixture, enantiomer 1, enantiomer 2);

(5R)-5-ethyl-5-methyl-3-{6-[(3-methyl-3,4-dihydro-2H-chromen-5-yl)oxy]-3-pyridinyl}-2,4-imidazolidinedione (diastereoisomeric mixture, diastereoisomer 1, diastereoisomer 2);

(5R)-5-ethyl-5-methyl-3-[6-(1,1a,2,7b-tetrahydrocyclopropa[c]chromen-7-yloxy)-3-pyridinyl]-2,4-imidazolidinedione (diastereoisomeric mixture, diastereoisomer 1, diastereoisomer 2);

3-{6-[(3-ethyl-1,3-dihydro-2-benzofuran-4-yl)oxy]-3-pyridinyl}-5,5-dimethyl-2,4-imidazolidinedione (racemate mixture, enantiomer 1, enantiomer 2);

or a pharmaceutically acceptable salt thereof.

In another embodiment of the disclosure the compound is selected from the group consisting of:

(5R)-5-ethyl-5-methyl-3-[2-(4-methylchroman-5-yl)oxypyrimidin-5-yl]imidazolidine-2,4-dione (diastereoisomeric mixture, diastereoisomer 1, diastereoisomer 2);

(5R)-5-ethyl-5-methyl-3-[2-(7-methylspiro[2H-benzofuran-3,1'-cyclopropane]-4-yl)oxypyrimidin-5-yl]imidazolidine-2,4-dione;

(5R)-3-[2-(3,3-dimethylisochroman-5-yl)oxypyrimidin-5-yl]-5-ethyl-5-methyl-imidazolidine-2,4-dione;
(5R)-5-ethyl-5-methyl-3-[2-(7-methylspiro[1H-isobenzofuran-3,1'-cyclobutane]-4-yl)oxypyrimidin-5-yl]imidazolidine-2,4-dione;
(5R)-5-ethyl-5-methyl-3-{2-[(3,3,7-trimethyl-2,3-dihydro-1-benzofuran-4-yl)oxy]-5-pyrimidinyl}-2,4-imidazolidinedione;
(5R)-3-{2-[(2,2-difluoro-7-methyl-1,3-benzodioxol-4-yl)oxy]-5-pyrimidinyl}-5-ethyl-5-methyl-2,4-imidazolidinedione;
(5R)-3-{2-[(2,2-difluoro-1,3-benzodioxol-4-yl)oxy]-5-pyrimidinyl}-5-ethyl-5-methyl-2,4-imidazolidinedione;
(5R)-5-ethyl-5-methyl-3-{2-[(2,4,4-trimethyl-4H-3,1-benzoxazin-5-yl)oxy]-5-pyrimidinyl}-2,4-imidazolidinedione;
5,5-dimethyl-3-[2-(7-methylspiro[2H-benzofuran-3,1'-cyclopropane]-4-yl)oxypyrimidin-5-yl]imidazolidine-2,4-dione; 3-[2-(3,3-dimethylisochroman-5-yl)oxypyrimidin-5-yl]-5,5-dimethyl-imidazolidine-2,4-dione;
5,5-dimethyl-3-[2-(7-methylspiro[1H-isobenzofuran-3,1'-cyclobutane]-4-yl)oxypyrimidin-5-yl]imidazolidine-2,4-dione;
(5R)-5-ethyl-3-[2-(7-methylspiro[2H-benzofuran-3,1'-cyclopropane]-4-yl)oxypyrimidin-5-yl]imidazolidine-2,4-dione;
(5R)-5-ethyl-3-[6-(7-methylspiro[2H-benzofuran-3,1'-cyclopropane]-4-yl)oxy-3-pyridyl]imidazolidine-2,4-dione;
(5R)-5-ethyl-3-{6-[(3,3,7-trimethyl-2,3-dihydro-1-benzofuran-4-yl)oxy]-3-pyridinyl}-2,4-imidazolidinedione;
(5R)-5-ethyl-3-{2-[(3,3,7-trimethyl-2,3-dihydro-1-benzofuran-4-yl)oxy]-5-pyrimidinyl}-2,4-imidazolidinedione;
(5R)-5-ethyl-5-methyl-3-[6-(7-methylspiro[2H-benzofuran-3,1'-cyclopropane]-4-yl)oxy-3-pyridyl]imidazolidine-2,4-dione;
(5R)-3-[6-(3,3-dimethylisochroman-5-yl)oxy-3-pyridyl]-5-ethyl-5-methyl-imidazolidine-2,4-dione;
(5R)-3-[6-[(3,3-diethyl-1H-isobenzofuran-4-yl)oxy]-3-pyridyl]-5-ethyl-5-methyl-imidazolidine-2,4-dione;
(5R)-5-ethyl-5-methyl-3-[6-[(2,4,4-trimethyl-3,1-benzoxazin-5-yl)oxy]-3-pyridyl]imidazolidine-2,4-dione;
(5R)-3-{6-[(3,3-dimethyl-1,3-dihydro-2-benzofuran-4-yl)oxy]-3-pyridinyl}-5-ethyl-5-methyl-2,4-imidazolidinedione;
5,5-dimethyl-3-[6-(7-methylspiro[2H-benzofuran-3,1-cyclopropane]-4-yl)oxy-3-pyridyl]imidazolidine-2,4-dione;
or a pharmaceutically acceptable salt thereof.

For the avoidance of doubt, the embodiments of any one feature of the compounds of the disclosure may be combined with any embodiment of another feature of compounds of the disclosure to create a further embodiment.

The term 'halo' or 'halogen' as used herein, refers to a fluorine, chlorine, bromine or iodine atom. Particular examples of halo are fluorine and chlorine, especially fluorine.

When the compound contains a $C_{1-4}$alkyl group, whether alone or forming part of a larger group, e.g. $C_{1-4}$alkoxy, the alkyl group may be straight chain, branched, cyclic, or a combination thereof. Examples of $C_{1-4}$alkyl are methyl, ethyl, n-propyl, isopropyl, n-butyl, isobutyl, sec-butyl, tert-butyl, cyclopropyl and cyclobutyl. A particular group of exemplary $C_{1-4}$alkyl groups are methyl, ethyl, n-propyl, isopropyl, n-butyl, isobutyl, sec-butyl, tert-butyl. An example of $C_{1-4}$alkoxy is methoxy.

The term 'halo$C_{1-4}$alkyl' as used herein, includes straight chain, branched chain or cyclic alkyl groups containing 1 to 4 carbon atoms substituted by one or more halo atoms, for example fluoromethyl, difluoromethyl and trifluoromethyl. A particular group of exemplary halo$C_{1-4}$ alkyl include methyl and ethyl groups substituted with one to three halo atoms, in particular one to three fluoro atoms.

The term 'halo$C_{1-4}$alkoxy' as used herein, includes straight chain, branched chain or cyclic alkoxy groups containing 1 to 4 carbon atoms substituted by one or more halo atoms, for example fluoromethoxy, difluoromethoxy and trifluoromethoxy. A particular group of exemplary halo$C_{1-4}$ alkyl include methoxy and ethoxy groups substituted with one to three halo atoms, in particular one to three fluoro atoms.

The term '5 or 6 membered saturated or unsaturated heterocycle, with at least one O atom' includes for example furan, oxazole, isoxazole, oxadiazole, terahydrofuran, pyran, tetrahydropyran, dioxolane, dioxan, morpholine, and oxazoline.

It will be appreciated that for use in medicine the salts of the compounds of formula (I) should be pharmaceutically acceptable. Suitable pharmaceutically acceptable salts will be apparent to those skilled in the art. Pharmaceutically acceptable salts include those described by Berge, Bighley and Monkhouse J. Pharm. Sci. (1977) 66, pp 1-19. Such pharmaceutically acceptable salts include acid addition salts formed with inorganic acids e.g. hydrochloric, hydrobromic, sulphuric, nitric or phosphoric acid and organic acids e.g. succinic, maleic, acetic, fumaric, citric, tartaric, benzoic, p-toluenesulfonic, methanesulfonic or naphthalenesulfonic acid. Other salts e.g. oxalates or formates, may be used, for example in the isolation of compounds of formula (I) and are included within the scope of this disclosure.

Certain of the compounds of formula (I) may form acid addition salts with one or more equivalents of the acid. The present disclosure includes within its scope all possible stoichiometric and non-stoichiometric forms.

The compounds of formula (I) may be prepared in crystalline or non-crystalline form and, if crystalline, may optionally be solvated, e.g. as the hydrate. This disclosure includes within its scope stoichiometric solvates (e.g. hydrates) as well as compounds containing variable amounts of solvent (e.g. water).

It will be understood that the disclosure includes pharmaceutically acceptable derivatives of compounds of formula (I) and that these are included within the scope of the disclosure.

As used herein "pharmaceutically acceptable derivative" includes any pharmaceutically acceptable ester or salt of such ester of a compound of formula (I) which, upon administration to the recipient is capable of providing (directly or indirectly) a compound of formula (I) or an active metabolite or residue thereof.

It is to be understood that the present disclosure encompasses all isomers of formula (I) and their pharmaceutically acceptable derivatives, including all geometric, tautomeric and optical forms, and mixtures thereof (e.g. racemic mixtures). Where additional chiral centres are present in compounds of formula (I), the present disclosure includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

The subject disclosure also includes isotopically-labeled compounds which are identical to those recited in formula (I) but for the fact that one or more atoms are replaced by an atom having an atomic mass or mass number different from the atomic mass or mass number most commonly found in nature. Examples of isotopes that can be incorporated into compounds of the disclosure include isotopes of hydrogen, carbon, nitrogen, oxygen, fluorine, iodine and chlorine such as $^3$H, $^{11}$C, $^{14}$C, $^{18}$F, $^{123}$I or $^{125}$I. Another isotope of interest is $^{13}$C.

Compounds of the present disclosure and pharmaceutically acceptable salts of said compounds that contain the aforementioned isotopes and/or other isotopes of other atoms are within the scope of the present disclosure. Isotopically labeled compounds of the present disclosure, for example those into which radioactive isotopes such as $^3$H or $^{14}$C have been incorporated, are useful in drug and/or substrate tissue distribution assays. Tritiated, i.e. $^3$H, and carbon-14, i.e. $^{14}$C, isotopes are particularly preferred for their ease of preparation and detectability. $^{11}$C and $^{18}$F isotopes are particularly useful in PET (positron emission tomography).

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

According to a further aspect of the present disclosure there is provided a process for the preparation of compounds of formula (I) and derivatives thereof. The following schemes detail some synthetic routes to compounds of the disclosure. In the following schemes reactive groups can be protected with protecting groups and deprotected according to well established techniques.

In general, the compounds of formula (I) may be made according to the organic synthesis techniques known to those skilled in this field, as well as by the representative methods set forth below, those in the Examples and modifications thereof.

Compounds of formula (I), and salts and solvates thereof, may be prepared by the general methods outlined hereinafter. In the following description, the groups A, $R_1$, $R_2$, X, Y, $R_3$, $R_4$ and $R_5$ have the meanings as previously defined for compounds of formula (I) unless otherwise stated.

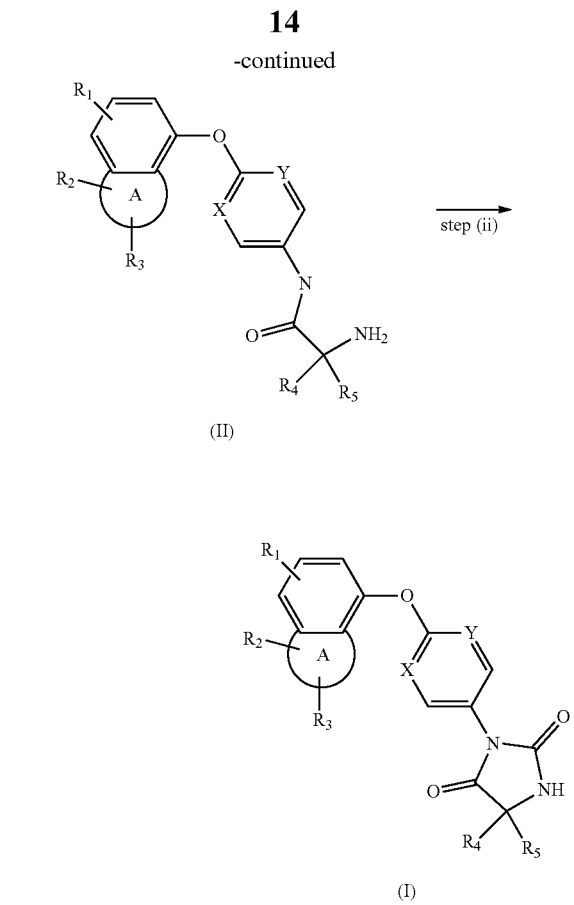

step (ii): Compounds of formula (I) can be prepared by cyclization of compounds of formula (II) in a solvent e.g. dichloromethane with a carbonylating agent e.g. triphosgene preferentially prediluted in the same solvent and added in a second time at 0° C. in presence of a base e.g. triethylamine. In some cases, ethyl acetate could be used as a solvent. Optionally a catalytic amount of DMAP can be added.

step (i): Compounds of formula (II) can be prepared from compounds of formula (III) by removal of the BOC protective group in acidic conditions e.g. TFA in a solvent e.g. dichloromethane at approximately 0° C. or RT.

Scheme 1a

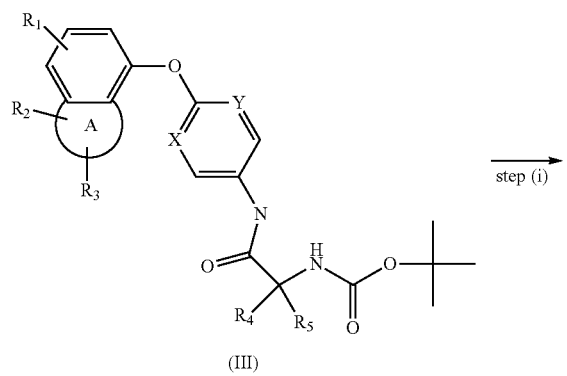

Scheme 1b

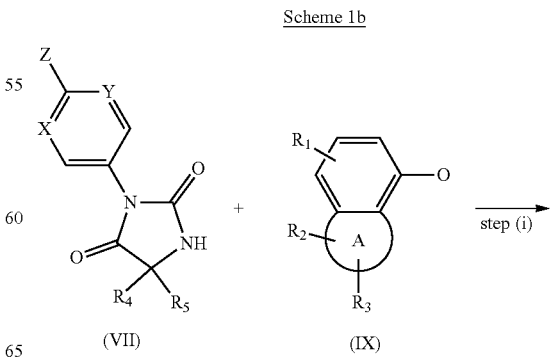

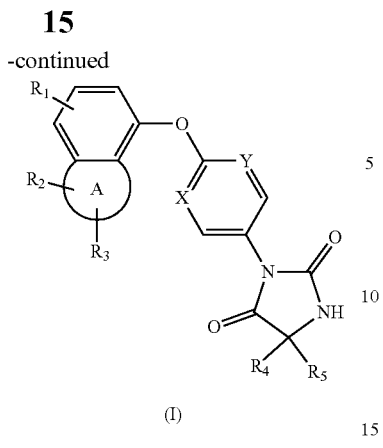

(I)

Compounds of formula (I), wherein X=Y=N or (X=C, Y=N) or (X=N, Y=C) and R$_4$ and R$_5$ are not H, can be prepared by nucleophilic aromatic substitution. In this reaction a halo-pyridyl or halo-pyrimidyl derivative of formula (VII) wherein typically Z=Cl and a phenol of formula (IX) are reacted in the presence of a base such as potassium carbonate in a suitable solvent, e.g. in N,N-dimethylformamide or in acetonitrile, with conventional heating or microwave heating.

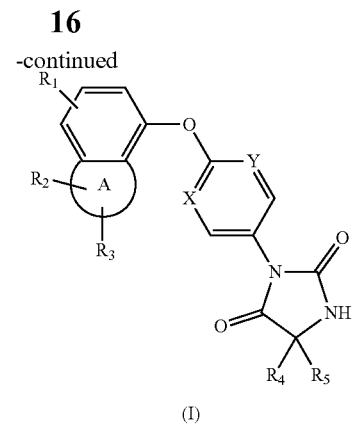

(I)

step (iii): Compounds of formula (I) wherein R$_4$ and R$_5$ are not H can be prepared by reaction of a urea of the type produced by step (ii) as shown above and a base such as sodium methoxide in a solvent such as Methanol at temperature ranging from 0° C. to 60° C.

step (ii): The urea product of step (ii) as shown above can be prepared by reaction of anilines of formula (IV) and amino esters (hydrochloride salt) of formula (XII) in a suitable solvent, e.g. dichloromethane or ethyl acetate, with a carbonylating agent, e.g. triphosgene, preferentially prediluted in the same solvent in presence of a base, e.g. triethylamine or diisopropylethylamine, at temperature ranging from 0° C. to 60° C., optionally adding a catalytic or stechiometric amount of DMAP.

step (i): Amino esters (hydrochloride salt) of formula (XII) (if not commercially available) can be prepared from commercially available amino acids (hydrochloride salt) of formula (XIII) by reaction with methanol in presence of a catalytic or stechiometric amount of thyonyl chloride at temperature ranging from r.t. to reflux.

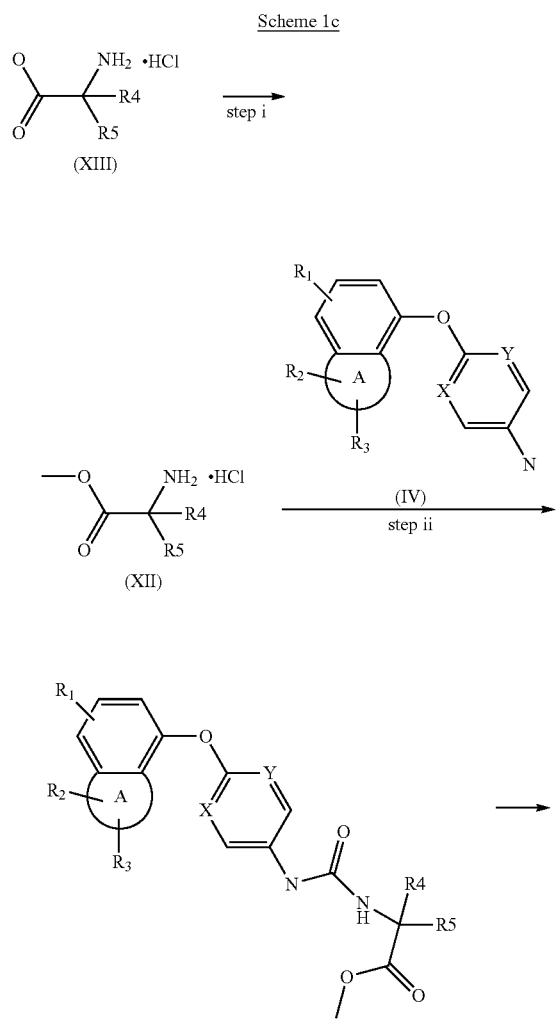

Scheme 1c

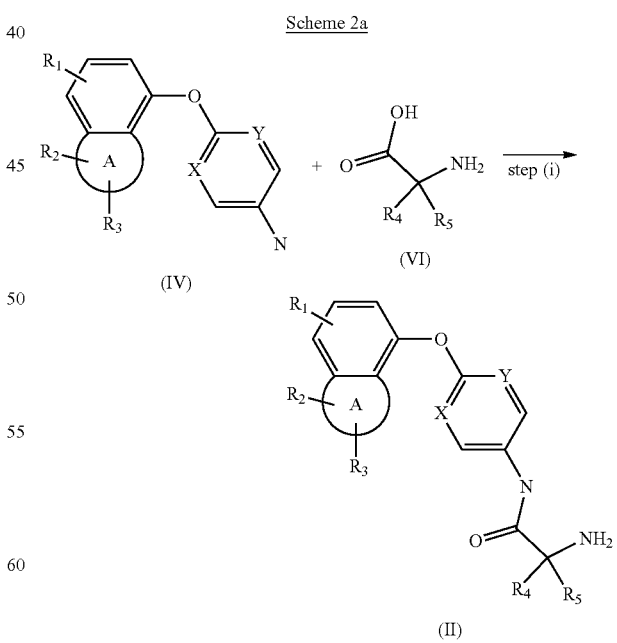

Scheme 2a step (i): Compounds of formula (II) can be prepared from anilines of formula (IV) and amino acids (as free base or hydrochloride salt) of formula (VI) by amidic coupling in the presence of a coupling agent e.g. T3P in a solvent such as ethyl acetate, acetonitrile or a mixture of them.

Scheme 2b

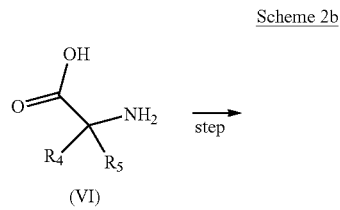

(VI)

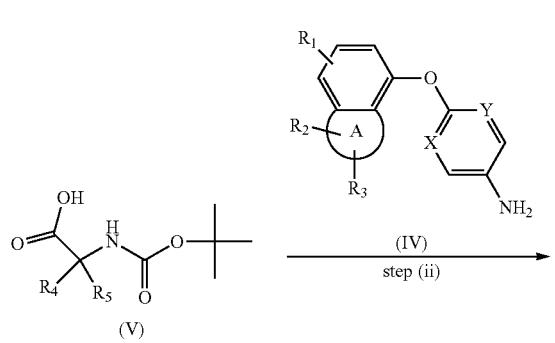

step (ii): Compounds of formula (III) can be prepared from anilines of formula (IV) and N-protected amino acids of formula (V) by amidic coupling in the presence of a base e.g. DIPEA and of a coupling agent e.g. HATU, TBTU in a solvent such as N,N-dimethylformamide.

step (i): Some N-Boc protected amino acids of formula (V) are commercially available e.g. N-{[(1,1-dimethylethyl)oxy]carbonyl}-2-methylalanine from for example Aldrich, N-{[(1,1-dimethylethyl)oxy]carbonyl}-D-alanine from for example Aldrich, (2R)-2-({[(1,1-dimethylethyl)oxy]carbonyl}amino)butanoic acid from for example Bachem UK Ltd, N-{[(1,1-dimethylethyl)oxy]carbonyl}-D-isovaline from for example Nagase & Co Ltd.

N-protected amino acids of formula (V) can also be prepared from compounds of formula (VI) for example with Boc-anhydride in presence of a base e.g. aqueous NaHCO$_3$, aqueous sodium hydroxide in a solvent such as THF, methanol, dioxane. Many descriptions are available in the literature (for example Tetrahedron, 2006, 62(42), 9966-9972)

Scheme 3

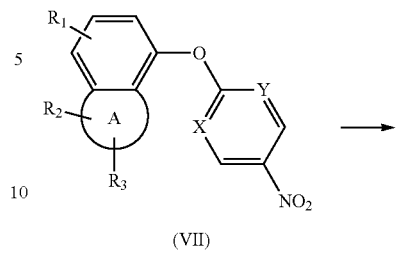

(VII)

↓

(IV)

Anilines of formula (IV) can be prepared from the nitro compounds (VII). Suitable reactions conditions to transform (VII) into (IV) are for example:

reduction in presence of Fe powder and ammonium chloride in a solvent such as a mixture THF/water for example at room temperature reduction with tin chloride hydrate in a solvent such as ethanol with heating for example at reflux.

Scheme 4

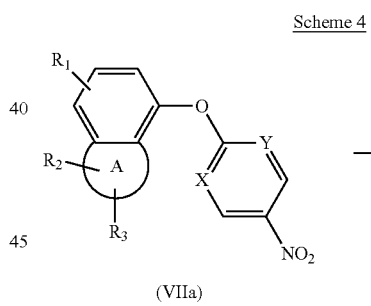

(VIIa)

↓

(IVa)

Anilines of formula (IVa), wherein R$_2$ is H, C$_{1-4}$ alkyl, C$_3$-C$_4$ spiro carbocycly and R$_3$ is H, C$_{1-4}$ alkyl and (X,Y) is not (N,N) can be prepared from the nitro compounds (VIIa) with the conditions described on Scheme 3 or also with the following conditions:

reduction with hydrazine hydrate and a catalytic amount of Pd/C in a solvent such as ethanol with heating for example at reflux.

Scheme 5

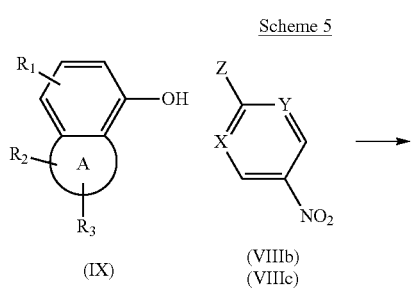

(VIIb), (VIIIb): X = Y = C or (X = C, Y = N) or (X = N, Y = C)
(VIIc), (VIIIc): X = Y = N

Compounds of formula (VIIb) wherein X=Y=C or (X=C, Y=N) or (X=N, Y=C) can be prepared by nucleophilic aromatic substitution. In this reaction are used a nitro derivative of formula (VIIIb) wherein Z=F (usually when [X=C, Y=C]) or Z=Cl (usually when [X=N, Y=C] or [X=C, Y=N]) and a phenol of formula (IX) in presence of a base such as potassium carbonate in a solvent e.g. in N,N-dimethylformamide or in acetonitrile with regular heating or microwave one.

Compounds of formula (VIIc) wherein X=Y=N can be prepared by nucleophilic aromatic substitution from phenol (IX) and nitro compound (VIIIc) wherein usually Z=Cl at room temperature using a base such as potassium carbonate in a solvent such as N,N-dimethylformamide. A further suitable solvent is acetonitrile.

Scheme 6

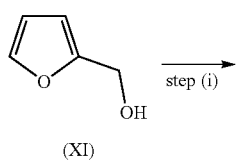

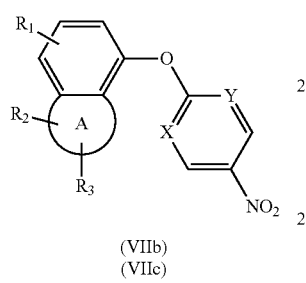

step (iii): Phenol of formula (IXa) corresponding to compound of formula (IX) wherein $R_1$ is H and A is the heterocycle depicted on Scheme 6 can be prepared by an intramolecular reaction from compounds of formula (X) in presence of a catalytic amount of $AuCl_3$ in acetonitrile at room temperature or a catalytic amount of $PtCl_2$ in acetone with heating (as described for that one in the Journal of the American Chemical Society 2003, 125, 5757-5766)

step (ii): Compound of formula (X) can be prepared from compound of formula (XI) with a similar method to the one described in the Journal of the American Chemical Society 2003, 125, 5757-5766 by nucleophilic substitution in presence of a base such as sodium hydride in a solvent e.g. DMF, with addition in a second time of an electrophile e.g. 3-bromo-1-propyne.

Scheme 7 step (ii): Phenols of formula (IXb), corresponding to compounds of formula (IX) wherein $R_1$ is H and A the heterocycles depicted on Scheme 7 ($R_6$ being Me or Et), can be prepared using the corresponding compounds of formula (XII) in presence of acidic conditions such as aqueous HCl in a solvent such as methanol.

step (i): Compounds of formula (XII) can be prepared by cyclization of compounds of formula (XIII) using a base such as nBuLi in a solvent such as THF e.g. at 0° C., adding in a second time 4-methylbenzenesulfonyl chloride e.g. at 0° C., then a second equivalent of a base such as nBuLi e.g. from 0° C. to room temperature and stopping the reaction with a diluted protic acid such as HCl.

Optionally the two steps (i) and (ii) can be carried out in a one pot fashion.

Scheme 8a

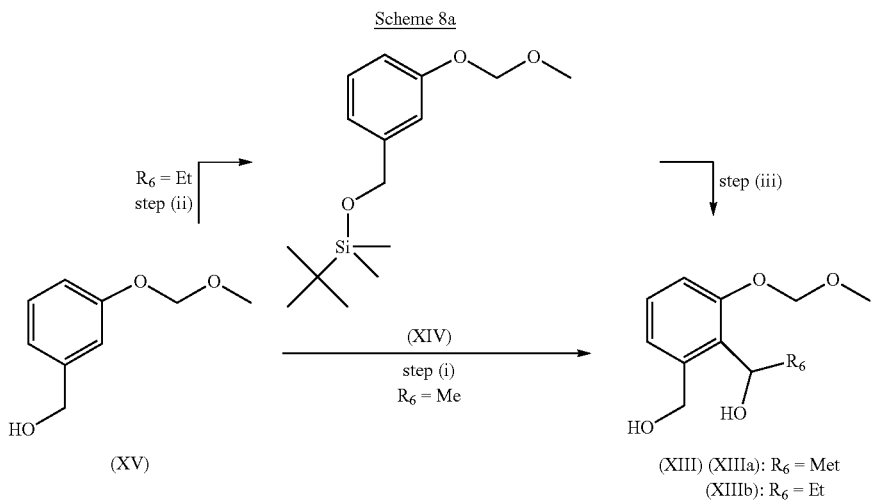

step (i): Compound of formula (XIIIa) wherein $R_6$=Met can be prepared directly from compound of formula (XV)
- by lithiation using for example nBuLi in a solvent such as hexane in presence of TMEDA from room temperature to 60° C.
- adding in a second time acetaldehyde for example at −78° C. and warming up the reaction mixture for example to room temperature.

step (iii): Compound of formula (XIIIb) wherein $R_6$=Et can be prepared from protected compound (XIV)
- by lithiation using for example nBuLi in a solvent such as hexane at room temperature
- adding in a second time propanal for example at 0° C. and warming up the reaction mixture for example to room temperature.

step (ii): Compound of formula (XIV) can be prepared from compound of formula (XV) by silylation, using for example chloro(1,1-dimethylethyl)dimethylsilane, 1H imidazole in a solvent such as dichloromethane at room temperature.

Scheme 8b

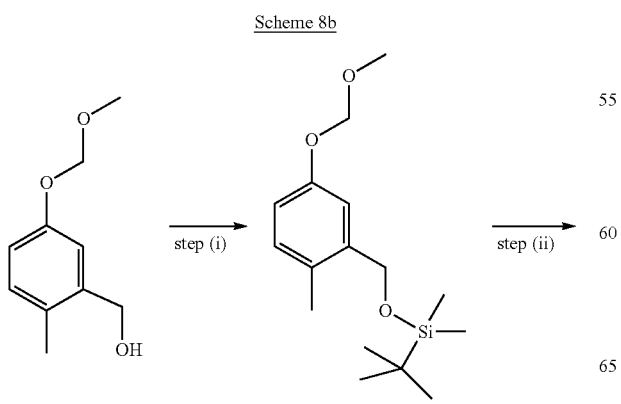

-continued

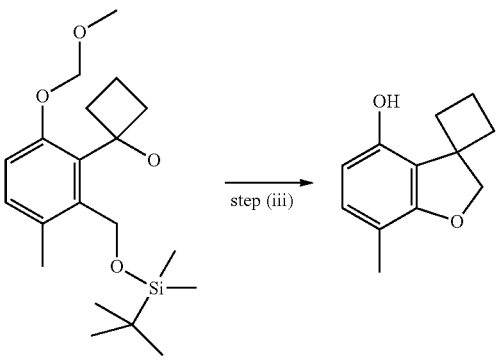

step (iii): phenol of the type produced by step (iii) as shown above can be obtained from alcohol of the type produced by step (ii) as shown above after treatment with a suitable acid such as $H_2SO_4$ or p-tolylsolphonic acid in a suitable solvent such as ethyl acetate, methanol or ethanol.

step (ii): The product of step (ii) as shown above can be prepared from the protected compound of the type produced by step (ii) as shown above
- by lithiation using for example nBuLi in a solvent such as hexane at room temperature (optionally adding $CeCl_3$ previously stirred in dry THF at room temperature under argon or hydrogen atmosphere)
- adding in a second stage cyclobutanone for example at 0° C. and warming up the reaction mixture for example to room temperature.

step (i): The product of step (i) as shown above can be prepared from the starting alcohol by silylation, using for example chloro(1,1-dimethylethyl)dimethylsilane, 1H imidazole in a solvent such as dichloromethane at room temperature.

Scheme 9a

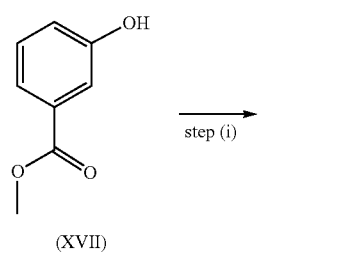

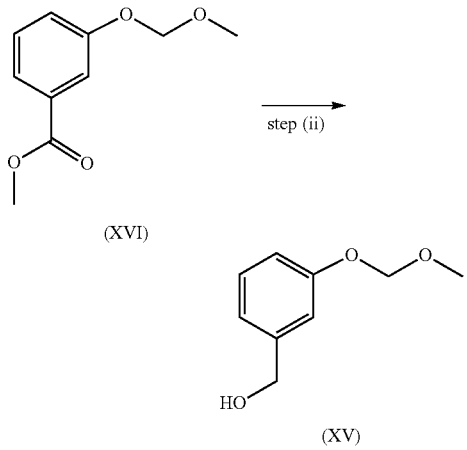

step (ii): Compounds of formula (XV) can be prepared from esters of formula (XVI) using a suitable reducing agent typically LiAlH$_4$ in a solvent such as tetrahydrofuran at a temperature such as 0° C.

step (i): Compounds of formula (XVI) can be prepared from phenols of formula (XVII) using chloro(methyloxy)methane, a base such as DIPEA in a solvent such as dichloromethane for example from 0° C. to room temperature.

Scheme 9b

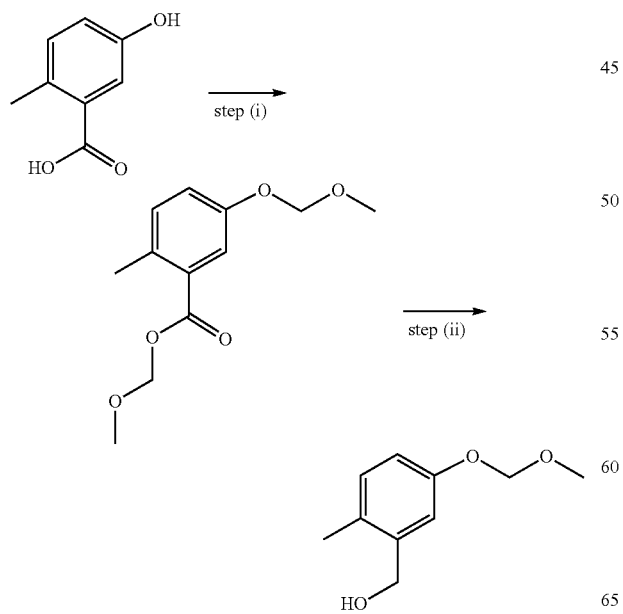

step (ii): The product of step (ii) as shown above can be prepared from esters of the type produced by step (i) as shown above using a suitable reducing agent typically LiAlH$_4$ in a solvent such as tetrahydrofuran at a temperature such as 0° C. or room temperature.

step (i): The product of step (i) as shown above can be prepared from the starting phenol using chloro(methyloxy)methane, a base such as NaH in a solvent such as DMF or THF for example from 0° C. to room temperature.

Optionally the two steps (i) and (ii) can be carried out in a one pot fashion.

Scheme 10

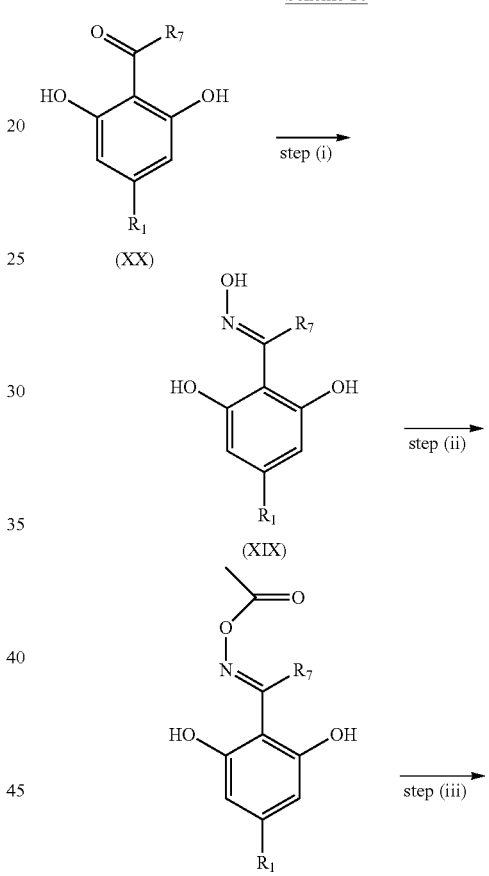

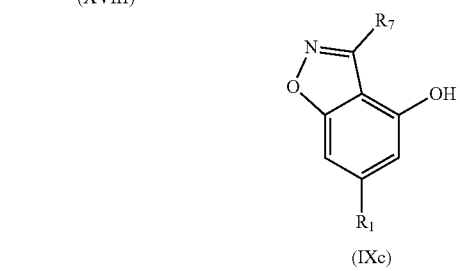

step (iii): Phenols of formula (IXc), corresponding to compounds of formula (IX) wherein A is the heterocycle depicted on Scheme 10, R$_1$ is H or methyl, R$_7$ is methyl, ethyl or isopropyl can be prepared from compound (XVIII) by cyclization in presence of an excess of a base such as pyridine with heating e.g. at reflux.

step (ii): Compounds of formula (XVIII) can be prepared from compounds of formula (XIX) by acylation for example with acetic anhydride at room temperature.

step (i): Compounds of formula (XIX) can be prepared from compounds of formula (XX) with hydroxylamine hydrochloride using a base such as sodium acetate heating e.g. at reflux in a solvent such as a mixture ethanol/water or using pyridine as solvent and base.

Scheme 11

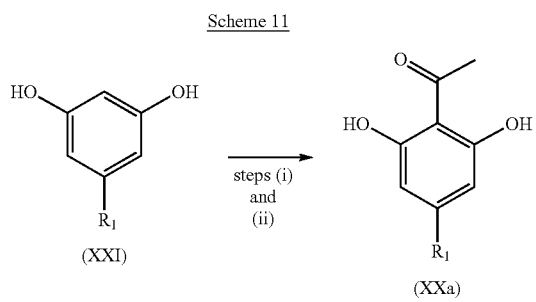

Amongst the ketones of formula (XX), 1-(2,6-dihydroxyphenyl)ethanone is commercially available e.g. from Aldrich. Ketones of formula (XXa) corresponding to ketones of formula (XX) wherein $R_7$=Me can be prepared from compounds of formula (XXI). Compounds of formula (XXI) undergoes
- first a bis-acylation using e.g. acetic anhydride in presence of a base e.g. triethylamine in a solvent e.g. dichloromethane
- followed by a Friedel Crafts acylation with intramolecular acyl transfer in presence of a Lewis acid such as $AlCl_3$ in a solvent such as chlorobenzene with heating e.g. at 90° C.

Scheme 12

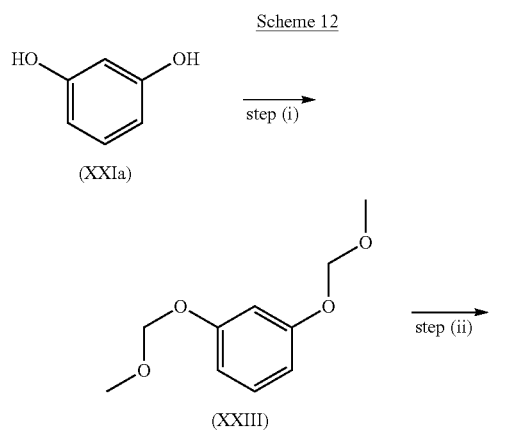

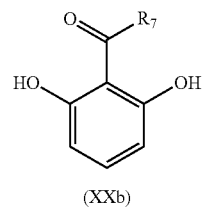

step (iii): Ketones of formula (XXb) corresponding to ketones of formula (XX) wherein $R_7$=Et or iPr and $R_1$=H can be prepared from compounds of formula (XXII) by removal of the two protective groups under acidic conditions such as aqueous HCl solution, with heating e.g. at reflux, in a solvent such as methanol.

step (ii): Compounds of formula (XXII) can be prepared from compounds of formula (XXIII) by—lithiation with for example BuLi in a solvent such as tetrahydrofuran at e.g. room temperature
- adding in a second time the suitable anhydride or acyl chloride for example at −78° C.

step (i): Compound of formula (XXIII) can be prepared from compound of formula (XXIa) corresponding to compound of formula (XXI) wherein $R_1$=H using a base such as sodium hydride in a solvent such as DMF for example at 0° C. adding in a second time chloro(methyloxy)methane for example from 0° C. to room temperature.

Scheme 13a

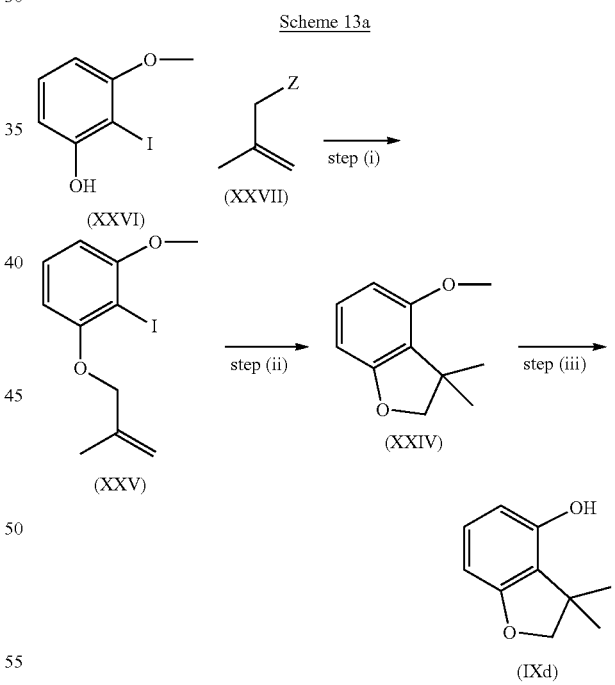

step (iii): Phenol of formula (IXd) corresponding to compound of formula (IX) wherein $R_1$ is H and A is the heterocycle depicted on Scheme 13a, can be prepared from the 0-methoxy precursor (XXIV) using a reaction of demethylation using for example $BBr_3$ in a solvent such as dichloromethane at 0° C.

step (ii): Compound of formula (XXIV) can be prepared by cyclization from compound of formula (XXV) using for example tributylstannane and AIBN in a solvent such as toluene e.g. at reflux.

step (i): Compound of formula (XXV) can be prepared from compound of formula (XXVI) in presence of a base such as sodium hydride in a solvent such as DMF adding in a second time the compound of formula (XXVII) wherein Z=Cl or Br e.g. at room temperature.

Scheme 13b

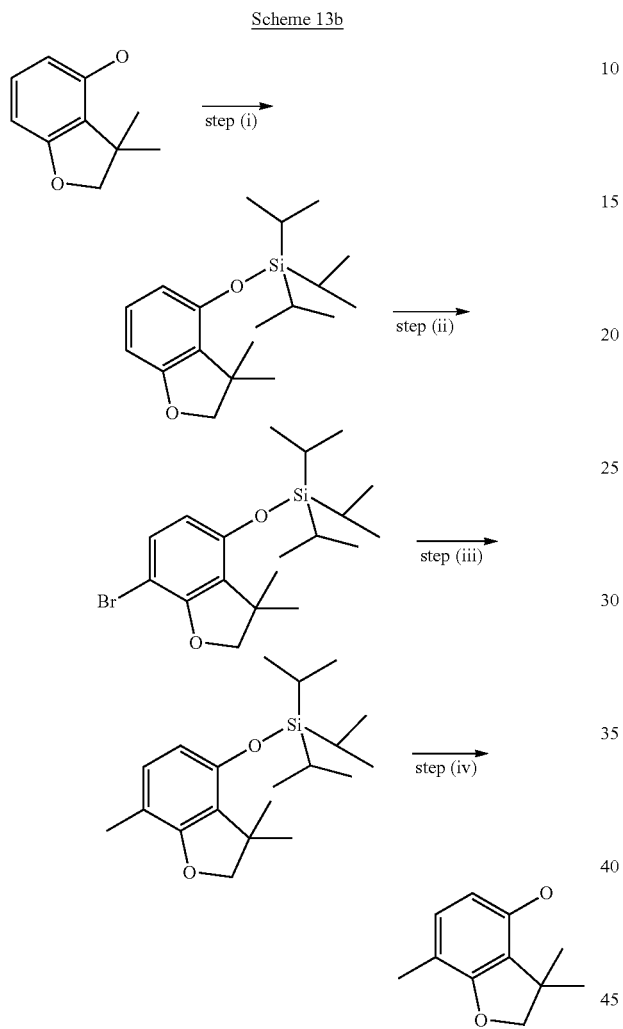

Step (iv): Phenol of the type produced by step (iv) as shown above can be prepared from TiPS protected compounds of the type produced by step (iii) as shown above removing the protective group in presence of a Fluoride source such as tetrabutylammonium fluoride in a suitable solvent such as THF at room temperature.

Step (iii): the compound of the type produced by step (iii) as shown above can be prepared by metal-halogen exchange using butyllithium or sec-butyllithium or tert-butyllithium in a suitable solvent such as THF or Et2O or n-hexane at temperature ranging from −78° C. to room temperature and adding in a second stage a methylating agent such as iodomethane at temperature ranging from −78° C. to room temperature.

Step (ii): the compound of the type produced by step (ii) as shown above can be prepared from a protected phenol of the type produced by step (i) as shown above by using a brominating agent such as NBS in a suitable solvent such as DMF or acetonitrile or THF at room temperature.

Step (i): The compound of the type produced by step (i) as shown above can be prepared from the starting phenol by silylation, using for example chloro triisopropylsilane in presence of a base such as butyllithium in a solvent such as THF at temperature ranging from 0° C. and room temperature.

Scheme 14

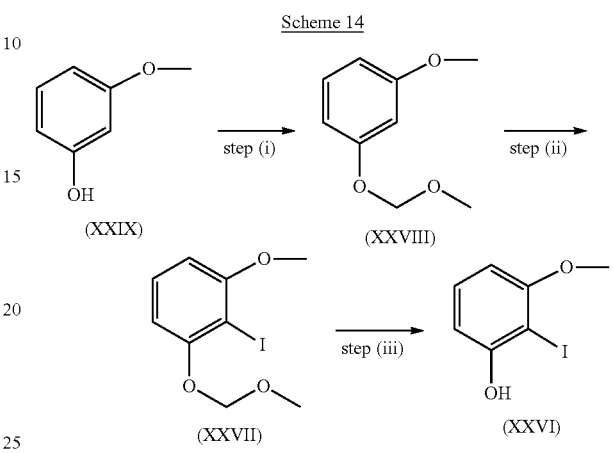

step (iii): Compound of formula (XXVI) can be prepared from compound of formula (XXVII) by removal of the protective group under acidic conditions using for example HCl gas in a solvent such as dichloromethane.

step (ii): Compound of formula (XXVII) can be prepared from compound of formula (XXVIII) by—lithiation with for example BuLi in a solvent such as tetrahydrofuran at e.g. −78° C.

adding in a second time a solution of iodine for example at −70° C. and leaving the reaction at room temperature.

step (i): Compound of formula (XXVIII) can be prepared from compound of formula (XXIX) by protection of the phenol using a base e.g. sodium hydride, in a solvent e.g. tetrahydrofuran, adding in a second time bromomethyl methyl ether e.g. at room temperature.

Scheme 15

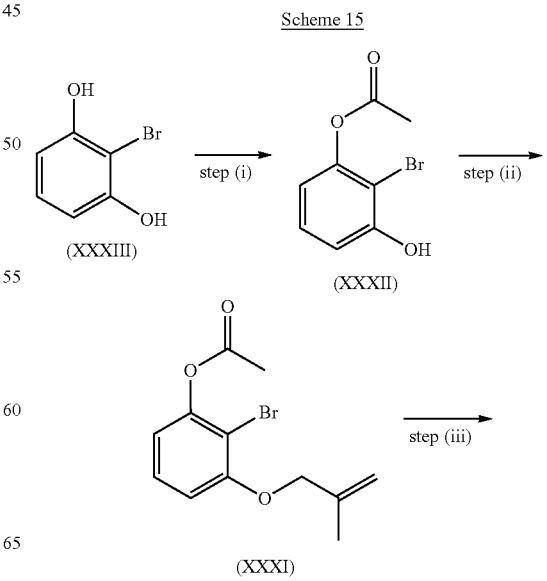

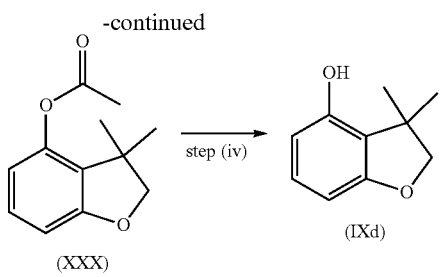

step (iv): Alternatively phenol of formula (IXd) corresponding to compound of formula (IX) wherein $R_1$ is H and A is the heterocycle depicted on Scheme 15 can be prepared from compound of formula (XXX) using an hydroxide base for example sodium hydroxide, in a solvent such as methanol, e.g. at room temperature.

step (iii): Compound of formula (XXX) can be prepared from compound of formula (XXXI) by cyclization with conditions presented on Scheme 13a in step (ii)

step (ii): Compound of formula (XXXI) can be prepared from compound of formula (XXXII) using a base such as potassium carbonate and an electrophile such as 3-bromo-2-methyl-1-propene, in a solvent such as acetonitrile e.g. at room temperature.

step (i): Compound of formula (XXXII) can be prepared from compound of formula (XXXIII) by acetylation using for example acetic anhydride, a base e.g. triethylamine in a solvent e.g. dichloromethane e.g. at room temperature.

step (v): Compound of formula (XXXIV) can be prepared from compound of formula (XXXV) by a Mitsonobu reaction using triphenylphosine in a solvent such as tetrahydrofuran and adding diisopropyl azodicarboxylate at room temperature.

step (iv): Compound of formula (XXXV) can be prepared from compound of formula (XXXVI) in a sequential mode—deprotection in acidic conditions such as HCl 2N in water in ethanol
- evaporation of the solvent and use of a strong base such as NaH in a solvent such as THE at 0° C.
- addition of MOMCl at 0° C.
- reduction with lithium aluminium hydride at 0° C.

step (iii): Compound of formula (XXXVI) can be prepared from compound of formula (XXXVII) using a Corey-Chaykovsky cyclopropanation reaction carried out at room temperature. To pre-form the dimethyloxosulfonium methylide, trimethylsulfoxonium iodide can be used in presence of a base such as NaH in a solvent such as DMSO, the compound of formula (XXXVII), (prediluted in DMSO) being added in a second time.

step (ii): Compound of formula (XXXVII) can be prepared from compound of formula (XXXVIII) using a Wittig reaction. In order to pre-form the ylide, a phosphonium salt such as methyltriphenylphosphonium bromide and a strong base such as KHMDS can be used in a solvent such as THE from 0° C. to room temperature. The compound of formula (XXXVIII) prediluted in a solvent such as THE can be added in a second time at 0° C.

Scheme 16

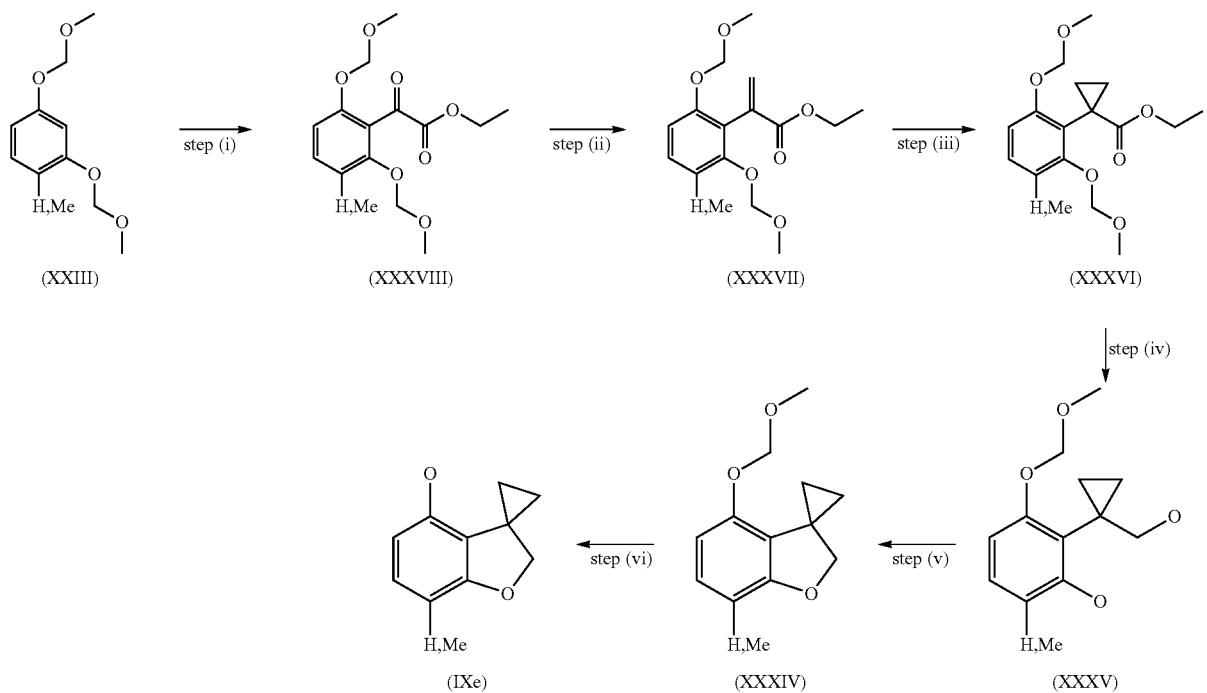

step (vi): Phenol of formula (IXe) corresponding to compound of formula (IX) wherein $R_1$ is H or methyl and A is the heterocycle depicted on Scheme 16 can be prepared from compound of formula (XXXIV) by removal of the MOM protective group under acidic conditions using for example aqueous HCl in a solvent such as methanol heating e.g. at 50° C.

step (i): Compound of formula (XXXVIII) can be prepared from compound (XXIII) by lithiation using BuLi in a solvent such as hexane at room temperature, this solution being added in a second time fn at −78° C. to the electrophile e.g. ethyl chloro(oxo)acetate (prediluted e.g. in THF).

Compounds of formula (XXIII) can be prepared in a similar fashion as described in Scheme 12 (step i).

Scheme 17a

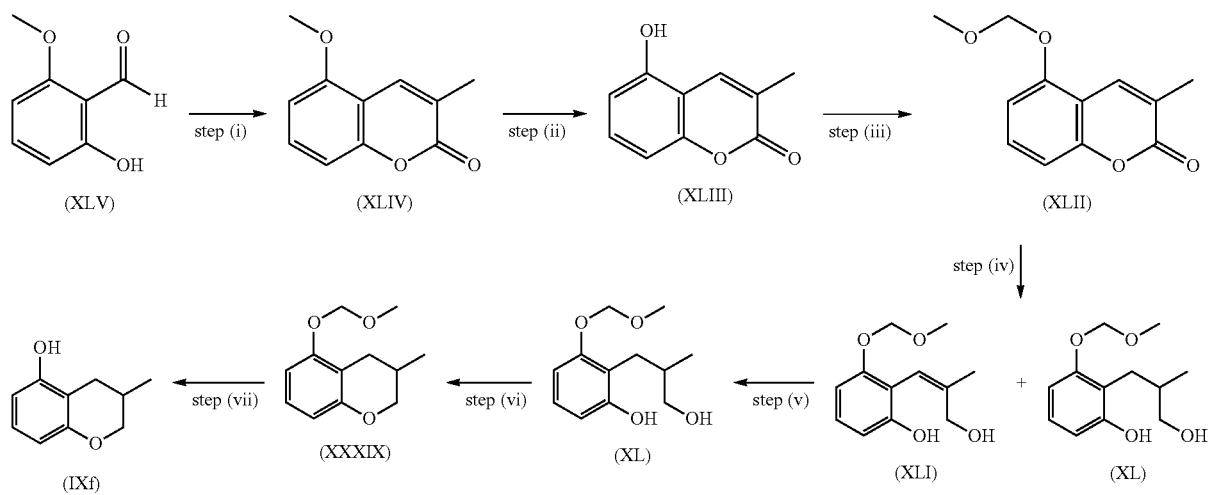

step (vii): Phenol of formula (IXf) corresponding to compound of formula (IX) wherein $R_1$ is H and A is the heterocycle depicted on Scheme 17a can be prepared from compound of formula (XXXIX) by removal of the MOM protective group under acidic conditions using for example aqueous HCl in a solvent such as methanol heating e.g. at 60° C.

step (vi): Compound of formula (XXXIX) can be prepared by cyclization of compounds of formula (XL) using a base such as triethylamine in a solvent such as THF e.g. at 0° C., adding in a second time methanesulfonyl chloride and in a third time a strong base such as potassium 2-methyl-2-propanolate.

step (v): Compound of formula (XL) can be prepared by hydrogenation of the mixture of compounds of formula (XLI) and (XL) in presence of a catalyst such as Pd/C at room temperature.

step (iv): The mixture of compounds of formula (XLI) and (XL) can be prepared from compound of formula (XLII) by reaction with a reducing agent such as lithium aluminium hydride in a solvent such as THF at 0° C.

step (iii): Compound of formula (XLII) can be prepared from phenol of formula (XLIII) using a base such as NaH and chloro(methyloxy)methane in a solvent such as DMF for example from 0° C. to room temperature. Alternatively the solvent used may be DCM and with a base such as DIPEA or TEA.

step (ii): Phenol of formula (XLIII) can be prepared from compound of formula (XLIV) by demethylation using for example boron tribromide in a solvent such as dichloromethane from 0° C. to room temperature.

step (i): Compound of formula (XLIV) can be prepared from compound of formula (XLV) by reaction with propanoic anhydride in presence of a base such as potassium carbonate heating e.g. at 70° C. in a solvent such as DMF followed by addition of water and heating e.g. at 120° C.

Scheme 17b

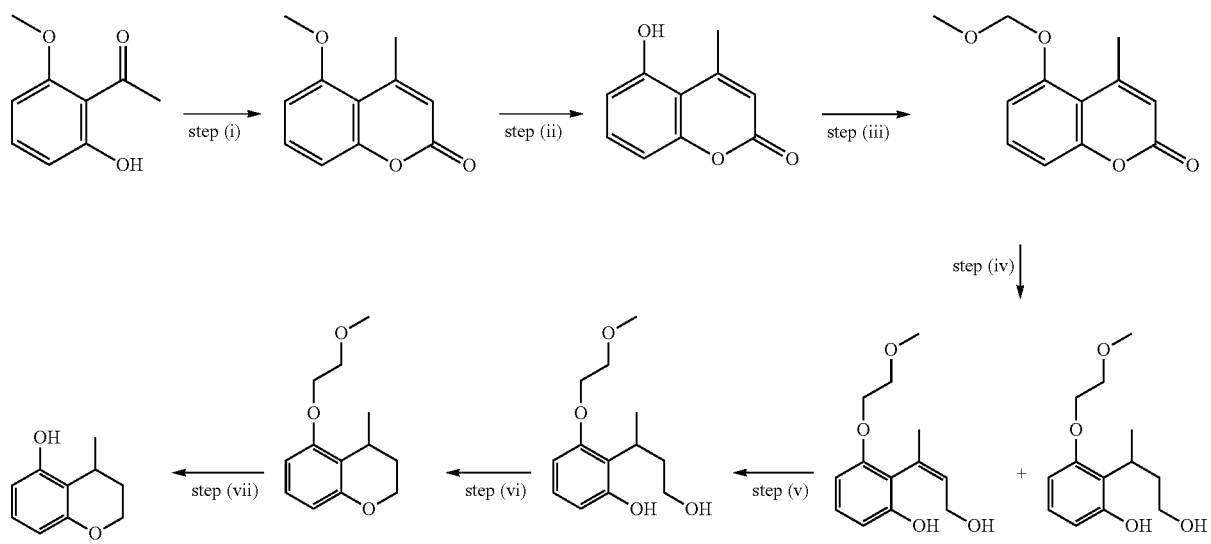

step (vii): Phenol of the type produced by step (vii) as shown above wherein $R_1$ is H and A is the heterocycle depicted on Scheme 17b can be prepared from a compound of the type produced by step (vi) as shown above by removal of the MOM protective group under acidic conditions using for example aqueous HCl in a solvent such as methanol heating e.g. at 60° C.

step (vi): Compound of the type produced by step (vi) as shown above can be prepared by cyclization of compounds of the type produced by step (v) as shown above using a base such as triethylamine in a solvent such as THF e.g. at 0° C., adding in a second time methanesulfonyl chloride and in a third time a strong base such as potassium 2-methyl-2-propanolate.

Alternatively Mitsunobu conditions can be used.

step (v): Compound of the type produced by step (v) as shown above can be prepared by hydrogenation of the mixture of compounds of the type produced by step (iv) as shown above in presence of a catalyst such as Pd/C at room temperature.

step (iv): The mixture of compounds of the type produced by step (iv) as shown above can be prepared from compound of the type produced by step (iii) as shown above by reaction with a reducing agent such as lithium aluminium hydride in a solvent such as THF at 0° C.

step (iii): Compound of the type produced by step (iii) as shown above can be prepared from phenol of the type produced by step (ii) as shown above using a base such as NaH and chloro(methyloxy)methane in a solvent such as DMF or THF for example from 0° C. to room temperature.

step (ii): Phenol of the type produced by step (ii) as shown above can be prepared from compound of the type produced by step (i) as shown above by demethylation using for example boron tribromide in a solvent such as dichloromethane from 0° C. to reflux.

step (i): Compound of the type produced by step (i) as shown above can be prepared from the starting alcohol by reaction with acetic anhydride in presence of a base such as potassium carbonate heating e.g. at 70° C. in a solvent such as DMF followed by addition of water and heating e.g. at 120° C.

Scheme 18a

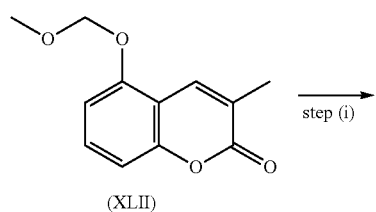

(XLII)

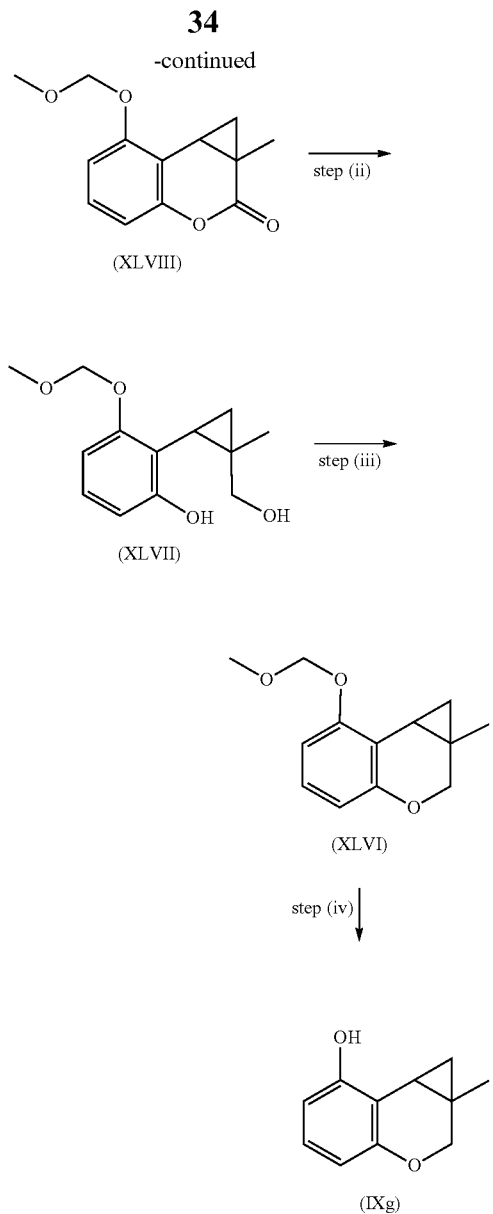

step (iv): Phenol of formula (IXg) corresponding to compound of formula (IX) wherein $R_1$ is H and A is the heterocycle depicted on Scheme 18a can be prepared from compound (XLVI) by removal of the MOM protective group as previously described on Scheme 16 (step vi).

step (iii): Compound of formula (XLVI) can be prepared from compound of formula (XLVII) by a Mitsonobu reaction using triphenylphosine in a solvent such as tetrahydrofuran and adding bis(1-methylethyl) (E)-1,2-diazenedicarboxylate at room temperature.

step (ii): Compound of formula (XLVII) can be prepared from compound of formula (XLVIII) by reaction with a reducing agent such as lithium aluminium hydride in a solvent such as THF at 0° C.

step (i): Compound of formula (XLVIII) can be prepared from compound of formula (XLII) by a Corey-Chaykovsky cyclopropanation reaction, carried out at room temperature as previously described on Scheme 16 (step (iii)).

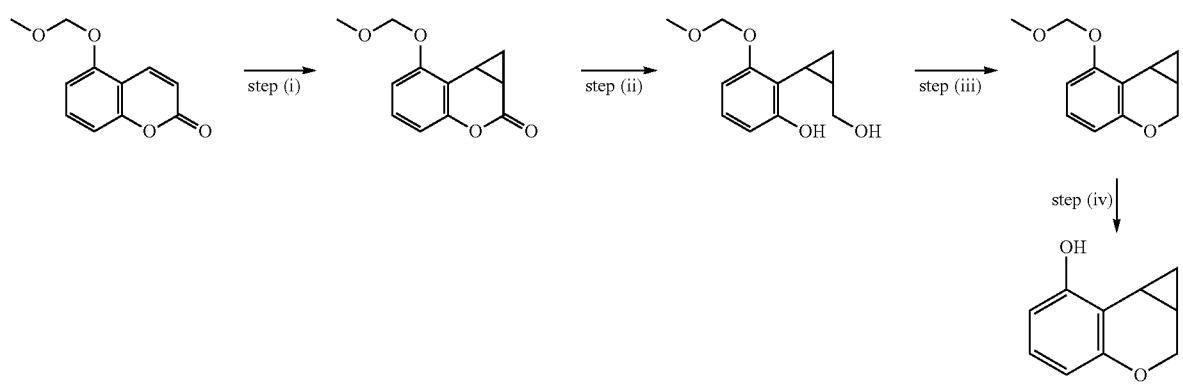

step (iv): Phenol of the type produced by step (iv) as shown above can be prepared from the compound the type produced by step (iii) as shown above by removal of the MOM protective group as previously described on Scheme 16 (step vi).

step (iii): Compound of the type produced by step (iii) as shown above can be prepared from compound of the type produced by step (ii) as shown above by a Mitsonobu reaction using triphenylphosine in a solvent such as tetrahydrofuran and adding bis(1-methylethyl) (E)-1,2-diazenedicarboxylate at room temperature.

step (ii): Compound of the type produced by step (ii) as shown above can be prepared from compound of the type produced by step (i) as shown above by reaction with a reducing agent such as lithium aluminium hydride in a solvent such as THE at 0° C.

step (i): Compound of the type produced by step (i) as shown above can be prepared from the starting compound by a Corey-Chaykovsky cyclopropanation reaction, carried out at room temperature as previously described on Scheme 16 (step (iii)).

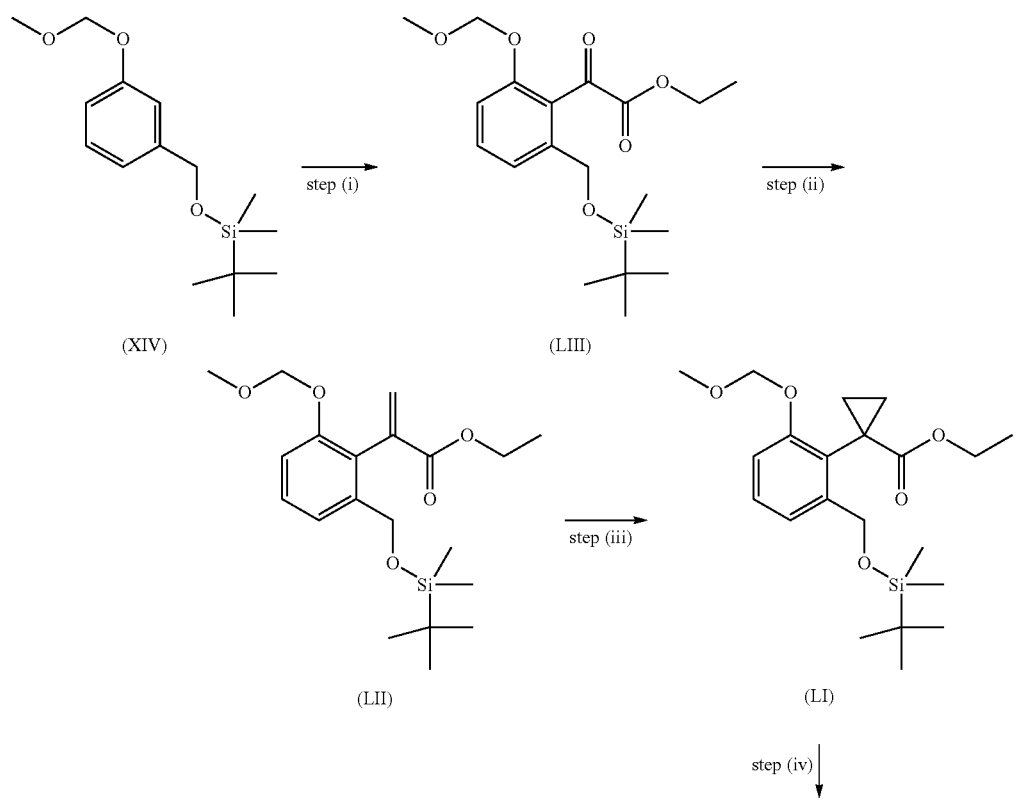

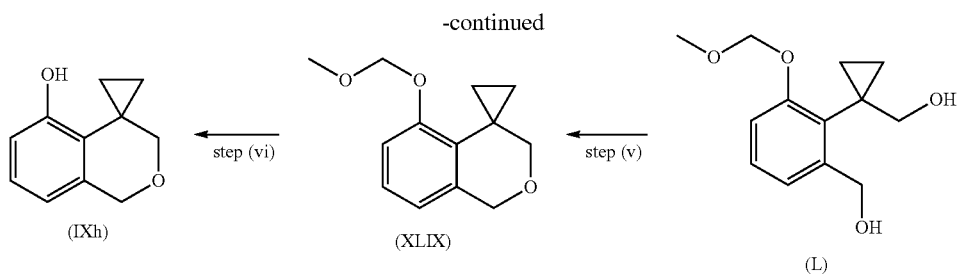

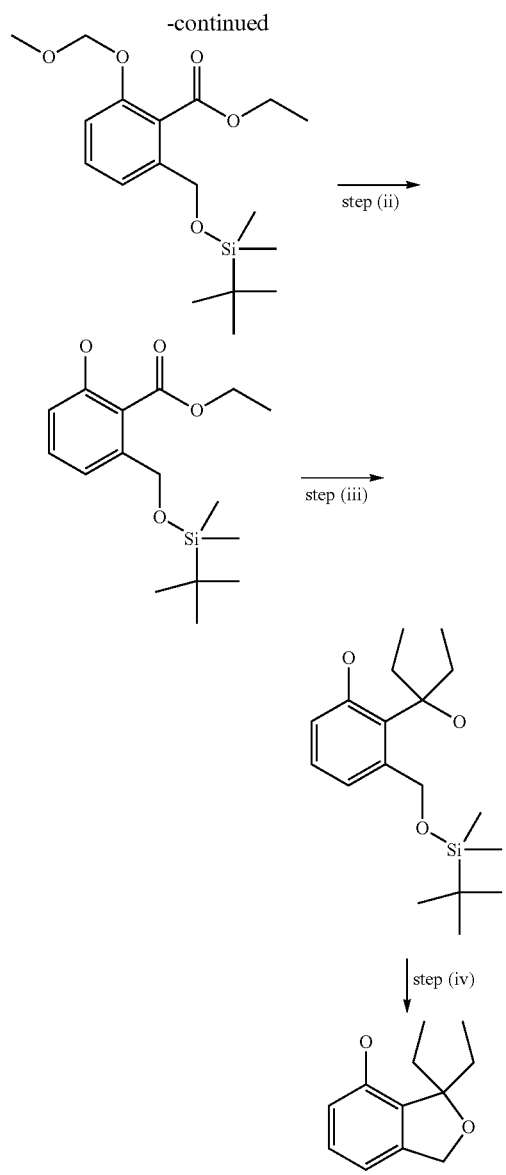

step (vi): Phenol of formula (IXh) corresponding to compound of formula (IX) wherein R₁ is H and A is the heterocycle depicted on Scheme 19a can be prepared from compound (XLIX) by removal of the MOM protective group as previously described on Scheme 16 (step vi).

step (v): Compound of formula (XLIX) can be prepared by cyclization of compound of formula (L) using a base such as BuLi in a solvent such as hexane e.g. at 0° C., adding in a second time 4-methylbenzenesulfonyl chloride e.g. at 0° C., then in a third time a second equivalent of a base such as nBuLi e.g. at 0° C.

step (iv): Compound of formula (L) can be prepared from compound of formula (LII) sequentially—by addition a reductive agent such as lithium aluminium hydride in a solvent such as THE e.g. at 0° C.

after work up and solvent evaporation addition of a desilylating agent such as TBAF in a solvent such as THE.

step (iii): Compound of formula (LI) can be prepared from compound of formula (LII) by a Corey-Chaykovsky cyclopropanation reaction carried out at room temperature as previously described on Scheme 16 (step (iii)).

step (ii): Compound of formula (LII) can be prepared from compound of formula (LIII) by olefination with for example a solution of dimethyl titanocene in a solvent such as toluene (e.g. 9% w/w) heating eg at 90° C. in a solvent such as toluene. The solution of dimethyl titanocene in toluene can be prepared by the reaction of titanocene dichloride with for example a solution of methyllithium at −10° C.

step (i): Compound of formula (LIII) can be prepared from compound (XIV) by lithiation using BuLi in a solvent such as hexane at room temperature, this solution being added in a second time at −78° C. to the electrophile e.g. ethyl chloro(oxo)acetate (prediluted e.g. in THF).

Scheme 19b

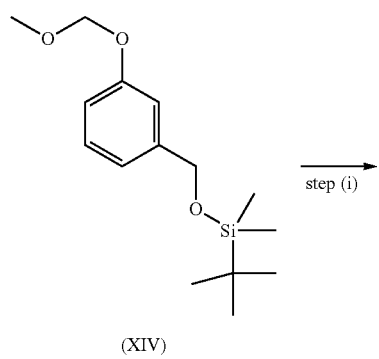

step (iv): phenol of the type produced by step (iv) as shown above can be prepared from alcohol of the type produced by step (iii) as shown above after treatment with a suitable acid such as H₂SO₄ or p-tolylsolphonic acid in a suitable solvent such as ethyl acetate, acetonitrile, methanol or ethanol.

step (iii): the compound of the type produced by step (iii) as shown above can be prepared from compounds of the type produced by step (ii) as shown above by reacting with ethyl magnesium bromide from 2 to 10 equivalents in a suitable solvent such as THF at temperature ranging from −78 C to room temperature.

step (ii): Phenol of the type produced by step (ii) as shown above can be prepared from the compound of the type produced by step (i) as shown above by removal of the MOM protective group using TFA in a suitable solvent such as DCM at temperature ranging from 0° C. to room temperature.

step (i): the compound of the type produced by step (i) as shown above can be prepared from the starting compound by lithiation using BuLi in a solvent such as hexane at room temperature, this solution being added in a second time at −78° C. to the electrophile e.g. ethyl chloroformate (prediluted e.g. in THF).

Scheme 20

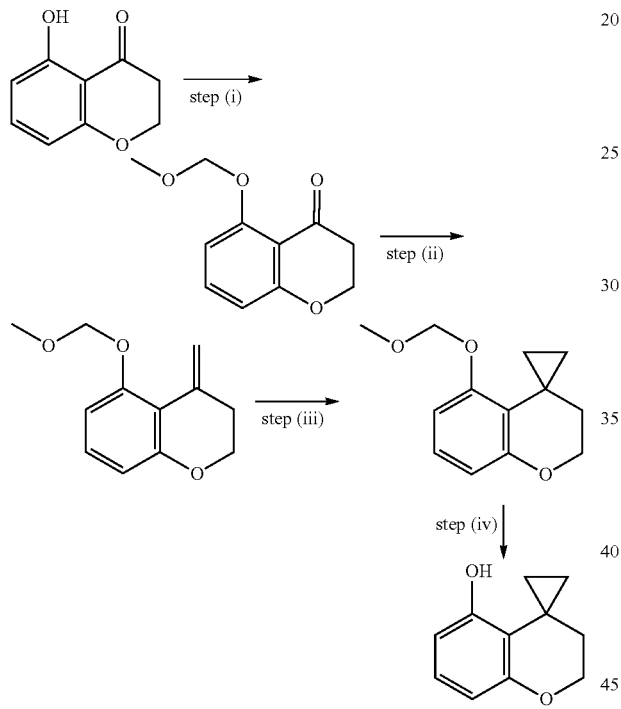

Step (iv): Phenol of the type produced by step (iv) as shown above can be prepared from a compound the type produced by step (iii) as shown above by removal of the MOM protective group as previously described on Scheme 16 (step vi).

Step (iii): the compound of the type produced by step (iii) as shown above can be prepared by cyclopropanation (Simmons-Smith conditions) of the unsaturated compound of the type produced by step (ii) as shown above using diethylzinc and diiodomethane (optionally 2,4,6-trichlorophenol is added) in a solvent such as dichloromethane at temperature ranging from −40° C. to room temperature.

Step (ii): the compound of the type produced by step (ii) as shown above can be prepared using a writing type reaction as described in Scheme 16 (step ii).

Step (i): Compound of the type produced by step (i) as shown above can be prepared from the starting phenol using a base such as NaH and chloro(methyloxy)methane in a solvent such as DMF or THF for example from 0° C. to room temperature.

Scheme 21

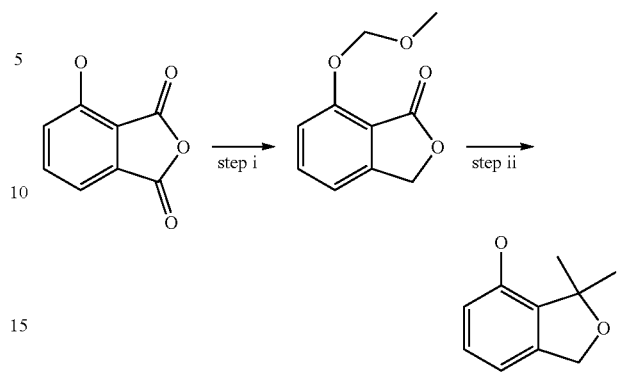

Step (ii): Phenol of the type produced by step (ii) as shown above can be prepared from lactone of the type produced by step (i) as shown above using Methylmagnesium bromide in a suitable solvent such as THF or diethyl ether at temperature ranging from −78° C. to room temperature. Obtained compound can be treated with a suitable acid such as H2SO4 or TsOH in a suitable solvent such as ethyl acetate or acetonitrile or methanol or ethanol.

Step (i): Lacton of the type produced by step (i) as shown above can be prepared by reaction of commercially available starting anhydride with a reducing agent such as K-selectride in a solvent such as THF at 0° C.; followed by MOM-protection using a base such as DIPEA and chloro(methyloxy)methane in a solvent such as DCM for example from 0° C. to room temperature.

Scheme 22

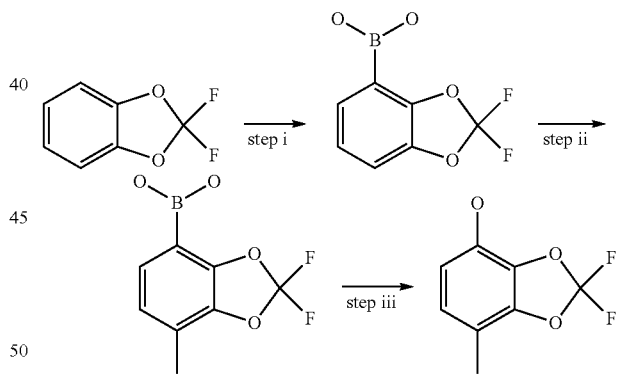

Step (iii): Phenol of the type produced by step (iii) as shown above can be prepared from a boronic acid of the type produced by step (ii) as shown above using $H_2O_2$ and NaOH in a suitable solvent such as THF or a combination of solvents such as water/THF at room temperature.

Step (ii): the boronic acid of the type produced by step (ii) as shown above can be prepared from boronic acid of the type produced by step (i) as shown above by lithiation using sec-BuLi in a solvent such as THF at temperature ranging from −78° C. to room temperature, followed by the addition in a second time of a methylating agent such as iodomethane at temperature ranging from −78° C. to room temperature.

Step (i): Boronic acid of the type produced by step (i) as shown above can be prepared from commercially available 2,2-Difluoro-1,3-benzodioxole by lithiation using sec-BuLi in a solvent such as THF at temperature ranging from −78° C. to room temperature, followed by the addition in a second time of trimethylborate.

Scheme 23

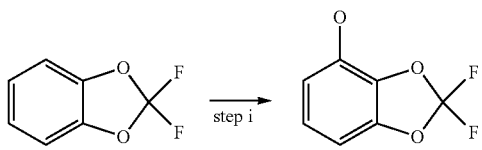

Step (i): Phenol of the type produced by step (i) as shown above can be prepared from commercially available 2,2-Difluoro-1,3-benzodioxole by lithiation using sec-BuLi in a solvent such as THF at temperature ranging from −78° C. to room temperature, followed by the addition in a second time of trimethylborate at temperature ranging from −78° C. to room temperature and followed by the addition in a third time of $H_2O_2$ and NaOH at room temperature.

Scheme 24

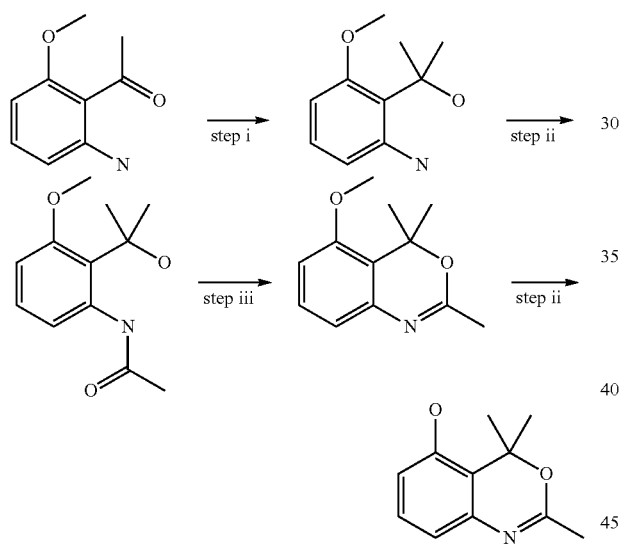

Step (iv): Phenol of the type produced by step (iv) as shown above can be prepared from compounds of the type produced by step (iii) as shown above by treatment with a demethylating agent such as $BBr_3$ in a suitable solvent such as dichloromethane or dichloroethane at temperature ranging from room temperature to reflux.

Step (iii): compound of the type produced by step (iii) as shown above can be prepared from compound of the type produced by step (ii) as shown above by treatment with a suitable acid such as polyphosphoric acid neat at suitable temperature such as 110° C.

Step (ii): compound of the type produced by step (ii) as shown above can be prepared from aminoalcohol of the type produced by step (i) as shown above by treatment with an acylating agent such as acetyl chloride in presence of a base such as triethylamine in a suitable solvent such as dichloromethane at a suitable temperature for example 0° C.

Step (i): Alcohol of the type produced by step (i) as shown above can be prepared from the commercially available starting ketone by treatment with Methyl magnesium bromide in a suitable solvent such as THF or diethyl ether at temperature ranging from 0° C. to room temperature.

Scheme 25

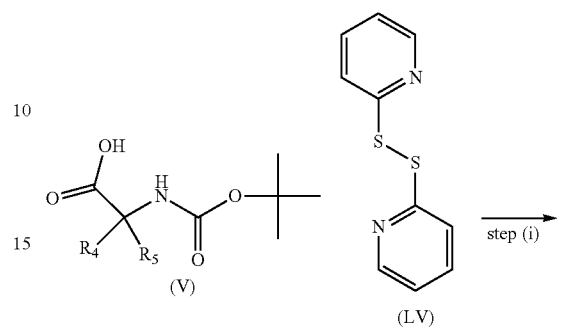

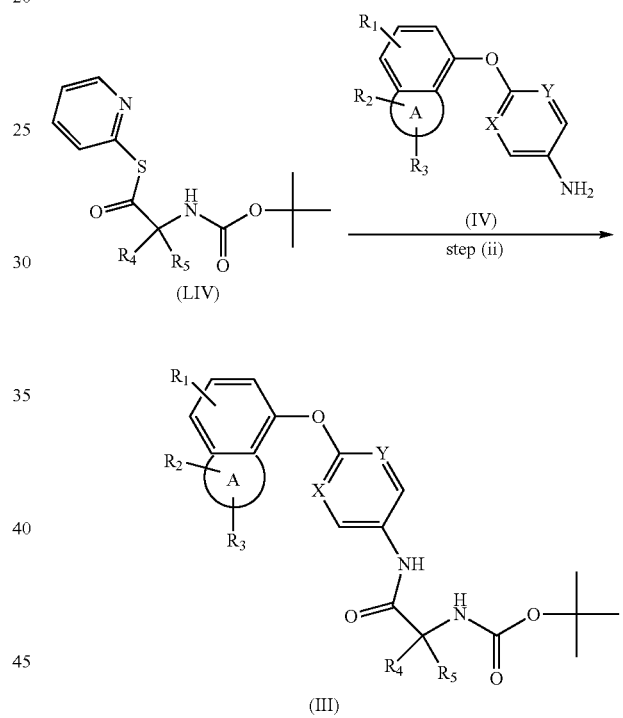

step (ii): Alternatively to the route described on Scheme 2b (step ii), compounds of formula (III) can be obtained by coupling between the aniline (IV) and the precursor (LIV) with heating e.g. at 150° C. in a solvent such as toluene.

step (i): Compounds of formula (LIV) can be prepared from N-protected amino acid (V) and 2,2′-dithiodipyridine (LV) in presence of triphenylphosphine at room temperature in a solvent such as THF.

Scheme 26

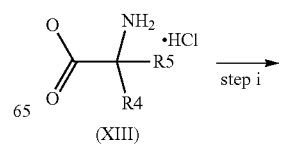

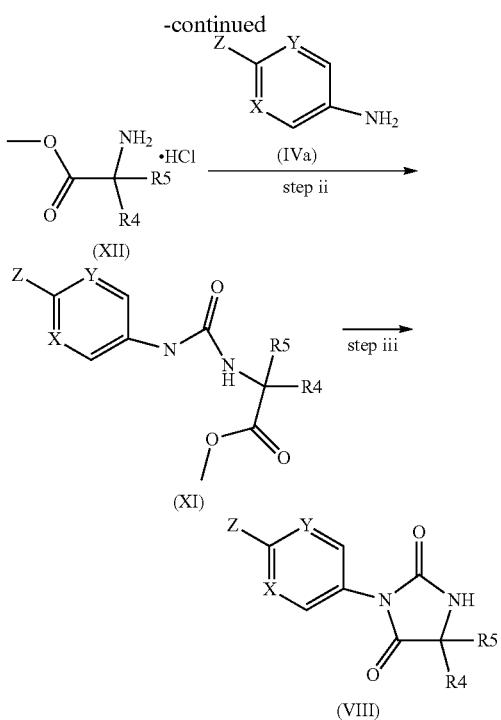

step (iii): Compounds of formula (VIII) can be prepared by reaction of ureas of formula (XI) and a base such as sodium methoxide in a solvent such as Methanol at temperature ranging from 0° C. to 60° C.

step (ii): Compounds of formula (XI) can be prepared by reaction of commercially available anilines of formula (IVa), wherein Z is Cl, and amino esters (hydrochloride salt) of formula (XII) in a solvent e.g. dichloromethane or ethyl acetate with a carbonylating agent e.g. triphosgene preferentially prediluted in the same solvent in presence of a base e.g. triethylamine or diisopropylethylamine at temperature ranging from 0° C. to 60° C., optionally adding a catalytic or stechiometric amount of DMAP.

step (i): Amino esters (hydrochloride salt) of formula (XII) can be prepared from commercially available amino-acids (hydrochloride salt) of formula (XIII) by reaction with methanol in presence of a catalytic or stechiometric amount of thyonyl chloride at temperature ranging from r.t. to reflux.

The present disclosure provides compounds of formula (I) or a pharmaceutically acceptable salt thereof for use in therapy.

The compounds of formula (I) or their pharmaceutically acceptable salts may be of use for the treatment or prophylaxis of a disease or disorder where a modulator of the Kv3.1 or Kv3.2 or Kv3.1 and Kv3.2 channels is required. As used herein, a modulator of Kv3.1 or Kv3.2 or Kv3.1 and Kv3.2 is a compound which alters the properties of these channels, either positively or negatively. The altered property of the channel may be the scale of response observed or the temporal behaviour of the channel.

Compounds of the disclosure may be tested in the assay of Biological Example 1 to determine their modulatory properties.

Diseases or conditions that may be mediated by modulation of Kv3.1 and/or Kv3.2 channels may be selected from the list below. The numbers in brackets after the listed diseases below refer to the classification code in Diagnostic and Statistical Manual of Mental Disorders, 4th Edition, published by the American Psychiatric Association (DSM-IV) and/or the International Classification of Diseases, 10th Edition (ICD-10).

The compounds of formula (I) or their pharmaceutically acceptable salts may be of use for the treatment or prophylaxis of depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90); Seasonal affective disorder.

The compounds of formula (I) or their pharmaceutically acceptable salts may be of use for the treatment or prophylaxis of schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

The compounds of formula (I) or their pharmaceutically acceptable salts may be of use for the treatment or prophylaxis of anxiety disorders including Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder, Separation Anxiety Disorder (309.21), Adjustment Disorders with Anxiety (309.24) and Anxiety Disorder Not Otherwise Specified (300.00).

The compounds of formula (I) or their pharmaceutically acceptable salts may be of use for the treatment or prophylaxis of substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide.

The compounds of formula (I) or their pharmaceutically acceptable salts may be of use for the enhancement of cognition including the treatment of cognition impairment in other diseases such as schizophrenia, bipolar disorder, depression, other psychiatric disorders and psychotic conditions associated with cognitive impairment, e.g. Alzheimer's disease.

The compounds of formula (I) or their pharmaceutically acceptable salts may be of use for the treatment or prophylaxis of sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; sleep apnea and jet-lag syndrome.

The compounds of formula (I) or their pharmaceutically acceptable salts may be of use for the treatment or prophylaxis of eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; Binge Eating Disorder; and Eating Disorder Not Otherwise Specified (307.50).

The compounds of formula (I) or their pharmaceutically acceptable salts may be of use for the treatment or prophylaxis of Autism Spectrum Disorders including Autistic Disorder (299.00), Asperger's Disorder (299.80), Rett's Disorder (299.80), Childhood Disintegrative Disorder (299.10) and Pervasive Disorder Not Otherwise Specified (299.80, including Atypical Autism).

The compounds of formula (I) or their pharmaceutically acceptable salts may be of use for the treatment or prophylaxis of Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23).

The compounds of formula (I) or their pharmaceutically acceptable salts may be of use for the treatment or prophylaxis of Personality Disorders including the subtypes Paranoid Personality Disorder (301.0), Schizoid Personality Disorder (301.20), Schizotypal Personality Disorder (301,22), Antisocial Personality Disorder (301.7), Borderline Personality Disorder (301,83), Histrionic Personality Disorder (301.50), Narcissistic Personality Disorder (301,81), Avoidant Personality Disorder (301.82), Dependent Personality Disorder (301.6), Obsessive-Compulsive Personality Disorder (301.4) and Personality Disorder Not Otherwise Specified (301.9).

The compounds of formula (I) or their pharmaceutically acceptable salts may be of use for the treatment or prophylaxis of Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

The compounds of formula (I) or their pharmaceutically acceptable salts may be of use for the treatment or prophylaxis of Impulse control disorder including: Intermittent Explosive Disorder (312.34), Kleptomania (312.32), Pathological Gambling (312.31), Pyromania (312.33), Trichotillomania (312.39), Impulse-Control Disorders Not Otherwise Specified (312.3), Binge Eating, Compulsive Buying, Compulsive Sexual Behaviour and Compulsive Hoarding.

The compounds of formula (I) or their pharmaceutically acceptable salts may be of use for the treatment or prophylaxis of hearing disorders including auditory neuropathy, auditory processing disorder, hearing loss, which includes sudden hearing loss, noise induced hearing loss, substance-induced hearing loss, and hearing loss in adults over 60 (presbycusis), and tinnitus.

The compounds of formula (I) or their pharmaceutically acceptable salts may be of use for the treatment or prophylaxis of Meniere's disease, disorders of balance, and disorders of the inner ear.

The compounds of formula (I) or their pharmaceutically acceptable salts may be of use for the treatment or prophylaxis of hyperacusis and disturbances of loudness perception, including Fragile-X syndrome and autism.

The compounds of formula (I) or their pharmaceutically acceptable salts may be of use for the treatment or prophylaxis of Epilepsy, (including, but not limited to, localization-related epilepsies, generalized epilepsies, epilepsies with both generalized and local seizures, and the like), seizures associated with Lennox-Gastaut syndrome, seizures as a complication of a disease or condition (such as seizures associated with encephalopathy, phenylketonuria, juvenile Gaucher's disease, Lundborg's progressive myoclonic epilepsy, stroke, head trauma, stress, hormonal changes, drug use or withdrawal, alcohol use or withdrawal, sleep deprivation, fever, infection, and the like), essential tremor, restless limb syndrome, partial and generalised seizures (including tonic, clonic, tonic-clonic, atonic, myoclonic, absence seizures), secondarily generalized seizures, temporal lobe epilepsy, absence epilepsies (including childhood, juvenile, myoclonic, photo- and pattern-induced), severe epileptic encephalopathies (including hypoxia-related and Rasmussen's syndrome), febrile convulsions, epilepsy partialis continua, progressive myoclonus epilepsies (including Unverricht-Lundborg disease and Lafora's disease), post-traumatic seizures/epilepsy including those related to head injury, simple reflex epilepsies (including photosensitive, somatosensory and proprioceptive, audiogenic and vestibular), metabolic disorders commonly associated with epilepsy such as pyridoxine-dependent epilepsy, Menkes' kinky hair disease, Krabbe's disease, epilepsy due to alcohol and drug abuse (e.g. cocaine), cortical malformations associated with epilepsy (e.g. double cortex syndrome or subcortical band heterotopia), chromosomal anomalies associated with seizures or epilepsy such as Partial monosomy (15Q)/Angelman syndrome) and the like.

In one embodiment of the disclosure, there is provided a compound of formula (I) or a pharmaceutically acceptable salt thereof for the treatment or prophylaxis of depression and mood disorders, hearing disorders, schizopherenea, substance abuse disorders, sleep disorders or epilepsy.

In one embodiment of the disclosure, there is provided a compound of formula (I) or a pharmaceutically acceptable salt thereof for the treatment or prophylaxis of bipolar disorder or mania.

The term "treatment" or "treating" as used herein includes the control, mitigation, reduction, or modulation of the disease state or its symptoms.

The term "prophylaxis" is used herein to mean preventing symptoms of a disease or disorder in a subject or preventing recurrence of symptoms of a disease or disorder in an afflicted subject and is not limited to complete prevention of an affliction.

The disclosure also provides a method of treating or preventing a disease or disorder where a modulator of Kv3 is required, for example those diseases and disorders mentioned hereinabove, which comprises administering to a subject in need thereof an effective amount of a compound of formula (I) or a pharmaceutically acceptable salt thereof.

The disclosure also provides a compound of formula (I), or a pharmaceutically acceptable salt thereof, for use in the treatment or prophylaxis of a disease or disorder where a modulator of Kv3 is required, for example those diseases and disorders mentioned hereinabove.

The disclosure also provides the use of a compound of formula (I), or a pharmaceutically acceptable salt thereof, in the manufacture of a medicament for the treatment or prophylaxis of a disease or disorder where a modulator of Kv3 is required, for example those diseases and disorders mentioned hereinabove.

The disclosure also provides a method of treating depression and mood disorders, schizopherenea, substance abuse disorders, sleep disorders or epilepsy, for example for those indications mentioned hereinabove, which comprises administering to a subject in need thereof an effective amount of a Kv3 modulator or a pharmaceutically acceptable salt thereof.

For use in therapy the compounds of the disclosure are usually administered as a pharmaceutical composition. The disclosure also provides a pharmaceutical composition comprising a compound of formula (I), or a pharmaceutically acceptable salt thereof, and a pharmaceutically acceptable carrier.

The compounds of formula (I) or their pharmaceutically acceptable salts may be administered by any convenient method, e.g. by oral, parenteral, buccal, sublingual, nasal, rectal or transdermal administration, and the pharmaceutical compositions adapted accordingly.

The compounds of formula (I) or their pharmaceutically acceptable salts which are active when given orally can be formulated as liquids or solids, e.g. as syrups, suspensions, emulsions, tablets, capsules or lozenges.

A liquid formulation will generally consist of a suspension or solution of the active ingredient in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient in a sterile aqueous carrier or parenterally acceptable oil, e.g. polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluorochlorohydrocarbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

In one embodiment the composition is in unit dose form such as a tablet, capsule or ampoule.

The composition may contain from 0.1% to 100% by weight, for example from 10 to 60% by weight, of the active material, depending on the method of administration. The composition may contain from 0% to 99% by weight, for example 40% to 90% by weight, of the carrier, depending on the method of administration. The composition may contain from 0.05 mg to 1000 mg, for example from 1.0 mg to 500 mg, of the active material, depending on the method of administration. The composition may contain from 50 mg to 1000 mg, for example from 100 mg to 400 mg of the carrier, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 500 mg, and such unit doses may be administered more than once a day, for example two or three a day. Such therapy may extend for a number of weeks or months.

The disclosure provides, in a further aspect, a combination comprising a compound of formula (I) or a pharmaceutically acceptable derivative thereof together with a further therapeutic agent or agents.

The disclosure provides a compound of formula (I), for use in combination with a further therapeutic agent or agents.

When the compounds are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above together with a pharmaceutically acceptable carrier or excipient comprise a further aspect of the disclosure. The individual components of such combinations may be administered either sequentially or simultaneously in separate or combined pharmaceutical formulations. The individual components of combinations may also be administered separately, through the same or different routes.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

A pharmaceutical composition of the disclosure, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

The present disclosure also provides Kv3 modulators, or their pharmaceutically acceptable salts, for use in the treatment or prophylaxis of depression and mood disorders, hearing disorders, schizopherenea, substance abuse disorders, sleep disorders or epilepsy.

In particular Kv3 modulators or their pharmaceutically acceptable salts may be particularly useful in the treatment or prophylaxis of depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90), Seasonal affective disorder.

The disclosure also provides a method of treating depression and mood disorders, hearing disorders, schizopherenea, substance abuse disorders, sleep disorders or epilepsy, including for example those disorders mentioned hereinabove, which comprises administering to a subject in need thereof an effective amount of Kv3 modulator or a pharmaceutically acceptable salt thereof.

The disclosure also provides a Kv3 modulator, or a pharmaceutically acceptable salt thereof, for use in the treatment or prophylaxis of depression and mood disorders, hearing disorders, schizopherenea, substance abuse disorders, sleep disorders or epilepsy, including for example those disorders mentioned hereinabove.

The disclosure also provides the use of a Kv3 modulator, or a pharmaceutically acceptable salt thereof, in the manufacture of a medicament for the treatment or prophylaxis of depression and mood disorders, hearing disorders, schizopherenea, substance abuse disorders, sleep disorders or epilepsy, including for example those disorders mentioned hereinabove.

For use in therapy the Kv3 modulators are usually administered as a pharmaceutical composition for example a composition comprising a Kv3 modulator or a pharmaceutically acceptable salt thereof, and a pharmaceutically acceptable carrier. Examples of such compositions, and methods of administration thereof, which compositions comprise a compound of formula (I) or a pharmaceutically acceptable salt thereof, are described hereinabove. Such compositions and methods of administration may also be used for other Kv3 modulators or pharmaceutically acceptable salts thereof, in the treatment of depression and mood disorders, hearing disorders, schizopherenea, substance abuse disorders, sleep disorders or epilepsy, including for example those disorders mentioned hereinabove.

Furthermore, the disclosure relates to a method for manufacturing compounds of formula I, to novel intermediates of use in the manufacture of compounds of formula I and to the manufacture of such intermediates.

Particular intermediates of interest include:
3,3-dimethyl-2,3-dihydro-1-benzofuran-4-ol (Intermediate 50)

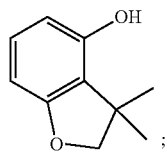

spiro[1-benzofuran-3,1'-cyclopropan]-4-ol (Intermediate 85)

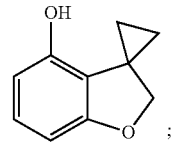

7-methylspiro[2H-benzofuran-3,1'-cyclopropane]-4-ol (Intermediate 156)

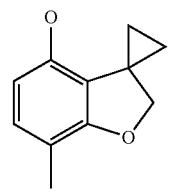

and
3,3,7-trimethyl-2,3-dihydro-1-benzofuran-4-ol (Intermediate 184)

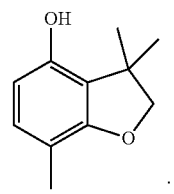

Other intermediates of interest are the anilides of formula (IV):

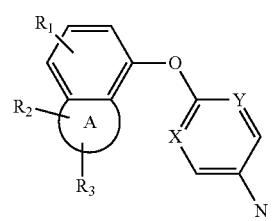

(IV)

Especially of interest are the anilides:

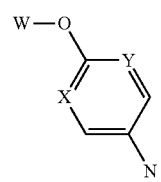

wherein:
X is C or N;
Y is C or N; and
the group W is selected from:

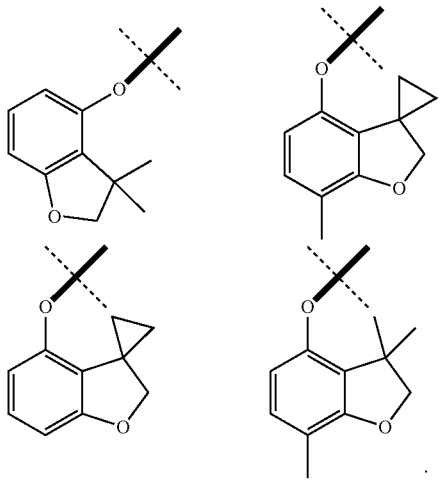

All publications, including but not limited to patents and patent applications, cited in this specification are herein incorporated by reference as if each individual publication were specifically and individually indicated to be incorporated by reference herein as though fully set forth.

BRIEF DESCRIPTION OF THE DRAWINGS

The present disclosure is illustrated, by way of example only, with reference to the following figures in which:

FIG. 6b Expression of Kv3.2 mRNA in the superchiasmatic nucleus.

EXPERIMENTAL

Figure 1A:
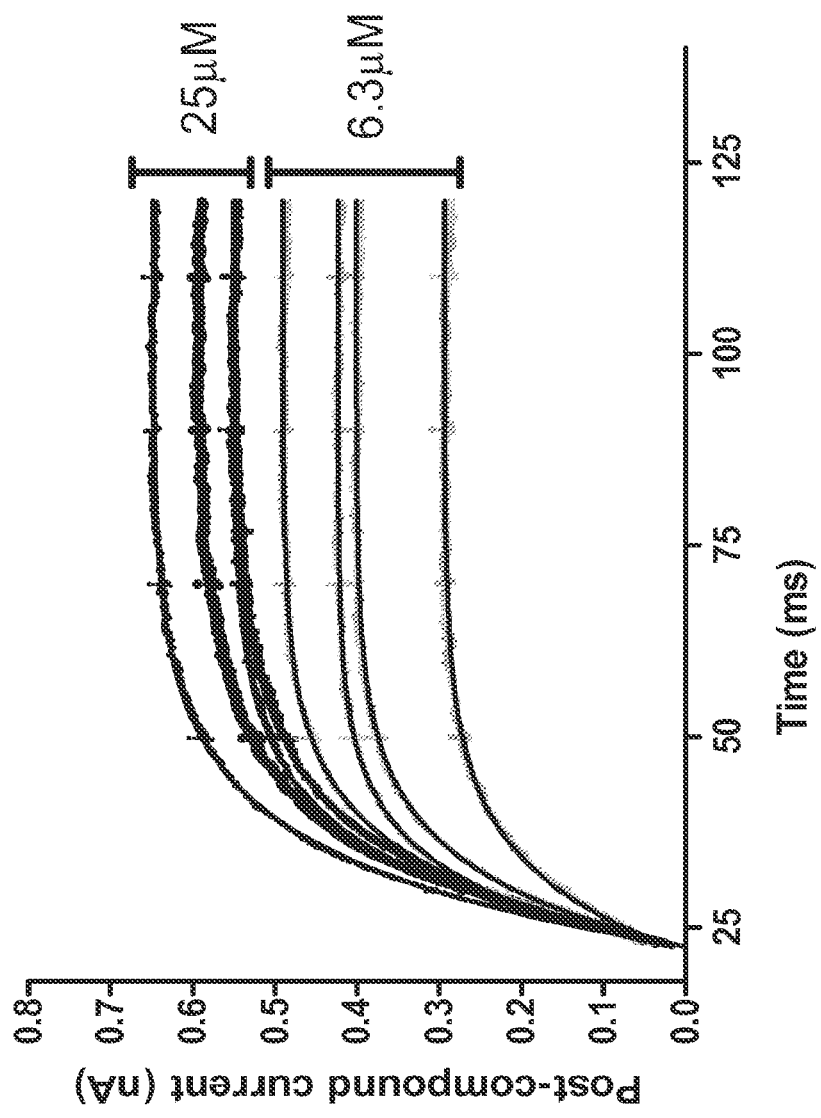
FIG. 1a hKv3.2 currents recorded using the assay described in Biological Example 1. Data shown are the individual currents over the period of the depolarising voltage step to −15 mV recorded from 4 different cells at two concentrations of the compound of Reference Example RE1. The data are fitted by a single exponential curve (solid lines) using the fitting procedure in Prism version 5 (Graphpad Software Inc).

The disclosure is illustrated by the Compounds described below. The following Examples describe the laboratory synthesis of specific compounds of the disclosure and are not meant to limit the scope of the disclosure in any way with respect to compounds or processes. It is understood that, although specific reagents, solvents, temperatures and time periods are used, there are many possible equivalent alternatives that can be used to produce similar results. This disclosure is meant to include such equivalents.

Analytical Equipment

Starting materials, reagents and solvents were obtained from commercial suppliers and used without further purification unless otherwise stated. Unless otherwise stated, all compounds with chiral centres are racemic. Where reactions are described as having been carried out in a similar manner to earlier, more completely described reactions, the general reaction conditions used were essentially the same. Work up conditions used were of the types standard in the art, but may have been adapted from one reaction to another. The starting material may not necessarily have been prepared from the batch referred to. Compounds synthesised may have various purities ranging from for example 85% to 98%. Calculations of number of moles and yield are in some cases adjusted for this.

Proton Magnetic Resonance (NMR) spectra were recorded either on Varian instruments at 300, 400, 500 or 600 MHz, or on Bruker instruments at 400 MHz. Chemical shifts are reported in ppm (δ) using the residual solvent line as internal standard. Splitting patterns are designed as s (singlet), br.s (broad singlet), d (doublet), t (triplet), q (quartet), dd (doublet of doublets), dt (doublet of triplets) and m (multiplet). The NMR spectra were recorded at temperatures ranging from 25 to 30° C.

HPLC analyses indicated by HPLC (walk-up): rt=x min, were performed on a Agilent 1100 series instrument using a Luna 3u C18(2) 100A column (50×2.0 mm, 3 µm particle size) [Mobile phase, solvent A: (water+0.05% TFA), solvent B: (acetonitrile+0.05% TFA), Gradient: 100% of (A) to 95% of (B) in 8 min. Column T=40° C. Flow rate=1 ml/min. UV detection wavelength=220 nm]. The use of this methodology is indicated by "HPLC" in the analytic characterization of the described compounds.

Direct infusion Mass spectra (MS) were run on an Agilent 1100 Series LC/MSD Mass Spectrometer, operating in ES (+) and ES (−) ionization mode [ES (+): Mass range: 100-1000 amu. Infusion solvent: water+0.1% HCO2H/CH3CN 50/50. ES (−): Mass range: 100-1000 amu. Infusion solvent: water+0.05% NH4OH/CH3CN 50/50]. The use of this methodology is indicated by "MS_1 (ESI)" in the analytic characterization of the described compounds.

Alternatively, Mass spectra (MS) were run on a mass spectrometer, operating in ES (+) and ES (−) ionization mode coupled with an HPLC instrument Agilent 1100 Series [LC/MS-ESI(+) analyses were performed on a Supelcosil ABZ+Plus (33×4.6 mm, 3 µm) (mobile phase: from 10% [CH$_3$CN+0.05% TFA] to 90%[CH$_3$CN+0.05% TFA] and 10% [water] in 2.2 min, under these conditions for 2.8 min. T=45° C., flux=0.9 mL/min)]. The use of this methodology is indicated by "MS_2 (ESI)" in the analytic characterization of the described compounds.

HPLC-Mass spectra (HPLC-MS) were taken on an Agilent 1100 Series LC/MSD Mass Spectrometer coupled with HPLC instrument Agilent 1100 Series, operating in positive or negative electrospray ionization mode and in both acidic and basic gradient conditions. Acidic gradient: LC/MS-ES (+ or −) analyses were performed on a Supelcosil ABZ+Plus column (33×4.6 mm, 3 μm). Mobile phase: A: (water+0.1% HCO2H)/B: CH3CN. Gradient (standard method): t=0 min 0% (B), from 0% (B) to 95% (B) in 5 min lasting for 1.5 min, from 95% (B) to 0% (B) in 0.1 min, stop time 8.5 min. Column T=r.t. Flow rate=1 ml/min. The use of this methodology is indicated by "LC-MS_A" in the analytic characterization of the described compounds. Basic gradient: LC/MS-ES (+ or −) analyses were performed on an XTerra MS C18 column (30×4.6 mm, 2.5 μm). Mobile phase: A: (5 mM aq. NH4HCO3+ammonia (pH 10))/B: CH3CN. Gradient: t=0 min 0% (B), from 0% (B) to 50% (B) in 0.4 min, from 50% (B) to 95% (B) in 3.6 min lasting for 1 min, from 95% (B) to 0% (B) in 0.1 min, stop time 5.8 min. Column T=r.t. Flow rate=1.5 mL/min]. Mass range ES (+ or −): 100-1000 amu. UV detection range: 220-350 nm. The use of this methodology is indicated by "LC-MS_B" in the analytic characterization of the described compounds.

Quality Control: LC/MS-ES+ under acidic conditions was performed on a Zorbax SB C18 column (1.8 μm 3×50 mm). Mobile phase: A: (H2O+0.05% TFA by vol.)/B: (CH3CN+ 0.05% TFA by vol). Gradient: t=0 min 0% (B), from 0 to 95% (B) in 2.5 min, 95% (B) for 0.2 min, from 95 to 100% (B) in 0.2 min, 100% (B) for 0.4 min, From 100% to 0% (B) in 0.1 min. Stop time 4 min. Column T=60° C. Flow rate: 1.5 ml/min. Mass range ES+: (100-1000 amu, F=60). UV detection wavelengths: DAD 1A=220.8, DAD 1B=254.8. The use of this methodology is indicated by "LC/MS: QC_3_MIN" in the analytic characterization of the described compounds. Ultra Performance Liquid Chromatography with an Acidic Gradient:

Total ion current (TIC) and DAD UV chromatographic traces together with MS and UV spectra associated with the peaks were taken on a UPLC/MS Acquity™ system equipped with 2996 PDA detector and coupled to a Waters Micromass ZQ™ mass spectrometer operating in positive or negative electrospray ionisation mode [LC/MS-ES (+ or −): analyses were performed using an Acquity™ UPLC BEH C18 column (50×2.1 mm, 1.7 μm particle size). General Method: Mobile phase: A: (water+0.1% HCO2H)/B: (CH3CN+0.06% HCO2H). Gradient: t=0 min 3% (B), t=0.05 min 6% (B), t=0.57 min 70% (B), t=1.06 min 99% (B) lasting for 0.389 min, t=1.45 min 3% (B), stop time 1.5 min. Column T=40° C. Flow rate=1.0 mL/min. Mass range: ES (+): 100-1000 amu. ES (−): 100-800 amu. UV detection range: 210-350 nm. The use of this methodology is indicated by "UPLC" in the analytic characterization of the described compounds. 1$^{st}$ Focused Method: Mobile phase: A: (water+ 0.1% HCO2H)/B: (CH3CN+0.1% HCO2H). Gradient: t=0 min 3% (B), t=1.06 min 99% (B), t=1.45 min 99% (B), t=1.46 min 3% (B), stop time 1.5 min. Column T=40° C. Flow rate=1.0 mL/min. Mass range: ES (+): 100-1000 amu. ES (−): 100-800 amu. UV detection range: 210-350 nm. The use of this methodology is indicated by "UPLC_s" in the analytic characterization of the described compounds. 2$^{nd}$ Focussed Method: Mobile phase: A: (water+0.1% HCO2H)/ B: (CH3CN+0.1% HCO2H). Gradient: t=0 min 3% (B), t=1.5 min 100% (B), t=1.9 min 100% (B), t=2 min 3% (B), stop time 2 min. Column T=40° C. Flow rate=1.0 mL/min. Mass range: ES (+): 100-1000 amu. ES (−): 100-800 amu. UV detection range: 210-350 nm. The use of this methodology is indicated by "UPLC_ipqc" in the analytic characterization of the described compounds.

Ultra Performance Liquid Chromatography with a Basic Gradient:

Total ion current (TIC) and DAD UV chromatographic traces together with MS and UV spectra associated with the peaks were taken on a UPLC/MS Acquity™ system equipped with PDA detector and coupled to a Waters SQD mass spectrometer operating in positive and negative alternate electrospray ionisation mode [LC/MS-ES+/−: analyses were performed using an Acquity™ UPLC BEH C18 column (50×2.1 mm, 1.7 μm particle size). Mobile phase: A: (10 mM aqueous solution of NH4HCO3 (adjusted to pH 10 with ammonia))/B: CH3CN. Gradient: t=0 min 3% (B), t=1.06 min 99% (B) lasting for 0.39 min, t=1.46 min 3% (B), stop time 1.5 min. Column T=40° C. Flow rate=1.0 mL/min. Mass range: ES (+): 100-1000 amu. ES (−): 100-1000 amu. UV detection range: 220-350 nm. The use of this methodology is indicated by "UPLC_B" in the analytic characterization of the described compounds.

For reactions involving microwave irradiation, a Personal Chemistry Emrys™ Optimizer was used or a Biotage Initiator In a number of preparations, purification was performed using Biotage manual flash chromatography (Flash+), Biotage automatic flash chromatography (Horizon, SP1 and SP4), Companion CombiFlash (ISCO) automatic flash chromatography, Flash Master Personal or Vac Master systems.

Flash chromatographies were carried out on silica gel 230-400 mesh (supplied by Merck AG Darmstadt, Germany) or on silica gel 300-400 mesh (supplied by Sinopharm Chemical Reagent Co., Ltd.), Varian Mega Be—Si pre-packed cartridges, pre-packed Biotage silica cartridges (e.g. Biotage SNAP cartridge), KP-NH prepacked flash cartridges, ISOLUTE NH$_2$ prepacked cartridges or ISCO RediSep Silica cartridges.

SPE-SCX cartridges are ion exchange solid phase extraction columns supplied by Varian. The eluent used with SPE-SCX cartridges is DCM and MeOH or only MeOH followed by ammonia solution in MeOH. The collected fractions are those eluted with the ammonia solution in MeOH unless otherwise stated.

SPE-Si cartridges are silica solid phase extraction columns supplied by Varian.

In a number of preparations, purification was performed on a Mass-Directed Autopurification (MDAP) system Fractionlynx™ equipped with Waters 2996 PDA detector and coupled with ZQ™ mass spectrometer (Waters) operating in positive and negative electrospray ionisation mode ES+, ES− (mass range 100-1000 or 100-900)

A set of semi-preparative gradients have been used:

METHOD A: Chromatographic Basic Conditions
Column: XTerra Prep MS C18 OBD (150 mm×30 mm 10 μm particle size) at room temperature
Mobile phase: A: (water+10 mM aqueous solution of ammonium bicarbonate (adjusted to pH 10 with ammonia)), B: acetonitrile
Flow rate: 40 ml/min
Gradient: 10% (B) for 0.5 min, from 10% (B) to 95% (B) in 12.5 min, from 95% (B) to 100% (B) in 3 min
METHOD B: Chromatographic Basic Conditions
Column: XTerra Prep MS C18 OBD (150 mm×30 mm 10 μm particle size) at room temperature
Mobile phase: A: water+10 mM aqueous solution of ammonium bicarbonate (adjusted to pH 10 with ammonia), B: acetonitrile
Flow rate: 40 ml/min
Gradient: from 20% to 25% (B) in 1 min, from 25% (B) to 65% (B) in 12 min, from 65% (B) to 100% (B) in 0.5 min METHOD C: Chromatographic Basic Conditions
Column: Waters Xbridge C18 OBD (50 mm×19 mm 5 μm particle size) at room temperature
Mobile phase: A: water+10 mM aqueous solution of ammonium bicarbonate (adjusted to pH 10 with ammonia), B: acetonitrile
Flow rate: 17 ml/min
Gradient: from 20% (B) to 25% (B) in 1 min, from 25% (B) to 55% (B) in 9 min, from 55% (B) to 100% (B) in 2 min, return to 20% (B) in 0.1 min
METHOD D: Chromatographic Acidic Conditions
Column: Waters Xbridge C18 OBD (50 mm×19 mm 5 μm particle size) at room temperature
Mobile phase: A: (water+0.1% formic acid in water); B: acetonitrile
Flow rate: 17 ml/min
Gradient: from 20% (B) to 25% B in 1 min, from 25% (B) to 55% (B) in 9 min, from 55% (B) to 100% (B) in 2 min, return to 20% (B) in 0.1 min
METHOD E: Chromatographic Basic Conditions
Column: Waters Xbridge C18 OBD (50 mm×19 mm 5 μm particle size) at room temperature
Mobile phase: A: (water+10 mM aqueous solution of ammonium bicarbonate (adjusted to pH 10 with ammonia)), B: acetonitrile
Flow rate: 17 ml/min
Gradient: from 10% (B) to 15% (B) in 1 min, from 15% (B) to 70% (B) in 7 min, from 70% (B) to 100% (B) in 1 min, 100% (B) for 2 min, return to 10% (B) in 0.1 min
METHOD F: Chromatographic Basic Conditions
Column: Phenomenex Gemini AXIA C18 (50×21.2 mm 5 μm particle size)
Mobile phase: A: water+10 mM aqueous solution of ammonium bicarbonate (adjusted to pH 10 with ammonia), B: acetonitrile
Flow rate: 17 ml/min
Gradient: from 10% (B) to 15% (B) in 1 min, from 15% (B) to 65% (B) in 8 min, from 65% (B) to 100% (B) in 1 min, return to 10% (B) in 1 min.
METHOD G: Chromatographic Basic Conditions
Column: Phenomenex Gemini AXIA C18 (50×21.2 mm 5 μm particle size)
Mobile phase: A: water+10 mM aqueous solution of ammonium bicarbonate (adjusted to pH 10 with ammonia), B: acetonitrile
Flow rate: 17 ml/min
Gradient: from 10% (B) to 15% (B) in 1 min, from 15% (B) to 70% (B) in 7 min, from 70% (B) to 100% (B) in 1 min, 100% (B) during 2 min, return to 10% (B) in 0.1 min.

Abbreviations

CDCl$_3$ deutrated chloroform
cHex cyclohexane
CV column volume
DCM dichloromethane
DIPEA N,N-diisopropylethylamine
DMAP 4-dimethylaminopyridine
DMF N,N-dimethylformamide
DMSO dimethylsulfoxide
DMSO-d$_6$ deutrated dimethylsulfoxide
EDC.HCl N-(3-dimethylaminopropyl)-N'-ethylcarbodiimide hydrochloride
Et$_2$O diethyl ether
EtOAc ethyl acetate
h hours
H$_2$ gaseous hydrogen
HATU (O-7-azabenzotriazol-1-yl)-N,N,N',N'-tetramethyl-uroniumhexafluoro phosphate)
HBTU O-benzotriazol-1-yl-tetramethyluronium hexafluorophosphate
HCO2H formic acid
HCl hydrogen chloride
HNO$_3$ nitric acid
HOBt.H$_2$O 1-hydroxybenzyltriazole hydrate
H$_2$SO$_4$ sulfuric acid
K$_2$CO$_3$ potassium carbonate
KHDMS potassium hexamethyldisilazide
KOH potassium hydroxide
MeCN/CH$_3$CN acetonitrile
MeOH methanol
MeOD deutrated methanol
MDAP mass-directed autopurification
MOM methoxymethyl
N$_2$ gaseous nitrogen
NaBH(OAc)$_3$ sodium triacethoxyborohydride
NaHCO$_3$ sodium hydrogenocarbonate
NaNO$_2$ sodium nitrite
Na$_2$CO$_3$ sodium carbonate
NaOH sodium hydroxide
NH4OH ammonium hydroxide
NH4 HCO3H ammonium bicarbonate
NMR Nuclear Magnetic Resonance
Pd/C palladium on charcoal
PE petroleum ether
r.t. room temperature
SCRC Sinopharm Chemical Reagent Co., Ltd
T3P Propylphosphonic anhydride
tBuOK potassium tert-butoxide
TBTU o-Benzotriazol-1-yl-n,n,n',n'-tetramethyluronium tetrafluoroborate
TEA triethylamine
TFA trifluoroacetic acid
THE tetrahydrofuran
TsOH*H$_2$O 4-methylbenzenesulfonic acid hydrate, p-toluenesulfonic acid hydrate Intermediate 1

2-[(2-propyn-1-yloxy)methyl]furan

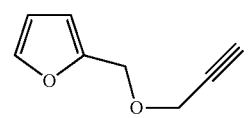

To a suspension of sodium hydride (1.570 g, 39.2 mmol) in DMF (46 ml) stirred under argon at 0° C. was dropped a solution of 2-furanylmethanol (3.5 g, 35.7 mmol) in DMF (4 ml) in 20 minutes. The reaction mixture was stirred at 0'C for 15 minutes. 3-bromo-1-propyne (4.24 g, 35.7 mmol) 80% in toluene was dropped in 10 minutes at 0'C, then the mixture was left stirring at room temperature overnight. Water was added and then the mixture was extracted with ethyl ether 3 times. The organic phase was dried over sodium sulphate and concentrated under vacuum. The residue was purified by flash chromatography on silica (Biotage SP1 instrument), eluting with a gradient cyclohexane/ethyl acetate 95/5 to 85/15. Evaporation afforded the title compound (1.63 g).

¹H NMR (400 MHz, DMSO-d₆): δ ppm 7.66 (1H, d), 6.41-6.49 (2H, m), 4.46 (2H, s), 4.12 (2H, d), 3.48 (1H, t); UPLC-MS: 0.66 min

Intermediate 2-3

1,3-dihydro-2-benzofuran-4-ol and 1,3-dihydro-2-benzofuran-5-ol

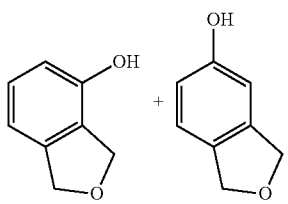 [SMILES: Oc1cccc2c1COC2 ; Oc1ccc2c(c1)COC2]

To a solution of [2-[(2-propyn-1-yloxy)methyl]furan] (Intermediate 1, 1.63 g) in acetonitrile (60 ml) stirred under argon at room temperature was added neat gold trichloride (0.182 g, 0.599 mmol). The reaction mixture was stirred overnight at room temperature. Gold trichloride was then added (120 mg) and after 2 hours another gold trichloride addition was carried out (226 mg). After 1 hour the mixture was concentrated and the crude was purified by flash chromatography (Biotage SP1), eluting with cyclohexane/ethyl acetate 90/10. Evaporation of the two fractions gave respectively the title compounds: 1,3-dihydro-2-benzofuran-4-ol (100 mg) and 1,3-dihydro-2-benzofuran-5-ol (356 mg)

Intermediate 2: 1,3-dihydro-2-benzofuran-4-ol: ¹H NMR (400 MHz, DMSO-d₆): δ ppm 9.59 (1H, s), 7.15-7.00 (1H, m), 6.78-6.60 (2H, m), 5.03-4.84 (4H, m); UPLC-MS: 0.41 min, 135 [M−H]−

Intermediate 3: 1,3-dihydro-2-benzofuran-5-ol: ¹H NMR (400 MHz, DMSO-d₆): δ ppm 9.36 (1H, s), 7.11-7.02 (1H, m), 6.70-6.61 (2H, m), 4.89 (4H, m); UPLC-MS: 0.42 min, 135 [M−H]−

Intermediate 4

4-[(4-nitrophenyl)oxy]-1,3-dihydro-2-benzofuran

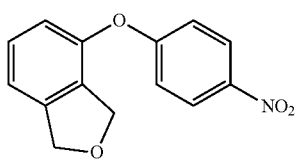

A suspension of potassium carbonate (670 mg, 4.85 mmol), 1,3-dihydro-2-benzofuran-4-ol (Intermediate 2, 110 mg) and 1-fluoro-4-nitrobenzene (114 mg, 0.808 mmol) in N,N-dimethylformamide (DMF) (5 ml) was heated under microwave irradiation at 100'C for 3×30 minutes. The mixture was concentrated. 2 ml of water were added and then dichloromethane. The phases were separated and the aqueous phase was extracted twice with dichloromethane. The organic phase was dried over sodium sulphate and concentrated under vacuum to afford the title compound, which was directly used in the next step.

¹H NMR (400 MHz, DMSO-d₆): δ ppm 8.30-8.20 (2H, m), 7.46-7.36 (1H, m), 7.32-7.22 (m, 1H), 7.18-7.10 (2H, m), 7.09-7.04 (1H, m), 5.14-4.79 (4H, m); UPLC-MS: 0.98 min

Intermediate 5

4-(1,3-dihydro-2-benzofuran-4-yloxy)aniline

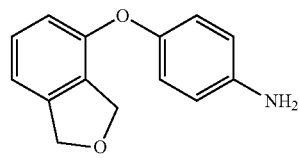 [SMILES: Nc1ccc(Oc2cccc3c2COC3)cc1]

A solution of 4-[(4-nitrophenyl)oxy]-1,3-dihydro-2-benzofuran (Intermediate 4, 208 mg), hydrazine hydrate (0.051 ml, 1.618 mmol) and Pd/C (172 mg, 0.162 mmol) in ethanol (6 ml) was stirred under argon at 90° C. After 1.5 hour the mixture was cooled to room temperature and then filtered over celite. The celite was washed with methanol. The organic phase was concentrated to afford title compound (136 mg).

¹H NMR (400 MHz, DMSO-d₆): δ ppm 7.20 (1H, s), 6.96 (1H, d), 6.79-6.73 (2H, m), 6.62-6.55 (3H, m), 5.00 (4H, s), 4.88 (2H, s); UPLC-MS: 0.72 min, 228 [M+1]+

Intermediate 6

1,1-dimethylethyl ((1R)-2-{[4-(1,3-dihydro-2-benzofuran-4-yloxy)phenyl]amino}-1-methyl-2-oxoethyl)carbamate

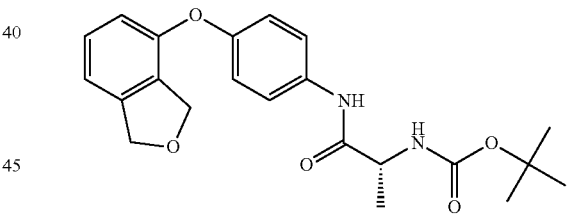

A suspension of N-{[(1,1-dimethylethyl)oxy]carbonyl}-D-alanine (97 mg, 0.515 mmol), DIPEA (0.138 ml, 0.792 mmol) and TBTU (191 mg, 0.594 mmol) in 1,2-dichloroethane (3 ml) was stirred under argon at room temperature for 45 min. 4-(1,3-dihydro-2-benzofuran-4-yloxy)aniline (Intermediate 5, 90 mg) was added and the mixture was left under stirring at room temperature overnight. Brine was added and the mixture was separated in a separator tube. The aqueous phase was extracted twice with dichloromethane. The organic phase was dried over sodium sulphate and concentrated under vacuum. The residue was purified by chromatography (Biotage SP1), using as eluents a gradient Cyclohexane/Ethyl acetate from 100:0 to 85:15 to afford the title compound (109 mg).

¹H NMR (400 MHz, DMSO-d₆): δ ppm 9.97 (1H, m), 7.67-7.57 (2H, m), 7.32-7.23 (1H, m), 7.11-7.04 (2H, m), 7.04-6.96 (2H, m), 6.79-6.71 (1H, m), 5.08-4.99 (2H, m), 4.93-4.83 (2H, m), 4.15-4.05 (1H, m), 1.39 (9H, s), 1.29-1.22 (3H, m); UPLC-MS: 0.85 min, 399 [M+H]+

Intermediate 7

N¹-[4-(1,3-dihydro-2-benzofuran-4-yloxy)phenyl]-D-alaninamide

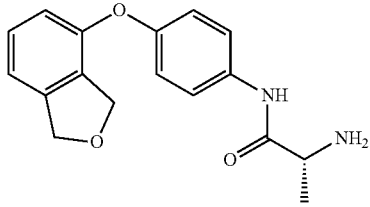 [SMILES: C[C@@H](N)C(=O)Nc1ccc(Oc2cccc3c2COC3)cc1]

A solution of 1,1-dimethylethyl ((1R)-2-{[4-(1,3-dihydro-2-benzofuran-4-yloxy) phenyl]amino}-1-methyl-2-oxoethyl)carbamate (Intermediate 6, 108 mg) and TFA (1 ml) in dichloromethane (4 ml) was stirred under argon at room temperature. The reaction mixture was stirred at room temperature for 1 hour. The mixture was concentrated and the residue was purified by SCX to afford the title compound (81 mg).

$^1$H NMR (400 MHz, DMSO-$d_6$): δ ppm: 7.66 (2H, d), 7.31-7.24 (1H, m), 7.09-7.04 (1H, m), 6.99 (2H, d), 6.71-6.77 (1H, m), 5.03 (2H, s), 4.87 (2H, s), 3.40-3.47 (1H, m), 1.21 (3H, d); UPLC-MS: 0.67 min, 299 [M+H]+

Intermediate 8

1-(2,6-dihydroxyphenyl)ethanone Oxime

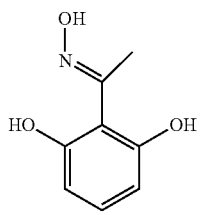

A solution of hydroxylamine hydrochloride (756 mg, 10.9 mmol) and sodium acetate trihydrate (1.71 g, 12.6 mmol) dissolved in 23 ml of a mixture of EtOH/H2O (7/3) was added to a solution of 2',6'-dihydroxyacetophenone (1.5 g, 9.9 mmol) in 12 ml of a 7/3 EtOH/H2O mixture. After refluxing and stirring under N2 for 2 hours, additional hydroxylamine hydrochloride (340 mg, 4.9 mmol) and sodium acetate trihydrate (570 mg, 4.19 mmol) dissolved in 7 ml of water were added and the reflux was continued for additional 30 minutes. After cooling down to room temperature, the volatiles were removed. Then water was added and the solid obtained was filtered, washed with water and dried. This afforded 1.3 g of the title compound.

$^1$H-NMR (400 MHz, DMSO-$d_6$): δ ppm 10.99 (1H, br. s), 9.63 (2H, br. s), 7.01-6.81 (1H, m), 6.44-6.19 (2H, m), 2.11 (3H, s).

Intermediate 9

1-(2,6-dihydroxyphenyl)ethanone O-acetyloxime

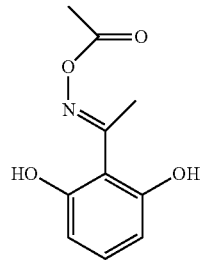

To 1-(2,6-dihydroxyphenyl)ethanone oxime (Intermediate 8, 588 mg), acetic anhydride (1.97 ml, 20.8 mmol) was added and the reaction mixture was stirred at room temperature for 15 minutes. After the removal of the volatiles, water was added and the solid obtained was filtered and dried under high vacuum affording 437 mg of the title compound.

$^1$H-NMR (400 MHz, DMSO-$d_6$): δ ppm 9.62 (2H, br. s), 7.07-6.96 (1H, m), 6.37 (2H, d), 2.19 (6H, s).

Intermediate 10

3-methyl-1,2-benzisoxazol-4-ol

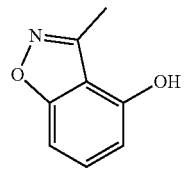

To 1-(2,6-dihydroxyphenyl)ethanone O-acetyloxime (Intermediate 9, 437 mg) pyridine (4.0 ml) was added and the reaction mixture was stirred at reflux for 2 hours. After the addition of HCl (4.0 ml of a 5M aqueous solution), the mixture was extracted 3 times with Et2O and the collected organic layers were washed with HCl (1M, aqueous solution). The organic phase was dried over sodium sulphate and filtered. Evaporation afforded the title compound (137 mg).

$^1$H-NMR (400 MHz, DMSO-$d_6$): δ ppm 10.67 (1H, br. s), 7.48-7.33 (1H, m), 7.08-6.99 (1H, m), 6.69-6.62 (1H, m), 2.58 (3H, s).

Intermediate 11

3-methyl-4-[(4-nitrophenyl)oxy]-1,2-benzisoxazole

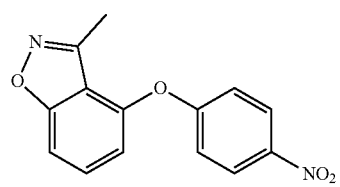 [SMILES: Cc1noc2cccc(Oc3ccc([N+](=O)[O-])cc3)c12]

3-methyl-1,2-benzisoxazol-4-ol (Intermediate 10, 137 mg) was stirred with 1-fluoro-4-nitrobenzene (130 mg, 0.92 mmol) in DMF (3.0 ml) with potassium carbonate (381 mg, 2.8 mmol). The reaction mixture was heated at 110° C. for 1 hour under microwave irradiation After removal of the volatiles, the residue was purified by silica gel chromatography eluting with CyHex/EtOAc (100%/0% to 0%/100%) to afford the title compound (100 mg).

$^1$H-NMR (400 MHz, DMSO-$d_6$): δ ppm 8.41-8.25 (2H, m), 7.78-7.57 (2H, m), 7.35-7.24 (2H, m), 7.09-6.98 (1H, m), 2.45 (3H, s); UPLC-MS: 0.83 min, 271 [M+H]+.

Intermediate 12

4-[(3-methyl-1,2-benzisoxazol-4-yl)oxy]aniline

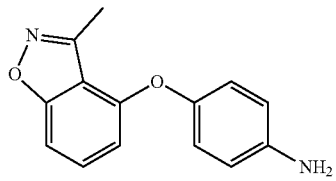

3-methyl-4-[(4-nitrophenyl)oxy]-1,2-benzisoxazole (Intermediate 11, 100 mg) was dissolved under nitrogen atmosphere in 5.0 ml of EtOH. Tin(II) chloride dihydrate (417 mg, 1.85 mmol) was added. The reaction mixture was then stirred at 90° C. for 5 hours. After removal of the volatiles, water was added and the reaction mixture was extracted two times with ethyl acetate. The collected organic layers were washed with a 5% aqueous solution of NaHCO$_3$, dried over sodium sulphate, filtered and evaporated. The crude obtained was purified by a NH column and eluted with DCM/MeOH (100/0, then a gradient from 100/0 to 90/10, then 90/10) to afford 30 mg of the title compound.

UPLC-MS: 0.63 min, 241 [M+H]+

Intermediate 13

1,1-dimethylethyl [(1R)-1-methyl-2-({4-[(3-methyl-1,2-benzisoxazol-4-yl)oxy]phenyl}amino)-2-oxoethyl]carbamate

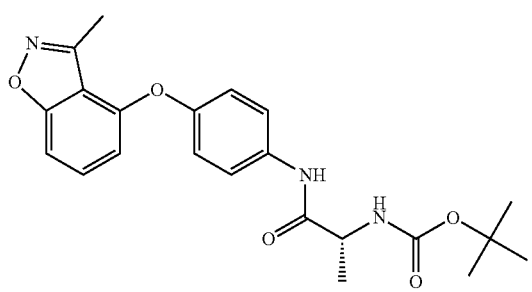 [SMILES: Cc1noc2cccc(Oc3ccc(NC(=O)[C@@H](C)NC(=O)OC(C)(C)C)cc3)c12]

{4-[(3-methyl-1,2-benzisoxazol-4-yl)oxy]phenyl}amine (Intermediate 12, 982 mg) was dissolved in 12.0 ml of DMF. DIPEA (1.07 ml, 6.1 mmol) and HATU (1865 mg, 4.9 mmol) were added. After stirring for 15 minutes, N-{[(1,1-dimethylethyl)oxy]carbonyl}-D-alanine (928 mg, 4.9 mmol) was added and the reaction mixture was stirred at 60° C. for 2 hours. After removal of the volatiles, the residue was purified by silica gel chromatography eluting with a gradient CyHex/EtOAc from 100/0% to 0/100%. This afforded the title compound (587 mg).

UPLC-MS_B: 0.89 min, 412 [M+H]+.

Intermediate 14

N$^1$-{4-[(3-methyl-1,2-benzisoxazol-4-yl)oxy]phenyl}-D-alaninamide

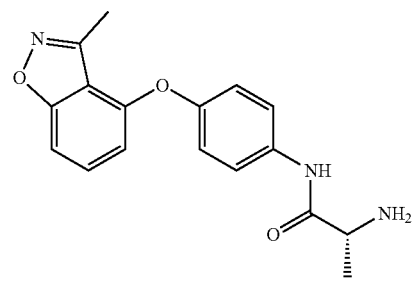 [SMILES: Cc1noc2cccc(Oc3ccc(NC(=O)[C@@H](C)N)cc3)c12]

1,1-dimethylethyl [(1R)-1-methyl-2-({4-[(3-methyl-1,2-benzisoxazol-4-yl)oxy]phenyl}amino)-2-oxoethyl]carbamate (Intermediate 13, 587 mg) was dissolved in 10.0 ml of DCM and then TFA (5.0 ml) was added. The reaction mixture was stirred at room temperature for 1 hour. After the removal of the volatiles, the residue was purified with an SCX cartridge and eluted with DCM/MeOH/NH3 (2.0 M solution in MeOH). Evaporation afforded 337 mg of the title compound.

UPLC-MS_B: 0.71 min, 312 [M+H]+.

Intermediate 15

5-methylbenzene-1,3-diyl Diacetate

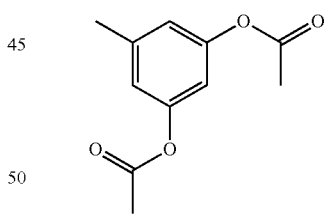

5-methyl-1,3-benzenediol (2.0 g, 16.11 mmol) was dissolved in 20.0 ml of dichloromethane and TEA (11.23 ml, 81.0 mmol) was added. Then, at 0° C., acetic anhydride (4.56 ml, 48.30 mmol) was added and the reaction mixture was stirred at room temperature for 50 hours. After the addition of water (20.0 ml) the reaction mixture was stirred for 3 hours. The phases were then separated and the aqueous one was extracted with dichloromethane (2 times). The gathered organic phases were washed with brine, dried over sodium sulphate, filtered and evaporated to afford the title compound (3.33 g).

$^1$H-NMR (400 MHz, CDCl$_3$): δ ppm 6.83 (2H, br. s), 6.75 (1H, br. s), 2.39 (3H, s), 2.31 (6H, s); UPLC-MS: 0.67 min, 209 [M+H]+.

Intermediate 16

1-(2,6-dihydroxy-4-methylphenyl)ethanone

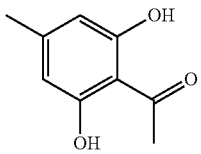

A solution of 5-methylbenzene-1,3-diyl diacetate (Intermediate 15, 3.33 g) in chlorobenzene (5.0 ml) was added dropwise to a suspension of AlCl$_3$ (6.40 g, 48.0 mmol) in chlorobenzene (15.0 ml). The reaction mixture was stirred at 90° C. for 1 hour, then it was cooled down to room temperature and pipetted onto a mixture of ice and 2 M HCl aqueous solution (16 ml). Ethyl acetate was added, the two phases were separated. The organic one was washed 2 times with brine, then dried over sodium sulphate, filtered and evaporated. The residue obtained was purified by silica gel chromatography eluting with a gradient Cy-Hex/EtOAc from 100/0 to 70/30 followed by an isochratic 70/30, another gradient from 70/30 to 50/50 and another isochratic 50/50. This afforded the title compound (940 mg).

$^1$H-NMR (400 MHz, DMSO-d$_6$): δ ppm 11.89 (2H, s), 6.22 (2H, s), 2.63 (3H, s), 2.19 (3H, s); UPLC-MS: 0.62 min, 167 [M+H]+.

Intermediate 17

1-(2,6-dihydroxy-4-methylphenyl)ethanone Oxime

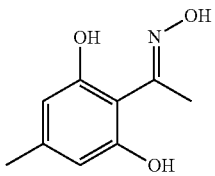

A solution of hydroxylamine hydrochloride (470 mg, 6.76 mmol) and sodium acetate trihydrate (590 mg, 4.34 mmol) dissolved in 20 ml of a mixture of EtOH/H2O (7/3) was added to a solution of 1-(2,6-dihydroxy-4-methylphenyl) ethanone (Intermediate 16, 940 mg) in 15 ml of a mixture of EtOH/H2O (7/3). After refluxing and stirring under N2 for 2 hours, additional hydroxylamine hydrochloride (159 mg, 2.29 mmol) and sodium acetate trihydrate (199 mg) dissolved in 5 ml of water were added. The reaction mixture was heated at reflux overnight. After cooling down to room temperature, the volatiles were removed. Water was added and the solid afforded was filtered, washed with water and dried giving 829 mg of the title compound.

$^1$H-NMR (400 MHz, DMSO-d$_6$): δ ppm 10.96 (1H, s), 9.80 (2H, s), 6.16 (2H, s), 2.13 (6H, br.s).

Intermediate 18

1-(2,6-dihydroxy-4-methylphenyl)ethanone O-acetyloxime

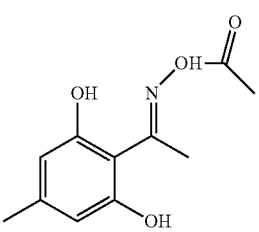 [SMILES: CC(=O)O/N=C(\C)c1c(O)cc(C)cc1O]

To 1-(2,6-dihydroxy-4-methylphenyl)ethanone oxime (Intermediate 17, 829 mg), acetic anhydride (2.6 ml, 27.5 mmol) was added and the reaction mixture was stirred at room temperature for 1 hour. After the removal of the volatiles, the residue was washed with water, filtered and dried. This afforded 1.0 g of the title compound.

$^1$H-NMR (400 MHz, DMSO-d$_6$): δ ppm 9.58 (2H, s), 6.20 (2H, s), 2.21-2.18 (6H, m), 2.16 (3H, s); acid UPLC-MS: 0.58 min, 224 [M+H]+.

Intermediate 19

3,6-dimethyl-1,2-benzisoxazol-4-ol

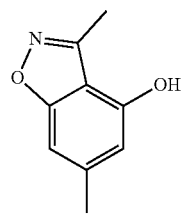

To 1-(2,6-dihydroxy-4-methylphenyl)ethanone O-acetyloxime (Intermediate 18, 1.0 g) pyridine (10 ml) was added and the reaction mixture was stirred at reflux under N2 for 2 hours. After the addition of HCl (10.0 ml of a 5M aqueous solution), the mixture was extracted 3 times with Et2O and the gathered organic phases were washed with HCl (1M). The separated organic phase was then dried over sodium sulphate, filtered and evaporated to afford 345 mg of the title compound.

$^1$H-NMR (400 MHz, DMSO-d$_6$): δ 10.55 (1H, s), 6.85 (1H, bs), 6.47 (1H, bs), 2.53 (3H, s), 2.35 (3H, s).

Intermediate 20

3,6-dimethyl-4-[(4-nitrophenyl)oxy]-1,2-benzisoxazole

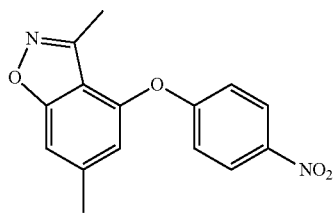

3,6-dimethyl-1,2-benzisoxazol-4-ol (Intermediate 19, 345 mg) was dissolved in acetonitrile (10.0 ml) and then 1-fluoro-4-nitrobenzene (298 mg, 2.11 mmol) and potassium carbonate (877 mg, 6.34 mmol) were added. The reaction mixture was stirred and heated at reflux overnight. After removal of the volatiles, the residue was purified by silica gel chromatography eluting with a gradient cHex/EtOAc from 100/0 to 50/50 to afford the title compound (208 mg).

$^1$H-NMR (400 MHz, DMSO-d$_6$): δ ppm 8.36-8.26 (2H, m), 7.46 (1H, s), 7.33-7.26 (2H, m), 6.91 (1H, s), 2.47 (3H, s), 2.39 (3H, s); UPLC-MS: 0.84 min, 285 [M+H]+.

Intermediate 21

{4-[(3,6-dimethyl-1,2-benzisoxazol-4-yl)oxy]phenyl}amine

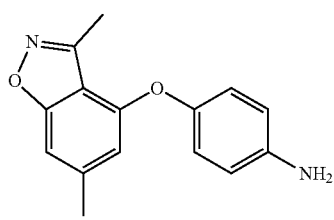 [SMILES: Cc1cc(Oc2ccc([N+](=O)[O-])cc2)c2c(C)noc2c1]

3,6-dimethyl-4-[(4-nitrophenyl)oxy]-1,2-benzisoxazole (Intermediate 20, 208 mg) was dissolved in ethanol (10.0 ml) and tin chloride dihydrate (991 mg, 4.39 mmol) was added. The reaction mixture was stirred and heated at reflux for 4 hours. After the removal of the volatiles, water was added and the reaction mixture was extracted two times with ethyl acetate. The collected organic were dried over sodium sulphate, filtered and evaporated to afford 260 mg of the title compound.

UPLC-MS: 0.60 min, 255 [M+H]+.

Intermediate 22

1,1-dimethylethyl [(1R)-2-({4-[(3,6-dimethyl-1,2-benzisoxazol-4-yl)oxy]phenyl}amino)-1-methyl-2-oxoethyl]carbamate)

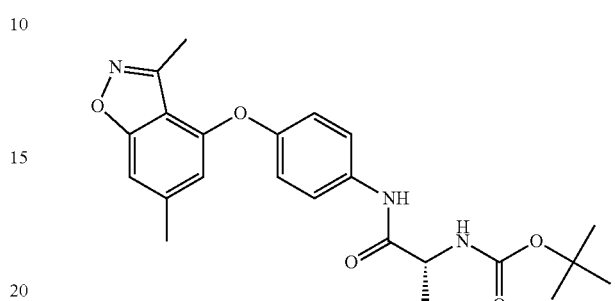

{4-[(3,6-dimethyl-1,2-benzisoxazol-4-yl)oxy]phenyl}amine (Intermediate 21, 260 mg) was dissolved in 8.0 ml of DMF. DIPEA (0.188 ml, 1.074 mmol) and HATU (327 mg, 0.86 mmol) were added. After stirring for 15 minutes, N-{[(1,1-dimethylethyl)oxy]carbonyl}-D-alanine (163 mg, 0.86 mmol) was added and the reaction mixture was stirred at 60° C. for 2 hours. After removal of the volatiles, the residue was purified by silica gel chromatography eluting with a gradient cHex/EtOAc from 100/0 to 0/100 to afford the title compound (74 mg).

UPLC-MS_B: 0.93 min, 426 [M+H]+.

Intermediate 23

N$^1$-{4-[(3,6-dimethyl-1,2-benzisoxazol-4-yl)oxy]phenyl}-D-alaninamide

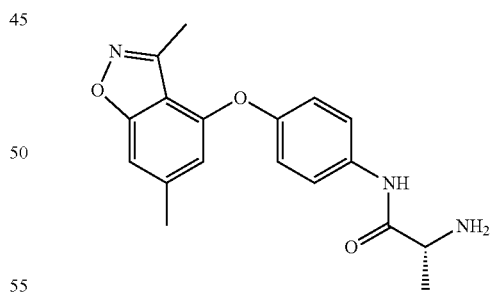

1,1-dimethylethyl [(1R)-2-({4-[(3,6-dimethyl-1,2-benzisoxazol-4-yl)oxy]phenyl}amino)-1-methyl-2-oxoethyl]carbamate) (Intermediate 22, 74 mg) was dissolved in 3.0 ml of dichloromethane. TFA (1.5 ml) was added and the reaction mixture was stirred at room temperature for 1 hour. After removal of the volatiles, the residue was purified with a SCX cartridge and eluted with DCM/MeOH/NH3 (2.0 M solution in MeOH). The evaporation of the volatiles, afforded 54 mg of the title compound.

UPLC-MS_B: 0.76 min, 326 [M+H]+.

Intermediate 24

1,1-dimethylethyl[1,1-dimethyl-2-({4-[(3-methyl-1,2-benzisoxazol-4-yl)oxy]phenyl}amino)-2-oxoethyl]carbamate

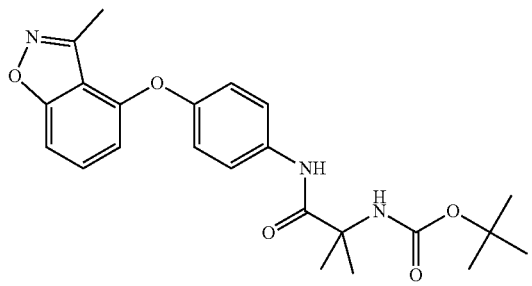 [SMILES: Cc1noc2cccc(Oc3ccc(NC(=O)C(C)(C)NC(=O)OC(C)(C)C)cc3)c12]

{4-[(3-methyl-1,2-benzisoxazol-4-yl)oxy]phenyl}amine (Intermediate 23, 30 mg) was dissolved in 5.0 ml of DMF. DIPEA (0.033 ml, 0.19 mmol) and HATU (57 mg, 0.15 mmol) were added. After stirring for 15 minutes, N-{[(1,1-dimethylethyl)oxy]carbonyl}-2-methylalanine (30.5 mg, 0.15 mmol) was added and the reaction mixture was stirred at 60° C. for 2 hours. After the removal of the volatiles, the residue was purified by silica gel chromatography eluting with a gradient cHex/EtOAc (from 100/0 to 0/100) to afford the title compound (34 mg).

UPLC-MS_B: 0.91 min, 426 [M+H]+.

Intermediate 25

2-methyl-$N^1$-{4-[(3-methyl-1,2-benzisoxazol-4-yl)oxy]phenyl}alaninamide

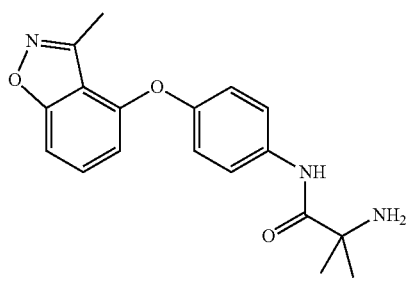 [SMILES: Cc1noc2cccc(Oc3ccc(NC(=O)C(C)(C)N)cc3)c12]

1,1-dimethylethyl [1,1-dimethyl-2-({4-[(3-methyl-1,2-benzisoxazol-4-yl)oxy]phenyl}amino)-2-oxoethyl]carbamate (Intermediate 24, 34 mg) was dissolved in 4.0 ml of dichloromethane and then TFA (1.0 ml) was added. The reaction mixture was stirred at room temperature for 1 hour. After removal of the volatiles, the residue was charged on a SCX cartridge and eluted successively with dichloromethane, MeOH, NH3 (2.0 M solution in MeOH). Evaporation afforded 18 mg of the title compound.

$^1$H-NMR (400 MHz, DMSO-$d_6$): δ ppm 7.84-7.70 (2H, m), 7.60-7.49 (1H, m), 7.45-7.36 (1H, m), 7.21-7.13 (2H, m), 6.61-6.51 (1H, m), 2.60 (3H, s), 1.33 (6H, s); basic UPLC-MS: 0.79 min, 326 [M+H]+.

Intermediate 26

1,3-bis{[(methyloxy)methyl]oxy}benzene

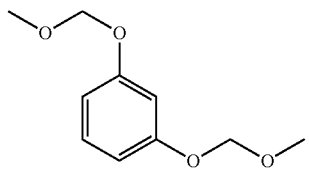

Resorcinol (3.0 g, 27.2 mmol) was dissolved in DMF (50.0 ml) and, at 0° C., NaH (4.36 g, 109 mmol, 60% Wt) was added. After stirring at that temperature for 30 minutes, chloromethyl methyl ether (8.28 ml, 109 mmol) was added and the reaction was allowed to reach room temperature and was stirred overnight. The mixture was quenched with a saturated aqueous solution of NaHCO3 and extracted with ethyl acetate. The collected organic layers were then washed with brine, dried, filtered and evaporated. The residue obtained was charged on a silica gel column and eluted with Cyclohexane/EtOAc (from 100/0 to 50/50) to afford the title compound (4.94 g).

$^1$H-NMR (400 MHz, DMSO-$d_6$): δ ppm 7.26-7.15 (1H, m), 6.71-6.65 (3H, m), 5.18 (4H, s) 3.39 (6H, s).

Intermediate 27

1-(2,6-bis{[(methyloxy)methyl]oxy}phenyl)-1-propanone

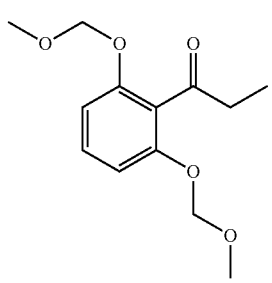 [SMILES: CCC(=O)c1c(OCOC)cccc1OCOC]

1,3-bis{[(methyloxy)methyl]oxy}benzene (Intermediate 26, 2.02 g) was dissolved under nitrogen in THF (7.0 mL) and a solution of BuLi (7.64 ml of a 1.6 M solution in hexane, 12.2 mmol) was added. After stirring at room temperature for 1 hour and cooling down at −78° C., propanoic anhydride (5.23 ml, 40.8 mmol) was added and the mixture was stirred at that temperature for 15 minutes. After quenching with water, the mixture was extracted with ethyl acetate. The collected organic layers were dried over sodium sulphate, filtered and evaporated. The crude afforded was then charged on a silica gel column and eluted with cyclohexane/EtOAc (from 10/0 to 9/1, then 9/1, then from 9/1 to 8/2, then 8/2) to afford the title compound (1.706 g).

$^1$H-NMR (400 MHz, DMSO-$d_6$): δ ppm 7.32-7.23 (1H, m), 6.81 (2H, d), 5.18 (4H, s) 3.34 (6H, s), 2.71 (2H, q), 1.06 (3H, t).

Intermediate 28

1-(2,6-dihydroxyphenyl)-1-propanone

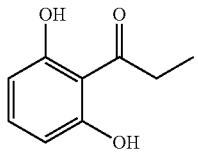

1-(2,6-bis{[(methyloxy)methyl]oxy}phenyl)-1-propanone (Intermediate 27, 1.7 g) was dissolved in methanol (50.0 ml) and an aqueous solution of HCl (26.7 ml, 53.5 mmol of a 2M aqueous solution) was added. The reaction mixture was refluxed for 2 hours. After quenching with water, the reaction mixture was extracted with ethyl acetate. The gathered organic layers were dried over sodium sulphate, filtered and evaporated to afford the title compound (1.11 g).

$^1$H-NMR (400 MHz, DMSO-$d_6$): δ ppm 11.59 (2H, br. s), 7.25-7.17 (1H, m), 6.37 (2H, d), 3.06 (2H, q), 1.07 (3H, t).

Intermediate 29

1-(2,6-dihydroxyphenyl)-1-propanone Oxime

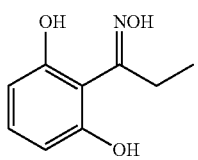

A solution of hydroxylamine hydrochloride (510 mg, 7.3 mmol) and sodium acetate trihydrate (629 mg, 4.6 mmol) dissolved in 20 ml of a mixture EtOH/H2O (7/3) was added to a solution of 1-(2,6-dihydroxyphenyl)-1-propanone (Intermediate 28, 1.0 g) in 15 ml of a mixture EtOH/H2O (7/3). After refluxing and stirring under N2 overnight, additional hydroxylamine hydrochloride (510 mg, 7.3 mmol) and sodium acetate trihydrate (629 mg, 4.6 mmol) dissolved in 4.5 mL of water were added. The reaction mixture was heated at reflux an additional 3 hours. After cooling down to room temperature, the volatiles were removed. Then water was added and reaction mixture was extracted with ethyl acetate. The gathered organic layers were dried over sodium sulphate, filtered and evaporated to afford the title compound (1.05 g).

UPLC: 0.41 min, 182 [M+H]+; 0.47 min, 182 [M+H]+.

Intermediate 30

1-(2,6-dihydroxyphenyl)-1-propanone O-acetyloxime

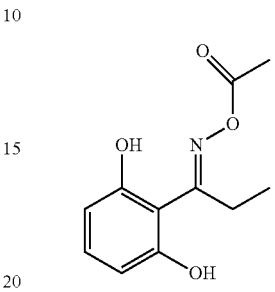

1-(2,6-dihydroxyphenyl)-1-propanone oxime (Intermediate 29, 716 mg) was stirred in acetic anhydride (2.24 ml, 23.7 mmol) at room temperature for 1 hour. After removal of the volatiles, the residue was washed with water, filtered and dried. The crude compound was charged on a silica gel column (Biotage SP1 system) and eluted with Cyclohexane/EtOAc (from 100/0 to all 0/100) to afford the title compound (269 mg).

$^1$H-NMR (400 MHz, DMSO-$d_6$): δ ppm 9.49 (2H, br. s), 7.01-6.91 (1H, m), 6.32 (2H, d), 2.54 (2H, q), 1.97 (3H, s), 1.02 (3H, t).

Intermediate 31

3-ethyl-1,2-benzisoxazol-4-ol and
2-ethyl-1,3-benzoxazol-4-ol

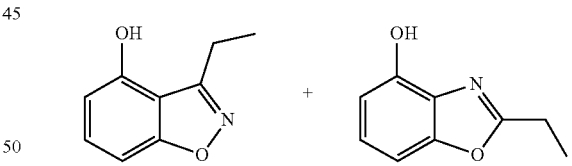

1-(2,6-dihydroxyphenyl)-1-propanone O-acetyloxime (Intermediate 30, 269 mg) was dissolved in pyridine (10.0 ml) and stirred at reflux for 2 days. After the addition of an aqueous solution of HCl (5M), the reaction mixture was extracted 3 times with ethyl acetate and the gathered organic layers were washed with an aqueous solution of HCl (1M). The organic phase was dried over sodium sulphate, filtered and evaporated. The residue obtained was charged on a silica gel column (Biotage SP1 system) and eluted with cyclohexane/EtOAc (from 1/0 to 1/1, then 1/1, then from 1/1 to 0/1) to afford the title compounds as mixture of 3-ethyl-1,2-benzisoxazol-4-ol and 2-ethyl-1,3-benzoxazol-4-ol (38 mg)

UPLC: 0.59 min, 164 [M+H]+; 0.61 min, 164 [M+H]+.

Intermediate 32

3-ethyl-4-[(5-nitro-2-pyridinyl)oxy]-1,2-benzisoxazole

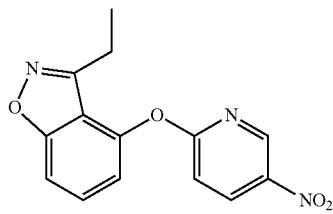 [SMILES: CCc1noc2cccc(Oc3ccc([N+](=O)[O-])cn3)c12]

A mixture of 3-ethyl-1,2-benzisoxazol-4-ol and 2-ethyl-1,3-benzoxazol-4-ol (Intermediate 31, 38 mg), was dissolved in DMF (3.0 mL) and 2-chloro-5-nitropyridine (36.9 mg, 0.23 mmol) was added, followed by potassium carbonate (97 mg, 0.70 mmol). The reaction mixture was heated under microwave irradiation at 110° C. for 1 hour. After removal of the volatiles, the crude was charged on a silica gel column and eluted with Cyclohexane/EtOAc (from 1/0 to 1/1) to afford the title compound (9.5 mg).

$^1$H-NMR (400 MHz, DMSO-d$_6$): δ ppm 9.06-9.01 (1H, m), 8.75-8.68 (1H, m), 7.76-7.65 (2H, m), 7.47 (1H, d), 7.27-7.22 (1H, m), 2.73-2.67 (2H, m), 1.20 (3H, t). UPLC: 0.77 min, 286 [M+H]+.

Intermediate 33

6-[(3-ethyl-1,2-benzisoxazol-4-yl)oxy]-3-pyridinamine

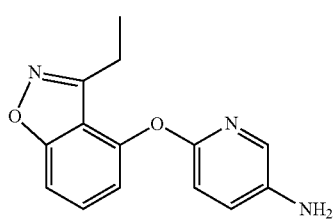 [SMILES: CCc1noc2cccc(Oc3ccc(N)cn3)c12]

3-ethyl-4-[(5-nitro-2-pyridinyl)oxy]-1,2-benzisoxazole (Intermediate 32, 9 mg) was dissolved in 3.0 ml of ethanol. Then tin(II) chloride dihydrate (21.4 mg, 0.095 mmol) was added and the reaction mixture was stirred at 80° C. for 3 hours. After quenching with water and extraction with ethyl acetate, the organic phase was dried over sodium sulphate, filtered and evaporated to afford the title compound.

UPLC: 0.62 min, 256 [M+H]+

Intermediate 34

1,1-dimethylethyl {(1R)-1-[({6-[(3-ethyl-1,2-benzisoxazol-4-yl)oxy]-3-pyridinyl}amino)carbonyl]propyl}carbamate

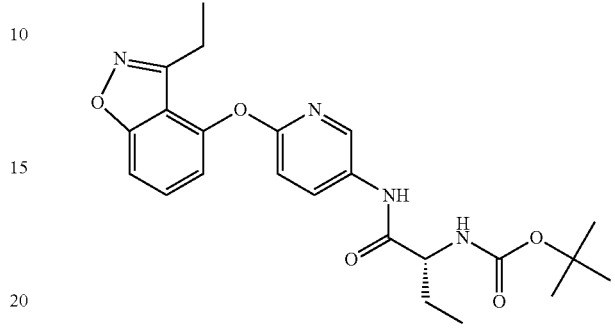

6-[(3-ethyl-1,2-benzisoxazol-4-yl)oxy]-3-pyridinamine (Intermediate 33) was dissolved in DMF (0.5 mL) and added to a mixture of (2R)-2-({[(1,1-dimethylethyl)oxy]carbonyl}amino)butanoic acid (7.7 mg, 0.038 mmol), DIPEA (0.008 mL, 0.047 mmol) and HATU (14.4 mg, 0.038 mmol) in 1 ml of DMF. The reaction mixture was then stirred at 50° C. for 2 hours. After the removal of DMF, water was added and the mixture was extracted with ethyl acetate. The gathered organic layers were dried over sodium sulphate, filtered and evaporated. The residue was then charged on a silica gel column (Biotage SP1 system) and eluted with Cyhexane/EtOAc (from all 10/0 to 7/3, then 7/3) to afford the title compound (4.4 mg).

$^1$H-NMR (400 MHz, CDCl$_3$): δ ppm 8.24-8.17 (2H, m), 7.55-7.47 (1H, m), 7.44-7.34 (1H, m), 7.08-7.00 (1H, m), 6.96-6.89 (1H, m), 5.00 (1H, br. s), 4.21-4.10 (1H, m), 2.94 (2H, q), 2.08-1.97 (1H, m), 1.80-1.70 (1H, m), 1.50 (9H, s), 1.38 (3H, t), 1.07 (3H, t). UPLC: 0.78 min, 441 [M+H]+.

Intermediate 35

(2R)-2-amino-N-{6-[(3-ethyl-1,2-benzisoxazol-4-yl)oxy]-3-pyridinyl}butanamide

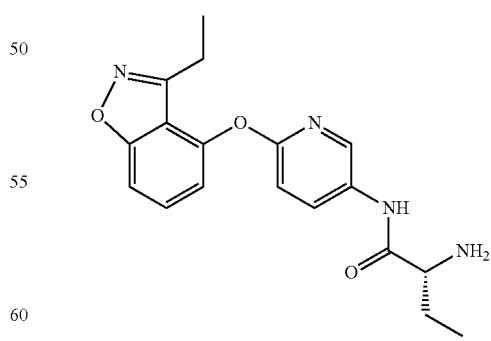

1,1-dimethylethyl {(1R)-1-[({6-[(3-ethyl-1,2-benzisoxazol-4-yl)oxy]-3-pyridinyl}amino)carbonyl]propyl}carbamate (Intermediate 34, 4.4 mg) was dissolved in dichloromethane (1.0 ml) and, at 0° C., TFA (0.100 ml, 1.3 mmol) was added. The reaction mixture was stirred at Intermediate 36

1-(2,6-bis{[(methyloxy)methyl]oxy}phenyl)-2-methyl-1-propanone

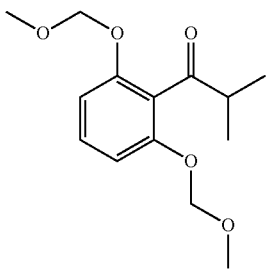 [SMILES: COCOc1cccc(OCOC)c1C(=O)C(C)C]

1,3-bis{[(methyloxy)methyl]oxy}benzene (Intermediate 35, 2.2 g) was dissolved under nitrogen in THF (8.0 mL) and a solution of BuLi (8.32 mL of a 1.6 M solution in hexane, 13.3 mmol) was added. After stirring at room temperature for 1 hour, cooling down to −78° C., 2-methylpropanoyl chloride (4.65 ml, 44.4 mmol) was added and the reaction mixture was stirred at that temperature for 1 hour. After quenching with water, the reaction mixture was extracted with ethyl acetate. The gathered organic layers were dried over sodium sulphate, filtered and evaporated. The residue obtained was then charged on a silica gel column (Biotage SP1 system) and eluted with Cyclohexane/EtOAc (from all 10/0 to 9/1, then 9/1, then from 9/1 to 8/2, then 8/2) to afford the title compound (825 mg).

$^1$H-NMR (400 MHz, DMSO-de): δ ppm 7.35-7.24 (1H, m), 6.87-6.77 (2H, m), 5.18 (4H, s), 3.36 (6H, s), 3.01-2.90 (1H, m), 1.12-1.06 (6H, m).

The title compound was also prepared by the following alternative way:

1,3-bis{[(methyloxy)methyl]oxy}benzene (Intermediate 35, 1.099 g) was dissolved under nitrogen in THF (5.0 mL) and a solution of BuLi (4.16 mL of a 1.6 M solution in hexane, 6.65 mmol) was added. After stirring at room temperature for 1 hour, cooling down at −78° C., isobutyric anhydride (3.68 ml, 22.2 mmol) was added and the reaction mixture was stirred at that temperature for 15 minutes. After quenching with water, the mixture was extracted with ethyl acetate. The gathered organic layers were dried over sodium sulphate, filtered and evaporated. The residue obtained was then charged on a silica gel column and eluted with Cyhexane/ethyl acetate (from all 10/0 to 9/1 then 9/1) to afford 759 mg of the title compound.

Intermediate 37

1-(2,6-dihydroxyphenyl)-2-methyl-1-propanone

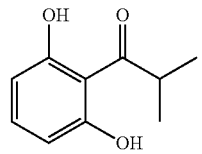

1-(2,6-bis{[(methyloxy)methyl]oxy}phenyl)-2-methyl-1-propanone (Intermediate 36, 1.58 g, 5.89 mmol) was dissolved in methanol (40.0 ml) and an aqueous solution of HCl (23.6 mL of a 2M aqueous solution, 47.1 mmol) was added. The reaction mixture was refluxed for 1 hour. After quenching with water, the reaction mixture was extracted with ethyl acetate. The gathered organic layers were dried over sodium sulphate, filtered and evaporated to afford the title compound (916 mg).

$^1$H-NMR (400 MHz, DMSO-d$_6$): δ ppm 11.01 (2H, br. s), 7.15 (1H, t), 6.39-6.34 (2H, m), 3.64-3.55 (1H, m), 1.09 (6H, d).

Intermediate 38

1-(2,6-dihydroxyphenyl)-2-methyl-1-propanone Oxime

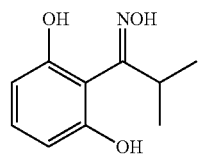

1-(2,6-dihydroxyphenyl)-2-methyl-1-propanone (Intermediate 37, 416 mg) was dissolved in pyridine (2.0 ml) and hydroxylamine hydrochloride (209 mg, 3.0 mmol) was added. The reaction mixture was then stirred at room temperature overnight. After night, additional hydroxylamine hydrochloride (64 mg, 0.92 mmol) was added and the mixture was heated at 100° C. for 3 hours. After removal of the volatiles, the crude was treated with water and extracted with ethyl acetate. The gathered organic layers were dried over sodium sulphate, filtered and evaporated to afford the title compound (370 mg).

UPLC: 0.47 min, 196 [M+H]+; 0.50 min, 196 [M+H]+.

Intermediate 39

1-(2,6-dihydroxyphenyl)-2-methyl-1-propanone O-acetyloxime

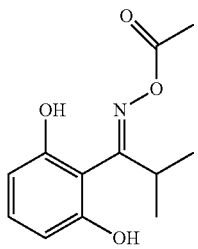 [SMILES: CC(=O)O/N=C(/c1c(O)cccc1O)C(C)C]

1-(2,6-dihydroxyphenyl)-2-methyl-1-propanone oxime (Intermediate 38, 320 mg) was stirred in acetic anhydride (0.928 ml, 9.84 mmol) at room temperature for 1 hour. After removal of the volatiles, the crude was washed with water, filtered and dried. The residue obtained was charged on a silica gel column (Biotage SP1 system) and eluted with Cyhexane/ethyl acetate (from 100/0 to 0/100) to afford the title compound (127 mg).

$^1$H-NMR (400 MHz, DMSO-$d_6$): δ ppm 9.42 (2H, br. s), 6.95 (1H, t), 6.31 (2H, d), 2.91-2.77 (1H, m), 1.97 (3H, s), 1.11 (6H, d).

Intermediate 40

3-(1-methylethyl)-1,2-benzisoxazol-4-ol and 2-(1-methylethyl)-1,3-benzoxazol-4-ol

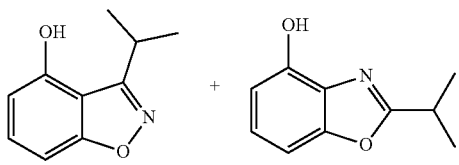

1-(2,6-dihydroxyphenyl)-2-methyl-1-propanone O-acetyloxime (Intermediate 39, 100 mg) was dissolved in pyridine (4.0 ml) and stirred at reflux for 5 days. After the addition of an aqueous solution of HCl (5M), the reaction mixture was extracted 3 times with ethyl acetate and the gathered organic layers were washed with an aqueous solution of HCl (1M). The organic phase was then dried over sodium sulphate, filtered and evaporated. The residue obtained was charged on a silica gel column (Biotage SP1 system) and eluted with Cyhexane/EtOAc (from 1/0 to 1/1 then 1/1, then from 1/1 to 0/1) to afford 13 mg of a mixture of the title compounds 3-(1-methylethyl)-1,2-benzisoxazol-4-ol and of 2-(1-methylethyl)-1,3-benzoxazol-4-ol.

UPLC: 0.64 min, 178 [M+H]+; 0.65 min, 178 [M+H]+.

Intermediate 41

3-(1-methylethyl)-4-[(5-nitro-2-pyridinyl)oxy]-1,2-benzisoxazole

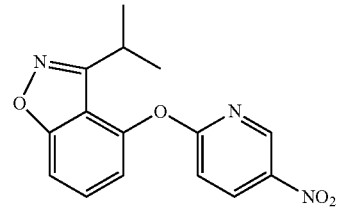 [SMILES: CC(C)c1noc2cccc(Oc3ccc([N+](=O)[O-])cn3)c12]

A mixture of 3-(1-methylethyl)-1,2-benzisoxazol-4-ol and 2-(1-methylethyl)-1,3-benzoxazol-4-ol (Intermediate 40, 13 mg), was dissolved in DMF (2.0 mL) and 2-chloro-5-nitropyridine (11.6 mg, 0.073 mmol) was added, followed by potassium carbonate (30 mg, 0.22 mmol). The reaction mixture was heated under microwave irradiation at 110° C. for 1 hour. After the removal of the volatiles, the residue obtained was charged on a silica gel column (Biotage SP1 system) and eluted with Cyhexane/EtOAc (from 10/0 to 9/1, then 9/1, then from 9/1 to 8/2) to afford the title compound (8.7 mg).

$^1$H-NMR (400 MHz, CDCl$_3$): δ ppm 9.08 (1H, d), 8.64-8.58 (1H, m), 7.65-7.57 (1H, m), 7.55-7.48 (1H, m), 7.23-7.19 (1H, m), 7.08 (1H, d), 3.24-3.13 (1H, m), 1.40 (6H, d). UPLC: 0.80 min, 300 [M+H]+.

Intermediate 42

6-{[3-(1-methylethyl)-1,2-benzisoxazol-4-yl]oxy}-3-pyridinamine

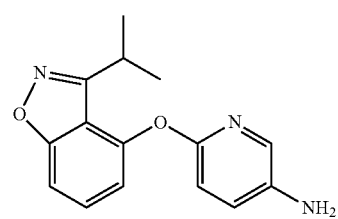

3-(1-methylethyl)-4-[(5-nitro-2-pyridinyl)oxy]-1,2-benzisoxazole (Intermediate 41, 8.7 mg) was dissolved in 3.0 ml of ethanol. Tin(II) chloride dihydrate (19.7 mg, 0.087 mmol) was added and the reaction mixture was stirred at 80° C. for 3 hours. After quenching with water and extraction with ethyl acetate, the gathered organic layers were dried over sodium sulphate, filtered and evaporated to afford the title compound.

UPLC: 0.67 min, 270 [M+H]+.

Intermediate 43

1,1-dimethylethyl ((1R)-1-{[(6-{[3-(1-methylethyl)-1,2-benzisoxazol-4-yl]oxy}-3-pyridinyl)amino]carbonyl}propyl)carbamate

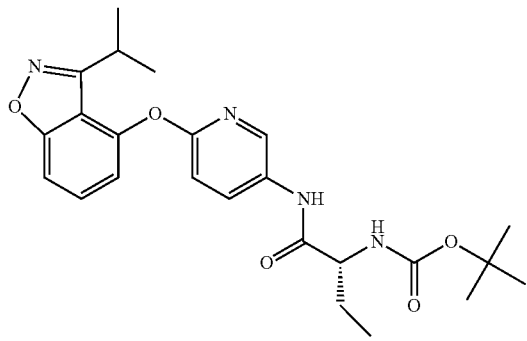 [SMILES: CC[C@@H](NC(=O)OC(C)(C)C)C(=O)Nc1ccc(Oc2cccc3onc(C(C)C)c23)nc1]

6-{[3-(1-methylethyl)-1,2-benzisoxazol-4-yl]oxy}-3-pyridinamine (Intermediate 42) was dissolved DMF (0.5 mL) and added to a mixture of (2R)-2-({[(1,1-dimethylethyl)oxy]carbonyl}amino)butanoic acid (7.09 mg, 0.035 mmol), DIPEA (7.6 μL, 0.044 mmol) and HATU (13.26 mg, 0.035 mmol) in 1 ml of DMF. The reaction mixture was then stirred at 50° C. for 1 hour. After removal of DMF, water was added and the mixture was extracted with ethyl acetate. The gathered organic layers were dried over sodium sulphate, filtered and evaporated. The residue was charged on a silica gel column (Biotage SP1 system) and eluted with Cyhexane/EtOAc (from 10/0 to 7/3, then 7/3) to afford the title compound (2 mg).

UPLC: 0.81 min, 455 [M+H]+.

Intermediate 44

(2R)-2-amino-N-(6-{[3-(1-methylethyl)-1,2-benzisoxazol-4-yl]oxy}-3-pyridinyl)butanamide

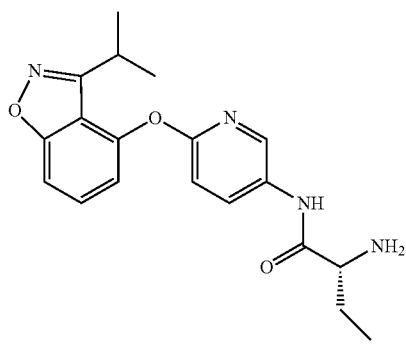 [SMILES: CC[C@@H](N)C(=O)Nc1ccc(Oc2cccc3onc(C(C)C)c23)nc1]

1,1-dimethylethyl ((1R)-1-{[(6-{[3-(1-methylethyl)-1,2-benzisoxazol-4-yl]oxy}-3-pyridinyl)amino]carbonyl}propyl)carbamate (Intermediate 43, 2.0 mg) was dissolved in dichloromethane (1.0 mL) and, at 0° C., TFA (0.05 mL, 0.65 mmol) was added. The reaction mixture was stirred at that temperature for 2 hours. After removal of the volatiles, the residue obtained was charged on a SCX cartridge and eluted with DCM/MeOH/NH3 (2.0 M in MeOH) to afford the title compound.

UPLC: 0.56 min, 355 [M+H]+.

Intermediate 45

1-(methyloxy)-3-{[(methyloxy)methyl]oxy}benzene

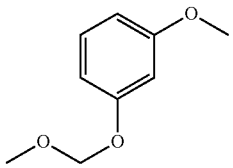

To a solution of 3-(methyloxy)phenol (10.38 g, 84 mmol) in tetrahydrofurane (100 ml, SCRC) was added NaH (60% wt., 1.824 g, 76 mmol, Aldrich) portionwise under ice-cooling. The reaction mixture was stirred at room temperature for 1 hour and bromomethyl methyl ether (9.5 g, 76 mmol, SCRC) was then added. The resulting mixture was stirred at room temperature for 2 hours and water (50 ml) was added. The reaction mixture was extracted with ethyl acetate (2 times 50 ml, SCRC) and the combined organic layers were dried over sodium sulphate, evaporated. The residue was purified by column chromatography on silica gel (EtOAc:PE=1:100) to afford the title compound (10.2 g) as a colorless liquid.

Intermediate 46

2-iodo-1-(methyloxy)-3-{[(methyloxy)methyl]oxy}benzene

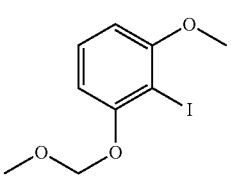

To a solution of 1-(methyloxy)-3-{[(methyloxy)methyl]oxy}benzene (Intermediate 45, 10 g, 59.5 mmol) in tetrahydrofurane (100 ml, SCRC) precooled to −78° C. was added dropwise BuLi (2.5 M in THF, 28.5 ml, 71.3 mmol, SCRC), maintaining the inner temperature lower than −70° C. After the addition was complete, the mixture was stirred at −70° C. for 2 hours and a solution of iodine (15.09 g, 59.5 mmol, SCRC) in THF (50 ml, SCRC) was added dropwise. The resulting mixture was stirred for 2 hours at room temperature and quenched with a saturated aqueous solution of ammonium chloride (100 ml). The mixture was extracted with ethyl acetate (3 times 300 ml, SCRC) and the combined organic layers were dried, evaporated and purified by silica gel chromatography with as eluents EtOAc:PE (1/100) to afford the title compound (16.2 g) as a yellow liquid.

Intermediate 47

2-iodo-3-(methyloxy)phenol

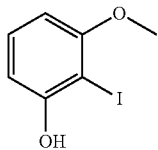

To a solution of 2-iodo-1-(methyloxy)-3-{[(methyloxy)methyl]oxy}benzene (Intermediate 46, 16.2 g, 55.1 mmol) in dichloromethane (100 ml, SCRC) was bubbled HCl (g) for 30 mins. TLC showed that the reaction was completed. The reaction mixture was poured into an aqueous saturated solution of NaHCO$_3$ (200 ml) and extracted with dichloromethane (3×200 ml, SCRC). The combined organic layers were dried, evaporated and purified by column chromatography on silica gel (EtOAc:PE=1:50) to afford the title compound as a yellow liquid (10.3 g).

Intermediate 48

2-iodo-1-(methyloxy)-3-[(2-methyl-2-propen-1-yl)oxy]benzene

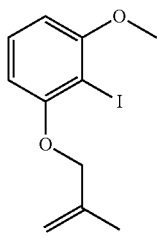

To a solution of 2-iodo-3-(methyloxy)phenol (Intermediate 47, 10.3 g) in DMF (100 ml, SCRC) was added NaH (60%, wt., 1.977 g, 49.4 mmol) portionwise. The reaction mixture was stirred at room temperature for 1 hour and 3-chloro-2-methyl-1-propene (3.73 g, 41.2 mmol, Aldrich) was added. The resulting mixture was stirred at room temperature for 2 hours and water (50 ml) was added. The reaction mixture was extracted with ethyl acetate (3 times 200 ml, SCRC) and the combined organic layer were dried, evaporated and purified by silica gel chromatography with as eluents EtOAc/PE (1/30) to afford the title compound as a yellow liquid (11.6 g)

$^1$H-NMR (400 MHz, CDCl$_3$) δ ppm: 7.25 (1H, t), 6.52-6.47 (2H, m), 5.21 (1H, s), 5.01 (1H, s), 4.49 (2H, s), 3.89 (3H, s), 1.87 (3H, s)

Intermediate 49

3,3-dimethyl-4-(methyloxy)-2,3-dihydro-1-benzofuran

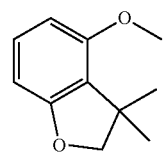

To a solution of 2-iodo-1-(methyloxy)-3-[(2-methyl-2-propen-1-yl)oxy]benzene (Intermediate 48, 6.08 g) in toluene (50 ml, SCRC) were added AIBN (3.61 g, 21.99 mmol, SCRC) and tributylstannane (11.60 g, 40.0 mmol, Aldrich). The reaction mixture was heated at reflux for 3 hours and then cooled to room temperature. Water (100 ml) was added and the mixture was extracted with ethyl acetate (3 times 200 ml, SCRC). The combined organic layers were dried, evaporated and purified by silica gel chromatography with as eluents EtOAc/PE (1/50) to afford the title compound as a yellow liquid (2.7 g).

$^1$H-NMR (400 MHz, DMSO-d$_6$) δ ppm: 7.05 (1H, t), 6.50 (1H, d), 6.39 (1H, d), 4.14 (2H, s), 3.77 (3H, s), 1.34 (6H, s);

Intermediate 50

3,3-dimethyl-2,3-dihydro-1-benzofuran-4-ol

To a solution of 3,3-dimethyl-4-(methyloxy)-2,3-dihydro-1-benzofuran (Intermediate 49, 4.0 g) in dichloromethane (100 ml, SCRC) was added BBr3 (6.37 ml, 67.3 mmol, SCRC) dropwise under ice-cooling. After the addition was complete, the reaction mixture was stirred for 2 hours at room temperature and then water (20 ml) was added. The resulting mixture was extracted with ethyl acetate (3 times 100 ml, SCRC) and the combined organic layers were dried, evaporated and purified by silica gel chromatography with EtOAc/PE as eluents (1/20) to afford the title compound (2.8 g).

$^1$H-NMR (400 MHz, CDCl$_3$) δ ppm: 6.98-6.94 (1H, t), 6.41-6.39 (1H, dd), 6.25-6.23 (1H, dd), 4.21 (2H, s), 1.45 (6H, s); MS_2: 163 [M−H]−.

Intermediate 51

2-bromo-3-hydroxyphenyl Acetate

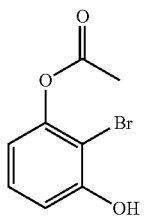

To a solution of 2-bromo-1,3-benzenediol (3.028 g, 16.02 mmol) in dichloromethane (70 ml), TEA (3.35 ml, 24.03 mmol) and acetic anhydride (1.512 ml, 16.02 mmol) were added under stirring. The reaction mixture was stirred at room temperature overnight. The reaction was quenched with a saturated solution of ammonium chloride (100 ml), and extracted with ethyl acetate (3 times 70 ml). The combined organic layers were dried over sodium sulphate, filtered and evaporated to afford the title compound as a black oil which was used directly used in the next step. (3.028 g)

UPLC_B: 0.41 min, 229 [M−H]−

Intermediate 52

2-bromo-3-[(2-methyl-2-propen-1-yl)oxy]phenyl Acetate

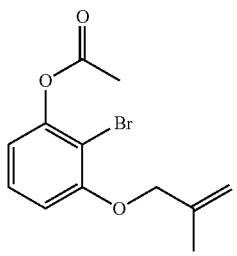 [SMILES: C=C(C)COc1cccc(OC(C)=O)c1Br]

To a solution of 2-bromo-3-hydroxyphenyl acetate (Intermediate 51, 3028 mg) in acetonitrile (60 ml) potassium carbonate (3623 mg, 26.2 mmol) and 3-bromo-2-methyl-1-propene (2123 mg, 15.73 mmol) were added. The reaction mixture was stirred at room temperature overnight. The mixture was washed with water (3 times 60 ml). The organic phase was separated, dried over sodium sulphate, filtered and evaporated. The residue was purified by flash chromatography on silica gel using a 100 g-SNAP column and cyclohexane/ethyl acetate from 100/0 to 80/20 as eluent to afford the title compound as a colourless oil (2.324 g).

$^1$H NMR (400 MHz, CDCl$_3$): δ ppm 7.27 (1H, t), 6.68 (1H, dd), 5.19 (1H, s), 5.04 (1H, s), 4.53 (2H, s), 2.38 (3H, s), 1.88 (3H, s); UPLC: 0.81 min, 285 [M+H]+

Intermediate 53

3,3-dimethyl-2,3-dihydro-1-benzofuran-4-yl Acetate

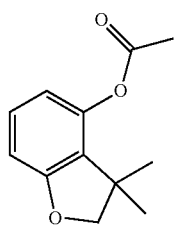

To a solution of 2-bromo-3-[(2-methyl-2-propen-1-yl)oxy]phenyl acetate (Intermediate 52, 2.324 g) in toluene (20 ml) AIBN (1.606 g, 9.78 mmol) and tributylstannane (4.73 g, 16.30 mmol) were added. The reaction mixture was stirred and heated at 100° C. for 2 hours, then was left at room temperature for 4 hours. The reaction was quenched with water (60 ml) and extracted with ethyl acetate (3 times 50 ml). The combined organic layers were dried over sodium sulphate, filtered and evaporated. The residue was purified by flash chromatography on silica gel using a 100 g-SNAP column and cyclohexane/ethyl acetate from 100/0 to 70/30 as eluent to afford the title compound as a colourless oil (1.290 g).

$^1$H NMR (400 MHz, CDCl$_3$): δ ppm 7.13 (1H, t), 6.68 (1H, d), 6.59 (1H, d), 4.22 (2H, s), 2.33 (3H, s), 1.39 (6H, s). UPLC: 0.72 min, 207 [M+H]+

Intermediate 50

3,3-dimethyl-2,3-dihydro-1-benzofuran-4-ol

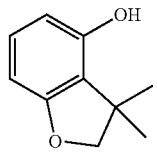

This is an alternative synthetic route to the one described previously for Intermediate 50.

To a solution of 3,3-dimethyl-2,3-dihydro-1-benzofuran-4-yl acetate (Intermediate 53, 1.290 g) in methanol (50 ml) a solution of sodium hydroxide (0.375 g, 9.38 mmol) in water (25.00 ml) was added. The reaction mixture was stirred at room temperature for 30 minutes. The mixture was then acidified with HCl 5% until pH=5 and extracted with ethyl acetate (3 times 50 ml). The combined organic layers were dried over sodium sulphate, filtered and evaporated. The residue was purified by flash chromatography on silica gel using a 25 g-SNAP column and cyclohexane/ethyl acetate from 100/0 to 80/20 as eluent to afford the title compound as a white solid (855 mg).

UPLC-MS: 0.65 min, 165 [M+H]+

Intermediate 54

3,3-dimethyl-4-[(4-nitrophenyl)oxy]-2,3-dihydro-1-benzofuran

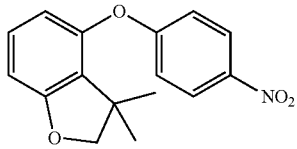 [SMILES: CC1(C)COc2cccc(Oc3ccc([N+](=O)[O-])cc3)c21]

To a solution of 3,3-dimethyl-2,3-dihydro-1-benzofuran-4-ol (Intermediate 50, 652 mg) and 1-fluoro-4-nitrobenzene (532 mg, 3.77 mmol) in acetonitrile (30 ml, SCRC) was added potassium carbonate (552 mg, 4 mmol, SCRC). The mixture was heated at reflux for 3 hours. After cooling, the reaction mixture was filtered and the filtrate was evaporated to afford the title compound as a yellow liquid (0.95 g), which was directly used in the next step.

Intermediate 55

4-[(3,3-dimethyl-2,3-dihydro-1-benzofuran-4-yl)oxy]aniline

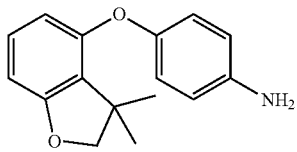

To a solution of 3,3-dimethyl-4-[(4-nitrophenyl)oxy]-2,3-dihydro-1-benzofuran (Intermediate 54, 0.9 g) in tetrahydrofuran (20 ml, SCRC) and water (10 ml) were added ammonium chloride (1.687 g, 31.5 mmol, SCRC) and zinc powder (1.031 g, 15.77 mmol, SCRC). The mixture was heated at 40° C. for 2 hours and then filtered through a pad of celite. The filtrate was partitioned with water (20 ml) and ethyl acetate (50 ml, SCRC). The organic layer was dried, evaporated and purified by column chromatography on silica gel (EtOAc/PE=from 1/50 to 1/30) to afford the title compound as a yellow liquid (0.625 g, 76%).
MS_2 (ESI): 256 [M+H]+

Intermediate 56

1,1-dimethylethyl [(1R)-2-({4-[(3,3-dimethyl-2,3-dihydro-1-benzofuran-4-yl)oxy]phenyl}amino)-1-methyl-2-oxoethyl]carbamate

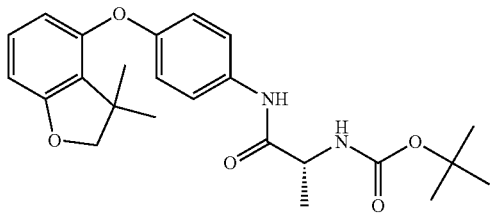 [SMILES: C[C@@H](NC(=O)OC(C)(C)C)C(=O)Nc1ccc(Oc2cccc3c2C(C)(C)CO3)cc1]

To a solution of 4-[(3,3-dimethyl-2,3-dihydro-1-benzofuran-4-yl)oxy]aniline (Intermediate 55, 255 mg) and N-{[(1,1-dimethylethyl)oxy]carbonyl}-D-alanine (227 mg, 1.199 mmol, SCRC) in DMF (10 ml, SCRC) were added HATU (570 mg, 1.498 mmol, SCRC) and DIPEA (0.523 ml, 3.00 mmol, SCRC). The mixture was heated at 100° C. in microwave for 1 hour. Water (20 ml) was added to the mixture and it was extracted with ethyl acetate (3 times 50 ml, SCRC). The combined organic layers were dried, evaporated and purified by column chromatography on silica gel (EtOAc/PE=from 1/50 to 1/20) to afford the title compound as a yellow solid (328 mg).
MS_2 (ESI): 371 [M−55]+

Intermediate 57

N$^1$-{4-[(3,3-dimethyl-2,3-dihydro-1-benzofuran-4-yl)oxy]phenyl}-D-alaninamide

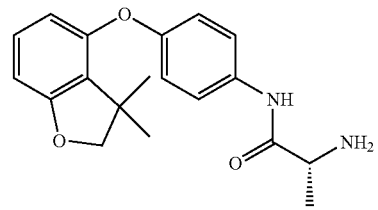 [SMILES: C[C@@H](N)C(=O)Nc1ccc(Oc2cccc3c2C(C)(C)CO3)cc1]

To a solution of 1,1-dimethylethyl [(1R)-2-({4-[(3,3-dimethyl-2,3-dihydro-1-benzofuran-4-yl)oxy]phenyl}amino)-1-methyl-2-oxoethyl]carbamate (Intermediate 56, 325 mg) in ethyl acetate (20 ml, SCRC) was bubbled into HCl (gas) for 0.5 hours. The reaction mixture was neutralized with a saturated aqueous solution of sodium carbonate pH=7 and it was extracted with ethyl acetate (3 times 100 ml, SCRC). The combined organic layers were dried and evaporated to afford the title compound as a yellow liquid (215 mg).
MS_2 (ESI): 327 [M−H]+

Intermediate 58

2-[(3,3-dimethyl-2,3-dihydro-1-benzofuran-4-yl)oxy]-5-nitropyridine

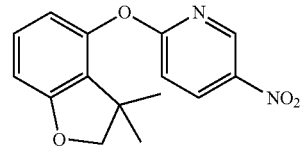

In a large microwave vial, 2-chloro-5-nitropyridine (386 mg, 2.436 mmol) was dissolved in 4 ml of dimethylformamide. 3,3-dimethyl-2,3-dihydro-1-benzofuran-4-ol (Intermediate 57, 400 mg) and potassium carbonate (2.02 g, 14.62 mmol) were added. The reaction mixture was heated under microwave irradiation during 30 minutes at 110 C (Biotage Initiator). The reaction mixture was filtered. The filtrated solid was washed with dichloromethane (30 ml). The volatiles were evaporated under vacuum. The residue was purified by silica gel chromatography (Companion instrument, 120 g cartridge) with cyclohexane as eluent to afford the title compound (470 mg).

¹H NMR (400 MHz, MeOD): δ ppm 9.00 (1H, d), 8.59 (1H, dd), 6.99-7.33 (2H, m), 6.66 (1H, d), 6.57 (1H, d), 4.20 (2H, s), 1.17-1.35 (6H, m); UPLC: 0.88 min, 287 [M+H]+

Intermediate 59

6-[(3,3-dimethyl-2,3-dihydro-1-benzofuran-4-yl)oxy]-3-pyridinamine

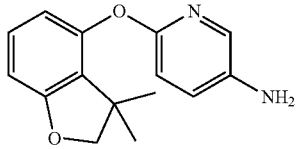

2-{[3-(1-methylethyl)phenyl]oxy}-5-nitropyridine (Intermediate 58, 465 mg) was dissolved in ethanol (8 ml). Hydrazine monohydrate (156 mg, 3.25 mmol, 2 equiv) and palladium on carbon (121 mg, 0.114 mmol) were added. The reaction mixture was heated at reflux under argon during 3 hours. The reaction was cooled down and then filtered on celite. The organic phase was evaporated under vacuum. Evaporation afforded the title compound as a yellow oil (300 mg).

¹H NMR (400 MHz, MeOD): δ ppm 7.65 (1H, d), 7.21 (1H, dd), 7.03 (1H, t), 6.73 (1H, d), 6.51 (1H, d), 6.26 (1H, d), 4.21 (2H, s), 1.40 (6H, s); UPLC: 0.64 min, 257 [M+H]+

Intermediate 60

1,1-dimethylethyl [(1R)-2-({6-[(3,3-dimethyl-2,3-dihydro-1-benzofuran-4-yl)oxy]-3-pyridinyl}amino)-1-methyl-2-oxoethyl]carbamate

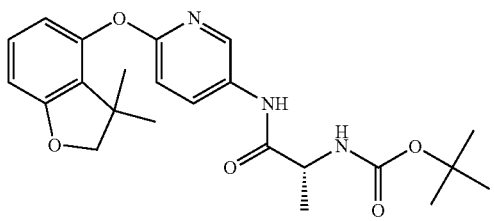 [SMILES: C[C@@H](NC(=O)OC(C)(C)C)C(=O)Nc1ccc(Oc2cccc3c2C(C)(C)CO3)nc1]

To a solution of N-{[(1,1-dimethylethyl)oxy]carbonyl}-D-alanine (35.4 mg, 0.156 mmol) in dry N,N-dimethylformamide (3 ml), DIPEA (0.041 ml, 0.264 mmol) and then HATU (71 mg, 0.187 mmol) were added and the reaction mixture was stirred for 15 minutes at room temperature under argon. Then 6-[(3,3-dimethyl-2,3-dihydro-1-benzofuran-4-yl)oxy]-3-pyridinamine (Intermediate 59, 40 mg) was added and the reaction mixture was stirred 3 hours at 60° C. under argon. The reaction mixture was evaporated. The residue obtained was purified by silica gel chromatography (Companion system, 2×12 g=24 g cartridge) with a gradient cyclohexane/ethyl acetate from 100/0 to 70/30. This afforded the title compound (43 mg).

¹H NMR (400 MHz, MeOD): δ ppm 8.35 (1H, d), 8.08 (1H, dd), 7.11 (1H, t), 6.93 (1H, d), 6.60 (1H, d), 6.45 (1H, d), 4.21 (2H, s), 4.15-4.04 (1H, m), 1.47-1.33 (18H, m); UPLC: 0.78 min, 428 [M+H]+

Intermediate 61

N¹-{6-[(3,3-dimethyl-2,3-dihydro-1-benzofuran-4-yl)oxy]-3-pyridinyl}-D-alaninamide

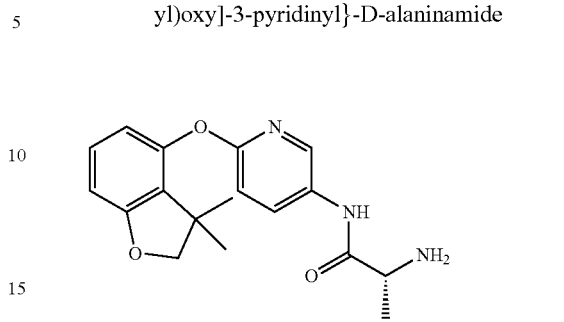

To a solution of 1,1-dimethylethyl [(1R)-2-({6-[(3,3-dimethyl-2,3-dihydro-1-benzofuran-4-yl)oxy]-3-pyridinyl}amino)-1-methyl-2-oxoethyl]carbamate (Intermediate 60, 35 mg) in dry dichloromethane (3 ml), TFA (0.189 ml, 2.456 mmol) was slowly added at 0° C. and the reaction mixture was stirred for 1.5 hours at room temperature. The solvent and the excess of TFA were evaporated and the residue was purified with an SCX cartridge. The cartridge was washed with 3 CV of methanol, then the compound was adsorbed on the cartridge, washed with 5 CV of methanol and desorbed with 2 CV of methanolic ammonia (1N). This afforded the title compound (32 mg).

¹H NMR (400 MHz, MeOD): δ ppm 8.41 (1H, d), 8.14 (1H, dd), 7.16 (1H, t), 6.97 (1H, d), 6.64 (1H, d), 6.48 (1H, d), 4.24 (2H, s), 3.62 (1H, m), 1.50-1.38 (9H, m); UPLC: 0.55 min, 328 [M+H]+

Intermediate 62

1,1-dimethylethyl {(1R)-1-[({6-[(3,3-dimethyl-2,3-dihydro-1-benzofuran-4-yl)oxy]-3-pyridinyl}amino)carbonyl]propyl}carbamate

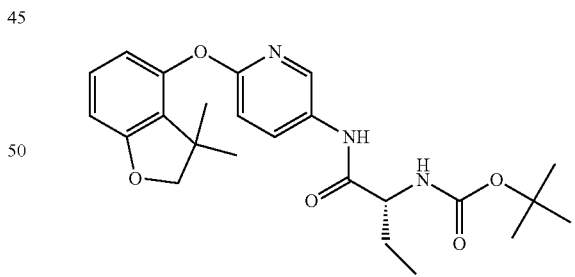

The title compound was made in a similar fashion to the preparation of Intermediate 60 replacing N-{[(1,1-dimethylethyl)oxy]carbonyl}-D-alanine with (2R)-2-({[(1,1-dimethylethyl)oxy]carbonyl}amino)butanoic acid (66.6 mg). This afforded 78 mg of the title compound.

¹H NMR (400 MHz, MeOD): δ ppm 8.37-8.32 (1H, m), 8.07 (1H, dd), 7.11 (1H, t), 6.93 (1H, d), 6.60 (1H, d), 6.44 (1H, d), 4.21 (2H, s), 4.12-4.05 (1H, m), 1.91-1.78 (1H, m), 1.74-1.64 (1H, m), 1.50-1.39 (12H, m), 1.37-1.30 (6H, s); UPLC: 0.81 min, 442 [M+H]+

Intermediate 63

(2R)-2-amino-N-{6-[(3,3-dimethyl-2,3-dihydro-1-benzofuran-4-yl)oxy]-3-pyridinyl}butanamide

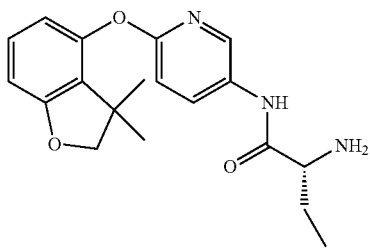 [SMILES: CC[C@@H](N)C(=O)Nc1ccc(Oc2cccc3c2C(C)(C)CO3)nc1]

The title compound was made in a similar fashion to the preparation of Intermediate 61 replacing 1,1-dimethylethyl [(1R)-2-({6-[(3,3-dimethyl-2,3-dihydro-1-benzofuran-4-yl)oxy]-3-pyridinyl}amino)-1-methyl-2-oxoethyl]carbamate with 1,1-dimethylethyl {(1R)-1-[({6-[(3,3-dimethyl-2,3-dihydro-1-benzofuran-4-yl)oxy]-3-pyridinyl}amino)carbonyl]propyl}carbamate (Intermediate 62, 74 mg). This afforded 60 mg of the title compound.

$^1$H NMR (400 MHz, MeOD): δ ppm 8.38 (1H, d), 8.12 (1H, dd), 7.11 (1H, t), 6.95 (1H, d), 6.61 (1H, d), 6.46 (1H, d), 4.21 (2H, s), 3.41 (1H, m), 1.81 (1H, m), 1.70 (1H, m), 1.35 (6H, s), 1.00 (3H, t); UPLC: 0.55 min, 342 [M+H]+

Intermediate 64

2-[(3,3-dimethyl-2,3-dihydro-1-benzofuran-4-yl)oxy]-5-nitropyrimidine

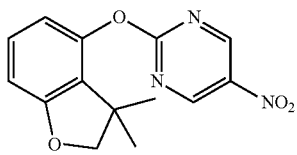 [SMILES: CC1(C)COc2cccc(Oc3ncc([N+](=O)[O-])cn3)c21]

To a solution of 3,3-dimethyl-2,3-dihydro-1-benzofuran-4-ol (Intermediate 50, 724 mg) in dry N,N-Dimethylformamide (40 mL) potassium carbonate and 2-chloro-5-nitropyrimidine (774 mg, 4.85 mmol) were added. The reaction mixture was stirred at room temperature overnight. The reaction was quenched with water (40 ml) and extracted with ethyl acetate (3×40 ml). The combined organic layers were washed with brine (2×50 ml), separated, dried over sodium sulphate, filtered and evaporated. The residue was purified by flash chromatography on silica gel using a column SNAP 50 g and cyclohexane/ethyl acetate as eluents from 100/0 to 70/30 to afford the title compound (1.257 g) as a yellow oil.

$^1$H NMR (400 MHz, DMSO-d$_6$): δ ppm 9.46 (2H, s), 7.22 (1H, t), 6.73 (2H, dd), 4.23 (2H, s), 1.24 (6H, s); UPLC: 0.75 min, 288 [M+H]+

Intermediate 65

2-[(3,3-dimethyl-2,3-dihydro-1-benzofuran-4-yl)oxy]-5-pyrimidinamine

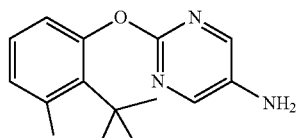

To a solution of 2-[(3,3-dimethyl-2,3-dihydro-1-benzofuran-4-yl)oxy]-5-nitropyrimidine (Intermediate 64, 1.257 g) in a mixture tetrahydrofuran/water (30 ml/15.00 ml) iron (1.222 g, 21.88 mmol) and ammonium chloride (1.170 g, 21.88 mmol) were added. The reaction mixture was stirred at room temperature for 48 hours. The catalyst was filtered off, and the filtrate was extracted with ethyl acetate (3×50 ml). The combined organic layers were dried over sodium sulphate, filtered and evaporated. The residue was recrystallized from ethyl acetate to afford the title compound (768 mg) as a white solid.

$^1$H NMR (400 MHz, DMSO-d$_6$): δ ppm 7.97 (2H, s), 6.94-7.16 (1H, m), 6.58 (1H, d), 6.44 (1H, d), 4.18 (2H, s), 3.32 (2H, br. s.), 1.25 (6H, s); UPLC: 0.60 min, 258 [M+H]+

Intermediate 66

1,1-dimethylethyl {(1R)-1-[({2-[(3,3-dimethyl-2,3-dihydro-1-benzofuran-4-yl)oxy]-5-pyrimidinyl}amino)carbonyl]propyl}carbamate

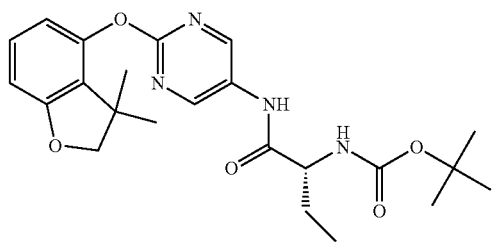

To a solution of (2R)-2-({[(1,1-dimethylethyl)oxy]carbonyl}amino)butanoic acid (20.14 mg, 0.099 mmol) in N,N-dimethylformamide (1.5 mL) DIPEA (0.029 mL, 0.165 mmol) and TBTU (33.9 mg, 0.106 mmol) were added. The mixture reaction was stirred during 15 minutes at room temperature, then 2-[(3,3-dimethyl-2,3-dihydro-1-benzofuran-4-yl)oxy]-5-pyrimidinamine (Intermediate 65, 17 mg) was added. The reaction mixture was stirred during 48 hours at room temperature. The mixture was diluted with ethyl acetate (5 ml) and washed with brine (3×5 ml). The organic layer was separated, dried over sodium sulphate, filtered and evaporated. The residue was purified by silica gel flash chromatography using a 10 g-SNAP column and cyclohexane/ethyl acetate from 100/0 to 40/60 as eluent to afford the title compound as a white solid (4.4 mg).

1H NMR (400 MHz, CDCl$_3$): δ ppm 8.78 (2H, s), 7.17 (1H, t), 6.71 (1H, d), 6.61 (1H, d), 4.97 (1H, d), 4.24 (2H, s), 4.18-4.11 (1H, m), 2.05-1.97 (1H, m), 1.77-1.70 (1H, m), 1.49 (9H, s), 1.37 (6H, s), 1.05 (3H, t). UPLC-MS: 0.78 min, 443 [M+H]+

Intermediate 67

(2R)-2-amino-N-{2-[(3,3-dimethyl-2,3-dihydro-1-benzofuran-4-yl)oxy]-5-pyrimidinyl}butanamide

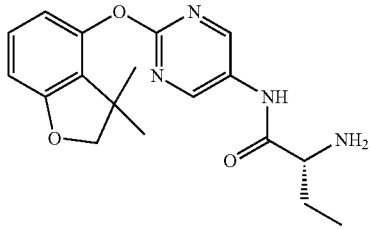 [SMILES: CC[C@@H](N)C(=O)Nc1cnc(Oc2cccc3c2C(C)(C)CO3)nc1]

To a solution of 1,1-dimethylethyl {(1R)-1-[({2-[(3,3-dimethyl-2,3-dihydro-1-benzofuran-4-yl)oxy]-5-pyrimidinyl}amino)carbonyl]propyl}carbamate (Intermediate 66, 4.4 mg) in dichloromethane (1 ml) cooled to 0° C. TFA (0.019 ml, 0.249 mmol) was added dropwise. The mixture reaction was stirred at 0° C. for 1.5 hours. The solvent and the TFA were evaporated. The mixture was diluted with dichloromethane (5 ml) and neutralized with an aqueous saturated solution of NaHCO₃ (5 ml). The organic layer was separated, dried over sodium sulphate, filtered end evaporated to afford the title compound (3 mg) which was directly used in the next step UPLC-MS: 0.98 min, 343 [M+H]+

Intermediate 68

1-({[(1,1-dimethylethyl)oxy]carbonyl}amino)cyclobutanecarboxylic Acid

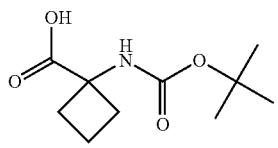

To a solution of 1-aminocyclobutanecarboxylic acid (626 mg, 5.44 mmol) in 5.6 ml of 1 M aqueous sodium hydroxide and 4 ml of methanol was added Boc-anhydride (1.425 g, 6.53 mmol) at 0° C. The reaction mixture was warmed to room temperature and stirred for 12 hours. After most of the methanol was evaporated, the solution was acidified to pH 2 with 1 M HCl and extracted with ethyl acetate. The organic extracts were combined and washed with brine. Evaporation of the solvent afforded the title compound (1.09 g).

$^1$H NMR (400 MHz, DMSO-d$_6$): δ ppm 12.21 (1H, s), 7.44 (1H, s), 2.29-2.47 (2H, m), 2.09 (2H, q), 1.74-1.94 (2H, m), 1.36 (9H, s); UPLC: 0.56 min, 216 [M+H]+

Intermediate 69

1,1-dimethylethyl {1-[({6-[(3,3-dimethyl-2,3-dihydro-1-benzofuran-4-yl)oxy]-3-pyridinyl}amino)carbonyl]cyclobutyl}carbamate

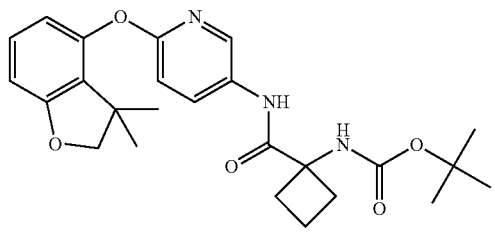 [SMILES: CC(C)(C)OC(=O)NC1(C(=O)Nc2ccc(Oc3cccc4c3C(C)(C)CO4)nc2)CCC1]

To a solution of 1-({[(1,1-dimethylethyl)oxy]carbonyl}amino)cyclobutanecarboxylic acid (Intermediate 68, 20.16 mg) in dry N,N dimethylformamide (3 ml), DIPEA (20.44 µl, 0.117 mmol) and then HATU (35.6 mg, 0.094 mmol) were added and the reaction mixture was stirred for 15 minutes at room temperature under argon. Then 6-[(3,3-dimethyl-2,3-dihydro-1-benzofuran-4-yl)oxy]-3-pyridinamine Intermediate 59, 20 mg) was added and the reaction mixture was stirred at 60° C. under argon during 12 hours. The reaction mixture was cooled down and a prestirred (15 min) solution of HATU (1 equiv), 1-({[(1,1-dimethylethyl)oxy]carbonyl}amino)cyclobutanecarboxylic acid (1 equiv) and DIPEA (1 equiv) in 1 mL of dry DMF was added. The reaction mixture was heated under argon an additional 12 hours at 60° C. The reaction mixture was evaporated. The residue obtained was purified on silica gel (Companion instrument) with cyclohexane/ethylacetate as eluents from 100/0 to 70/30. This afforded the title compound (14 mg)

$^1$H NMR (400 MHz, MeOD): δ ppm 8.29 (1H, s), 8.13-7.86 (1H, m), 7.11 (1H, t), 7.04-6.76 (1H, m), 6.60 (1H, d), 6.45 (1H, d), 4.21 (2H, s) 2.85-2.52 (2H, m), 2.26-2.09 (2H, m), 2.07-1.80 (2H, m), 1.45 (6H, s), 1.35 (9H, s); UPLC: 0.95 min, 454 [M+H]+

Intermediate 70

1-amino-N-{6-[(3,3-dimethyl-2,3-dihydro-1-benzofuran-4-yl)oxy]-3-pyridinyl}cyclobutanecarboxamide

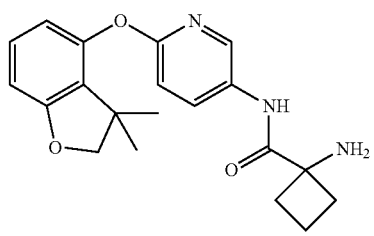 [SMILES: CC1(C)COc2cccc(Oc3ccc(NC(=O)C4(N)CCC4)cn3)c21]

To a solution of 1,1-dimethylethyl {1-[({6-[(3,3-dimethyl-2,3-dihydro-1-benzofuran-4-yl)oxy]-3-pyridinyl}amino)carbonyl]cyclobutyl}carbamate (Intermediate 69, 23.5 mg) in dry dichloromethane (3.5 ml), TFA (159 µl, 2.07 mmol) was slowly added at 0° C. and the reaction mixture was stirred for 2 hours at room temperature.

The solvent and the excess of TFA were evaporated and the residue was purified with an SCX cartridge. The cartridge was washed with 3 CV of methanol, then the compound was adsorbed on the cartridge, washed with 5 CV of methanol and desorbed with 2 CV of methanolic ammonia (1N). This afforded the title compound (18 mg).

¹H NMR (400 MHz, MeOD): δ ppm 8.43 (1H, d), 8.11 (1H, dd), 7.11 (1H, t), 6.94 (1H, d), 6.61 (1H, d), 6.45 (1H, d), 4.20 (2H, s), 2.75-2.70 (2H, m), 2.18-2.00 (4H, m), 1.34 (6H, m); UPLC: 0.82 min, 354 [M+H]+

Intermediate 71

1-({[(1,1-dimethylethyl)oxy]carbonyl}amino)cyclopropanecarboxylic Acid

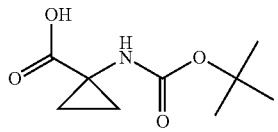

The title compound (998 mg) was made in a similar fashion to the preparation of Intermediate 68 replacing 1-aminocyclobutanecarboxylic acid WITH 1-aminocyclopropanecarboxylic acid (550 mg).

¹H NMR (400 MHz, DMSO-d₆): δ ppm 12.26 (1H, s), 7.40 (1H, s), 1.38 (9H, s), 1.26 (2H, m), 0.96 (2H, m); UPLC: 0.52 min, 202 [M+H]+

Intermediate 72

1,1-dimethylethyl {1-[({6-[(3,3-dimethyl-2,3-dihydro-1-benzofuran-4-yl)oxy]-3-pyridinyl}amino)carbonyl]cyclopropyl}carbamate

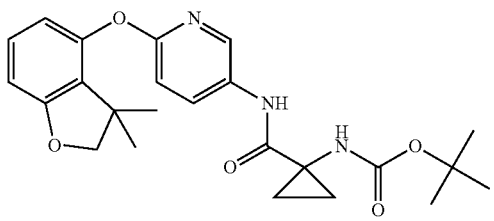 [SMILES: CC(C)(C)OC(=O)NC1(C(=O)Nc2ccc(Oc3cccc4c3C(C)(C)CO4)nc2)CC1]

The title compound (14 mg) was made in a similar fashion to the preparation of Intermediate 69 replacing 1-({[(1,1-dimethylethyl)oxy]carbonyl}amino)cyclobutanecarboxylic acid with 1-({[(1,1-dimethylethyl)oxy]carbonyl}amino)cyclopropanecarboxylic acid (Intermediate 71, 18.84 mg, 0.094 mmol).

¹H NMR (400 MHz, MeOD): δ ppm 8.30 (1H, s), 8.08-7.93 (1H, m), 7.11 (1H, t) 6.92 (1H, d), 6.60 (1H, d), 6.45 (1H, d), 4.22 (2H, s), 1.58-1.51 (2H, m), 1.45 (9H, s), 1.35 (6H, s), 1.12 (2H, m); UPLC: 0.78 min, 440 [M+H]+

Intermediate 73

1-amino-N-{6-[(3,3-dimethyl-2,3-dihydro-1-benzofuran-4-yl)oxy]-3-pyridinyl}cyclopropanecarboxamide

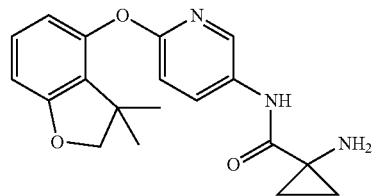 [SMILES: CC1(C)COc2cccc(Oc3ccc(NC(=O)C4(N)CC4)cn3)c21]

The title compound (10 mg) was made in a similar fashion to the preparation of Intermediate 70 replacing 1,1-dimethylethyl {1-[({6-[(3,3-dimethyl-2,3-dihydro-1-benzofuran-4-yl)oxy]-3-pyridinyl}amino)carbonyl]cyclobutyl}carbamate with 1,1-dimethylethyl {1-[({6-[(3,3-dimethyl-2,3-dihydro-1-benzofuran-4-yl)oxy]-3-pyridinyl}amino)carbonyl]cyclopropyl}carbamate (Intermediate 72, 13 mg).

¹H NMR (400 MHz, MeOD): δ ppm 8.39 (1H, d), 8.07 (1H, dd), 7.10 (1H, t), 6.92 (1H, d), 6.59 (1H, d), 6.44 (1H, d), 4.20 (2H, s), 1.40-1.31 (8H, m), 1.04-0.96 (2H, m); UPLC: 0.51 min, 340 [M+H]+

Intermediate 74

1,1-dimethylethyl [2-({6-[(3,3-dimethyl-2,3-dihydro-1-benzofuran-4-yl)oxy]-3-pyridinyl}amino)-1,1-dimethyl-2-oxoethyl]carbamate

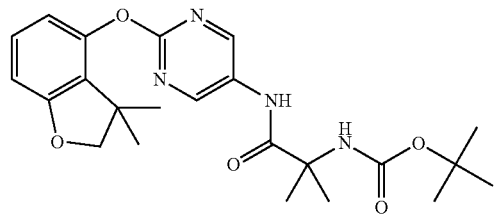 [SMILES: CC(C)(C)OC(=O)NC(C)(C)C(=O)Nc1cnc(Oc2cccc3c2C(C)(C)CO3)nc1]

To a solution of (N-{[(1,1-dimethylethyl)oxy]carbonyl}-2-methylalanine (39.0 mg, 0.192 mmol) in dry N,N dimethylformamide (3 mL), DIPEA (0.042 mL, 0.240 mmol) and then HATU (73.0 mg, 0.192 mmol) were added and the reaction mixture was stirred for 15 minutes at room temperature under argon. Then 6-[(3,3-dimethyl-2,3-dihydro-1-benzofuran-4-yl)oxy]-3-pyridinamine (Intermediate 59, 41 mg) was added and the reaction mixture was stirred at 60° C. under argon. The reaction was left under heating 4 hours and was stop before completion. The reaction mixture was evaporated. The residue obtained was purified on silica gel (Companion instrument) with a gradient cyclohexane/ethylacetate from 100/0 to 70/30. This afforded the title compound (13 mg).

¹H NMR (400 MHz, MeOH): δ ppm 9.66 (1H, s), 8.28 (1H, s), 8.04 (1H, s), 7.80-7.51 (1H, m), 7.11 (1H, t), 6.92 (1H, d), 6.60 (1H, d), 6.45 (1H, d), 4.21 (2H, s), 1.48 (6H, s), 1.43 (6H, s), 1.35 (9H, s); UPLC: 0.79 min, 442 [M+H]+

Intermediate 75

N¹-{6-[(3,3-dimethyl-2,3-dihydro-1-benzofuran-4-yl)oxy]-3-pyridinyl}-2-methylalaninamide

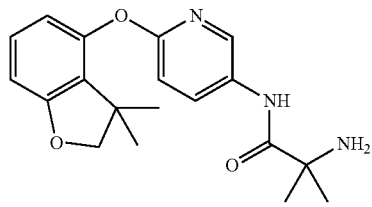 [SMILES: CC(C)(N)C(=O)Nc1ccc(Oc2cccc3c2C(C)(C)CO3)nc1]

To a solution of 1,1-dimethylethyl [2-({6-[(3,3-dimethyl-2,3-dihydro-1-benzofuran-4-yl)oxy]-3-pyridinyl}amino)-1,1-dimethyl-2-oxoethyl]carbamate (Intermediate 74, 11 mg) in dry dichloromethane (2 ml), TFA (0.077 ml, 0.997 mmol) was slowly added at 0° C. and the reaction mixture was stirred for 2 hours at room temperature. The solvent and the excess of TFA were evaporated and the residue was purified with an SCX cartridge. The cartridge was washed with 3 CV of methanol and then the compound was adsorbed on the cartridge, washed with 5 CV of methanol and desorbed with 2 CV of methanolic ammonia (1N). This afforded the title compound (8.5 mg).

¹H NMR (400 MHz, MeOD): δ ppm 8.39 (1H, d), 8.07 (1H, dd), 7.11 (1H, t), 6.92 (1H, d), 6.59 (1H, d), 6.43 (1H, d), 4.21 (2H, s), 1.45 (6H, s), 1.35 (6H, s); UPLC: 0.50 min, 342 [M+H]+

Intermediate 76

N-{[(1,1-dimethylethyl)oxy]carbonyl}-3-methyl-D-valine

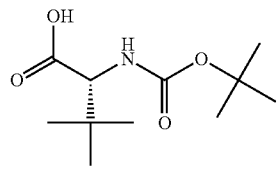 [SMILES: CC(C)(C)OC(=O)N[C@@H](C(=O)O)C(C)(C)C]

To a solution of 3-methyl-D-valine (900 mg, 6.86 mmol) in 7 ml of 1 M aqueous sodium hydroxide and 7 ml of methanol was added Boc-anhydride (1.797 g, 8.23 mmol) at 0° C. The reaction mixture was warmed to room temperature and stirred overnight. After most of the methanol was evaporated, the solution was acidified to pH 2 with an aqueous solution of HCl (1M) and extracted 3 times with ethylacetate (3×20 ml). The organic layers were combined and washed with brine (2×5 ml). Evaporation of the solvent afforded the title compound as a white solid (1.36 g).

¹H NMR (400 MHz, DMSO-d₆): δ ppm 12.44 (1H, s), 6.82 (1H, d), 3.76 (1H, d), 1.38 (9H, s), 0.93 (9H, s); UPLC: 0.64 min, 232 [M+H]+

Intermediate 77

1,1-dimethylethyl {(1R)-1-[({2-[(3,3-dimethyl-2,3-dihydro-1-benzofuran-4-yl)oxy]-5-pyrimidinyl}amino)carbonyl]-2,2-dimethylpropyl}carbamate

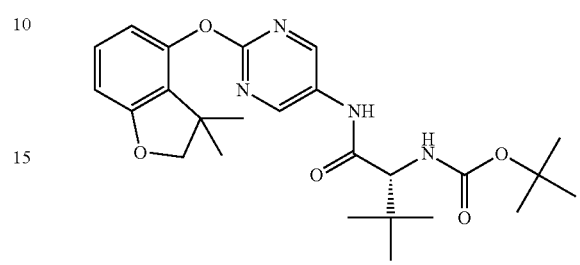

To a solution of N-{[(1,1-dimethylethyl)oxy]carbonyl}-3-methyl-D-valine (Intermediate 76, 53.9 mg) in dry N,N dimethylformamide (1 ml), DIPEA (50.9 µl, 0.292 mmol) and then HATU (102 mg, 0.268 mmol) were added and the reaction mixture was stirred for 15 minutes at room temperature under argon. Then 2-[(3,3-dimethyl-2,3-dihydro-1-benzofuran-4-yl)oxy]-5-pyrimidinamine (Intermediate 65, 30 mg) was added and the reaction mixture was stirred at 60° C. under argon during 12 hours. The reaction was quenched with brine (1 ml), diluted with water (2 ml) and extracted with ethyl acetate (2×5 ml). The organic layer was dried over sodium sulphate and evaporated. The residue obtained was purified on silica gel (Companion instrument) with a gradient cyclohexane/ethylacetate 100/0 to 70/30. This afforded the title compound (17 mg).

¹H NMR (400 MHz, CDCl₃): δ ppm 8.74 (2H, s), 7.14 (1H, t), 6.67 (1H, d), 6.57 (1H, d), 4.53 (1H, d), 4.20 (2H, s), 1.40 (6H, s) 1.06 (9H, s), 0.98 (9H, s); UPLC: 0.83 min, 371 [M+H]+

Intermediate 78

N¹-{2-[(3,3-dimethyl-2,3-dihydro-1-benzofuran-4-yl)oxy]-5-pyrimidinyl}-3-methyl-D-valinamide

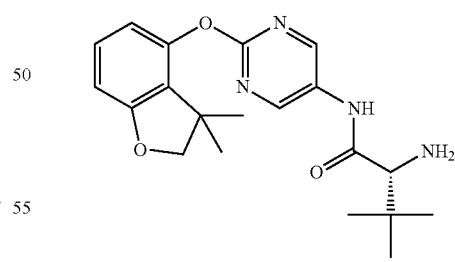

To a solution of 1,1-dimethylethyl {(1R)-1-[({2-[(3,3-dimethyl-2,3-dihydro-1-benzofuran-4-yl)oxy]-5-pyrimidinyl}amino)carbonyl]-2,2-dimethylpropyl}carbamate (Intermediate 77, 13 mg) in dry dichloromethane (0.5 ml) cooled to 0° C., TFA (85 µl, 1.105 mmol) was added dropwise and the solution was stirred for 3 hours at that temperature. The volatiles were evaporated. The residue was dissolved with dichloromethane (2 ml) and an aqueous saturated solution of NaHCO₃ was added (4 ml).

The layers were separated and the aqueous layer was extracted twice with dichloromethane. The gathered organic layers were dried over sodium sulphate and evaporated to afford the title compound (10.9 mg).

¹H NMR (400 MHz, CDCl₃): δ ppm 8.68 (2H, s), 7.14 (1H, t), 6.68 (1H, d), 6.59 (1H, d), 4.21 (2H, s), 3.30 (1H, s), 1.70 (2H, br s), 1.35 (6H, s) 1.07 (9H, s); UPLC: 0.53 min, 377 [M+H]+

Intermediate 79

1,3-bis{[(methyloxy)methyl]oxy}benzene

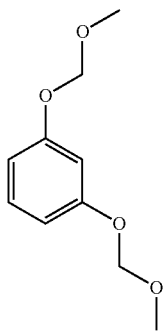

To a solution of 1,3-benzenediol (1.5 g, 13.62 mmol) in dry N,N-Dimethylformamide (13.62 ml) at 0° C. sodium hydride (0.981 g, 40.9 mmol) was added and the reaction mixture was stirred for 15 minutes at the same temperature. MOM-Cl (3.10 ml, 40.9 mmol) was quickly added and the reaction mixture was stirred for 1 hour while the temperature was allowed to reach room temperature. The reaction was quenched with brine (20 ml) and extracted with ethyl acetate (3×50 ml). The organic layer was washed with brine (2×30 ml), dried over sodium sulphate, filtered and evaporated and the residue was purified by flash chromatography (Biotage system) on silica gel using a 50 g SNAP column and cyclohexane to cyclohexane/ethyl acetate 8:2 as eluents affording the title compound (1.59 g, 8.02 mmol) as a colourless oil.

¹H NMR (400 MHz, DMSO-d₆): δ ppm 7.16-7.23 (1H, d), 6.69-6.64 (3H, m), 5.17 (4H, s), 3.38 (6H, s).

Intermediate 80 ethyl (2,6-bis{[(methyloxy)methyl]oxy}phenyl)(oxo)acetate

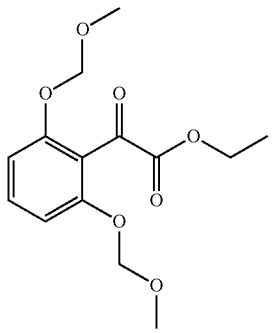 [SMILES: CCOC(=O)C(=O)c1c(OCOC)cccc1OCOC]

To a solution of 1,3-bis{[(methyloxy)methyl]oxy}benzene (Intermediate 79, 2.19 g) in dry tetrahydrofuran (10 ml) at room temperature BuLi 1.6M in hexane (8.29 ml, 13.26 mmol) was added and the reaction mixture was stirred for 30 minutes at the same temperature. The mixture was cooled to −78° C. and it was added (via cannulation) to a solution of ethyl chloro(oxo)acetate (2.263 g, 16.57 mmol) in dry tetrahydrofuran (10 ml) at −78° C. The reaction mixture was stirred at −78° C. for 30 minutes. The reaction was quenched with an aqueous saturated solution of ammonium chloride (10 ml) and extracted with ethyl acetate (2×30 ml). Combined organic layers were dried over sodium sulphate, filtered and evaporated. The residue was purified by flash chromatography (Biotage system) on silica gel using a 100 g SNAP column and cyclohexane to cyclohexane/ethyl acetate 8:2 as eluent affording the title compound as a light yellow oil (1.75 g).

¹H NMR (400 MHz, DMSO-d₆): δ ppm 7.46 (1H, t), 6.87 (2H, d), 5.20 (4H, s), 4.29 (2H, q), 3.34 (6H, s), 1.27 (3H, t).

Intermediate 81 ethyl 2-(2,6-bis{[(methyloxy)methyl]oxy}phenyl)-2-propenoate

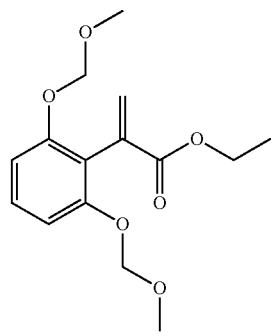 [SMILES: C=C(C(=O)OCC)c1c(OCOC)cccc1OCOC]

To a suspension of methyltriphenylphosphonium bromide (3.13 g, 8.75 mmol) in dry tetrahydrofuran (30 ml) at 0° C. KHMDS (1.745 g, 8.75 mmol) was slowly added and the reaction mixture was stirred for 15 minutes at 0° C. and for 45 minutes at room temperature. The reaction mixture was cooled to 0° C. and a solution of ethyl (2,6-bis{[(methyloxy)methyl]oxy}phenyl)(oxo)acetate (Intermediate 80, 1.74 g) in dry tetrahydrofuran (10 mL) was slowly added and the reaction mixture was stirred for 2 hours at 0° C. The reaction was quenched with an aqueous saturated solution of ammonium chloride (10 ml), diluted with water (20 ml) and extracted with ethyl acetate (2×50 ml). The organic layer was dried over sodium sulphate, filtered and evaporated. The residue was purified by flash chromatography (Biotage system) on silica gel using a 100 g SNAP column and cyclohexane to cyclohexane/ethyl acetate 8:2 as eluents affording the title compound as a colourless oil (1.37 g).

¹H NMR (400 MHz, DMSO-d₆): δ ppm 7.21 (1H, t), 6.78 (2H, d), 6.44 (1H, d), 5.74 (1H, d), 5.12 (4H, s), 4.12 (2H, q), 3.32 (6H, s), 1.17 (3H, t).

Intermediate 82 ethyl 1-(2,6-bis{[(methyloxy)methyl]oxy}phenyl) cyclopropanecarboxylate

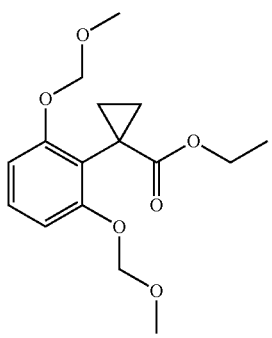 [SMILES: CCOC(=O)C1(c2c(OCOC)cccc2OCOC)CC1]

To a solution of trimethylsulfoxonium iodide (1.805 g, 8.20 mmol) in dry dimethyl sulfoxide (20 mL) sodium hydride 60% dispersion in mineral oil (0.310 g, 7.75 mmol) was added and the reaction mixture was stirred for 1 hour at room temperature. A solution of ethyl 2-(2,6-bis{[(methyloxy)methyl]oxy}phenyl)-2-propenoate (Intermediate 81, 1.35 g) in dry dimethyl sulfoxide (10 mL) was slowly added and the reaction mixture was stirred for 1 hour at room temperature. The reaction was quenched with an aqueous saturated solution of ammonium chloride (10 ml), diluted with water (20 ml) and extracted with ethyl acetate (2×50 ml). The organic layer was washed with water (50 ml), dried over sodium sulphate, filtered and evaporated. The residue was purified by flash chromatography (Biotage system) on silica gel using a 50 g SNAP column and cyclohexane to cyclohexane/ethyl acetate 8:2 as eluents affording the title as a colourless oil (1.14 g).

$^1$H NMR (400 MHz, DMSO-d$_6$): δ ppm 7.15 (1H, t), 6.71 (2H, d), 5.18 (4H, s), 3.97 (2H, q), 3.36 (6H, s), 1.53-1.58 (2H, m), 1.09-1.14 (2H, m), 1.04 (3H, t).

Intermediate 83

2-[1-(hydroxymethyl)cyclopropyl]-3-{[(methyloxy) methyl]oxy}phenol

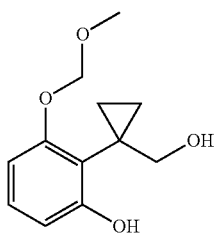 [SMILES: COCOc1cccc(O)c1C1(CO)CC1]

To a solution of ethyl 1-(2,6-bis{[(methyloxy)methyl] oxy}phenyl)cyclopropanecarboxylate (Intermediate 82, 490 mg) in ethanol (10 ml) HCl 2N in water (0.789 mL, 1.579 mmol) was added and the reaction mixture was stirred overnight at 50° C. Toluene (20 mL) was added and the combined solvents were removed under reduced pressure. The residue was re-suspended in toluene (20 ml) and the solvent evaporated. The obtained residue was dissolved in dry tetrahydrofuran (20 ml), the mixture was cooled to 0° C. and NaH 60% dispersion in mineral oil (126 mg, 3.16 mmol) was added and the reaction mixture was stirred for 30 minutes at the same temperature. MOM-Cl (0.120 mL, 1.579 mmol) was then added and the reaction mixture was stirred for 2 hours at 0° C. LiAlH4 (1M in THF, 1.579 ml, 1.579 mmol) was added and the reaction mixture was further stirred for 1 hour at the same temperature. The reaction was quenched with an aqueous saturated solution of ammonium chloride (10 ml), diluted with water (10 ml) and extracted with ethyl acetate (2×50 ml). Combined organic layers were dried over sodium sulphate, filtered and evaporated and the residue was purified by flash chromatography (Biotage system) on silica gel using a 25 g SNAP column and cyclohexane to cyclohexane/ethyl acetate 7:3 as eluents affording the title compound as a colourless oil (191 mg).

$^1$H NMR (400 MHz, DMSO-d$_6$): δ ppm 8.90 (1H, br.s) 6.96 (1H, t), 6.50 (1H, d), 6.45 (1H, d), 5.16 (2H, s), 4.93 (1H, br.s), 3.45 (2H, s), 3.40 (3H, s), 0.86-0.93 (2H, m), 0.56-0.62 (2H, m); UPLC: 0.59 min, 225 [M+H]+.

Intermediate 84

4-{[(methyloxy)methyl]oxy}spiro[1-benzofuran-3, 1'-cyclopropane]

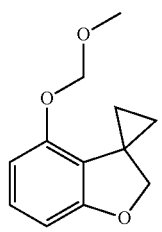

To a solution of 2-[1-(hydroxymethyl)cyclopropyl]-3-{[(methyloxy)methyl]oxy}phenol (Intermediate 83, 190 mg) in dry tetrahydrofuran (10 ml) triphenylphosphine (333 mg, 1.271 mmol) was added and the reaction mixture was stirred until complete dissolution of PPh3. DIAD (0.198 ml, 1.017 mmol) was then added dropwise and the reaction mixture was stirred for 30 minutes at room temperature The solvent was removed under reduced pressure. The residue was purified by flash chromatography (Biotage system) on silica gel using a 25 g SNAP column and cyclohexane to cyclohexane/ethyl acetate 9:1 as eluents affording the title compound as a light yellow oil (120 mg).

$^1$H NMR (400 MHz, DMSO-d$_6$): δ ppm 6.97 (1H, t), 6.51 (1H, d), 6.43 (1H, d), 5.12 (2H, s), 4.40 (2H, s), 3.35 (3H, s), 1.43-1.48 (2H, m), 0.85-0.90 (2H, m); UPLC_B: 0.88 min, 207 [M+H]+.

Intermediate 85

Spiro[1-benzofuran-3,1'-cyclopropan]-4-ol

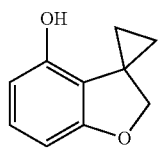 [SMILES: Oc1cccc2c1C1(CC1)CO2]

To a solution of 4-{[(methyloxy)methyl]oxy}spiro[1-benzofuran-3,1'-cyclopropane] (Intermediate 84, 118 mg) in methanol (5 ml), HCl 2N in water (0.286 mL, 0.572 mmol) was added and the reaction mixture was stirred overnight at 50° C. Combined solvents were removed under reduced pressure and the residue was re-dissolved in toluene (10 ml) and the solvent was removed. The residue was purified by flash chromatography (Biotage system) on silica gel using a 10 g SNAP column and cyclohexane to cyclohexane/ethyl acetate 7:3 as eluents affording the title compound as a white solid (70 mg).

$^1$H NMR (400 MHz, DMSO-d$_6$): δ ppm 9.28 (1H, s), 6.81 (1H, t), 6.24 (1H, d), 6.22 (1H, d), 4.34 (2H, s), 1.40-1.45 (2H, m), 0.77-0.82 (2H, m).

Intermediate 86

5-nitro-2-(spiro[1-benzofuran-3,1'-cyclopropan]-4-yloxy)pyridine

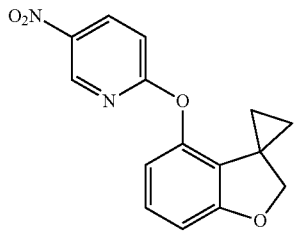

To a solution of spiro[1-benzofuran-3,1'-cyclopropan]-4-ol (Intermediate 85, 70 mg) in dry N,N-dimethylformamide (2 ml) potassium carbonate (89 mg, 0.647 mmol) and then 2-chloro-5-nitropyridine (75 mg, 0.475 mmol) were added and the reaction mixture was stirred for 3 hours at 100° C. The reaction was quenched with brine (1 ml), diluted with water (2 ml) and extracted with ethyl acetate (3×10 ml). The organic layer was dried over sodium sulphate, filtered and evaporated. The residue was purified by flash chromatography (Biotage system) on silica gel using a 10 g SNAP column and cyclohexane to cyclohexane/ethyl acetate 9:1 as eluents affording the title compound as a white solid (100 mg).

$^1$H NMR (400 MHz, DMSO-d$_6$): δ ppm 9.05 (1H, d), 8.63 (1H, dd), 7.23 (1H, d), 7.13 (1H, t), 6.73 (1H, d), 6.60 (1H, d), 4.45 (2H, s), 1.05-1.10 (2H, m), 0.88-0.93 (2H, m); UPLC: 0.79 min, 285 [M+H]+.

Intermediate 87

6-(spiro[1-benzofuran-3,1'-cyclopropan]-4-yloxy)-3-pyridinamine

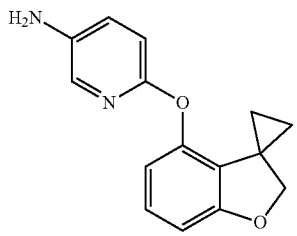 [SMILES: O=[N+]([O-])c1ccc(Oc2cccc3c2C2(CC2)CO3)nc1]

To a solution of 5-nitro-2-(spiro[1-benzofuran-3,1'-cyclopropan]-4-yloxy)pyridine (Intermediate 86, 99 mg) in tetrahydrofuran (5 ml)/water (2.5 ml) iron (97 mg, 1.741 mmol) and then ammonium chloride (93 mg, 1.741 mmol) were added and the reaction mixture was stirred for 4 hours at room temperature. The catalyst was filtered off and the residue was diluted with an aqueous saturated solution of NaHCO3 (5 ml) and extracted with ethyl acetate (3×10 ml). The organic layer was dried over sodium sulphate, filtered and evaporated and the residue was purified by flash chromatography (Biotage system) on silica gel using a 10 g SNAP column and cyclohexane/ethyl acetate 8:2 to cyclohexane/ethyl acetate 1:1 as eluents affording the title compound as a light yellow solid (85 mg).

$^1$H NMR (400 MHz, DMSO-d$_6$): δ ppm 7.52 (1H, d), 7.06 (1H, dd), 6.97 (1H, t), 6.70 (1H, d), 6.53 (1H, d), 6.23 (1H, d), 5.08 (2H, s), 4.43 (2H, s), 1.28-1.33 (2H, m), 0.86-0.91 (2H, m); UPLC: 0.62 min, 255 [M+H]+.

Intermediate 88

1,1-dimethylethyl [(1R)-1-({[6-(spiro[1-benzofuran-3,1'-cyclopropan]-4-yloxy)-3-pyridinyl]amino}carbonyl)propyl]carbamate

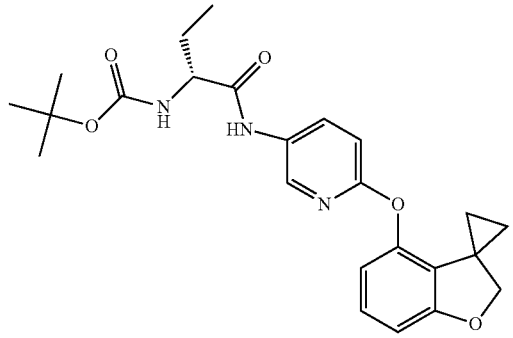 [SMILES: CC[C@@H](NC(=O)OC(C)(C)C)C(=O)Nc1ccc(Oc2cccc3c2C2(CC2)CO3)nc1]

To a solution of (2R)-2-({[(1,1-dimethylethyl)oxy]carbonyl}amino)butanoic acid (94 mg, 0.462 mmol) in dry N,N-Dimethylformamide (2 mL) DIPEA (0.115 mL, 0.661 mmol) and then TBTU (159 mg, 0.496 mmol) were added and the reaction mixture was stirred for 15 minutes at room temperature. 6-(spiro[1-benzofuran-3,1'-cyclopropan]-4-yloxy)-3-pyridinamine (Intermediate 87, 84 mg) was added and the reaction mixture was stirred for 6 hours at the same temperature. The reaction was quenched with brine (2 ml), diluted with water (5 ml) and extracted with ethyl acetate (2×10 ml). The organic layer was washed with ice cold brine (2×5 ml), dried over sodium sulphate, filtered and evaporated. The residue was purified by flash chromatography (Biotage system) on silica gel using a 10 g SNAP column and cyclohexane to cyclohexane/ethyl acetate 7:3 as eluents affording the title compound as a colourless oil (130 mg).

$^1$H NMR (400 MHz, DMSO-d$_6$): δ ppm 10.14 (1H, br.s), 8.32 (1H, d), 8.08 (1H, dd), 7.02-7.09 (2H, m), 6.96 (1H, d), 6.63 (1H, d), 6.42 (1H, d), 4.44 (2H, s), 3.93-4.01 (1H, m), 1.52-1.75 (2H, m), 1.39 (9H, s), 1.15-1.22 (2H, m), 0.85-0.95 (5H, m); UPLC: 0.80 min, 440 [M+H]+.

Intermediate 89

(2R)-2-amino-N-[6-(spiro[1-benzofuran-3,1'-cyclopropan]-4-yloxy)-3-pyridinyl]butanamide

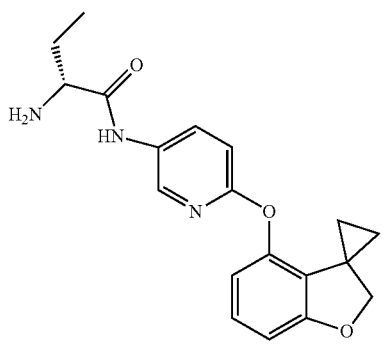 [SMILES: CC[C@@H](N)C(=O)Nc1ccc(Oc2cccc3c2C2(CC2)CO3)nc1]

To a solution of 1,1-dimethylethyl [(1R)-1-({[6-(spiro[1-benzofuran-3,1'-cyclopropan]-4-yloxy)-3-pyridinyl]amino}carbonyl)propyl]carbamate (Intermediate 88, 128 mg) in dry dichloromethane (3 ml) at 0° C. TFA (0.9 mL, 11.68 mmol) was slowly added and the reaction mixture was stirred for 2 hours at the same temperature. The reaction was diluted with dichloromethane (10 ml) and an aqueous saturated solution of NaHCO$_3$ was added while the pH was allowed to reach ~8. Two phases were separated and the aqueous layer was re-extracted with dichloromethane (10 ml). The organic layers were combined, dried over sodium sulphate, filtered and evaporated affording the title compound as a colourless oil (92 mg).

$^1$H NMR (400 MHz, DMSO-d$_6$): δ ppm 8.37 (1H, d), 8.13 (1H, dd), 7.05 (1H, t), 6.95 (1H, d), 6.63 (1H, d), 6.42 (1H, d), 4.44 (2H, s), 3.24 (1H, m), 1.61-1.72 (1H, m), 1.44-1.55 (1H, m), 1.16-1.21 (2H, m), 0.91 (3H, t), 0.86-0.91 (2H, m); UPLC_B: 0.74 min, 340 [M+H]+.

Intermediate 90

1,1-dimethylethyl (1,1-dimethyl-2-oxo-2-{[6-(spiro[1-benzofuran-3,1'-cyclopropan]-4-yloxy)-3-pyridinyl]amino}ethyl)carbamate

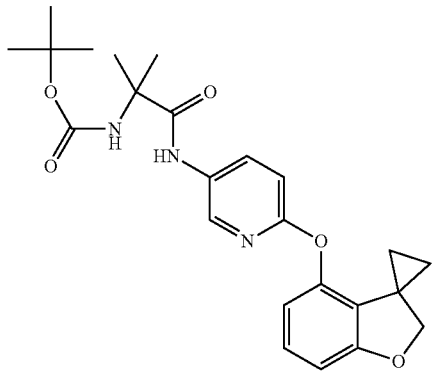 [SMILES: CC(C)(C)OC(=O)NC(C)(C)C(=O)Nc1ccc(Oc2cccc3c2C2(CC2)CO3)nc1]

To a solution of N-{[(1,1-dimethylethyl)oxy]carbonyl}-2-methylalanine (80 mg, 0.393 mmol) in dry N,N-dimethylformamide (1.5 mL) DIPEA (0.096 mL, 0.551 mmol) and then HATU (150 mg, 0.393 mmol) were added and the reaction mixture was stirred for 15 minutes at room temperature This solution was added to a solution of 6-(spiro[1-benzofuran-3,1'-cyclopropan]-4-yloxy)-3-pyridinamine (Intermediate 89, 40 mg) in dry N,N-dimethylformamide (0.5 ml) and the reaction mixture was stirred overnight at room temperature. The reaction was quenched with water (2 ml), diluted with brine (10 ml) and extracted with ethyl acetate (2×20 ml). The organic layer was dried over sodium sulphate, filtered and evaporated and the residue was purified by flash chromatography (Biotage system) on silica gel using a 10 g SNAP column and cyclohexane/ethyl acetate 8:2 to cyclohexane/ethyl acetate 1:1 as eluents affording the title compound as a white solid (52 mg).

$^1$H NMR (400 MHz, DMSO-d$_6$): δ ppm 9.62 (1H, br.s), 8.24-8.42 (1H, br.m), 8.05 (1H, d), 6.98-7.10 (2H, m), 6.92 (1H, d), 6.61 (1H, d), 6.40 (1H, d), 4.44 (2H, s), 1.42 (6H, s), 1.36 (9H, s), 1.15-1.21 (2H, m), 0.85-0.91 (2H, m); UPLC: 0.81 min, 440 [M+H]+.

Intermediate 91

2-methyl-N$^1$-[6-(spiro[1-benzofuran-3,1'-cyclopropan]-4-yloxy)-3-pyridinyl]alaninamide

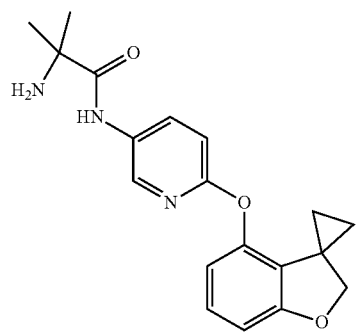 [SMILES: CC(C)(N)C(=O)Nc1ccc(Oc2cccc3c2C2(CC2)CO3)nc1]

To a solution of 1,1-dimethylethyl (1,1-dimethyl-2-oxo-2-{[6-(spiro[1-benzofuran-3,1'-cyclopropan]-4-yloxy)-3-pyridinyl]amino}ethyl)carbamate (Intermediate 90, 50 mg) in dry dichloromethane (4 mL) at 0° C. TFA (1 ml, 12.98 mmol) was slowly added and the reaction mixture was stirred for 2 hours at the same temperature. The reaction was diluted with dichloromethane (10 ml) and an aqueous saturated solution of NaHCO$_3$ was added while the pH was allowed to reach ~8. Two phases were separated and the organic layer was dried over sodium sulphate, filtered and evaporated affording the title compound (35 mg) as a colourless oil.

$^1$H NMR (400 MHz, DMSO-d$_6$): δ ppm 8.40 (1H, d), 8.15 (1H, dd), 7.04 (1H, t), 6.94 (1H, d), 6.62 (1H, d), 6.41 (1H, d), 4.43 (2H, s), 1.28 (6H, s), 1.15-1.20 (2H, m), 0.86-0.91 (2H, m); UPLC: 0.56 min, 340 [M+H]+.

Intermediate 92

1,1-dimethylethyl [(1R)-1-methyl-1-({[6-(spiro[1-benzofuran-3,1'-cyclopropan]-4-yloxy)-3-pyridinyl]amino}carbonyl)propyl]carbamate

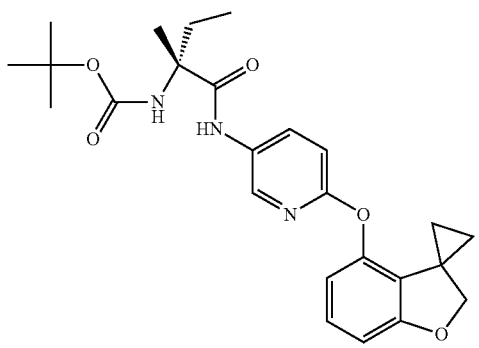 [SMILES: CC[C@@](C)(NC(=O)OC(C)(C)C)C(=O)Nc1ccc(Oc2cccc3c2C2(CC2)CO3)nc1]

6-(spiro[1-benzofuran-3,1'-cyclopropan]-4-yloxy)-3-pyridinamine (Intermediate 91, 127 mg), N-{[(1,1-dimethylethyl)oxy]carbonyl}-D-isovaline (Nagase & Co Ltd, 109 mg, 0.499 mmol), DIPEA (0.131 mL, 0.749 mmol) and HATU (247 mg, 0.649 mmol) were dissolved in dry N,N-dimethylformamide (3 ml) and the mixture obtained was stirred at room temperature for 2 days. A saturated aqueous NaHCO3 solution was then added and the mixture was extracted twice with diethyl ether. The organic phase was washed with brine, dried over sodium sulphate and concentrated under vacuum to give 300 mg of crude. This was purified by flash chromatography (Biotage KP-Sil 25 g SNAP column, eluant cyclohexane/ethyl acetate from 90/10 to 20/80 in 12CV) to give 106 mg of the title compound as a brown solid.

$^1$H NMR (400 MHz, CDCl$_3$): δ ppm 8.13-8.18 (2H, m), 7.06 (1H, t), 6.85 (1H, d), 6.66 (1H, d), 6.45 (1H, d), 4.85 (1H, br.s), 4.48 (2H, s), 1.90-2.11 (2H, m), 1.53 (3H, s), 1.48 (9H, s), 1.42-1.47 (2H, m), 0.97 (3H, t), 0.81-0.86 (2H, m); UPLC: 1.19 min, 454 [M+H]+.

Intermediate 93

N$^1$-[6-(spiro[1-benzofuran-3,1'-cyclopropan]-4-yloxy)-3-pyridinyl]-D-isovalinamide

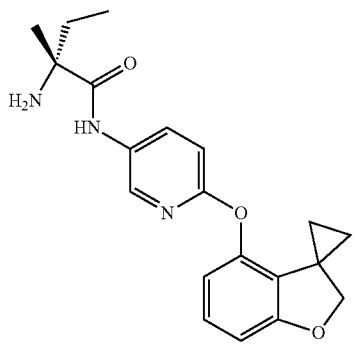 [SMILES: CC[C@@](C)(N)C(=O)Nc1ccc(Oc2cccc3c2C2(CC2)CO3)nc1]

To a solution of 1,1-dimethylethyl [(1R)-1-methyl-1-({[6-(spiro[1-benzofuran-3,1'-cyclopropan]-4-yloxy)-3-pyridinyl]amino}carbonyl)propyl]carbamate (Intermediate 92, 106 mg) in dry dichloromethane (2 ml) at 0° C. TFA (0.360 ml, 4.67 mmol) was added. The mixture was stirred at this temperature for 5 minutes, then allowed to warm up at room temperature. After 2 hours UPLC/MS showed the absence of the starting material and the presence of the desired compound: toluene (5 ml) was added and the mixture was concentrated under vacuum. The residue was loaded on a SCX cartridge (1 g), which was eluted with methanol and a 1M NH$_3$ solution in methanol. The basic eluate was concentrated under vacuum to afford the title compound as a brown oil (68 mg) which was used in the following experiment without further purification.

$^1$H NMR (400 MHz, CDCl$_3$): δ ppm 9.93 (1H, s), 8.21-8.31 (2H, m), 7.06 (1H, t), 6.85 (1H, d), 6.65 (1H, d), 6.45 (1H, d), 4.48 (2H, s), 1.94-2.04 (1H, m), 1.59-1.69 (1H, m), 1.44-1.48 (2H, m), 1.43 (3H, s), 0.95 (3H, t), 0.81-0.85 (2H, m); UPLC: 0.71 min, 354 [M+H]+.

Intermediate 94

Methyl 3-{[(methyloxy)methyl]oxy}benzoate

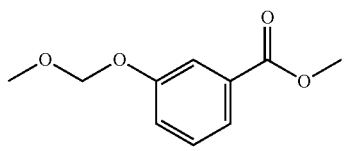

In a 500 ml round-bottomed flask, under argon flush, methyl 3-hydroxybenzoate (5 g, 32.9 mmol) was dissolved in dichloromethane (100 ml) to give a white suspension. The reaction mixture was cooled at 0° C. At that temperature chloro(methyloxy)methane (2.75 ml, 36.1 mmol) and DIPEA (6.89 ml, 39.4 mmol) were added. The reaction mixture was stirred overnight. During that time, the reaction temperature was allowed to reach room temperature. The reaction mixture was then evaporated under vacuum to afford the crude product as a yellow oil which was purified by silica gel chromatography (Biotage SP1 system, 50 g SNAP column) with Cyclohexane/EtOAc as eluents (from 10/0 to 3/1 in 10 CV; then 3/1 for 5 CV). The collected fractions afforded the title compound (5.088 g).

$^1$H NMR (400 MHz, CDCl$_3$): δ ppm 7.76-7.68 (2H, m), 7.41-7.34 (1H, m), 7.27-7.22 (1H, m), 5.24 (2H, s), 3.93 (3H, s), 3.51 (3H, s); UPLC_ipqc: 0.92 min, 197 [M+H]+

Intermediate 95

(3-{[(methyloxy)methyl]oxy}phenyl)methanol

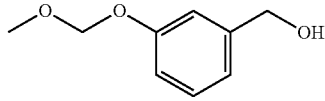

In a 250 ml round-bottomed flask, under argon flush, methyl 3-{[(methyloxy)methyl]oxy}benzoate (Intermediate 94, 5.0875 g) was dissolved in tetrahydrofuran (20 ml) to give a colourless solution. The reaction mixture was cooled at 0° C. In those conditions, a solution of LiAlH$_4$ in (1M) (25.9 ml, 25.9 mmol) was added dropwise and the reaction mixture was stirred at 0° C. After 45 min, the reaction mixture was quenched with a 2M hydrochloric acid solution until pH ~2 and diluted with 100 ml of dichloromethane. Phases were separated through a phase separator cartridge. The organic phase was evaporated under vacuum to afford the title compound (4.348 g).

$^1$H NMR (400 MHz, CDCl$_3$): δ ppm 7.30 (1H, t), 7.10-7.05 (1H, m), 7.04-7.00 (1H, m), 7.00-6.95 (1H, m), 5.20 (2H, s), 4.69 (2H, d), 3.50 (3H, s), 1.80-1.70 (1H, m).

UPLC_ipqc: 0.63 min, 151 [M−OH]$^+$

Intermediate 96

1-(2-(hydroxymethyl)-6-{[(methyloxy)methyl]oxy}phenyl)ethanol

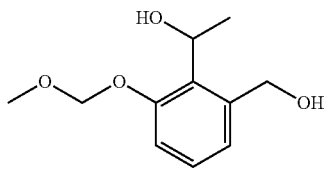

Under argon flush, in a 2-necked 100 ml round-bottomed flask equipped with a reflux condenser (flamed for 5 min under vacuum and then 3 cycles of Ar/vacuum) (3-{[(methyloxy)methyl]oxy}phenyl)methanol (Intermediate 95, 1 g) was dissolved in hexane (20 ml) to give a colourless solution. N,N,N',N'-tetramethyl-1,2-ethanediamine (1.872 mL, 12.49 mmol) was added. To the obtained reaction mixture a solution of BuLi (1.6M/hexane) (7.80 ml, 12.49 mmol) was added dropwise. The reaction mixture was then heated at 60° C. and stirred in those conditions. After 5 hours stirring in those conditions, acetaldehyde (1.090 ml, 19.30 mmol) in 6 ml of dry hexane was added dropwise at −78° C. The reaction mixture was stirred at that temperature for 1 hour and then warmed to room temperature. After overnight stirring at that temperature, the reaction was quenched with an aqueous solution of 2M hydrochloric acid and diluted with 100 ml of dichloromethane. The phases were separated through a phase separator cartridge. The organic phase was evaporated under vacuum to afford the crude product which was purified by silica gel chromatography (Biotage SP1 system, 25 g-SNAP Silica column) with Cyclohexane/EtOAc as eluents (from 5/1 to 1/1 in 15 CV; then 1/1 for 5 CV). The collected fractions afforded (3-{[(methyloxy)methyl]oxy}phenyl)methanol (532.4 mg, recovered Intermediate 95) and the title compound (184.7 mg).

$^1$H NMR (400 MHz, CDCl$_3$): δ ppm 7.20 (1H, t), 7.10 (1H, dd), 7.00 (1H, dd), 5.26 (1H, d), 5.37 (1H, q), 5.26 (1H, d), 5.25 (1H, d), 4.83 (1H, d), 4.63 (1H, d), 3.51 (3H, s), 3.55 (1H, br. s.), 2.66 (1H, br. s.), 1.60 (3H, d); UPLC_ipqc: 0.60 min, 195 [M-OH]+

Intermediate 97

1-methyl-7-{[(methyloxy)methyl]oxy}-1,3-dihydro-2-benzofuran

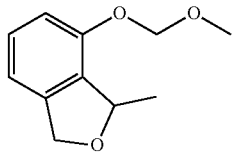

Under argon flush, in a 8 ml vial 1-(2-(hydroxymethyl)-6-{[(methyloxy)methyl]oxy}phenyl)ethanol (Intermediate 96, 50.3 mg) was dissolved in tetrahydrofuran (1 ml) to give a pale yellow solution. The reaction mixture was cooled at 0° C. In that conditions, a solution of BuLi (1.6M/hexane) (0.148 ml, 0.237 mmol) was added. The reaction mixture was stirred at 0° C. After 30 minutes, 4-methylbenzenesulfonyl chloride (45.2 mg, 0.237 mmol) was added at 0° C. The reaction was stirred at that temperature. After 1 h, an additional quantity of the BuLi solution (1.6M/hexane) (0.148 ml, 0.237 mmol) was added at 0° C. The reaction mixture was stirred at 0° C. for 1 hour, then at room temperature for 30 minutes. The reaction mixture was then quenched with 2 ml of 2M hydrochloric acid and diluted with 5 ml of dichloromethane. The phases were separated through a phase separator cartridge. The organic phase was evaporated under vacuum to afford the crude product which was purified by silica gel chromatography (Biotage SP1 system, 10 g-SNAP Silica column) with Cyclohexane/EtOAc as eluents (from 1/0 to 3/1 in 10 CV; then 3/1 for 5 CV; then from 3/1 to 1/1 in 5 CV; then 1/1 for 5 CV). The collected fraction afforded the title compound (25.2 mg).

$^1$H NMR (400 MHz, CDCl$_3$): δ ppm 7.25 (1H, t), 6.99 (1H, d), 6.88 (1H, d), 5.53-5.43 (1H, m), 5.26 (1H, d), 5.23 (1H, d), 5.20 (1H, dd), 5.10-5.02 (1H, m), 3.51 (3H, s), 1.57 (3H, d); UPLC_ipqc: 0.92 min, 195 [M+H]+

And also the corresponding deprotected phenol (Intermediate 98, 11.1 mg). $^1$H NMR (400 MHz, CDCl$_3$): δ ppm 7.17-7.11 (1H, m), 6.79 (1H, d), 6.63 (1H, d), 5.55-5.40 (1H, m), 5.20-5.14 (2H, m), 5.04 (1H, d), 1.57 (3H, d); UPLC_ipqc: 0.66 min, 149 [M−H]−

Intermediate 98

3-methyl-1,3-dihydro-2-benzofuran-4-ol

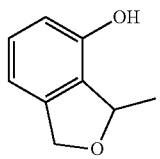

In a 8 ml vial 1-methyl-7-{[(methyloxy)methyl]oxy}-1,3-dihydro-2-benzofuran (Intermediate 97, 25.2 mg) was dissolved in methanol (1 ml) to give a colourless solution. A solution of HCl (2M/H$_2$O) (0.259 ml, 0.519 mmol) was added. The reaction mixture was shaken at 80° C. After 30 minutes, the reaction mixture was diluted with 10 ml of dichloromethane. The phases were separated through a phase separator cartridge. The organic phase was mixed with the fraction obtained before and evaporated under vacuum to afford a residue which was purified by silica gel chromatography (Biotage SP1 system, 10 g-SNAP Silica column) with Cyclohexane/EtOAc as eluents (from 100/0 to 3/1 in 10 CV; then 3/1 for 5 CV; then from 3/1 to 1:1 in 5 CV; then 1:1 for 5 CV). The collected fractions afforded the title compound (24 mg).

$^1$H NMR (400 MHz, CDCl$_3$): δ ppm 7.14 (1H, t), 6.79 (1H, d), 6.64 (1H, d), 5.55-5.42 (1H, m), 5.23 (1H, s), 5.17 (1H, dd), 5.04 (1H, d), 1.57 (3H, d); UPLC_ipqc: 0.66 min, 149 [M−H]−

Intermediate 99

2-[(3-methyl-1,3-dihydro-2-benzofuran-4-yl)oxy]-5-nitropyridine

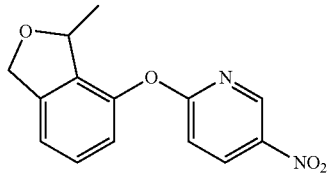 [SMILES: CC1OCc2cccc(Oc3ccc([N+](=O)[O-])cn3)c21]

In a microwave vial 3-methyl-1,3-dihydro-2-benzofuran-4-ol (Intermediate 98, 24 mg) was dissolved in N,N-dimethylformamide (1.5 ml) to give a pale yellow solution. 2-chloro-5-nitropyridine (24.07 mg, 0.152 mmol) and potassium carbonate (62.9 mg, 0.455 mmol) were added. The reaction vessel was sealed and heated in a microwave Biotage Initiator at 110° C. for 1 hour. After cooling, the reaction mixture was quenched with 5 ml of water and diluted with 25 ml of Et$_2$O. The organic phase was washed with water (3×10 mL) and the phases were separated. The organic phase was passed through a phase separator cartridge and evaporated under vacuum to give the title compound (38.3 mg).

$^1$H NMR (400 MHz, CDCl$_3$): δ ppm 9.06 (1H, d), 8.53 (1H, dd), 7.39 (1H, t), 7.18 (1H, d), 7.10 (1H, d), 7.04 (1H, d), 5.37-5.26 (1H, m), 5.26-5.18 (1H, m), 5.12 (1H, d), 1.41 (3H, d); UPLC_B: 0.84 min, 273. [M+H]+

Intermediate 100

6-[(3-methyl-1,3-dihydro-2-benzofuran-4-yl)oxy]-3-pyridinamine

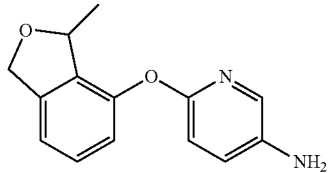 [SMILES: CC1OCc2cccc(Oc3ccc(N)cn3)c21]

In a 50 ml round-bottomed flask 2-[(3-methyl-1,3-dihydro-2-benzofuran-4-yl)oxy]-5-nitropyridine (Intermediate 99, 38.3 mg) was dissolved in ethanol (10 ml) to give a pale yellow solution. Pd/C (14.22 mg, 0.013 mmol) and hydrazine hydrate (0.026 ml, 0.267 mmol) were added. The reaction mixture was stirred at 90° C. After 45 minutes, the reaction mixture was filtered and the organic phase was evaporated under vacuum to afford the title compound (32 mg).

$^1$H NMR (400 MHz, CDCl$_3$): δ ppm 7.70 (1H, d), 7.25 (1H, t), 7.09 (1H, dd), 6.99 (1H, d), 6.88 (1H, d), 6.76 (1H, d), 5.28-5.39 (1H, m), 5.18 (1H, dd), 5.07 (1H, d), 3.53 (2H, br. s.), 1.47 (3H, d); UPLC_B: 0.64 min, 243 [M+H]+

Intermediate 101

1,1-dimethylethyl {(1R)-1-[({6-[(3-methyl-1,3-dihydro-2-benzofuran-4-yl)oxy]-3-pyridinyl}amino)carbonyl]propyl}carbamate

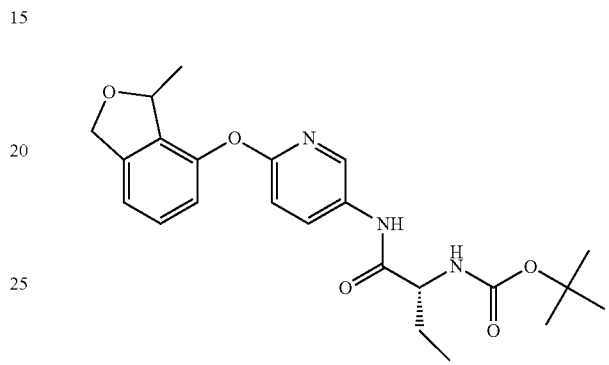

In a 8 ml vial (2R)-2-({[(1,1-dimethylethyl)oxy]carbonyl}amino)butanoic acid (32.2 mg, 0.158 mmol) was dissolved in N,N-dimethylformamide (0.5 ml) to give a colourless solution. DIPEA (0.035 ml, 0.198 mmol) and HATU (60.3 mg, 0.158 mmol) were added. The reaction mixture was stirred at room temperature for 30 minutes. 6-[(3-methyl-1,3-dihydro-2-benzofuran-4-yl)oxy]-3-pyridinamine (Intermediate 100, 32 mg) was dissolved in 1.5 ml of DMF and the obtained solution was added to the reaction mixture. It was shaken at 60° C. After 2 hours, no reaction occurred. Additional 0.5 ml of a solution [obtained dissolving in 0.5 ml of DMF (2R)-2-({[(1,1-dimethylethyl)oxy]carbonyl}amino)butanoic acid (32.2 mg, 0.158 mmol), DIPEA (0.035 mL, 0.198 mmol) and HATU (60.3 mg, 0.158 mmol)] was added to the reaction mixture. It was shaken at 60° C. over weekend. After that time, only traces of the title compound along with the Intermediate 100 was detected. The reaction mixture was evaporated under vacuum using the Vaportec V10 to give the crude product which was purified by silica gel chromatography (Biotage SP1 system, 10 g-SNAP Silica column) with Cyclohexane/EtOAc as eluents (from 3/1 to 1/1 in 10 CV; then 1/1 for 10 CV). The collected fractions afforded 4.9 mg of the title compound mixed with the amino acid and 61 mg of a mixture of starting material (Intermediate 100) and the amino acid.

This was dissolved in 10 ml of dichloromethane and washed with 10 ml of saturated aqueous solution of sodium bicarbonate. The phases were separated through a phase separator cartridge. The organic phases were evaporated under vacuum to afford 64 mg of the same mixture. This latter was dissolved in 1.0 ml of DMF and added to a stirring DMF solution (0.5 ml) of (2R)-2-({[(1,1-dimethylethyl)oxy]carbonyl}amino)butanoic acid (61.4 mg, 0.302 mmol), DIPEA (0.066 mL, 0.378 mmol) and TBTU (97 mg, 0.302 mmol). The obtained mixture was warmed at 60° C. and was shaken. After 1 h30 min the reaction mixture was evaporated under vacuum using the Vaportec V10 to give the crude product as a yellow oil which was dissolved in 10 ml of EtOAc and quenched with 10 ml of a saturated aqueous solution of sodium bicarbonate. The aqueous phase was extracted with EtOAc (3×10 ml). The collected organic phases were dried using a hydrophobic frit, mixed with the title compound obtained before and purified by silica gel chromatography (Biotage SP1 system, 10 g-SNAP Silica column) with Cyclohexane/EtOAc as eluents (from 3/1 to 1/1 in 10 CV; then 1:1 for 10 CV). The collected fractions afforded the title compound, as a 1:1 mixture of diastereoisomers (62.3 mg).

$^1$H NMR (400 MHz, CDCl$_3$): δ ppm 8.20-8.16 (1H, m), 8.15-8.08 (1H, m), 7.31 (1H, t), 7.06 (1H, d), 6.95 (1H, d), 6.89 (1H, d), 5.37-5.25 (1H, m), 5.20 (1H, dd), 5.15-5.02 (2H, m), 4.23-4.08 (1H, m), 2.03-1.81 (2H, m), 1.47 (9H, s), 1.43 (3H, d), 1.08-0.99 (3H, m). UPLC_ipqc: 1.05 min, 428 [M+H]+

Intermediate 102

(2R)-2-amino-N-{6-[(3-methyl-1,3-dihydro-2-benzofuran-4-yl)oxy]-3-pyridinyl}butanamide

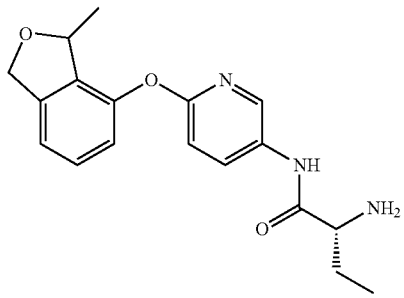 [SMILES: CC[C@@H](N)C(=O)Nc1ccc(Oc2cccc3c2C(C)OC3)nc1]

In a 25 ml round-bottomed flask 1,1-dimethylethyl {(1R)-1-[({6-[(3-methyl-1,3-dihydro-2-benzofuran-4-yl)oxy]-3-pyridinyl}amino)carbonyl]propyl}carbamate (Intermediate 101, 62.3 mg) was dissolved in dichloromethane (3 ml) to give a pale yellow solution. The reaction mixture was cooled at 0° C. At that temperature TFA (0.5 ml, 6.49 mmol) was added dropwise to the reaction mixture. The reaction mixture was stirred at 0° C. After 1 hour, the reaction mixture was evaporated under vacuum to afford the crude product which was charged on a 2 g SCX cartridge. It was then flushed with 50 ml of MeOH followed by 25 ml of a 2M solution of ammonia in MeOH. The ammonia eluate was evaporated under vacuum to afford 34.4 mg of a yellow oil which was a mixture of the title compound and the deprotected amino acid. This mixture was dissolved in 20 ml of Et2O and was washed with a saturated aqueous solution of NaHCO$_3$ (3×10 ml). The organic phase was dried using a phase separator cartridge and evaporated under vacuum to afford the title compound as a 1:1 mixture of diastereoisomers (24.4 mg).

$^1$H NMR (400 MHz, CDCl$_3$): δ ppm 9.58 (1H, br. s.), 8.32-8.25 (1H, m), 8.23 (1H, t), 7.32 (1H, t), 7.08 (1H, d), 6.98 (1H, d), 6.94 (1H, d), 5.40-5.29 (1H, m), 5.22 (1H, dd), 5.11 (1H, d), 3.49 (1H, dd), 2.11-1.94 (1H, m), 1.85-1.60 (3H, m), 1.46 (3H, d), 1.12-1.01 (3H, m); UPLC_ipqc: 0.64 min, 328 [M+H]+

Intermediate 103

(1,1-dimethylethyl)(dimethyl){[(3-{[(methyloxy)methyl]oxy}phenyl)methyl]oxy}silane

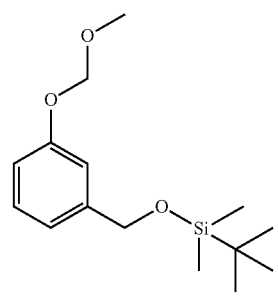 [SMILES: COCOc1cccc(CO[Si](C)(C)C(C)(C)C)c1]

In a 100 ml round-bottomed flask (3-{[(methyloxy)methyl]oxy}phenyl)methanol (Intermediate 95, 3.5 g) was dissolved in dichloromethane (20 ml) to give a colourless solution. 1H-imidazole (1.700 g, 24.97 mmol) and chloro (1,1-dimethylethyl)dimethylsilane (3.64 g, 24.14 mmol) were added. The reaction mixture immediately became a white suspension and was stirred at room temperature. After overnight stirring the reaction was completed. The reaction mixture was then quenched with 10 ml of water and diluted with 10 ml of dichloromethane. The phases were separated through a separating funnel. The organic phase was dried using a hydrophobic frit and evaporated under vacuum to give 6.0082 g of the crude product as a colourless oil which was purified via Biotage SP1 (with cyclohexane/EtOAc as eluents from 1:0 to 5:1 in 10 CV; then 5:1 for 5 CV; then from 5:1 to 1:1 in 5 CV; 100 g SNAP Silica column). Two fractions of the title compound were collected: 1.70 g of a colourless oil (purity: 93%) and 3.70 g of a colourless oil (purity: 98%).

$^1$H NMR (400 MHz, CDCl$_3$) δ ppm 7.26 (1H, t), 7.04-7.08 (1H, m), 6.96-7.01 (1H, m), 6.91-6.96 (1H, m), 5.20 (2H, s), 4.75 (2H, s), 3.50 (3H, s), 0.92-1.02 (9H, m), 0.12 (6H, s). UPLC-MS_ipqc: 1.49 min, 281 [M–H]–.

Intermediate 104

1-(2-({[(1,1-dimethylethyl)(dimethyl)silyl]oxy}methyl)-6-{[(methyloxy)methyl]oxy}phenyl)-1-propanol

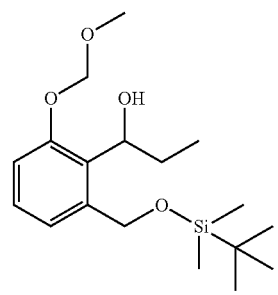 [SMILES: CCC(O)c1c(CO[Si](C)(C)C(C)(C)C)cccc1OCOC]

Under argon flush, in a 2-necked 100 ml round-bottomed flask equipped with a reflux condenser (flamed for 5 minutes under vacuum and then 3 cycles of Ar/vacuum) (1,1-dimethylethyl)(dimethyl){[(3-{[(methyloxy)methyl]oxy}phenyl)methyl]oxy}silane (Intermediate 103, 0.2 g) was dissolved in hexane (2 ml) to give a colourless solution. A 1.6M/Hexane solution of BuLi (0.487 ml, 0.779 mmol) was added dropwise. The reaction mixture was stirred at room temperature. After 2 hours stirring in those conditions, to the pale yellow reaction mixture propanal (0.061 mL, 0.850 mmol) was added at 0° C. After 1 h30 min, the reaction was quenched with 2M hydrochloric acid until pH ~2 and diluted with 25 ml of dichloromethane. The phases were separated through a phase separator cartridge. The organic phase was evaporated under vacuum affording the crude product as a green/grey oil that was purified via Biotage SP1 (with Cyclohexane/EtOAc as eluents from 1:0 to 5:1 in 5 CV; then 5:1 for 5 CV; then from 5:1 to 3:1 in 5 CV; then 3:1 for 5 CV; 10 g SNAP Silica column.) This afforded the title compound as a pale yellow oil (132.1 mg).

$^1$H NMR (400 MHz, CDCl$_3$) δ ppm 7.18 (1H, t), 7.02-7.12 (2H, m), 5.26 (1H, d), 5.25 (1H, d), 4.78-4.89 (2H, m), 4.75 (1H, d), 3.63 (1H, d), 3.51 (3H, s), 1.89-2.06 (1H, m), 1.74-1.88 (1H, m), 1.02 (3H, t), 0.94 (9H, s), 0.12 (3H, s), 0.10 (3H, s). UPLC-MS_ipqc: 1.45 min, 363 [M+Na]+.

Intermediate 105

1-(2-(hydroxymethyl)-6-{[(methyloxy)methyl]oxy}phenyl)-1-propanol

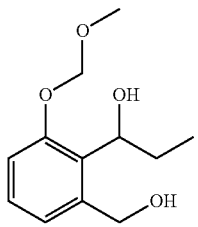 [SMILES: CCC(O)c1c(CO)cccc1OCOC]

In a 50 ml round-bottomed flask 1-(2-({[(1,1-dimethylethyl)(dimethyl)silyl]oxy}methyl)-6-{[(methyloxy)methyl]oxy}phenyl)-1-propanol (Intermediate 104, 132.1 mg) was dissolved in Tetrahydrofuran (2 ml) to give a pale yellow solution. 1M/THF sol of TBAF (0.388 ml, 0.388 mmol) was added. The reaction mixture was stirred at room temperature. After over night stirring, the reaction was completed. The reaction mixture was evaporated under vacuum to give the crude product as a pale yellow oil which was purified via Biotage SP1 (with Cyclohexane/EtOAc as eluents from 3:1 to 2:1 in 10 CV; then 2:1 for 5 CV; then from 2:1 to 2:1 in 5 CV; then 1:1 for 5 CV; 25 g SNAP Silica column). The collected fractions afforded a residue which was purified again in the same conditions to afford the title compound as a pale yellow oil.

$^1$H NMR (400 MHz, CDCl$_3$) δ ppm 7.16-7.24 (1H, m), 7.10 (1H, dd), 7.02 (1H, dd), 5.23 (2H, dd), 5.08 (1H, dd), 4.81 (1H, d), 4.61 (1H, d), 3.50 (3H, s), 2.41-3.05 (2H, m), 1.91-2.07 (1H, m), 1.82 (1H, s), 1.00 (3H, t). UPLC-MS_ipqc: 0.70 min, 249 [M+Na]+.

Intermediate 106

3-ethyl-1,3-dihydro-2-benzofuran-4-ol

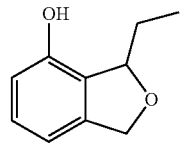

Under argon flush, in a 8 ml vial 1-(2-(hydroxymethyl)-6-{[(methyloxy)methyl]oxy}phenyl)-1-propanol (Intermediate 105, 99 mg) was dissolved in tetrahydrofuran (2 ml) to give a pale yellow solution. The reaction mixture was cooled at 0° C. In those conditions, a solution of BuLi in hexane (1.6M, 0.246 ml, 0.394 mmol) was added. The reaction mixture was stirred at 0° C. After 30 minutes, 4-methylbenzenesulfonyl chloride (75 mg, 0.394 mmol) was added at 0° C. The reaction was stirred at that temperature. After 1 hour, additional BuLi in hexane (1.6M, 0.246 ml, 0.394 mmol) was added at 0° C. The reaction mixture was stirred at 0° C. for 1 h, then at room temperature for 30 minutes. After that time the reaction mixture was quenched with 2 ml of 2M hydrochloric acid and diluted with 5 ml of dichloromethane. The phases were separated through a phase separator cartridge. The organic phase was evaporated under vacuum to afford the crude product as a pale yellow oil which was dissolved in methanol (3.00 ml). HCl (0.788 ml, 1.575 mmol) was added thereto. The obtained reaction mixture was warmed at 80° C. and shaken. After 30 minutes, the reaction was completed. The reaction mixture was quenched with 5 ml of water and diluted with 25 ml of dichloromethane. The phases were separated through a phase separator cartridge. The organic phase was evaporated under vacuum to afford the crude product as a pale yellow oil which was purified via Biotage SP1 (with Cyclohexane/EtOAc as eluents from 1:0 to 3:1 in 10 CV; then 3:1 for 5 CV; then from 3:1 to 1:1 in 5 CV; then 1:1 for 5 CV; 10 g SNAP Silica column). The collected fractions afforded the title compound as a colourless oil (49.7 mg).

$^1$H NMR (400 MHz, CDCl$_3$) δ ppm 7.14 (1H, t), 6.79 (1H, d), 6.64 (1H, d), 5.51 (1H, br. s.), 5.37-5.45 (1H, m), 5.16 (1H, dd), 5.07 (1H, d), 1.99-2.15 (1H, m), 1.78-1.92 (1H, m), 0.91-1.00 (3H, m). UPLC-MS_ipqc: 0.77 min, 163 [M−H]−.

Intermediate 107

2-[(3-ethyl-1,3-dihydro-2-benzofuran-4-yl)oxy]-5-nitropyridine

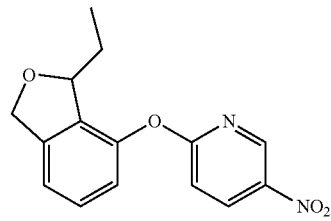 [SMILES: CCC1OCc2cccc(Oc3ccc([N+](=O)[O-])cn3)c21]

In a 0.5-2.0 ml micro-wave vial 3-ethyl-1,3-dihydro-2-benzofuran-4-ol (Intermediate 106, 49.7 mg) was dissolved in N,N-dimethylformamide (1.5 ml) to give a pale yellow solution. 2-chloro-5-nitropyridine (48.0 mg, 0.303 mmol) and potassium carbonate (125 mg, 0.908 mmol) were added. The reaction vessel was sealed and heated in micro-wave Biotage Initiator at 110° C. for 1 hour. After cooling, the reaction completed. The reaction mixture was then quenched with 5 ml of water and diluted with 25 mt of Et$_2$O. The aqueous phase was extracted with 3×10 ml of Et$_2$O. The collected organic phases were passed through a phase separator cartridge and evaporated under vacuum to give the title compound as a pale yellow oil (97.6 mg).

$^1$H NMR (400 MHz, CDCl$_3$) δ ppm 9.05 (1H, d), 8.51 (1H, dd), 7.37 (1H, t), 7.16 (1H, d), 7.06 (1H, d), 7.02 (1H, d), 5.16-5.25 (2H, m), 5.13 (1H, d), 1.77-1.90 (1H, m), 1.60-1.72 (1H, m), 0.82-0.91 (3H, m). UPLC_B: 0.90 min, 287 [M+H]+.

Intermediate 108

6-[(3-ethyl-1,3-dihydro-2-benzofuran-4-yl)oxy]-3-pyridinamine

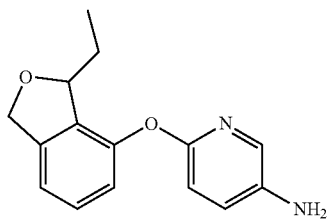

In a 50 ml round-bottomed flask 2-[(3-ethyl-1,3-dihydro-2-benzofuran-4-yl)oxy]-5-nitropyridine (Intermediate 107, 97.6 mg) was dissolved in ethanol (10 ml) to give a pale yellow solution. Pd/C (26.1 mg, 0.245 mmol) and hydrazine hydrate (12.29 mg, 0.245 mmol) were added. The reaction mixture was stirred at 90° C. After 45 minutes, the reaction was completed. The reaction mixture was filtered and the organic phase was evaporated under vacuum affording the crude product which was charged on a 2 g SCX cartridge. It was then flushed with 15 ml of methanol followed by 15 ml of a 2M solution of ammonia in methanol. The ammonia eluate was evaporated under vacuum affording nothing. The methanol eluate was then evaporated under vacuum to afford the title compound as a colourless oil.

$^1$H NMR (400 MHz, CDCl$_3$) δ ppm 7.70 (1H, d), 7.24 (1H, t), 7.09 (1H, dd), 6.99 (1H, d), 6.87 (1H, d), 6.75 (1H, d), 5.21-5.29 (1H, m), 5.17 (1H, dd), 5.09 (1H, d), 3.57 (2H, br. s.), 1.88-2.04 (1H, m), 1.68-1.82 (1H, m), 0.89 (3H, t). UPLC_B: 0.71 min, 257 [M+H]+.

Intermediate 109

1,1-dimethylethyl {(1R)-1-[({6-[(3-ethyl-1,3-dihydro-2-benzofuran-4-yl)oxy]-3-pyridinyl}amino)carbonyl]propyl}carbamate

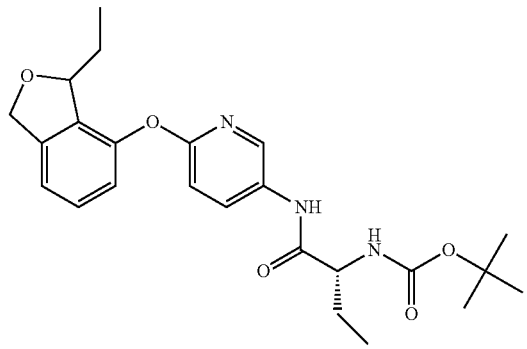 [SMILES: CCC1OCc2cccc(Oc3ccc(NC(=O)[C@@H](CC)NC(=O)OC(C)(C)C)cn3)c21]

In a 8 ml vial 6-[(3-ethyl-1,3-dihydro-2-benzofuran-4-yl)oxy]-3-pyridinamine (Intermediate 108, 10 mg) was dissolved in N,N-dimethylformamide (1 ml) to give a colourless solution. DIPEA (10.22 µl, 0.059 mmol), (2R)-2-({[(1,1-dimethylethyl)oxy]carbonyl}amino)butanoic acid (9.52 mg, 0.047 mmol) and, finally, TBTU (15.03 mg, 0.047 mmol) were added. The reaction mixture was shaken at 60° C. After overnight shaking, the reaction was completed. The reaction mixture was evaporated under vacuum to give the crude product as a yellow oil which was purified via Biotage SP1 (with Cyclohexane/EtOAc as eluents from 2:1 to 1:1 in 10 CV; then 2:1 for 5 CV; 10 g SNAP Silica column). The collected fractions afforded the title compound as a colourless oil (12.7 mg).

$^1$H NMR (400 MHz, CDCl$_3$) δ ppm 8.40 (1H, br. s.), 8.15-8.18 (1H, m), 8.08-8.14 (1H, m), 7.30 (1H, t), 7.05 (1H, d), 6.95 (1H, d), 6.88 (1H, d), 5.20-5.26 (1H, m), 5.17 (1H, dd), 5.10 (1H, d), 4.99 (1H, br. s.), 4.05-4.19 (1H, m), 1.82-2.08 (2H, m), 1.64-1.79 (2H, m), 1.47 (9H, s), 1.03 (3H, t), 0.88 (3H, t). UPLC_B: 0.91 min, 442 [M+H]+.

Intermediate 110

(2R)-2-amino-N-{6-[(3-ethyl-1,3-dihydro-2-benzofuran-4-yl)oxy]-3-pyridinyl}butanamide

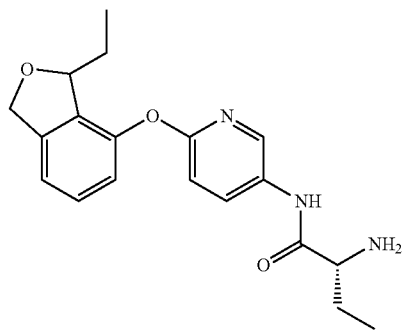 [SMILES: CCC1OCc2cccc(Oc3ccc(NC(=O)[C@H](N)CC)cn3)c21]

In a 50 ml round-bottomed flask 1,1-dimethylethyl {(1R)-1-[({6-[(3-ethyl-1,3-dihydro-2-benzofuran-4-yl)oxy]-3-pyridinyl}amino)carbonyl]propyl}carbamate (Intermediate 109, 12.7 mg) was dissolved in dichloromethane (3 ml) to give a colourless solution. The reaction mixture was cooled at 0° C. TFA (1.5 ml, 19.47 mmol) was added at that temperature. The reaction mixture was stirred at 0° C. After 1 hour, the reaction was completed. The reaction mixture was evaporated under vacuum affording the crude product which was charged on a 2 g SCX cartridge. It was then flushed with 15 ml of MeOH followed by 15 ml of a solution of ammonia in MeOH (2M). The ammonia eluate was evaporated under vacuum to afford the title compound as a colourless oil (9.0 mg).

$^{1}$H NMR (400 MHz, CDCl$_3$) δ ppm 9.59 (1H, br. s.), 8.18-8.28 (2H, m), 7.30 (1H, t), 7.05 (1H, d), 6.95 (1H, d), 6.90 (1H, d), 5.21-5.26 (1H, m), 5.18 (1H, dd), 5.10 (1H, d), 3.50 (1H, dd), 1.79-2.07 (4H, m), 1.62-1.78 (2H, m), 1.04 (3H, t), 0.88 (3H, t); UPLC_B: 0.72 min, 342 [M+H]+.

Intermediate 111

3-methyl-5-(methyloxy)-2H-chromen-2-one

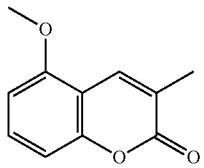

To a solution of 2-hydroxy-6-(methyloxy)benzaldehyde (3 g, 19.72 mmol) in dry N,N-dimethylformamide (30 ml), propanoic anhydride (12.98 ml, 101 mmol) and K$_2$CO$_3$ (3.00 g, 21.69 mmol) were added and the reaction mixture was warmed to 70° C. At this temperature water (0.036 ml, 1.972 mmol) was added and the reaction mixture was warmed to 120° C. and stirred overnight under nitrogen. The reaction was then quenched with 60 ml of water. A precipitate was formed and the crude material was filtered, the solid dissolved in DCM/water and the two phases were separated through a phase separator cartridge. The organic phase was evaporated under vacuum affording the title compound as a white solid (3.25 g, 85% yield).

$^{1}$H NMR (400 MHz, CDCl$_3$): δ ppm 7.91 (1H, s), 7.37 (1H, t), 6.92 (1H, d), 6.71 (1H, d), 3.94 (3H, s), 2.22 (3H, s); UPLC_ipqc: 0.95 min, 191 [M+H]+.

Intermediate 112

5-hydroxy-3-methyl-2H-chromen-2-one

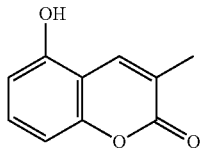

To a solution of 3-methyl-5-(methyloxy)-2H-chromen-2-one (Intermediate 111, 2.5 g) in dry dichloromethane (45 ml) cooled to 0° C. was added BBr3 (39.4 ml, 39.4 mmol). The reaction mixture was warmed to room temperature and stirred at room temperature overnight under nitrogen. The reaction was then cooled to 0° C. and quenched with ice. The obtained mixture was diluted with diethyl ether and the two phases obtained were separated through a separating funnel. The aqueous phase was back-extracted with diethyl ether. The collected organic phases were dried over sodium sulphate, filtered and evaporated under vacuum to give the title compound as a light brown solid (2.225 g).

$^{1}$H NMR (400 MHz, CDCl$_3$): δ ppm 7.92 (1H, s), 7.30 (1H, t), 6.93 (1H, d), 6.67 (1H, d), 5.54 (1H, s), 2.26 (3H, s); UPLC_ipqc: 0.70 min, 177 [M+H]+.

Intermediate 113

3-methyl-5-{[(methyloxy)methyl]oxy}-2H-chromen-2-one

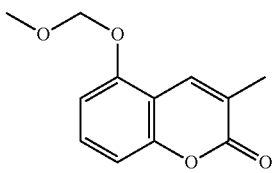 [SMILES: COCOc1cccc2oc(=O)c(C)cc12]

To a solution of 5-hydroxy-3-methyl-2H-chromen-2-one (Intermediate 112, 2.225 g) in dry N,N-Dimethylformamide (60 ml) cooled to 0° C. was added sodium hydride (60%, 0.532 g, 13.89 mmol) followed by the addition of chloro (methyloxy)methane (1.919 ml, 25.3 mmol). The reaction mixture was warmed to room temperature and stirred for 30 minutes under nitrogen. It was then quenched by the addition of a saturated solution of NH$_4$Cl, the product was extracted with diethyl ether, washed with brine, dried over sodium sulphate, filtered and concentrated under vacuum. The residue obtained was purified by silica gel chromatography (Biotage system, with a gradient from pure cyclohexane to cyclohexane/ethyl acetate 5/1) to give the title compound as a white solid (2.15 g).

$^{1}$H NMR (400 MHz, CDCl$_3$): δ ppm 7.94 (1H, s), 7.38 (1H, t), 6.93-7.05 (2H, m), 5.33 (2H, s), 3.55 (3H, s), 2.26 (3H, s); UPLC_ipqc: 0.94 min, 221 [M+H]+.

Intermediate 114

3:1 Mixture of 2-[3-hydroxy-2-methyl-1-propen-1-yl]-3-{[(methyloxy)methyl]oxy}phenol and 2-(3-hydroxy-2-methylpropyl)-3-{[(methyloxy)methyl]oxy}phenol

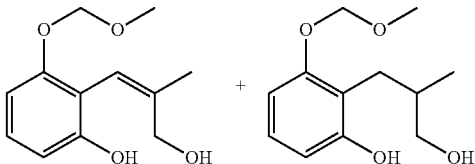 [SMILES: COCOc1cccc(O)c1/C=C(/C)CO ; COCOc1cccc(O)c1CC(C)CO]

In a 50 ml round-bottomed flask 3-methyl-5-{[(methyloxy)methyl]oxy}-2H-chromen-2-one (Intermediate 113, 461.1 mg) was dissolved in tetrahydrofuran (3 ml) to give a colourless solution. The reaction mixture was cooled at 0° C. A solution of LiAlH$_4$ (1M/THF, 4.19 ml, 4.19 mmol) was then added dropwise. The reaction mixture was stirred at 0° C. After 30 minutes, the reaction mixture was quenched with 5 ml of hydrochloric acid (2M) and diluted with 10 ml of dichloromethane. Phases were separated through a phase separator cartridge. The organic phase was evaporated under vacuum to afford a 3:1 mixture of 2-[3-hydroxy-2-methyl-1-propen-1-yl]-3-{[(methyloxy)methyl]oxy}phenol and 2-(3-hydroxy-2-methylpropyl)-3-{[(methyloxy)methyl]oxy}phenol (548 mg) as a pale yellow oil.

$^1$H NMR (400 MHz, CDCl$_3$) major component of the mixture δ ppm 7.11 (1H, t), 6.67 (1H, d), 6.63 (1H, d), 6.08-6.16 (1H, m), 5.81 (1H, br. s.), 5.15 (2H, s), 4.74 (1H, br. s.), 4.00 (2H, s), 3.47 (3H, s), 2.08 (3H, d); $^1$H NMR (400 MHz, CDCl$_3$) minor component of the mixture δ ppm 7.05 (1H, t), 6.97 (1H, br. s.), 6.66 (1H, d), 6.58 (1H, d), 5.19 (2H, s), 3.51-3.59 (1H, m), 3.49 (3H, s), 3.41-3.49 (1H, m), 2.78 (1H, dd), 2.66 (1H, dd), 2.13 (1H, br. s.), 1.94-2.07 (1H, m), 1.09 (3H, d); UPLC-MS_ipqc: major component of the mixture: 0.70 min, 223 [M−H]−; minor component of the mixture: 0.78 min, 225 [M−H]−.

Intermediate 115

2-(3-hydroxy-2-methylpropyl)-3-{[(methyloxy)methyl]oxy}phenol

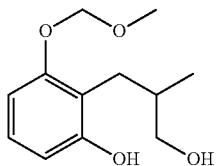 [SMILES: COCOc1cccc(O)c1CC(C)CO]

In a 100 ml round-bottomed flask a 3:1 mixture of 2-[3-hydroxy-2-methyl-1-propen-1-yl]-3-{[(methyloxy)methyl]oxy}phenol and 2-(3-hydroxy-2-methylpropyl)-3-{[(methyloxy)methyl]oxy}phenol (Intermediate 114, 548 mg) was dissolved in methanol (10 ml) to give a colourless solution. Three cycles of vacuum/N$_2$ were performed then Pd/C (129 mg, 0.122 mmol) was added to the reaction mixture. Again three cycles of vacuum/N$_2$ were performed before three cycles of vacuum/H$_2$. Finally, the reaction mixture was allowed to stir at room temperature in H$_2$ atmosphere (no pressure). The reaction mixture was stirred at room temperature. After 1 h30 min the reaction was completed. The reaction mixture was filtered over a celite pad. The filtrate was evaporated under vacuum affording the crude product which was purified on the Biotage SP1 system with Cyclohexane/EtOAc as eluents from 1:0 to 5:1 in 10 CV; then 5:1 for 5 CV; then from 5:1 to 3:1 in 5 CV; then 3:1 for 5 CV; then from 3:1 to 1:1 in 5 CV; then 1:1 for 5 CV (25 g SNAP Silica column). The collected fractions afforded the title compound as a colourless oil.

$^1$H NMR (400 MHz, CDCl$_3$) δ ppm 7.05 (1H, t), 6.97 (1H, br. s.), 6.66 (1H, d), 6.58 (1H, d), 5.19 (2H, s), 3.51-3.59 (1H, m), 3.49 (3H, s), 3.41-3.49 (1H, m), 2.78 (1H, dd), 2.66 (1H, dd), 2.13 (1H, br. s.), 1.94-2.07 (1H, m), 1.09 (3H, d). UPLC-MS_ipqc: 0.79 min, 225 [M−H]−.

Intermediate 116

3-methyl-5-{[(methyloxy)methyl]oxy}-3,4-dihydro-2H-chromene

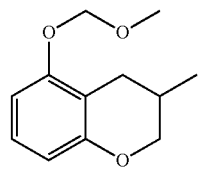

In a 50 ml round-bottomed flask under argon, 2-(3-hydroxy-2-methylpropyl)-3-{[(methyloxy)methyl]oxy}phenol (Intermediate 115, 377.9 mg) was dissolved in tetrahydrofuran (5 ml) to give a colourless solution. TEA (0.409 ml, 2.93 mmol) was added and the reaction mixture was cooled at 0° C. At that temperature methanesulfonyl chloride (0.124 ml, 1.591 mmol) was added. The reaction mixture was stirred at 0° C. After 45 minutes, additional methanesulfonyl chloride (0.124 ml, 1.591 mmol) was added. After additional 45 minutes, potassium 2-methyl-2-propanolate (422 mg, 3.76 mmol) was added. After 15 minutes from this latter addition, additional potassium 2-methyl-2-propanolate (422 mg, 3.76 mmol) was added. After 15 minutes the reaction was completed. The reaction was then quenched with 10 ml of a saturated aqueous solution of NH$_4$Cl, acidified until pH ~2 with 2M hydrochloric acid and diluted with 25 ml of dichloromethane. Phases were separated through a phase separator cartridge. The organic phase was evaporated under vacuum to afford the title compound.

$^1$H NMR (400 MHz, CDCl$_3$) δ ppm 7.04 (1H, t), 6.63 (1H, d), 6.53 (1H, d), 5.21 (2H, s), 4.13-4.19 (1H, m), 3.60-3.71 (1H, m), 3.50 (3H, s), 2.84-2.95 (1H, m), 2.19-2.30 (1H, m), 2.04-2.18 (1H, m), 1.08 (3H, d); UPLC-MS_ipqc: 1.16 min, 209 [M+H]+.

Intermediate 117

3-methyl-3,4-dihydro-2H-chromen-5-ol

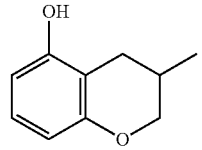

In a 8 ml vial 3-methyl-5-{[(methyloxy)methyl]oxy}-3,4-dihydro-2H-chromene (Intermediate 116, 103.6 mg) was dissolved in methanol (3 ml) to give a colourless solution. A 2M/H$_2$O solution of HCl (0.224 ml, 0.448 mmol) was added. The reaction mixture was shaken at 60° C. After 2 h30 min, the reaction mixture was diluted with 10 ml of dichloromethane. The phases were separated through a phase separator cartridge. The organic phase was evaporated under vacuum to afford the crude product which was purified via Biotage SP1 (with Cyclohexane/EtOAc as eluents from 1:0 to 5:1 in 10 CV; then 5:1 for 5 CV; then from 5:1 to 3:1 in 5 CV; (10 g SNAP Silica column). The collected fractions afforded the title compound as a white solid (53.0 mg).

¹H NMR (400 MHz, CDCl₃) δ ppm 6.96 (1H, t), 6.46 (1H, d), 6.35 (1H, dd), 4.79 (1H, s), 4.10-4.22 (1H, m), 3.61-3.73 (1H, m), 2.78-2.90 (1H, m), 2.19-2.30 (1H, m), 2.16 (1H, d), 1.09 (3H, d). UPLC-MS_ipqc: 0.90 min, 165 [M+H]+.

Intermediate 118

2-[(3-methyl-3,4-dihydro-2H-chromen-5-yl)oxy]-5-nitropyridine

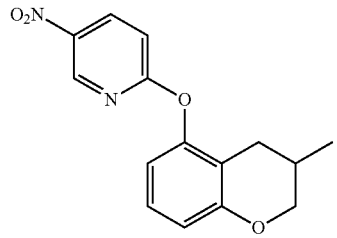 [SMILES: CC1COc2cccc(Oc3ccc([N+](=O)[O-])cn3)c2C1]

In a microwave vial, 3-methyl-3,4-dihydro-2H-chromen-5-ol (Intermediate 117, 53 mg), potassium carbonate (134 mg, 0.968 mmol) and 2-chloro-5-nitropyridine (51.2 mg, 0.323 mmol) were dissolved in N,N-dimethylformamide (2 ml) to give a light brown solution. The reaction vessel was sealed and heated in Biotage Initiator at 110° C. for 1 hour. After cooling, the reaction mixture was quenched with 5 ml of water and diluted with 10 ml of Et₂O. Phases were separated by a separating funnel. The aqueous phase was extracted with 3×10 ml of Et₂O. The collected organic phase were dried using a hydrophobic frit and evaporated under vacuum to give the title compound as a brown oil (181 mg).

¹H NMR (400 MHz, CDCl₃) δ ppm 9.06 (1H, d), 8.48 (1H, dd), 7.17 (1H, t), 7.02 (1H, d), 6.80 (1H, d), 6.66 (1H, dd), 4.16-4.24 (1H, m), 3.63-3.75 (1H, m), 2.62-2.74 (1H, m), 2.04-2.18 (2H, m), 1.00 (3H, d). UPLC_B: 0.95 min, 287 [M+H]+.

Intermediate 119

6-[(3-methyl-3,4-dihydro-2H-chromen-5-yl)oxy]-3-pyridinamine

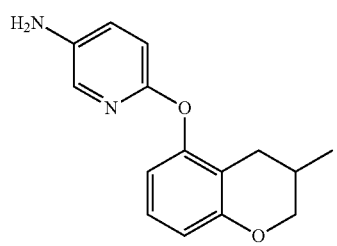

In a 50 ml round-bottomed flask 2-[(3-methyl-3,4-dihydro-2H-chromen-5-yl)oxy]-5-nitropyridine (Intermediate 118, 181 mg) was dissolved in ethanol (10 ml) to give a pale yellow solution. Pd/C (33.0 mg, 0.031 mmol) and hydrazine hydrate (0.030 ml, 0.310 mmol) were added. The reaction mixture was stirred at 90° C. After 1 hour, the reaction mixture was filtered and evaporated under vacuum to give the title compound (131.4 mg).

¹H NMR (400 MHz, CDCl₃) δ ppm 7.72 (1H, d), 7.02-7.13 (2H, m), 6.72 (1H, d), 6.65 (1H, d), 6.51 (1H, dd), 4.11-4.20 (1H, m), 3.67 (1H, s), 3.52 (2H, br. s.), 2.81-2.89 (1H, m), 2.16-2.25 (1H, m), 2.05-2.16 (1H, m), 1.02 (3H, d). UPLC_B: 0.75 min, 257 [M+H]+.

Intermediate 120

1,1-dimethylethyl [1,1-dimethyl-2-({6-[(3-methyl-3,4-dihydro-2H-chromen-5-yl)oxy]-3-pyridinyl}amino)-2-oxoethyl]carbamate

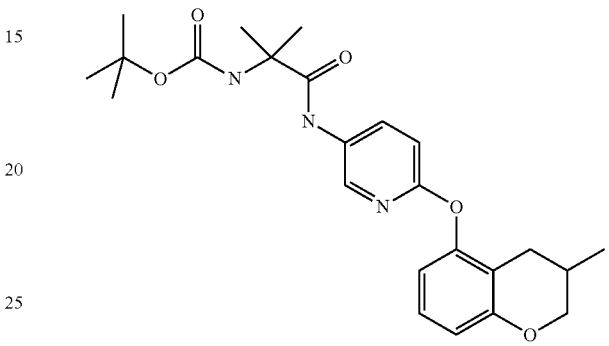

In a 8 ml vial 6-[(3-methyl-3,4-dihydro-2H-chromen-5-yl)oxy]-3-pyridinamine (Intermediate 119, 131.4 mg) was dissolved in N,N-dimethylformamide (2 ml) to give a pale yellow solution. DIPEA (0.215 ml, 1.230 mmol), N-{[(1,1-dimethylethyl)oxy]carbonyl}-2-methylalanine (188 mg, 0.923 mmol) and HATU (351 mg, 0.923 mmol) were added. The reaction mixture was shaken at 60° C. After 3 hours, the reaction mixture was evaporated under a vacuum to give the crude product which was purified via Biotage SP1 (with Cyclohexane/EtOAc as eluents from 3:1 to 1:2 in 15 CV; then 1:2 for 5 CV; 25 g SNAP Silica column.) The collected fractions afforded the title as a white solid (104.0 mg).

¹H NMR (400 MHz, DMSO-d₆) δ ppm 9.58 (1H, br. s.), 8.29 (1H, br. s.), 7.97-8.13 (1H, m), 7.08 (1H, t), 7.00 (1H, br. s.), 6.93 (1H, d), 6.63 (1H, dd), 6.53 (1H, dd), 4.08-4.17 (1H, m), 3.62 (1H, dd), 2.58-2.71 (1H, m), 1.92-2.13 (2H, m), 1.36 (15H, br. s.), 0.93 (3H, d). UPLC_B: 0.91 min, 442 [M+H]+.

Intermediate 121

2-methyl-N1-{6-[(3-methyl-3,4-dihydro-2H-chromen-5-yl)oxy]-3-pyridinyl}alaninamide

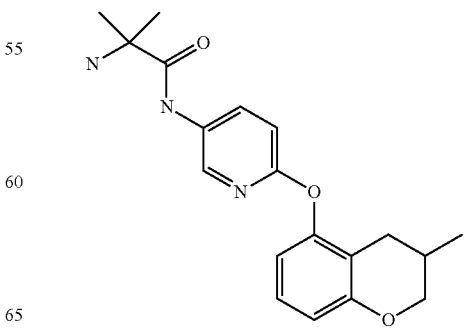

In a 50 ml round-bottomed flask 1,1-dimethylethyl [1,1-dimethyl-2-({6-[(3-methyl-3,4-dihydro-2H-chromen-5-yl)oxy]-3-pyridinyl}amino)-2-oxoethyl]carbamate (Intermediate 120, 104.0 mg) was dissolved in dichloromethane (6 ml) to give a pale yellow solution. The reaction mixture was cooled at 0° C. and TFA (2 ml, 26.0 mmol) was added. The reaction mixture was stirred at 0° C. After 2 h 30 min, the mixture was evaporated under vacuum to give the crude product which was charged on a 5 g SCX cartridge. It was then flushed with 40 ml of methanol followed by 40 ml of a 2M solution of ammonia in methanol. The ammonia eluate was evaporated under vacuum to give the title compound as a colourless oil (72.6 mg).

¹H NMR (400 MHz, CDCl₃) δ ppm 9.90 (1H, br. s.), 8.17-8.26 (2H, m), 7.10 (1H, t), 6.84 (1H, d), 6.70 (1H, d), 6.56-6.62 (1H, m), 4.12-4.22 (1H, m), 3.67 (1H, t), 2.70-2.85 (1H, m), 2.13 (2H, s), 1.47 (6H, s), 1.00 (3H, d), NH2 Missed. UPLC_B: 0.78 min, 342 [M+H]+.

Intermediate 122

1a-methyl-7-{[(methyloxy)methyl]oxy}-1a,7b-dihydrocyclopropa[c]chromen-2(1H)-one

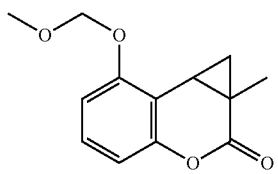 [SMILES: COCOc1cccc2c1C1CC1(C)C(=O)O2]

To a solution of trimethylsulfoxonium iodide (4.52 g, 20.55 mmol) in dry dimethyl sulfoxide (50 ml) stirred under nitrogen at room temperature was added neat sodium hydride (60%, 0.822 g, 20.55 mmol). The reaction mixture was stirred at room temperature for 1 hour before adding 3-methyl-5-{[(methyloxy)methyl]oxy}-2H-chromen-2-one (Intermediate 113, 1.81 g) dissolved into 15 ml of DMSO. The reaction mixture turned yellow and was heated and stirred at 100° C. for 4 h. The reaction was then worked up by the addition of a saturated solution of NH₄Cl and extracted with diethyl ether, washed with brine, dried over sodium sulphate, filtered and concentrated under vacuum. The residue obtained was purified by silica gel chromatography (Biotage system, with a gradient from pure cyclohexane to cyclohexane/ethyl acetate 5/1) to give the title compound as a white solid (360 mg).

¹H NMR (400 MHz, CDCl₃): δ ppm 7.10 (1H, t), 6.88 (1H, d), 6.67 (1H, d), 5.26 (2H, s), 3.53 (3H, s), 2.71 (1H, dd), 1.58 (1H, dd), 1.44 (3H, s), 1.08 (1H, t); UPLC_ipqc: 0.96 min, 235 [M+H]+.

Intermediate 123

2-[2-(hydroxymethyl)-2-methylcyclopropyl]-3-{[(methyloxy)methyl]oxy}phenol

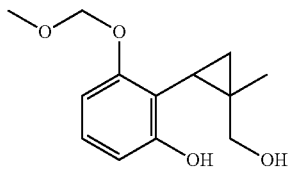 [SMILES: COCOc1cccc(O)c1C1CC1(C)CO]

To a solution of 1a-methyl-7-{[(methyloxy)methyl]oxy}-1a,7b-dihydrocyclopropa[c]chromen-2(1H)-one (Intermediate 122, 360 mg) in dry tetrahydrofuran (15 ml) stirred under nitrogen at 0° C. was added a solution of lithium aluminium hydride (1.0 M in THF, 1.537 ml, 1.537 mmol) and the reaction mixture was stirred at that temperature for 20 minutes. The reaction was then diluted with THF (20 ml) and quenched with the addition of Na₂SO₄.10H₂O (10 eq) leaving the mixture under stirring for 30 minutes. The reaction was diluted with ethyl acetate, dried over Na₂SO₄, filtered and concentrated under vacuum. The residue obtained was purified by silica gel chromatography (Companion system, with a gradient from cyclohexane/ethyl acetate 5/1 to cyclohexane/ethyl acetate 1/1) to give the title compound as a white solid (307 mg).

¹H NMR (400 MHz, CDCl₃): δ ppm 7.40 (1H, br. s.), 7.06 (1H, t), 6.67 (1H, d), 6.59 (1H, d), 5.12-5.27 (2H, m), 3.57-3.68 (1H, m), 3.53 (3H, s), 3.42-3.51 (1H, m), 2.98 (1H, d), 1.54 (1H, dd), 1.41 (3H, s), 1.05 (1H, dd), 0.86 (1H, dd); UPLC_ipqc: 0.73 min, 237 [M−H]+.

Intermediate 124

1a-methyl-7-{[(methyloxy)methyl]oxy}-1,1a,2,7b-tetrahydrocyclopropa[c]chromene

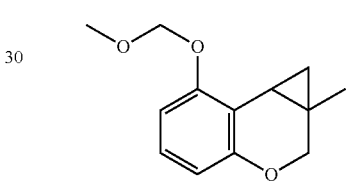

To a solution of 2-[2-(hydroxymethyl)-2-methylcyclopropyl]-3-{[(methyloxy)methyl]oxy}phenol (Intermediate 123, 307 mg) in dry tetrahydrofuran (10 ml) were added triphenylphosphine (338 mg, 1.288 mmol) and bis(1-methylethyl) (E)-1,2-diazenedicarboxylate (261 mg, 1.288 mmol). The reaction turned yellow and was stirred for 20 minutes at room temperature under nitrogen. The solvent was then evaporated under vacuum to give the crude product as pale yellow oil. The residue obtained was purified by silica gel chromatography (Companion system, with a gradient from pure Cyclohexane to cyclohexane/ethyl acetate 10/1) to give the title compound as a white solid (280 mg).

¹H NMR (400 MHz, CDCl₃): δ ppm 6.97 (1H, t), 6.73 (1H, d), 6.53 (1H, d), 5.15-5.30 (2H, m), 4.17 (1H, d), 3.67 (1H, d), 3.54 (3H, s), 2.15 (1H, dd), 1.27 (3H, s), 1.20 (1H, t), 0.94 (1H, dd); UPLC_ipqc: 1.15 min, 221 [M+H]+.

Intermediate 125

1a-methyl-1,1a,2,7b-tetrahydrocyclopropa[c]chromen-7-ol

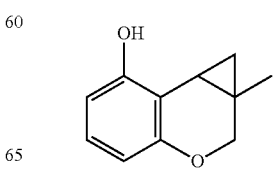

To a solution of 1a-methyl-7-{[(methyloxy)methyl]oxy}-1,1a,2,7b-tetrahydrocyclopropa[c]chromene (Intermediate 124, 280 mg) in methanol (16 ml) of a 2.0 M aqueous solution of HCl (1.271 ml, 2.54 mmol) was added. The reaction mixture was stirred at 50° C. for 2 hours and then at room temperature overnight at which time the reaction still showed some unreacted starting material, therefore more 2.0 M HCl was added (2 eq.) and stirring was continued at 50° C. for 2 hours. The reaction mixture was then quenched with water and diluted and extracted with dichloromethane, washed with brine, dried over sodium sulphate, filtered and concentrated under vacuum. The residue obtained was purified by silica gel chromatography (Companion system, with a gradient from pure cyclohexane to cyclohexane/ethyl acetate 5/1) to give the title compound as a white solid (192 mg).

$^1$H NMR (400 MHz, CDCl$_3$): δ ppm 6.91 (1H, t), 6.40-6.53 (2H, m), 5.00 (1H, s), 4.18 (1H, d), 3.72 (1H, d), 2.00 (1H, dd), 1.29 (3H, s), 1.20 (1H, t), 0.98 (1H, dd); UPLC_ipqc: 0.91 min, 177 [M+H]+.

Intermediate 126

2-[(1a-methyl-1,1a,2,7b-tetrahydrocyclopropa[c]chromen-7-yl)oxy]-5-nitropyridine

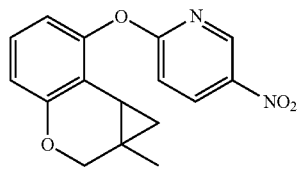 [SMILES: CC12COc3cccc(Oc4ccc([N+](=O)[O-])cn4)c3C1C2]

To a solution of 1a-methyl-1,1a,2,7b-tetrahydrocyclopropa[c]chromen-7-ol (Intermediate 125, 190 mg) in dry N,N-dimethylformamide (10 ml) were added K$_2$CO$_3$ (447 mg, 3.23 mmol) and 2-chloro-5-nitropyridine (171 mg, 1.078 mmol) to give a light brown solution. The reaction was heated at 110° C. for 1 hour and then quenched with water, extracted with ethyl acetate, washed with brine, dried over sodium sulphate, filtered and concentrated under vacuum. The residue obtained was purified by silica gel chromatography (Companion system, with a gradient from pure Cyclohexane to cyclohexane/ethyl acetate 5/1) to give the title compound as a light brown solid (250 mg).

$^1$H NMR (400 MHz, CDCl$_3$): δ ppm 9.12 (1H, d), 8.51 (1H, dd), 7.12 (1H, t), 7.04 (1H, d), 6.81 (1H, d), 6.75 (1H, dd), 4.22 (1H, d), 3.74 (1H, d), 1.73 (1H, dd), 1.23 (1H, t), 1.21 (3H, s), 0.85 (1H, dd); UPLC_ipqc: 1.21 min, 299 [M+H]+.

Intermediate 127

6-[(1a-methyl-1,1a,2,7b-tetrahydrocyclopropa[c]chromen-7-yl)oxy]-3-pyridinamine

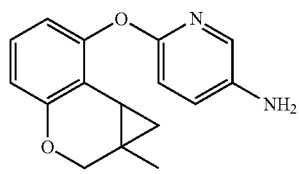 [SMILES: CC12COc3cccc(Oc4ccc(N)cn4)c3C1C2]

To a solution of 2-[(1a-methyl-1,1a,2,7b-tetrahydrocyclopropa[c]chromen-7-yl)oxy]-5-nitropyridine (Intermediate 126, 250 mg) in tetrahydrofuran (6 ml)/water (3 ml) were added iron (234 mg, 4.19 mmol) and ammonium chloride (224 mg, 4.19 mmol). The reaction mixture was stirred at room temperature overnight at which time UPLC showed partial formation of the target compound with some hydroxyl-amine intermediate, therefore additional 3 equivalents of ammonium chloride and iron were added and the reaction was left stirring for an other 5 hours. The iron was then filtered off over a pad of celite and the solution was diluted with an aqueous saturated solution of NaHCO$_3$ (100 ml) and ethyl acetate (200 ml). Two phases were separated and the aqueous layer was extracted with ethyl acetate. Organic layers were combined, dried over sodium sulphate, filtered and evaporated. The residue was purified by silica gel chromatography (Companion system, with a gradient from cyclohexane/ethyl acetate 8:2 to cyclohexane/ethyl acetate 1:1) to give the title compound as a light brown solid (150 mg).

$^1$H NMR (400 MHz, CDCl$_3$): δ ppm 7.75 (1H, d), 7.08 (1H, dd), 6.99 (1H, t), 6.73 (1H, d), 6.64 (1H, d), 6.59 (1H, d), 4.17 (1H, d), 3.70 (1H, d), 3.50 (2H, br. s.), 2.00 (1H, dd), 1.17-1.23 (4H, m), 0.85 (1H, dd); UPLC_ipqc: 0.88 min, 269 [M+H]+.

Intermediate 128

1,1-dimethylethyl [1,1-dimethyl-2-({6-[(1a-methyl-1,1a,2,7b-tetrahydrocyclopropa[c]chromen-7-yl)oxy]-3-pyridinyl}amino)-2-oxoethyl]carbamate

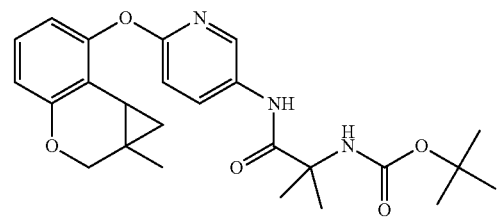 [SMILES: CC(C)(C)OC(=O)NC(C)(C)C(=O)Nc1ccc(Oc2cccc3c2C2CC2(C)CO3)nc1]

To a solution of 6-[(1a-methyl-1,1a,2,7b-tetrahydrocyclopropa[c]chromen-7-yl)oxy]-3-pyridinamine (Intermediate 127, 150 mg) in dry N,N-dimethylformamide (10 ml) DIPEA (0.352 ml, 2.013 mmol), N-{[(1,1-dimethylethyl)oxy]carbonyl}-2-methylalanine (307 mg, 1.509 mmol) and HATU (574 mg, 1.509 mmol) were added. The reaction mixture was heated at 60° C. for 2.5 hours. The organic phase was washed with saturated brine, extracted with diethyl ether, dried over sodium sulphate, filtered and concentrated under vacuum. The residue was purified by silica gel chromatography (Companion system, with a gradient from cyclohexane/ethyl acetate 8:2 to cyclohexane/ethyl acetate 1:1) to give the title compound as a white solid (135 mg).

$^1$H NMR (400 MHz, CDCl$_3$): δ ppm 8.17 (1H, d), 8.13 (1H, dd), 7.03 (1H, t), 6.86 (1H, d), 6.69 (2H, t), 5.86 (1H, br. s.), 4.89 (1H, br. s.), 4.18 (1H, d), 3.71 (1H, d), 1.90 (1H, dd), 1.60 (6H, s), 1.45 (9H, s), 1.15-1.23 (4H, m), 0.84 (1H, dd); UPLC_ipqc: 1.18 min, 454 [M+H]+.

Intermediate 129

2-methyl-$N^1$-{6-[(1a-methyl-1,1a,2,7b-tetrahydrocyclopropa[c]chromen-7-yl)oxy]-3-pyridinyl}alaninamide

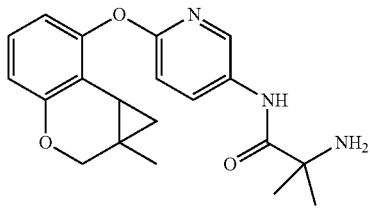 [SMILES: CC(C)(N)C(=O)Nc1ccc(Oc2cccc3c2C2CC2(C)CO3)nc1]

To a solution of 1,1-dimethylethyl [1,1-dimethyl-2-({6-[(1a-methyl-1,1a,2,7b-tetrahydrocyclopropa[c]chromen-7-yl)oxy]-3-pyridinyl}amino)-2-oxoethyl]carbamate (Intermediate 128, 135 mg, 0.298 mmol) in dry dichloromethane (10 ml) at 0° C. TFA (5 ml, 64.9 mmol) was slowly added and the reaction mixture was stirred for 2 hours at the same temperature. The solvent and the excess of TFA were evaporated and the residue was dissolved in dichloromethane and a saturated solution of $NaHCO_3$ was slowly added while the pH was allowed to reach 8. Two phases were separated and the organic layer was dried over sodium sulphate, filtered and evaporated affording the title compound as a colourless oil used as it was without any further purification (105 mg).

$^1$H NMR (400 MHz, $CDCl_3$): δ ppm 9.94 (1H, br. s.), 8.19-8.30 (2H, m), 7.03 (1H, t), 6.85 (1H, d), 6.70 (1H, d), 6.67 (1H, d), 4.18 (1H, d), 3.71 (1H, d), 1.91 (1H, dd), 1.72 (2H, br. s.), 1.48 (6H, s), 1.15-1.23 (4H, m), 0.84 (1H, dd); UPLC_ipqc: 0.76 min, 354 [M+1]+.

Intermediate 130 ethyl (2-({[(1,1-dimethylethyl)(dimethyl)silyl]oxy}methyl)-6-{[(methyloxy)methyl]oxy}phenyl)(oxo)acetate

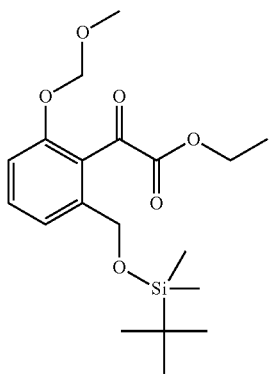 [SMILES: CCOC(=O)C(=O)c1c(CO[Si](C)(C)C(C)(C)C)cccc1OCOC]

To a solution of (1,1-dimethylethyl)(dimethyl){[(3-{[(methyloxy)methyl]oxy}phenyl)methyl]oxy}silane (Intermediate 103, 3 g) in dry n-hexane (30 mL) a solution of BuLi in hexane (1.6M, 7.63 mL, 12.21 mmol) was added and the reaction mixture was stirred for 2 hours at room temperature The reaction mixture was cooled to −78° C. and it was added (via cannulation) to a solution of ethyl chloro(oxo)acetate (1.780 mL, 15.93 mmol) in dry tetrahydrofuran (20 mL) at −78° C. The reaction was quenched with water (20 ml) and extracted with ethyl acetate (2×30 ml). The organic layer was dried over sodium sulphate, filtered and evaporated and the residue was purified by flash chromatography (Biotage system) on silica gel using a 100 g SNAP column and cyclohexane to cyclohexane/ethyl acetate 8:2 as eluents. This afforded the title compound as a yellow pale oil (2.67 g).

$^1$H NMR (400 MHz, DMSO-$d_6$): δ ppm 7.53 (1H, t), 7.20 (1H, d), 7.15 (1H, d), 5.21 (2H, s), 4.76 (2H, s), 4.27 (2H, q), 3.34 (3H, s), 1.27 (3H, t), 0.86 (9H, s), 0.05 (6H, s).

Intermediate 131

Dimethyltitanocene

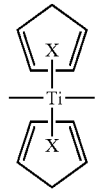

To a suspension of dichlorotitanocene (8.3 g, 33.3 mmol) in dry toluene (100 mL) at −10° C. a solution of methyllithium in $Et_2O$ (1.6M, 47.3 mL, 76 mmol) was slowly added (20 minutes) and the reaction mixture was stirred for 45 minutes at the same temperature. The reaction mixture was added (via cannulation) to a solution of ammonium chloride (1.2 g) in water (24 ml) cooled to −10° C. Two phases were separated and the organic layer was washed with cool water (3×20 ml) and brine (1×20 ml), dried over sodium sulphate filtered and concentrated under reduced pressure to 60 ml containing 9% w/w of dimethyltitanocene (5.04 g, 24 mmol) in toluene.

$^1$H NMR (400 MHz, DMSO-$d_6$): δ ppm 6.10 (10H, s), −0.11 (6H, s).

Intermediate 132 ethyl2-(2-({[(1,1-dimethylethyl)(dimethyl)silyl]oxy}methyl)-6-{[(methyloxy)methyl]oxy}phenyl)-2-propenoate

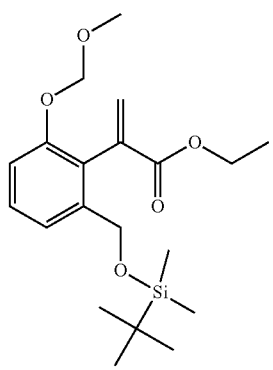 [SMILES: C=C(C(=O)OCC)c1c(CO[Si](C)(C)C(C)(C)C)cccc1OCOC]

To a solution of ethyl (2-({[(1,1-dimethylethyl)(dimethyl)silyl]oxy}methyl)-6-{[(methyloxy)methyl]oxy}phenyl)(oxo)acetate (Intermediate 130, 1.4 g) in dry toluene (8 ml) dimethyl titanocene 9% w/w in toluene (Intermediate 131, 30 ml) was added and the reaction mixture was stirred for 1.5 hours at 90° C. After cooling the reaction was diluted with water (20 ml) and ethyl acetate (30 ml). Two phases were separated and the organic layer was dried over sodium sulphate, filtered and evaporated and the residue was purified by flash chromatography (Biotage system) on silica gel using a 100 g SNAP column and cyclohexane to cyclohexane/ethyl acetate 9:1 as eluents. This afforded the title compound as a yellow pale oil (865 mg).

$^1$H NMR (400 MHz, DMSO-$d_6$): δ ppm 7.30 (1H, t), 7.12 (1H, d), 7.02 (1H, d), 6.46 (1H, d), 5.74 (1H, d), 5.12 (2H, s), 4.54 (2H, s), 4.12 (2H, q), 3.32 (3H, s), 1.16 (3H, t), 0.88 (9H, s), 0.04 (6H, s); UPLC_IPQC: 1.54 min, 381 [M+H]+.

Intermediate 133 ethyl 1-(2-({[(1,1-dimethylethyl)(dimethyl)silyl]oxy}methyl)-6-{[(methyloxy)methyl]oxy}phenyl)cyclopropanecarboxylate

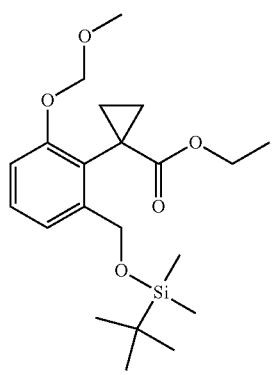 [SMILES: CCOC(=O)C1(c2c(CO[Si](C)(C)C(C)(C)C)cccc2OCOC)CC1]

To a solution of Trimethylsulfoxonium Iodide (816 mg, 3.71 mmol) in dry Dimethyl Sulfoxide (10 mL) NaH 60% disp in mineral oil (140 mg, 3.49 mmol) was added and the reaction mixture was stirred for 30 minutes at room temperature. A solution of ethyl 2-(2-({[(1,1-dimethylethyl)(dimethyl)silyl]oxy}methyl)-6-{[(methyloxy)methyl]oxy}phenyl)-2-propenoate (Intermediate 132, 830 mg) in dry dimethyl sulfoxide (5 mL) was added and the reaction mixture was stirred for 30 minutes at room temperature The reaction was quenched with ice, diluted with brine (10 ml) and water (10 ml) and extracted with ethyl acetate (2×30 ml). The organic layer was washed with water (3×15 ml) and brine (1×20 ml), dried over sodium sulphate, filtered and evaporated and the residue was purified by flash chromatography (Biotage system) on silica gel using a 50 g SNAP column and cyclohexane to cyclohexane/ethyl acetate 7:3 as eluent. This afforded the title compound as a colourless oil (780 mg).

$^1$H NMR (400 MHz, DMSO-$d_6$, 65° C.): δ ppm 7.25 (1H, t), 7.12 (1H, d), 6.98 (1H, d), 5.19 (2H, s), 4.78 (2H, br.s), 4.01 (2H, q), 3.41 (3H, s), 1.55-1.65 (2H, m), 1.13-1.21 (2H, m), 1.08 (3H, t), 0.94 (9H, s), 0.11 (6H, s); UPLC_IPQC: 1.57 min, 395 [M+H]+.

Intermediate 134

(2-[1-(hydroxymethyl)cyclopropyl]-3-{[(methyloxy)methyl]oxy}phenyl)methanol

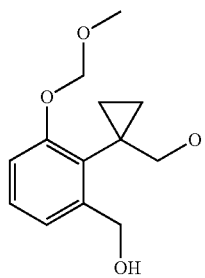 [SMILES: COCOc1cccc(CO)c1C1(CO)CC1]

To a solution of ethyl 1-(2-({[(1,1-dimethylethyl)(dimethyl)silyl]oxy}methyl)-6-{[(methyloxy)methyl]oxy}phenyl)cyclopropanecarboxylate (Intermediate 133, 780 mg) in dry tetrahydrofuran (20 ml) at 0° C., a solution of LiAlH4 in THF (1M, 2.076 mL, 2.076 mmol) was slowly added and the reaction mixture was stirred for 2 hours at the same temperature. The reaction was quenched with water (10 ml) and brine (10 ml) and diluted with ethyl acetate (30 ml). The solid was filtered off and two phases were separated. The aqueous layer was extracted with ethyl acetate (30 ml) and the combined organic layers were dried over sodium sulphate, filtered and evaporated to afford the alcohol intermediate as a colourless oil. It was dissolved in dry tetrahydrofuran (20.00 mL) and TBAF 1M solution in THF (2.076 mL, 2.076 mmol) was slowly added at 0° C. The reaction mixture was stirred for 1 hour at the same temperature. The reaction was quenched with water (10 ml) and brine (10 ml) and extracted with ethyl acetate (2×30 ml). The organic layer was dried over sodium sulphate, filtered and evaporated and the residue was purified by flash chromatography (Biotage system) on silica gel using a 50 g SNAP column and cyclohexane/ethyl acetate as eluents from 7:3 to 3:7. This afforded the title compound (450 mg) as a white crystal solid.

$^1$H NMR (400 MHz, DMSO-$d_6$): δ ppm 7.16 (1H, t), 7.07 (1H, d), 6.92 (1H, d), 5.17-5.24 (2H, m), 5.00 (1H, t), 4.67-4.74 (3H, m), 3.65-3.76 (1H, m), 3.41 (3H, s), 3.11-3.21 (1H, m), 0.83-0.94 (2H, m), 0.65-0.77 (1H, m), 0.51-0.61 (1H, m).

Intermediate 135

5-{[(methyloxy)methyl]oxy}-1H-spiro[2-benzopyran-4,1'-cyclopropane]

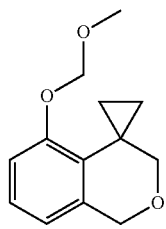 [SMILES: COCOc1cccc2c1C1(CC1)COC2]

To a solution of (2-[1-(hydroxymethyl)cyclopropyl]-3-{[(methyloxy)methyl]oxy}phenyl)methanol (Intermediate 134, 450 mg) in dry tetrahydrofuran (10 ml) at 0° C., a solution of BuLi in hexane (1.6M, 1.180 mL, 1.889 mmol) was slowly added and the reaction mixture was stirred for 15 minutes at the same temperature. A solution of tosyl chloride (360 mg, 1.889 mmol) in dry tetrahydrofuran (5 ml) was slowly added and the reaction mixture was stirred for 15 minutes at 0° C. A second equivalent of a solution of BuLi in hexane (1.6M, 1.180 mL, 1.889 mmol) was added and the reaction mixture was stirred for 30 minutes at the same temperature. The reaction was quenched with an aqueous saturated solution of NaHCO$_3$ (10 ml) diluted with water (10 ml) and extracted with ethyl acetate (2×30 ml). The organic layer was dried over sodium sulphate, filtered and evaporated and the residue was purified by flash chromatography (Biotage system) on silica gel using a 25 g SNAP column and cyclohexane/ethyl acetate as eluents from 100:0 to 8:2. This afforded the title compound 5-{[(methyloxy)methyl]oxy}-1H-spiro[2-benzopyran-4,1'-cyclopropane] as a colourless oil (385 mg).

$^1$H NMR (400 MHz, DMSO-d$_6$): δ ppm 7.04 (1H, t), 6.83 (1H, d), 6.68 (1H, d), 5.11 (2H, s), 4.75 (2H, s), 3.49 (2H, s), 3.37 (3H, s), 1.64-1.70 (2H, m), 0.56-0.61 (2H, m).

Intermediate 136

1H-spiro[2-benzopyran-4,1'-cyclopropan]-5-ol

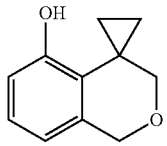

To a solution of 5-{[(methyloxy)methyl]oxy}-1H-spiro[2-benzopyran-4,1'-cyclopropane] (Intermediate 135, 380 mg) in methanol (10 mL) HCl 10% in water (1.048 mL, 3.45 mmol) was added and the reaction mixture was stirred overnight at 50° C. The combined solvents were evaporated and the residue was purified by flash chromatography (Biotage system) on silica gel using a 25 g SNAP column and cyclohexane/ethyl acetate as eluents from 100:0 to 8:2. This afforded the title compound as a white solid (260 mg).

$^1$H NMR (400 MHz, DMSO-d$_6$): δ ppm 9.18 (1H, s), 6.88 (1H, t), 6.56 (1H, d), 6.47 (1H, d), 4.71 (2H, s), 3.47 (2H, s), 1.69-1.74 (2H, m), 0.47-0.52 (2H, m).

Intermediate 137

5-nitro-2-(1H-spiro[2-benzopyran-4,1'-cyclopropan]-5-yloxy)pyridine

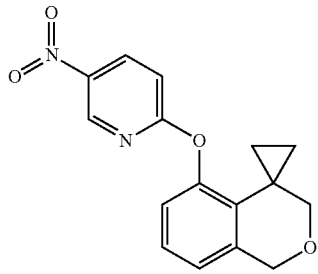 [SMILES: O=[N+]([O-])c1ccc(Oc2cccc3c2C2(CC2)COC3)nc1]

To a solution of 1H-spiro[2-benzopyran-4,1'-cyclopropan]-5-ol (Intermediate 136, 150 mg) in dry N,N-dimethylformamide (4 ml) potassium carbonate (176 mg, 1.277 mmol) and then 2-chloro-5-nitropyridine (148 mg, 0.936 mmol) were added and the reaction mixture was stirred for 1 h at 110° C. After cooling the reaction was quenched with brine (1 ml), diluted with water (5 ml) and extracted with ethyl acetate (3×15 ml). The organic layer was washed with ice cold brine (2×10 ml), dried over sodium sulphate, filtered and evaporated and the residue was purified by flash chromatography (Biotage system) on silica gel using a 25 g SNAP column and cyclohexane/ethyl acetate as eluents from 100:0 to 7:3. This afforded the title compound as a colourless gum (240 mg).

$^1$H NMR (400 MHz, DMSO-d$_6$): δ ppm 9.05 (1H, d), 8.64 (1H, dd), 7.24 (1H, d), 7.20 (1H, t), 7.01 (1H, d), 6.88 (1H, d), 4.86 (2H, s), 3.53 (2H, s), 1.23-1.27 (2H, m), 0.63-0.68 (2H, m); UPLC_IPQC: 1.08 min, 299 [M+H]+.

Intermediate 138

6-(1H-spiro[2-benzopyran-4,1'-cyclopropan]-5-yloxy)-3-pyridinamine

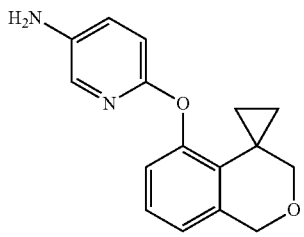 [SMILES: Nc1ccc(Oc2cccc3c2C2(CC2)COC3)nc1]

To a solution of 5-nitro-2-(1H-spiro[2-benzopyran-4,1'-cyclopropan]-5-yloxy)pyridine (Intermediate 137, 238 mg) in tetrahydrofuran (10 mL)/water (5 mL) iron (223 mg, 3.99 mmol) and then ammonium chloride (213 mg, 3.99 mmol) were added and the reaction mixture was stirred overnight at room temperature. The catalyst was filtered off and the solution was diluted with an aqueous saturated solution of NaHCO$_3$ and extracted with ethyl acetate (2×30 ml). The organic layer was dried over sodium sulphate filtered and evaporated and the residue was purified by flash chromatography (Biotage system) on silica gel using a 25 g SNAP column and cyclohexane/ethyl acetate as eluents from 7:3 to 3:7. This afforded the title compound (180 mg) as a light yellow solid.

$^1$H NMR (400 MHz, DMSO-d$_6$): δ ppm 7.51 (1H, d), 7.07 (1H, dd), 7.04 (1H, t), 6.80 (1H, d), 6.69 (1H, d), 6.53 (1H, d), 5.06 (2H, br.s), 4.81 (2H, s), 3.53 (2H, s), 1.49-1.53 (2H, m), 0.58-0.62 (2H, m).

Intermediate 139

S-2-pyridinyl (2R)-2-({[(1,1-dimethylethyl)oxy]carbonyl}amino)-2-methylbutanethioate

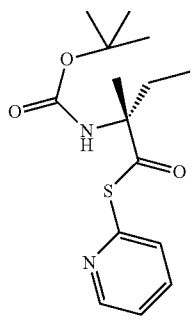 [SMILES: CC[C@@](C)(NC(=O)OC(C)(C)C)C(=O)Sc1ccccn1]

To a solution of N-{[(1,1-dimethylethyl)oxy]carbonyl}-D-isovaline (100 mg, 0.460 mmol) in dry tetrahydrofuran (THF) (10 ml) 2,2'-dithiodipyridine (254 mg, 1.151 mmol) and triphenylphosphine (302 mg, 1.151 mmol) were added. The mixture was stirred at room temperature for 3 hours. THE was evaporated under vacuum. The residue was purified by flash chromatography on silica gel using a 25 g the title compound (78 mg, 0.251 mmol) as a white solid.

$^1$H NMR (400 MHz, DMSO-$d_6$) δ ppm 8.59 (1H, d), 7.87 (1H, t), 7.70 (1H, br.s.), 7.51 (1H, d), 7.41 (t, 1H), 2.02-1.84 (1H, m), 1.74-1.60 (1H, m), 1.43 (9H, s), 1.33 (3H, s), 0.81 (3H, t).

UPLC_IPQC: 1.01 min, 311 [M+H]+.

Intermediate 140

1,1-dimethylethyl [(1R)-1-methyl-1-({[6-(1H-spiro[2-benzopyran-4,1'-cyclopropan]-5-yloxy)-3-pyridinyl]amino}carbonyl)propyl]carbamate

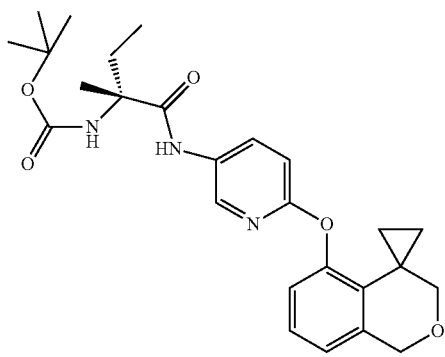 [SMILES: CC[C@@](C)(NC(=O)OC(C)(C)C)C(=O)Nc1ccc(Oc2cccc3c2C2(CC2)COC3)nc1]

To a solution of 6-(1H-spiro[2-benzopyran-4,1'-cyclopropan]-5-yloxy)-3-pyridinamine (Intermediate 138, mg, 0.242 mmol) in dry toluene (4 mL) S-2-pyridinyl (2R)-2-({[(1,1-dimethylethyl)oxy]carbonyl}amino)-2-methylbutanethioate (Intermediate 139, 75 mg, 0.242 mmol) was added and the reaction mixture was stirred for 3 hours at 150° C. After cooling the solvent was removed under reduced pressure and the residue was purified by flash chromatography (Biotage system) on silica gel using a 10 g SNAP column and cyclohexane/ethyl acetate 9:1 to cyclohexane/ethyl acetate 1:1 as eluent affording the title compound as a white solid (64 mg).

$^1$H NMR (400 MHz, DMSO-$d_6$): δ ppm 9.63 (1H, br.s), 8.30 (1H, br.s), 8.01-8.16 (1H, m), 7.11 (1H, t), 6.87-6.95 (3H, m), 6.69 (1H, d), 4.83 (2H, s), 3.53 (2H, s), 1.70-1.90 (2H, m), 1.26-1.47 (14H, m), 0.78 (3H, t), 0.58-0.65 (2H, m); UPLC_IPQC: 1.14 min, 468 [M+H]+.

Intermediate 141

N$^1$-[6-(1H-spiro[2-benzopyran-4,1'-cyclopropan]-5-yloxy)-3-pyridinyl]-D-isovalinamide

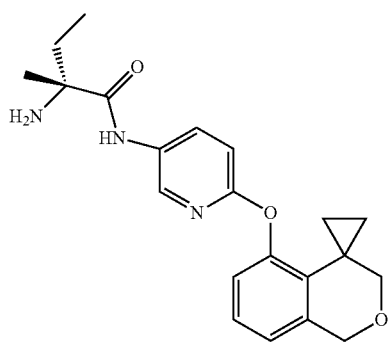 [SMILES: CC[C@@](C)(N)C(=O)Nc1ccc(Oc2cccc3c2C2(CC2)COC3)nc1]

To a solution of 1,1-dimethylethyl [(1R)-1-methyl-1-({[6-(1H-spiro[2-benzopyran-4,1'-cyclopropan]-5-yloxy)-3-pyridinyl]amino}carbonyl)propyl]carbamate (Intermediate 140, 62 mg) in dry dichloromethane (6 mL) at 0° C. TFA (2 ml, 26.0 mmol) was slowly added and the reaction mixture was stirred for 3 hours at the same temperature. The reaction mixture was diluted with dichloromethane (15 ml) and an aqueous saturated solution of NaHCO$_3$ was added while the pH was allowed to reach ~8. Two phases were separated and the organic layer was dried over sodium sulphate, filtered and evaporated and the residue was purified by flash chromatography (Biotage system) on silica gel using a 10 g SNAP column and dichloromethane/methanol as eluents from 99:1 to 95:5. This afforded the title compound as a white solid (42 mg, 86% yield).

$^1$H NMR (400 MHz, DMSO-$d_6$): δ ppm 8.40 (1H, d), 8.16 (1H, dd), 7.11 (1H, t), 0.94 (1H, d), 6.90 (1H, d), 6.69 (1H, d), 4.84 (2H, s), 3.53 (2H, s), 1.66-1.78 (1H, m), 1.46-1.58 (1H, m), 1.37-1.42 (2H, m), 1.24 (3H, s), 0.83 (3H, t), 0.59-0.64 (2H, m); UPLC_IPQC: 0.69 min, 368 [M+H]+.

Intermediate 142

1,1-dimethylethyl [2-({2-[(3,3-dimethyl-2,3-dihydro-1-benzofuran-4-yl)oxy]-5-pyrimidinyl}amino)-1,1-dimethyl-2-oxoethyl]carbamate

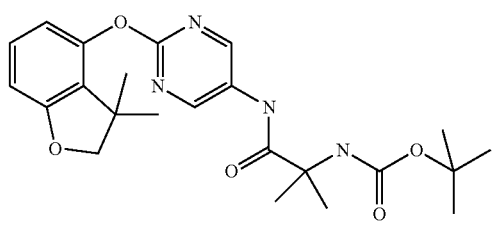 [SMILES: CC(C)(C)OC(=O)NC(C)(C)C(=O)Nc1cnc(Oc2cccc3c2C(C)(C)CO3)nc1]

To a solution of N-{[(1,1-dimethylethyl)oxy]carbonyl}-2-methylalanine (59.2 mg, 0.292 mmol) DIPEA (0.068 mL, 0.389 mmol) and then HATU (111 mg, 0.292 mmol) were added and the reaction mixture was stirred for 15 minutes at r.t. 2-[(3,3-dimethyl-2,3-dihydro-1-benzofuran-4-yl)oxy]-5-pyrimidinamine (Intermediate 65, 50 mg, 0.194 mmol) was then added and the reaction mixture was stirred for 18 hours at 50° C. The reaction was quenched with brine (1 ml), diluted with water (2 ml) and extracted with ethyl acetate (2×5 ml). The organic layer was dried (Na$_2$SO$_4$), filtered and evaporated and The residue was purified by flash chromatography (Biotage system) on silica gel using a column SNAP 25 g and cyclohexane to cyclohexane/ethyl acetate 7:3 as eluents affording the title compound (31 mg) as a white solid.

UPLC: 0.75 min, 443 [M+H]+.

Intermediate 143

N1-{2-[(3,3-dimethyl-2,3-dihydro-1-benzofuran-4-yl)oxy]-5-pyrimidinyl}-2-methylalaninamide

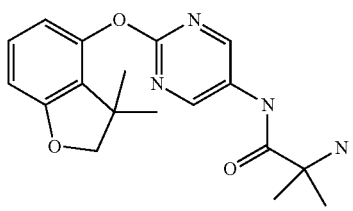 [SMILES: CC(C)(N)C(=O)Nc1cnc(Oc2cccc3c2C(C)(C)CO3)nc1]

To a solution of 1,1-dimethylethyl [2-({2-[(3,3-dimethyl-2,3-dihydro-1-benzofuran-4-yl)oxy]-5-pyrimidinyl}amino)-1,1-dimethyl-2-oxoethyl]carbamate (Intermediate 142, 30 mg, 0.068 mmol) in dry Dichloromethane (DCM) (1.6 mL) at 0° C. TFA (0.4 ml, 5.19 mmol) was slowly added and the reaction mixture was stirred for 1 h at the same temperature. The solvent and the excess of TFA were evaporated end the residue was dissolved in DCM (5 ml) and an aqueous saturated solution of NaHCO$_3$ was added while the pH was allowed to reach ~8-9. Two phases were separated and the organic layer was dried (Na$_2$SO$_4$), filtered and evaporated affording the title compound (20 mg) as a white solid.

UPLC: 0.51 min, 343 [M+H]+.

Intermediate 144

1,1-dimethylethyl{(1R)-1-[({2-[(3,3-dimethyl-2,3-dihydro-1-benzofuran-4-yl)oxy]-5-pyrimidinyl}amino)carbonyl]-2-methylpropyl}carbamate

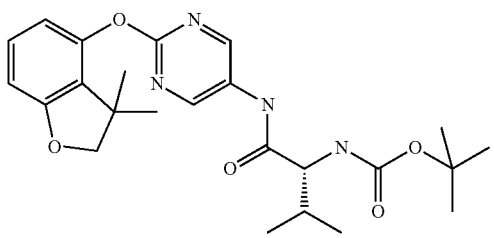 [SMILES: CC(C)[C@@H](NC(=O)OC(C)(C)C)C(=O)Nc1cnc(Oc2cccc3c2C(C)(C)CO3)nc1]

To a solution of Boc-D-Valine (63.3 mg, 0.292 mmol) in N,N-Dimethylformamide (DMF) (2 mL) DIPEA (0.068 mL, 0.389 mmol) and then HATU (111 mg, 0.292 mmol) were added and the reaction mixture was stirred for 15 minutes at r.t. 2-[(3,3-dimethyl-2,3-dihydro-1-benzofuran-4-yl)oxy]-5-pyrimidinamine (Intermediate 65, 50 mg, 0.194 mmol) was then added and the reaction mixture was stirred for 5 hours at 50° C. The reaction was quenched with brine (1 ml), diluted with water (2 ml) and extracted with ethyl acetate (2×5 ml). The organic layer was dried (Na$_2$SO$_4$), filtered and evaporated and The residue was purified by flash chromatography (Biotage system) on silica gel using a column SNAP 25 g and cyclohexane to cyclohexane/ethyl acetate 7:3 as eluent affording the title compound 1,1-dimethylethyl{(1R)-1-[({2-[(3,3-dimethyl-2,3-dihydro-1-benzofuran-4-yl)oxy]-5-pyrimidinyl}amino)carbonyl]-2-ethylpropyl}carbamate (55 mg, 0.120 mmol, 62.0% yield) as a white solid.

Intermediate 145

(2R)-2-amino-N-[2-[(3,3-dimethyl-2H-benzofuran-4-yl)oxy]pyrimidin-5-yl]-3-methyl-butanamide

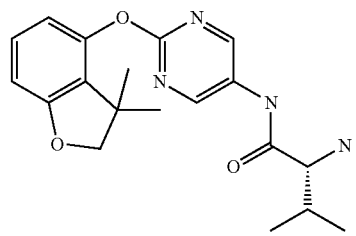 [SMILES: CC(C)[C@@H](N)C(=O)Nc1cnc(Oc2cccc3c2C(C)(C)CO3)nc1]

To a solution of 1,1-dimethylethyl {(1R)-1-[({2-[(3,3-dimethyl-2,3-dihydro-1-benzofuran-4-yl)oxy]-5-pyrimidinyl}amino)carbonyl]-2-methylpropyl}carbamate (Intermediate 144, 52 mg, 0.114 mmol) in dry Dichloromethane (DCM) (2 mL) at 0° C. TFA (0.5 ml, 6.49 mmol) was slowly added and the reaction mixture was stirred for 1 h at the same temperature. The solvent and the excess of TFA were evaporated end the residue was dissolved in DCM (5 ml) and an aqueous saturated solution of NaHCO$_3$ was added while the pH was allowed to reach ~8-9. Two phases were separated and the organic layer was dried (Na$_2$SO$_4$), filtered and evaporated affording the title compound (40 mg) as a white solid.

UPLC: 0.53 min, 357 [M+H]+.

Intermediate 146

Tert-butyl N-[(1R)-1-methyl-1-[[6-(3-methylchroman-5-yl)oxy-3-pyridyl]carbamoyl]propyl]carbamate

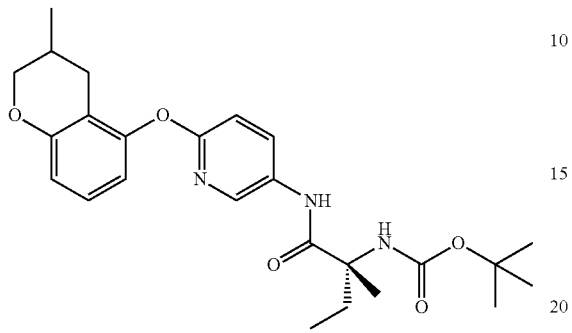

In a 8 mL 6-[(3-methyl-3,4-dihydro-2H-chromen-5-yl)oxy]-3-pyridinamine (Intermediate 119, 82.4 mg, 0.0305 mmol), (2R)-2-(tert-butoxycarbonylamino)-2-methyl-butanoic acid (59.7 mg, 0.275 mmol) and DIPEA (0.080 mL, 0.458 mmol) were dissolved in N,N-Dimethylformamide (DMF) (2 mL) to give a pale yellow solution. HATU (151 mg, 0.397 mmol) was added. The reaction mixture was stirred at room temperature over week-end. The reaction mixture was evaporated in vacuo and the residue was purified by flash chromatography on silica gel using a column SNAP 25 g and cyclohexane/ethyl acetate from 3:1 to 1:2 as eluents affording the title compound (55.8 mg) as white solid.

$^1$H NMR (400 MHz, CDCl$_3$) δ ppm 8.08-8.16 (2H, m), 7.10 (1H, t), 6.84 (1H, d), 6.70 (1H, d), 6.59 (1H, d), 6.13 (1H, br. s.), 4.90 (1H, br. s.), 4.12-4.22 (1H, m), 3.59-3.75 (1H, m), 2.59-2.92 (1H, m), 1.85-2.25 (3H, m), 1.69-1.84 (1H, m), 1.51 (3H, s), 1.45 (9H, s), 0.91-1.05 (6H, m). UPLC_ipqc: 1.22 min, 456 [M+H]+.

Intermediate 147

(2R)-2-amino-2-methyl-N-[6-(3-methylchroman-5-yl)oxy-3-pyridyl]butanamide

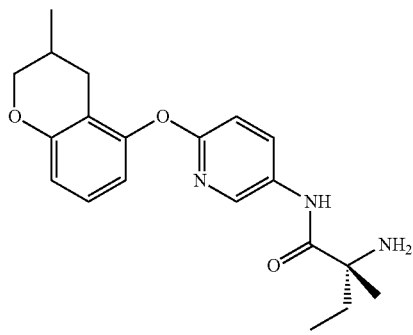 [SMILES: CC[C@@](C)(N)C(=O)Nc1ccc(Oc2cccc3c2CC(C)CO3)nc1]

In a 50 mL round-bottomed flask tert-butyl N-[(1R)-1-methyl-1-[[6-(3-methylchroman-5-yl)oxy-3-pyridyl]carbamoyl]propyl]carbamate (Intermediate 146, 55.8 mg, 0.104 mmol) was dissolved in Dichloromethane (3 mL) to give a pale yellow solution. The reaction mixture was cooled at 0° C. and TFA (2 mL, 26.0 mmol) was added. The reaction mixture was stirred at 0° C. for 2 hours. The reaction mixture was evaporated in vacuo to give the crude product as a yellow oil. The sample was charged on a 2 g SCX cartridge. It was then flushed with 36 mL of MeOH followed by 25 mL of 2M solution of ammonia in MeOH. The ammonia eluate was evaporated in vacuo affording the title compound (32.9 mg) as pale yellow oil.

$^1$H NMR (400 MHz, CDCl$_3$) δ ppm 9.88 (1H, br. s.), 8.14-8.28 (2H, m), 7.10 (1H, t), 6.83 (1H, d), 6.70 (1H, dd), 6.59 (1H, dd), 4.12-4.21 (1H, m), 3.61-3.72 (1H, m), 2.72-2.84 (1H, m), 2.04-2.24 (2H, m), 1.92-2.04 (1H, m), 1.52-1.84 (6H, m), 1.00 (3H, d), 0.94 (3H, t). UPLC_ipqc: 0.76 min, 356 [M+H]+.

Intermediate 148

1,1-dimethylethyl [2-({6-[(3-ethyl-1,3-dihydro-2-benzofuran-4-yl)oxy]-3-pyridinyl}amino)-1,1-dimethyl-2-oxoethyl]carbamate

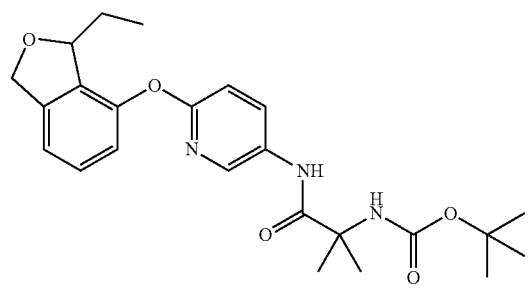 [SMILES: CCC1OCc2cccc(Oc3ccc(NC(=O)C(C)(C)NC(=O)OC(C)(C)C)cn3)c21]

In a 8 mL vial 6-[(3-ethyl-1,3-dihydro-2-benzofuran-4-yl)oxy]-3-pyridinamine (Intermediate 108, 55 mg, 0.215 mmol) was dissolved in N,N-Dimethylformamide (2 mL) to give a colourless solution. DIPEA (0.056 mL, 0.322 mmol), N-{[(1,1-dimethylethyl)oxy]carbonyl}-2-methylalanine (52.3 mg, 0.258 mmol) and, TBTU (83 mg, 0.258 mmol) were added. The reaction mixture was shakeNat 60° C. overnight. Additional DIPEA (0.1 mL), N-{[(1,1-dimethylethyl)oxy]carbonyl}-2-methylalanine (105 mg) and TBTU (170 mg) were added. The reaction mixture was shaken at 60° C. for additional 10 hours. The reaction mixture was evaporated in vacuo and the residue was purified by flash chromatography on silica gel using a column SNAP 25 g and cyclohexane/ethyl acetate from 2:1 to 1:1 as eluents affording the title compound (36.5 mg) as colorless oil solid.

$^1$H NMR (400 MHz, CDCl$_3$) δ ppm 8.12-8.17 (2H, m), 7.30 (1H, t), 7.05 (1H, d), 6.95 (1H, d), 6.89 (1H, d), 6.16 (1H, br. s.), 5.20-5.27 (1H, m), 5.17 (1H, dd), 5.10 (1H, d), 4.92 (1H, br. s.), 1.84-1.97 (1H, m), 1.66-1.78 (1H, m), 1.63 (6H, s), 1.45 (9H, s), 0.88 (3H, t). UPLC_B: 0.89 min, 442 [M+H]+.

Intermediate 149

N1-{6-[(3-ethyl-1,3-dihydro-2-benzofuran-4-yl)oxy]-3-pyridinyl}-2-methylalaninamide

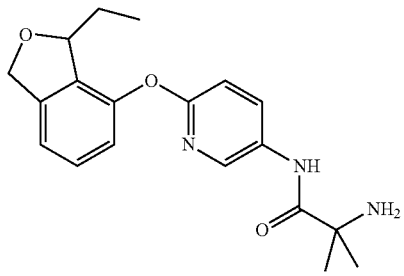 [SMILES: CCC1OCc2cccc(Oc3ccc(NC(=O)C(C)(C)N)cn3)c21]

In a 50 mL round-bottomed flask 1,1-dimethylethyl [2-({6-[(3-ethyl-1,3-dihydro-2-benzofuran-4-yl)oxy]-3-pyridinyl}amino)-1,1-dimethyl-2-oxoethyl]carbamate (Intermediate 148, 36.5 mg, 0.066 mmol) was dissolved in Dichloromethane (3 mL) to give a colourless solution. The reaction mixture was cooled at 0° C. and TFA (1.5 mL, 19.47 mmol) was added at that temperature. The reaction mixture was stirred at 0° C. for 1.5 hours. The reaction mixture was evaporated in vacuo affording and the residue was charged on a 2 g SCX cartridge. It was then flushed with 15 mL of MeOH followed by 15 mL of 2M solution of ammonia in MeOH. The ammonia eluate was evaporated in vacuo affording the title compound (17.2 mg) as colorless oil.

$^1$H NMR (400 MHz, CDCl$_3$) δ ppm 9.91 (1H, br. s.), 8.26 (1H, dd), 8.20 (1H, d), 7.30 (1H, t), 7.05 (1H, d), 6.94 (1H, d), 6.90 (1H, d), 5.21-5.27 (1H, m), 5.17 (1H, dd), 5.10 (1H, d), 1.83-1.98 (1H, m), 1.68-1.79 (1H, m), 1.47 (6H, s), 0.88 (3H, t). UPLC_B: 0.74 min, 342 [M+H]+.

Intermediate 150

2,4-bis(methoxymethoxy)-1-methyl-benzene

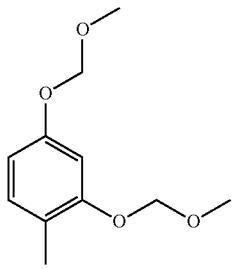

To a solution of 4-methylbenzene-1,3-diol (4 g, 32.26 mmol) in dry N,N-Dimethylformamide (30 ml) at 0° C. sodium hydride (60% dispersion in mineral oil) (3.87 g, 96.78 mmol) was added and the reaction mixture was stirred for 15 minutes at the same temperature. MOM-Cl (7.35 ml, 96.78 mmol) was quickly added and the reaction mixture was stirred for 1 hour while the temperature was allowed to reach room temperature. The reaction was quenched with brine (40 ml) and extracted with ethyl acetate (3×80 ml). The organic layer was washed with ice cold brine (2×50 ml), dried over sodium sulphate, filtered and evaporated and the residue was purified by flash chromatography (Biotage system) on silica gel using a 100 g SNAP column and cyclohexane to cyclohexane/ethyl acetate 8:2 as eluents affording the title compound (6.1 g) as a colourless oil.
LC/MS: QC_3_MIN: Rt=1.811 min; 213 [M+H]+.

Intermediate 151 ethyl 2-[2,6-bis(methoxymethoxy)-3-methyl-phenyl]-2-oxo-acetate

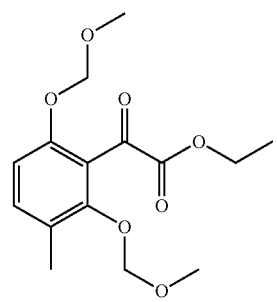 [SMILES: CCOC(=O)C(=O)c1c(OCOC)ccc(C)c1OCOC]

To a solution of 2,4-bis(methoxymethoxy)-1-methyl-benzene (Intermediate 150, 5.5 g, 25.94 mmol) in dry tetrahydrofuran (50 ml) at room temperature BuLi 1.6M in hexane (19.45 ml, 31.13 mmol) was added and the reaction mixture was stirred for 30 minutes at the same temperature. The mixture was cooled to −78° C. and it was added (via cannulation) to a solution of ethyl chlorooxoacetate (4.35 ml, 38.9 mmol) in dry tetrahydrofuran (30 ml) at −78° C. The reaction mixture was stirred at −78° C. for 30 minutes. The reaction was quenched with water (20 ml), diluted with brine (50 ml) and extracted with ethyl acetate (2×100 ml). Combined organic layers were dried over sodium sulphate, filtered and evaporated. The residue was purified by flash chromatography (Biotage system) on silica gel using a 100 g SNAP column and cyclohexane to cyclohexane/ethyl acetate 8:2 as eluent affording the title compound (4.65 g) as a light yellow oil.
LC/MS: QC_3_MIN: Rt=1.865 min.

Intermediate 152 ethyl 2-[2,6-bis(methoxymethoxy)-3-methyl-phenyl]prop-2-enoate

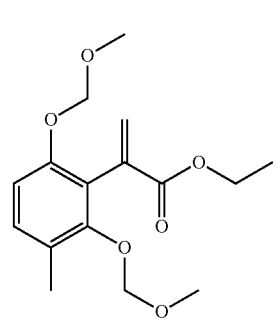 [SMILES: C=C(C(=O)OCC)c1c(OCOC)ccc(C)c1OCOC]

To a suspension of methyltriphenylphosphonium bromide (8.78 g, 24.6 mmol) in dry tetrahydrofuran (50 ml) at 0° C. KHMDS 0.5M solution in toluene (44.22 ml, 22.11 mmol) was slowly added and the reaction mixture was stirred for 15 minutes at 0° C. and for 45 minutes at room temperature. The reaction mixture was cooled to 0° C. and it was slowly added to a solution of ethyl 2-[2,6-bis(methoxymethoxy)-3-methyl-phenyl]-2-oxo-acetate (Intermediate 151, 4.6 g, 14.74 mmol) in dry tetrahydrofuran (25 mL) at 0° C. and the reaction mixture was stirred for 2 hours at 0° C. The reaction was quenched with water (50 ml), diluted with brine (50 ml) and extracted with ethyl acetate (2×100 ml). The organic layer was dried over sodium sulphate, filtered and evaporated. The residue was purified by flash chromatography (Biotage system) on silica gel using a 100 g SNAP column and cyclohexane to cyclohexane/ethyl acetate 8:2 as eluents affording the title compound (3.8 g) as a colourless oil.

LC/MS: QC_3_MIN: Rt=1.930 min.

Intermediate 153 ethyl 1-[2,6-bis(methoxymethoxy)-3-methyl-phenyl]cyclopropanecarboxylate

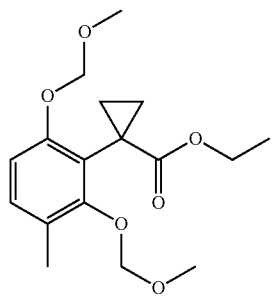 [SMILES: CCOC(=O)C1(c2c(OCOC)ccc(C)c2OCOC)CC1]

To a solution of trimethylsulfoxonium iodide (4.4 g, 20 mmol) in dry dimethyl sulfoxide (30 mL) sodium hydride (60% dispersion in mineral oil) (0.720 g, 18 mmol) was added and the reaction mixture was stirred for 1 hour at room temperature. A solution of ethyl 2-[2,6-bis(methoxymethoxy)-3-methyl-phenyl]prop-2-enoate (Intermediate 152, 3.5 g, 11.29 mmol) in dry dimethyl sulfoxide (15 mL) was slowly added and the reaction mixture was stirred for 1 hour at room temperature. The reaction was quenched with an aqueous saturated solution of ammonium chloride (10 ml), diluted with water (40 ml) and extracted with ethyl acetate (2×100 ml). The organic layer was washed with water (2×50 ml), dried over sodium sulphate, filtered and evaporated. The residue was purified by flash chromatography (Biotage system) on silica gel using a 100 g SNAP column and cyclohexane to cyclohexane/ethyl acetate 8:2 as eluents affording the title compound (3.1 g) as a colourless oil.

LC/MS: QC_3_MIN: Rt=2.028 min.

Intermediate 154

2-[1-(hydroxymethyl)cyclopropyl]-3-(methoxymethoxy)-6-methyl-phenol

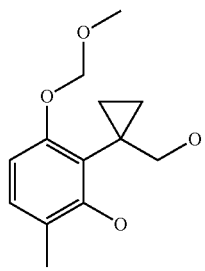 [SMILES: COCOc1ccc(C)c(O)c1C1(CO)CC1]

To a solution of ethyl 1-[2,6-bis(methoxymethoxy)-3-methyl-phenyl]cyclopropanecarboxylate (Intermediate 153, 300 mg, 0.93 mmol) in ethanol (10 ml) HCl 6N in water (0.4 mL, 2.4 mmol) was added and the reaction mixture was stirred overnight at 50° C. Combined solvents were removed under reduced pressure. The residue was suspended in dry toluene (10 mL) and the solvent evaporated. The obtained residue was dissolved in dry tetrahydrofuran (10 ml), the mixture was cooled to 0° C. and NaH (60% dispersion in mineral oil) (80 mg, 2 mmol) was added and the reaction mixture was stirred for 30 minutes at the same temperature. MOM-Cl (0.083 mL, 1.1 mmol) was then added and the reaction mixture was stirred for 1 hour at 0° C. LiAlH$_4$ (1M in THF, 1.2 ml, 1.2 mmol) was added and the reaction mixture was further stirred for 1 hour at the same temperature. The reaction was quenched with an aqueous saturated solution of ammonium chloride (10 ml), diluted with water (20 ml) and extracted with ethyl acetate (2×50 ml). Combined organic layers were dried over sodium sulphate, filtered and evaporated and the residue was purified by flash chromatography (Biotage system) on silica gel using a 25 g SNAP column and cyclohexane to cyclohexane/ethyl acetate 7:3 as eluents affording the title compound (70 mg) as a white solid.

LC/MS: QC_3_MIN: Rt=1.690 min; 239 [M+H]+.

Intermediate 155

4-(methoxymethoxy)-7-methyl-spiro[2H-benzofuran-3,1'-cyclopropane]

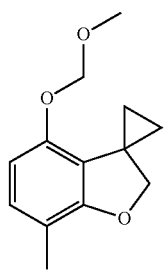 [SMILES: COCOc1ccc(C)c2c1C1(CC1)CO2]

To a solution of 2-[1-(hydroxymethyl)cyclopropyl]-3-(methoxymethoxy)-6-methyl-phenol (Intermediate 154, 65 mg, 0.27 mmol) in dry tetrahydrofuran (5 ml) triphenylphosphine (84 mg, 0.32 mmol) was added and the reaction mixture was stirred until complete dissolution of PPh3. DIAD (0.056 ml, 0.285 mmol) was then added dropwise and the reaction mixture was stirred for 30 minutes at room temperature. The solvent was removed under reduced pressure and the residue was purified by flash chromatography (Biotage system) on silica gel using a 10 g SNAP column and cyclohexane to cyclohexane/ethyl acetate 8:2 as eluents affording the title compound (40 mg) as a light yellow oil.

LC/MS: QC_3_MIN: Rt=2.024 min; 221 [M+H]+.

Intermediate 156

7-methylspiro[2H-benzofuran-3,1'-cyclopropane]-4-ol

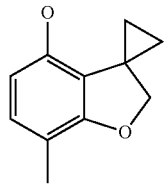

To a solution of 4-(methoxymethoxy)-7-methyl-spiro[2H-benzofuran-3,1'-cyclopropane] (Intermediate 155, 38 mg, 0.17 mmol) in ethanol (5 ml), HCl 6N in water (0.1 mL, 0.6 mmol) was added and the reaction mixture was stirred for 4 days at room temperature. Combined solvents were removed under reduced pressure and the residue was purified by flash chromatography (Biotage system) on silica gel using a 10 g SNAP column and cyclohexane to cyclohexane/ethyl acetate 7:3 as eluents affording the title compound (24 mg) as a light orange solid.

$^1$H-NMR (400 MHz, DMSO-$d_6$) δ ppm: 9.02 (1H, s), 6.65 (1H, d), 6.06 (1H, d), 4.36 (2H, s), 2.02 (3H, s), 1.40-1.44 (2H, m), 0.77-0.82 (2H, m). ROESY (400 MHz, DMSO-$d_6$): NOE correlation between proton at 6.65 ppm and protons (CH3) at 2.02 ppm, NOE correlation between proton at 9.02 ppm and proton at 6.06 ppm. LC/MS: QC_3_MIN: Rt=1.647 min; 177 [M+H]+.

Intermediate 157

2-(7-methylspiro[2H-benzofuran-3,1'-cyclopropane]-4-yl)oxy-5-nitro-pyridine

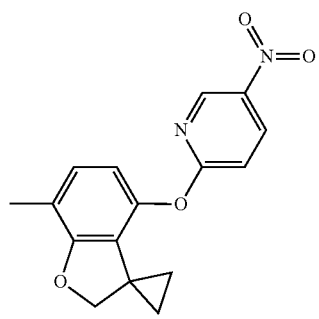 [SMILES: Cc1ccc(Oc2ccc([N+](=O)[O-])cn2)c2c1OCC21CC1]

To a solution of 7-methylspiro[2H-benzofuran-3,1'-cyclopropane]-4-ol (Intermediate 156, 176 mg, 1 mmol) in dry DMF (4 ml) potassium carbonate (207 mg, 1.5 mmol) and then 2-chloro-5-nitropyridine (158 mg, 1 mmol) were added and the reaction mixture was stirred for 2 hours at 80° C. After cooling the reaction mixture was quenched with water (2 ml), diluted with brine (10 ml) and extracted with ethyl acetate (2×20 ml). The organic layer was dried over sodium sulfate, filtered and evaporated affording the title compound (270 mg) as an orange solid that was used in the next step as crude material without further purification.

LC/MS: QC_3_MIN: Rt=2.138 min; 299 [M+H]+.

Intermediate 158

6-(7-methylspiro[2H-benzofuran-3,1'-cyclopropane]-4-yl)oxypyridin-3-amine

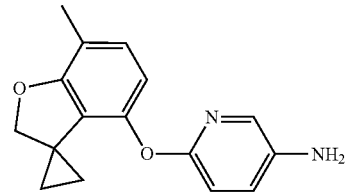 [SMILES: Cc1ccc(Oc2ccc(N)cn2)c2c1OCC21CC1]

To a solution of 2-(7-methylspiro[2H-benzofuran-3,1'-cyclopropane]-4-yl)oxy-5-nitro-pyridine (Intermediate 157, 265 mg) in tetrahydrofuran (5 ml)/water (2.5 ml) iron (245 mg, 4.45 mmol) and then ammonium chloride (238 mg, 4.45 mmol) were added and the reaction mixture was stirred overnight at room temperature. The catalyst was filtered off and the residue was diluted with an aqueous saturated solution of NaHCO$_3$ (5 ml) and extracted with ethyl acetate (3×10 ml). The organic layer was dried over sodium sulphate, filtered and evaporated and the residue was purified by flash chromatography (Biotage system) on silica gel using a 10 g SNAP column and cyclohexane/ethyl acetate 8:2 to cyclohexane/ethyl acetate 1:1 as eluents affording the title compound (203 mg) as a light yellow solid.

LC/MS: QC_3_MIN: Rt=1.740 min; 269 [M+H]+.

Intermediate 159

Tert-butyl N-[(1R)-1-[[6-(7-methylspiro[2H-benzofuran-3,1'-cyclopropane]-4-yl)oxy-3-pyridyl]carbamoyl]propyl]carbamate

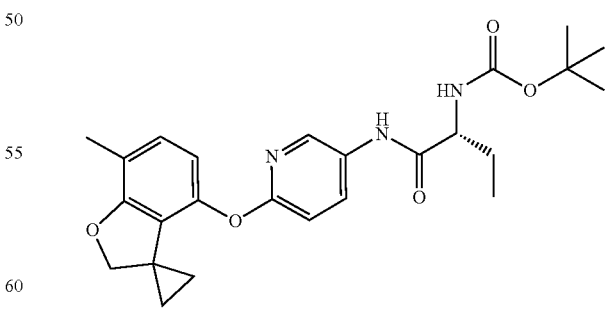

To a solution of (2R)-2-({[(1,1-dimethylethyl)oxy]carbonyl}amino)butanoic acid (36 mg, 0.18 mmol) in dry DMF (1 ml) DIPEA (521, 0.3 mmol) and then HATU (65 mg, 0.17 mmol) were added and the reaction mixture was stirred for 15 minutes at r.t. 6-(7-methylspiro[2H-benzofuran-3,1'-cyclopropane]-4-yl)oxypyridin-3-amine (Intermediate 158, 40 mg, 0.15 mmol) was then added and the reaction mixture was stirred for 4 hours at room temperature. The reaction was quenched with water (2 ml) diluted with brine (5 ml) and extracted with ethyl acetate (2×10 ml). The organic layer was dried (Na₂SO₄), filtered and evaporated and the residue was purified by flash chromatography (Biotage system) on silica gel using a 10 g SNAP column and cyclohexane/ethyl acetate 90:10 to cyclohexane/ethyl acetate 60:40 as eluents affording the title compound (57 mg) as a white solid.

LC/MS: QC_3_MIN: Rt=2.190 min; 454 [M+H]+.

Intermediate 160

(2R)-2-amino-N-[6-(7-methylspiro[2H-benzofuran-3,1'-cyclopropane]-4-yl)oxy-3-pyridyl]butanamide

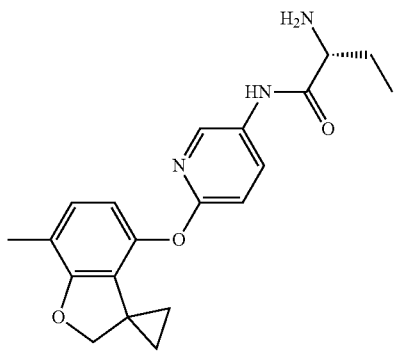 [SMILES: CC[C@@H](N)C(=O)Nc1ccc(Oc2ccc(C)c3c2C2(CC2)CO3)nc1]

To a solution of tert-butyl N-[(1R)-1-[[6-(7-methylspiro [2H-benzofuran-3,1'-cyclopropane]-4-yl)oxy-3-pyridyl]carbamoyl]propyl]carbamate (Intermediate 159, 55 mg) in dry DCM (3 ml) at 0° C. TFA (1 ml) was slowly added and the reaction mixture was stirred for 3 hours at the same temperature. The solvent and the excess of TFA were removed under reduced pressure and the residue was diluted with DCM (10 ml) and an aqueous saturated solution NaHCO₃ was added while the pH was allowed to reach ~8. Two phases were separated and the organic layer was dried (Na₂SO₄), filtered and evaporated affording the title compound (41 mg) as white solid.

LC/MS: QC_3_MIN: Rt=1.792 min; 354 [M+H]+.

Intermediate 161

2-(7-methylspiro[2H-benzofuran-3,1'-cyclopropane]-4-yl)oxy-5-nitro-pyrimidine

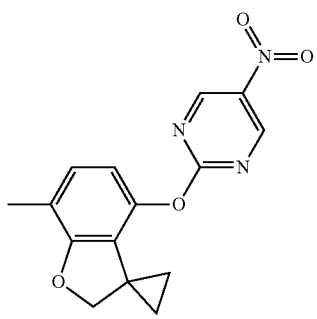 [SMILES: Cc1ccc(Oc2ncc([N+](=O)[O-])cn2)c2c1OCC21CC1]

To a solution of 7-methylspiro[2H-benzofuran-3,1'-cyclopropane]-4-ol (Intermediate 156, 176 mg, 1 mmol) in dry Acetonitrile (4 ml) potassium carbonate (207 mg, 1.5 mmol) and then 2-chloro-5-nitropyrimidine (159 mg, 1 mmol) were added and the reaction mixture was stirred for 24 hours at 80° C. After cooling the reaction mixture was quenched with water (2 ml), diluted with brine (10 ml) and extracted with ethyl acetate (2×20 ml). The organic layer was dried over sodium sulfate, filtered and evaporated affording the title compound (258 mg) as an orange solid that was used in the next step as crude material without further purification.

LC/MS: QC_3_MIN: Rt=2.007 min; 300 [M+H]+.

Intermediate 162

2-(7-methylspiro[2H-benzofuran-3,1'-cyclopropane]-4-yl)oxypyrimidin-5-amine

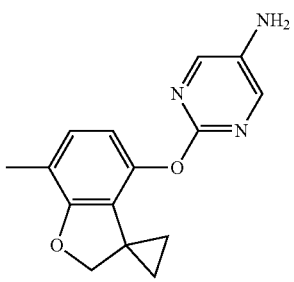 [SMILES: Cc1ccc(Oc2ncc(N)cn2)c2c1OCC21CC1]

To a solution of 2-(7-methylspiro[2H-benzofuran-3,1'-cyclopropane]-4-yl)oxy-5-nitro-pyrimidine (Intermediate 161, 255 mg) in tetrahydrofuran (5 ml)/water (2.5 ml) iron (234 mg, 4.25 mmol) and then ammonium chloride (227 mg, 4.25 mmol) were added and the reaction mixture was stirred for 48 hours at room temperature. The catalyst was filtered off and the residue was diluted with an aqueous saturated solution of NaHCO₃ (5 ml) and extracted with ethyl acetate (3×10 ml). The organic layer was dried over sodium sulphate, filtered and evaporated and the residue was purified by flash chromatography (Biotage system) on silica gel using a 10 g SNAP column and cyclohexane/ethyl acetate 8:2 to cyclohexane/ethyl acetate 4:6 as eluents affording the title compound (52 mg) as a light orange solid.

LC/MS: QC_3_MIN: Rt=1.746 min; 270 [M+H]+.

Intermediate 163

Tert-butyl N-[(1R)-1-[[2-(7-methylspiro[2H-benzofuran-3,1'-cyclopropane]-4-yl)oxypyrimidin-5-yl]carbamoyl]propyl]carbamate

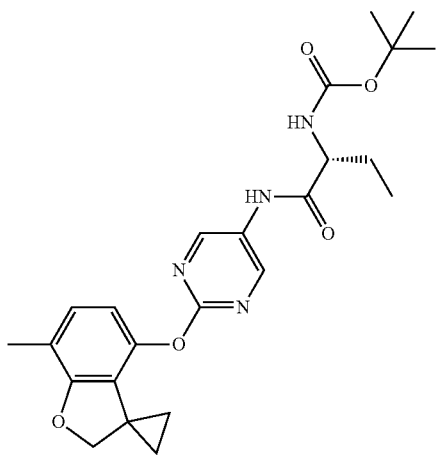 [SMILES: CC[C@@H](NC(=O)OC(C)(C)C)C(=O)Nc1cnc(Oc2ccc(C)c3c2C2(CC2)CO3)nc1]

To a solution of (2R)-2-({[(1,1-dimethylethyl)oxy]carbonyl}amino)butanoic acid (45 mg, 0.222 mmol) in dry DMF (1 ml) DIPEA (871, 0.5 mmol) and then HATU (80 mg, 0.21 mmol) were added and the reaction mixture was stirred for 15 minutes at r.t. 2-(7-methylspiro[2H-benzofuran-3,1'-cyclopropane]-4-yl)oxypyrimidin-5-amine (Intermediate 162, 50 mg, 0.185 mmol) was then added and the reaction mixture was stirred for 6 hours at room temperature. The reaction was quenched with water (2 ml) diluted with brine (5 ml) and extracted with ethyl acetate (2×10 ml). The organic layer was dried (Na$_2$SO$_4$), filtered and evaporated and the residue was purified by flash chromatography (Biotage system) on silica gel using a 10 g SNAP column and cyclohexane/ethyl acetate 90:10 to cyclohexane/ethyl acetate 60:40 as eluents affording the title compound (45 mg) as a white solid.

LC/MS: QC_3_MIN: Rt=2.109 min; 455 [M+H]+.

Intermediate 164

(2R)-2-amino-N-[2-(7-methylspiro[2H-benzofuran-3,1'-cyclopropane]-4-yl)oxypyrimidin-5-yl]butanamide

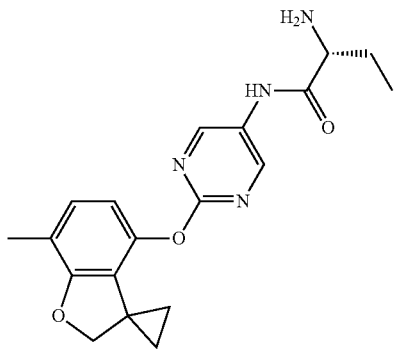 [SMILES: CC[C@@H](N)C(=O)Nc1cnc(Oc2ccc(C)c3c2C2(CC2)CO3)nc1]

To a solution of tert-butyl N-[(1R)-1-[[2-(7-methylspiro[2H-benzofuran-3,1'-cyclopropane]-4-yl)oxypyrimidin-5-yl]carbamoyl]propyl]carbamate (Intermediate 163, 42 mg) in dry DCM (3 ml) at 0° C. TFA (1 ml) was slowly added and the reaction mixture was stirred for 3 hours at the same temperature. The solvent and the excess of TFA were removed under reduced pressure and the residue was diluted with DCM (10 ml) and an aqueous saturated solution NaHCO$_3$ was added while the pH was allowed to reach ~8. Two phases were separated and the organic layer was dried (Na$_2$SO$_4$), filtered and evaporated affording the title compound (25 mg) as light yellow gum.

LC/MS: QC_3_MIN: Rt=1.688 min; 355 [M+H]+.

Intermediate 165

(5R)-3-(2-chloropyrimidin-5-yl)-5-ethyl-5-methyl-imidazolidine-2,4-dione

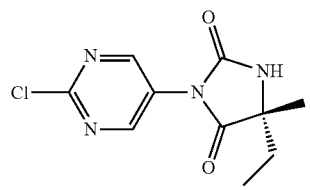 [SMILES: CC[C@@]1(C)NC(=O)N(c2cnc(Cl)nc2)C1=O]

To a solution of triphosgene (1.38 g, 4.65 mmol) in Ethyl acetate (20 ml) at 0° C. a solution of 2-chloro-5-aminopyrimidine (1 g, 7.75 mmol)/DIPEA (8 ml, 4.65 mmol) in ethyl acetate (40 ml) was slowly added (20 minutes) and the reaction mixture was stirred for 15 minutes at the same temperature. Maintaining the reaction mixture at 0° C., vacuum was applied (10 minutes) for removing the excess of phosgene. A solution of DMAP (0.945 g, 7.75 mmol) in ethyl acetate/dichloromethane 1:1 (8 ml) was added and the reaction mixture was stirred for 5 minutes at the same temperature. A solution of methyl (R)-2-amino-2-methyl-butyrate hydrochloride (2.59 g, 15.5 mmol) in ethyl acetate (30 ml) was slowly added (15 minutes) at 0° C. and the reaction mixture was stirred for 30 minutes at the same temperature. The reaction was quenched with aqueous buffer (pH3) while the pH was allowed to reach ~5-6 and two phases were separated. The organic layer was washed with aqueous buffer (pH3) (2×20 ml) and then brine (20 ml), dried (Na$_2$SO$_4$), filtered and evaporated affording the urea intermediate as orange foam.

The urea was dissolved in MeOH (20 ml), NaOMe (0.41 g, 7.75 mmol) was added and the reaction mixture was stirred for 15 minutes at r.t. The mixture was quenched with an aqueous saturated solution of ammonium chloride (25 ml) and diluted with ethyl acetate (50 ml). Two phases were separated and the organic layer was washed with brine (2×20 ml), dried (Na$_2$SO$_4$), filtered and evaporated. The residue was triturated with Et$_2$O (10 ml) and the solid collected affording the title compound (1.22 g) as a beige solid.

LC/MS: QC_3_MIN: Rt=1.341 min; 255 [M+H]+.

Intermediate 166

3-(2-chloropyrimidin-5-yl)-5,5-dimethyl-imidazolidine-2,4-dione

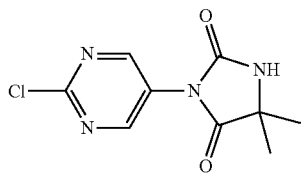 [SMILES: CC1(C)NC(=O)N(c2cnc(Cl)nc2)C1=O]

To a solution of triphosgene (1.38 g, 4.65 mmol) in Ethyl acetate (20 ml) at 0° C. a solution of 2-chloro-5-aminopyrimidine (1 g, 7.75 mmol)/DIPEA (8 ml, 4.65 mmol) in ethyl acetate (40 ml) was slowly added (20 minutes) and the reaction mixture was stirred for 15 minutes at the same temperature. Maintaining the reaction mixture at 0° C., vacuum was applied (10 minutes) for removing the excess of phosgene. A solution of DMAP (0.945 g, 7.75 mmol) in ethyl acetate/dichloromethane 1:1 (8 ml) was added and the reaction mixture was stirred for 5 minutes at the same temperature. 2,2-Dimethylglycine methyl ester hydrochloride (2.37 g, 15.5 mmol) in ethyl acetate (30 ml) was slowly added (15 minutes) at 0° C. and the reaction mixture was stirred for 30 minutes at the same temperature. The reaction was quenched with aqueous buffer (pH3) while the pH was allowed to reach ~5-6 and two phases were separated. The organic layer was washed with aqueous buffer (pH3) (2×20 ml) and then brine (20 ml), dried ($Na_2SO_4$), filtered and evaporated affording the urea intermediate as orange foam.

The urea was dissolved in MeOH (20 ml), NaOMe (0.41 g, 7.75 mmol) was added and the reaction mixture was stirred for 15 minutes at r.t. The mixture was quenched with an aqueous saturated solution of ammonium chloride (25 ml) and diluted with ethyl acetate (50 ml). Two phases were separated and the organic layer was washed with brine (2×20 ml), dried ($Na_2SO_4$), filtered and evaporated. The residue was triturated with $Et_2O$ (10 ml) and the solid collected affording the title compound (1.08 g) as an orange solid.

LC/MS: QC_3_MIN: Rt=1.062 min; 241 [M+H]+.

Intermediate 167

Methyl 3-(2-methylallyloxy)benzoate

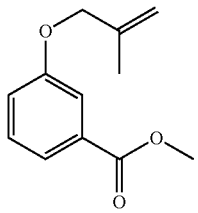

Methyl 3-hydroxybenzoate (1 g, 6.57 mmol) was dissolved in DMF (10 ml) to give a colorless solution. To the solution potassium carbonate (1.089 g, 7.88 mmol) and 3-Bromo-2-methylpropene (0.729 ml, 7.23 mmol) were added. The reaction mixture was heated to 90° C. and stirred for 1 h. After cooling the reaction mixture was diluted with water and extracted with ethyl acetate. The organic phase was washed with water, dried over $Na_2SO_4$ and evaporated under vacuum to afford the title compound (1.180 mg)

LC/MS: QC_3_MIN: Rt=2.073 min; 207 [M+H]+.

Intermediate 168

Methyl 3-hydroxy-2-(2-methylallyl)benzoate

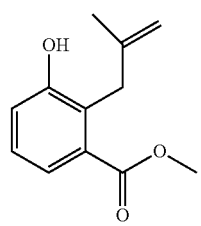

Methyl 3-(2-methylallyloxy)benzoate (Intermediate 167, 1.100 g, 5.3 mmol) was dissolved in 1-Methyl-2-pyrrolidinone (12 ml) and heated to 200° C. The solution was stirred for 30 h at the same temperature. After cooling, the mixture was diluted with water and extracted with ethyl acetate. Organic phase was dried over $Na_2SO_4$ and evaporated in vacuo to afford a crude product that was purified via Biotage SP1 with Cyclohexane/EtOAc as eluents (from 10/0 to 7/3 for 12 CV, 50 g SNAP Silica column). Fractions were collected and evaporated to afford the title compound (507 mg).

LC/MS: QC_3_MIN: Rt=1.772 min; 207 [M+H]+.

Intermediate 169

3-(hydroxymethyl)-2-(2-methylallyl)phenol

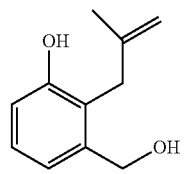

Methyl 3-hydroxy-2-(2-methylallyl)benzoate (Intermediate 168, 410 mg, 1.99 mmol) was dissolved in tetrahydrofuran (5 ml) to give a colourless solution. The reaction mixture was cooled at 0° C. A solution of $LiAlH_4$ 2M in THF (1.09 ml, 2.19 mmol) was added dropwise and the reaction mixture was stirred at 0° C. for 30 min. After this time the reaction mixture was poured into ice and diluted with 60 ml of ethyl acetate. Phases were separated, the organic phase was dried over $Na_2SO_4$ and evaporated under vacuum to afford the title compound (360 mg) as a colorless oil.

LC/MS: QC_3_MIN: Rt=1.192 min.

Intermediate 170

3,3-dimethylisochroman-5-ol

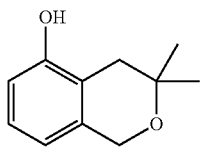

3-(hydroxymethyl)-2-(2-methylallyl)phenol (Intermediate 169, 360 mg, 2 mmol) was dissolved in ethyl acetate (20 ml), two drops of sulfuric acid were added to the solution that was stirred for 4 hours at room temperature. After this time the reaction was diluted with water (40 ml) and ethyl acetate (40 ml). Phases were separated and the organic layer was dried over $Na_2SO_4$ and evaporated in vacuo to afford a colourless oil. The oil was triturated with cyclohexane to obtain a white solid that was filtered, washed with cyclohexane (20 ml) and dried in vacuo to afford the title compound (130 mg).

LC/MS: QC_3_MIN: Rt=1.441 min.

Intermediate 171

2-(3,3-dimethylisochroman-5-yl)oxy-5-nitro-pyridine

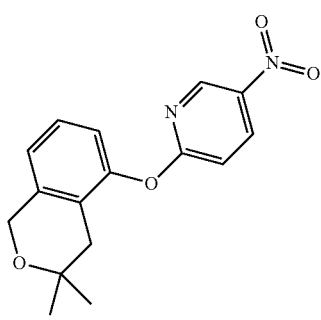 [SMILES: CC1(C)Cc2c(cccc2Oc2ccc([N+](=O)[O-])cn2)CO1]

To a solution of 3,3-dimethylisochroman-5-ol (Intermediate 170, 65 mg, 0.36 mmol) in dry DMF (3 ml) potassium carbonate (207 mg, 1.5 mmol) and then 2-chloro-5-nitropyridine (50.8 mg, 0.32 mmol) were added and the reaction mixture was stirred for 2 hours at 80° C. After cooling the reaction mixture was quenched with water (2 ml), diluted with brine (10 ml) and extracted with ethyl acetate (2×20 ml). The organic layer was dried over sodium sulfate, filtered and evaporated affording the title compound (80 mg) as an orange solid that was used in the next step as crude without further purification.

LC/MS: QC_3_MIN: Rt=2.027 min; 301 [M+H]+.

Intermediate 172

6-(3,3-dimethylisochroman-5-yl)oxypyridin-3-amine

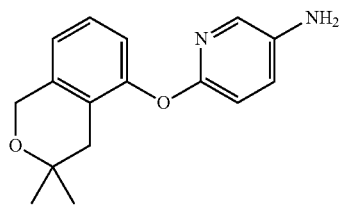 [SMILES: CC1(C)Cc2c(cccc2Oc2ccc(N)cn2)CO1]

To a solution of 2-(3,3-dimethylisochroman-5-yl)oxy-5-nitro-pyridine (Intermediate 171, 80 mg) in tetrahydrofuran (5 ml)/water (2.5 ml) iron (70 mg, 1.3 mmol) and then ammonium chloride (70 mg, 1.3 mmol) were added and the reaction mixture was stirred overnight at room temperature. The catalyst was filtered off and the residue was diluted with an aqueous saturated solution of $NaHCO_3$ (5 ml) and extracted with ethyl acetate (3×10 ml). The organic layer was dried over sodium sulfate, filtered and evaporated and the residue was purified by flash chromatography (Biotage system) on silica gel using a 10 g SNAP column and cyclohexane/ethyl acetate 8:2 to cyclohexane/ethyl acetate 4:6 as eluents affording the title compound (25 mg) as a white solid.

LC/MS: QC_3_MIN: Rt=1.586 min; 271 [M+H]+.

Intermediate 173

[5-(methoxymethoxy)-2-methyl-phenyl]methanol

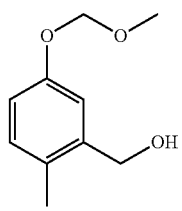

5-Hydroxy-2-methyl-benzoic acid (2 g, 13.3 mmol) was dissolved in tetrahydrofuran (40 ml). The reaction mixture was cooled to 0° C. and sodium hydride (60% dispersion in mineral oil) (1.8 g, 39.5 mmol) was added portionwise. Chloro(methyloxy)methane (4 ml, 52 mmol) was added. The reaction mixture was stirred for 30 min at 0° C. The mixture was poured into ice and extracted with ethyl acetate, two phases were separated and the organic layer was dried over $Na_2SO_4$ and evaporated under vacuum to give the crude product as a yellow oil. To this material, dissolved in THF (20 ml), cooled at 0° C., $LiAlH_4$ 1M in THF (15 ml, 15 mmol) was added dropwise and the reaction mixture was stirred at 0° C. for 30 min. After this time the reaction mixture was poured into ice and diluted with 60 ml of ethyl acetate. Phases were separated, the organic phase was dried over $Na_2SO_4$ and evaporated under vacuum to afford a colorless oil that was purified by flash chromatography (Biotage system) on silica gel using a 100 g SNAP column and cyclohexane to cyclohexane/ethyl acetate 75:25 as eluents affording the title compound (1.9 g) as a colorless oil.

LC/MS: QC_3_MIN: Rt=1.351 min

Intermediate 174

Tert-butyl-[[5-(methoxymethoxy)-2-methyl-phenyl]methoxy]-dimethyl-silane

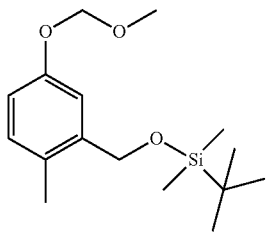 [SMILES: COCOc1ccc(C)c(CO[Si](C)(C)C(C)(C)C)c1]

[5-(methoxymethoxy)-2-methyl-phenyl]methanol (Intermediate 173, 1.9 g, 10 mmol) was dissolved in dichloromethane (10 ml) to give a colourless solution. 1H-imidazole (1.137 g, 16.7 mmol) and chloro(1,1-dimethylethyl)dimethylsilane (2.095 g, 13.9 mmol) were added. The reaction mixture immediately became a white suspension and was stirred at room temperature for 30 minutes. The reaction mixture was quenched with 10 ml of water and diluted with 10 ml of dichloromethane. Two phases were separated through a separating funnel. The organic phase was dried over $Na_2SO_4$ and evaporated under vacuum and the residue was purified by flash chromatography (Biotage system) on silica gel using a 100 g SNAP column and cyclohexane to cyclohexane/ethyl acetate 50:50 as eluents affording the title compound (2.9 g) as a colorless oil.

LC/MS: QC_3_MIN: Rt=2.437 min

Intermediate 175

1-[2-[[tert-butyl(dimethyl)silyl]oxymethyl]-6-(methoxymethoxy)-3-methyl-phenyl]cyclobutanol

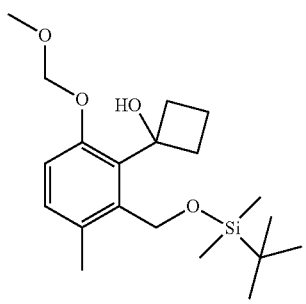 [SMILES: COCOc1ccc(C)c(CO[Si](C)(C)C(C)(C)C)c1C1(O)CCC1]

To a solution of tert-butyl-[[5-(methoxymethoxy)-2-methyl-phenyl]methoxy]-dimethyl-silane (Intermediate 174, 0.3 g, 1 mmol) in hexane (5 ml), BuLi (1.6M in hexane, 0.9 ml, 1.4 mmol) was added at room temperature. The reaction mixture was stirred for 2 h and then added dropwise at −30° C. to a suspension of $CeCl_3$ (0.37 g, 1.5 mmol) in dry THF (5 ml) that was previously stirred at room temperature overnight. After 45 min at −30° C., cyclobutanone (0.07 g, 1 mmol) dissolved in THF (1 ml) was added. The reaction was stirred at the same temperature for and then quenched with ammonium chloride (20 ml) and extracted with Ethyl Acetate (2×20 ml). Combined organic layers were dried over $Na_2SO_4$ and evaporated under vacuum to afford a colorless oil that was purified by flash chromatography (Biotage system) on silica gel using a 25 g SNAP column and cyclohexane to cyclohexane/ethyl acetate 75:25 as eluents affording the title compound (0.05 g) as a colorless oil.

LC/MS: QC_3_MIN: Rt=2.437 min

Intermediate 176

7-methylspiro[1H-isobenzofuran-3,1'-cyclobutane]-4-ol

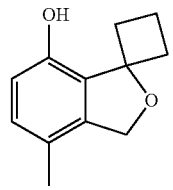

To a solution of 1-[2-[[tert-butyl(dimethyl)silyl]oxymethyl]-6-(methoxymethoxy)-3-methyl-phenyl]cyclobutanol (Intermediate 175, 0.05 g, 0.136 mmol) in Ethyl Acetate (5 ml), Sulphuric Acid (96%, 2 drops) was added at room temperature and the reaction mixture was stirred for 2 h. Ethyl Acetate (20 ml) was added and the organic phase was washed with brine (2×50 ml), dried over sodium sulphate and evaporated. The residue was purified by flash chromatography (Biotage system) on silica gel using a 10 g SNAP column and cyclohexane to cyclohexane/ethyl acetate 7:3 as eluents affording the title compound (0.02 g) as a colourless oil.

LC/MS: QC_3_MIN: Rt=1.720 min

Intermediate 177 ethyl 2-[[tert-butyl(dimethyl)silyl]oxymethyl]-6-(methoxymethoxy)benzoate

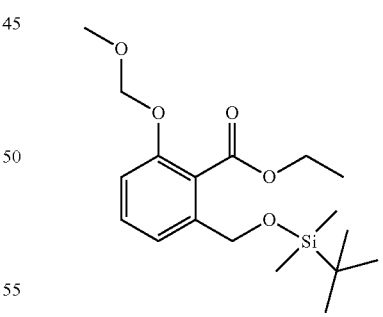

Under nitrogen flush, in a 2-necked 100 ml round-bottomed flask equipped with a reflux condenser (flamed for 5 minutes under vacuum and then 3 cycles of N2/vacuum), (1,1-dimethylethyl)(dimethyl){[(3-{[(methyloxy)methyl]oxy}phenyl)methyl]oxy}silane (Intermediate 103, 1.5 g, 5.31 mmol) was dissolved in hexane (20 ml) to give a colourless solution. Butyllithium 1.6N in hexane (4.31 ml, 6.9 mmol) was added dropwise and the reaction mixture was stirred at room temperature. After 2 hours stirring in those conditions, the pale yellow reaction mixture was added to a solution of ethyl chloroformate (1.015 ml, 10.62 mmol) in tetrahydrofuran at −78° C. After 30 min, the reaction was quenched with a 2M aqueous solution of hydrochloric acid while the pH was allowed to reach ~2 and diluted with 10 ml of ethyl acetate. Two phases were separated and the organic layer was dried over Na$_2$SO$_4$ and evaporated under vacuum affording the crude product as a yellowish oil that was purified by flash chromatography (Biotage system) on silica gel using cyclohexane to cyclohexane/ethyl acetate 8:2 as eluents affording the title compound (1.396 g) as a yellow pale oil.

LC/MS: QC_3_MIN: Rt=2.413 min; 355 [M+H]+.

Intermediate 178 ethyl 2-[[tert-butyl(dimethyl)silyl]oxymethyl]-6-hydroxy-benzoate

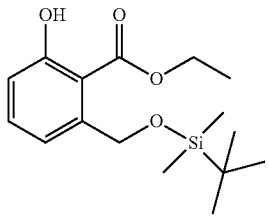 [SMILES: CCOC(=O)c1c(O)cccc1CO[Si](C)(C)C(C)(C)C]

Ethyl 2-[[tert-butyl(dimethyl)silyl]oxymethyl]-6-(methoxymethoxy)benzoate (Intermediate 177, 950 mg, 2.68 mmol) was dissolved in dichloromethane (30 ml), the solution was cooled to 0° C. and trifluoroacetic acid (2 ml) was added. After 3 h stirring at 0° C. water (20 ml) was added at 0° C. and two phases were separated. The organic layer was dried over Na$_2$SO$_4$ and evaporated in vacuo to afford a colourless oil that was purified by flash chromatography (Biotage system) on silica gel using cyclohexane to cyclohexane/ethyl acetate 7:3 as eluents affording the title compound (0.345 g) as a colorless oil.

LC/MS: QC_3_MIN: Rt=2.463 min; 311 [M+H]+.

Intermediate 179

3,3-diethyl-1H-isobenzofuran-4-ol

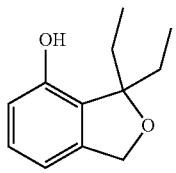

To a 1M solution in THE of Ethylmagnesium bromide (10 ml, 5 mmol) in dry THE (5 ml) at 0° C. a solution of ethyl 2-[[tert-butyl(dimethyl)silyl]oxymethyl]-6-hydroxy-benzoate (Intermediate 178, 0.31 g, 1 mmol) in Et$_2$O (10 ml) was added in 15 min. The reaction mixture was stirred for 1.5 h at the same temperature and then for additional 2 hours while the temperature was allowed to reach room temperature. The reaction was quenched with an aqueous saturated solution of ammonium chloride (40 ml) and extracted with ethyl acetate (3×80 ml). The organic layer was washed with brine (2×50 ml), dried over sodium sulphate, filtered and evaporated. The residue was dissolved in THE (5 ml) and tetrabutylammonium fluoride (1M in THF, 1.5 ml, 1.5 mmol) was added and the reaction mixture was stirred for 15 minutes. Ethyl Acetate (50 ml) was added and the combined organic layers were washed with Ammonium Chloride (2×50 ml), dried over sodium sulphate, and concentrated. The yellow solid obtained was triturated with Ethyl Acetate and Pentane (1:1, 5 ml) to give a white solid.

The solid was dissolved in Ethyl Acetate (5 ml) and Sulphuric Acid (96%, 4 drops) was added at room temperature. The reaction was stirred for 2 h, then Ethyl Acetate (20 ml) was added and the organic phase washed with brine (2×50 ml), dried over sodium sulphate and evaporated. The residue was purified by flash chromatography (Biotage system) on silica gel using a 10 g SNAP column and cyclohexane to cyclohexane/ethyl acetate 7:3 as eluents affording the title compound (0.05 g) as a colourless oil.

LC/MS: QC_3_MIN: Rt=1.683 min.

Intermediate 180

6-[(3,3-diethyl-1H-isobenzofuran-4-yl)oxy]pyridin-3-amine

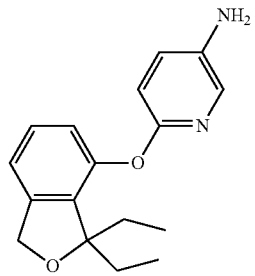 [SMILES: CCC1(CC)OCc2cccc(Oc3ccc(N)cn3)c21]

To a solution of 3,3-diethyl-1H-isobenzofuran-4-ol (Intermediate 179, 0.03 g, 0.15 mmol) in dry DMF (3 ml) potassium carbonate (0.08 g, 0.6 mmol) and then 2-Chloro-5-Nitropyridine (0.026 g, 0.17 mmol) were added and the reaction mixture was stirred for 2 hours at 80° C. After cooling the reaction mixture was quenched with water (1 ml), diluted with brine (5 ml) and extracted with ethyl acetate (2×10 ml). The organic layer was dried over sodium sulfate, filtered and evaporated. The residue was dissolved in tetrahydrofuran (5 ml)/water (2.5 ml), iron (0.04 g, 0.75 mmol) and then ammonium chloride (0.4 g, 0.75 mmol) were added and the reaction mixture was stirred overnight at room temperature. The catalyst was filtered off and the residue was diluted with an aqueous saturated solution of NaHCO$_3$ (5 ml) and extracted with ethyl acetate (3×10 ml). The organic layer was dried over sodium sulphate, filtered and evaporated and the residue was purified by flash chromatography (Biotage system) on silica gel using a 10 g SNAP column and cyclohexane/ethyl acetate 8:2 to cyclohexane/ethyl acetate 1:1 as eluents affording the title compound (0.025 g) as a light yellow solid.

LC/MS: QC_3_MIN: Rt 1.735 min, 285 [M+H]+.

Intermediate 181

[(3,3-dimethyl-2,3-dihydro-1-benzofuran-4-yl)oxy][tris(1-methylethyl)]silane

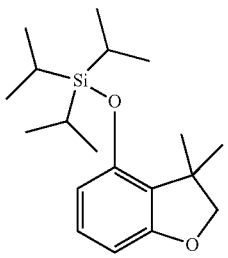 [SMILES: CC(C)[Si](Oc1cccc2c1C(C)(C)CO2)(C(C)C)C(C)C]

3,3-Dimethyl-2,3-dihydro-1-benzofuran-4-ol (Intermediate 50, 3.6 g, 21.91 mmol) was dissolved in anhydrous THF (20.0 mL) and the colorless solution was cooled to 0° C. stirring under nitrogen. A 2M n-BuLi solution in cyclohexane (13.2 mL, 26.4 mmol) was added drop wise and the resulting yellow solution was stirred at 0° C. for 10 min. Triisopropylsislyltriflate (7.7 mL, 28.5 mmol) was added drop wise: the solution discolored almost completely. This was allowed to warm to room temperature and stirred over night. Water (1.0 mL) was added to and volatiles evaporated under reduced pressure. The residue was dissolved in ethyl acetate and washed with brine three times. The organic layer was dried over anhydrous Na$_2$SO$_4$ and evaporated to dryness to give yellow oil which was re-dissolved in TBME and washed twice with water. The organic solution was dried over Na$_2$SO$_4$ and evaporated to dryness to give the title compound (7.4 g) as a yellow oil.

$^1$H NMR (400 MHz, DMSO-d$_6$) δ ppm 6.94 (1H, t), 6.31-6.36 (1H, m), 6.29 (1H, d), 4.14 (2H, s), 1.28-1.40 (9H, m), 1.09 (18H, d).

Intermediate 182

[(7-bromo-3,3-dimethyl-2,3-dihydro-1-benzofuran-4-yl)oxy][tris(1-methylethyl)]silane

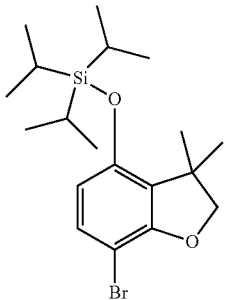 [SMILES: CC(C)[Si](Oc1ccc(Br)c2c1C(C)(C)CO2)(C(C)C)C(C)C]

[(3,3-dimethyl-2,3-dihydro-1-benzofuran-4-yl)oxy][tris(1-methylethyl)]silane (Intermediate 181, 7.4 g, 23.19 mmol) was dissolved in THF (70.0 mL). N-Bromosuccinimide (4.2 g, 23.88 mmol) was added dissolving in few minutes. This mixture was stirred at room temperature for 3 hrs. More NBS (0.64 g, 3.48 mmol) was added and the reaction mixture was stirred at room temperature for a further hour. CCl$_4$ (50 mL) was added to the reaction mixture and the solution was evaporated to dryness. The residue was re-suspended in CCl$_4$ and stirred at room temperature for 15 min. The white solid was removed by filtration and the wet cake was washed with more CCl$_4$. The CCl$_4$ was swapped with ethyl acetate and the organic solution was washed three times with 2.5% w/w aqueous NaHCO$_3$ and finally with water. The organic solution was dried on anhydrous Na$_2$SO$_4$ and evaporated to dryness to give the title compound (8.6 g) as a brown oil.

$^1$H NMR (400 MHz, DMSO-d$_6$) δ ppm 7.14 (1H, d), 6.29 (1H, d), 4.24 (2H, s), 1.27-1.41 (9H, m), 1.08 (18H, d).

Intermediate 183

Tris(1-methylethyl)[(3,3,7-trimethyl-2,3-dihydro-1-benzofuran-4-yl)oxy]silane

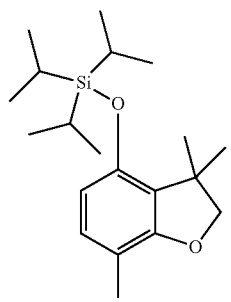 [SMILES: Cc1ccc(O[Si](C(C)C)(C(C)C)C(C)C)c2c1OCC2(C)C]

[(7-bromo-3,3-dimethyl-2,3-dihydro-1-benzofuran-4-yl)oxy][tris(1-methylethyl)]silane (Intermediate 182, 7.1 g, 17.72 mmol) was dissolved in anhydrous THF (72 mL) and cooled to 0° C. Tetramethylethylenediamine (8.0 mL, 53.16 mmol) was added and the yellow solution was stirred at 0° C. for 10 min. A solution of 1.6 M butyllithium in hexane (22.5 mL, 35.4 mmol) was added drop wise over 10 minutes and then stirred at 0° C. for 15 min. Methyl iodide (11 mL, 177.2 mmol) was added drop wise over 6 min. The white solid was removed by filtration and the wet cake was washed in with THF. The combined organic layers were evaporated to dryness. The residue was dissolved in ethyl acetate and washed twice with aqueous NaHCO$_3$ and once with water. The organic solution was dried on anhydrous Na$_2$SO$_4$ and evaporated to dryness. to give brown oil. The residue was purified by flash chromatography on silica gel using cyclohexane to cyclohexane/ethyl acetate 1:1 as eluents affording the title compound (3.6 g) as a brown oil.

$^1$H NMR (400 MHz, DMSO-d$_6$) δ ppm 6.76 (1H, d), 6.20 (1H, d), 4.14 (2H, s), 2.02 (3H, s), 1.28-1.39 (9H, m), 1.09 (18H, d).

Intermediate 184

3,3,7-trimethyl-2,3-dihydro-1-benzofuran-4-ol

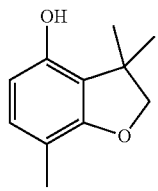

Tris(1-methylethyl)[(3,3,7-trimethyl-2,3-dihydro-1-benzofuran-4-yl)oxy]silane (Intermediate 183, 3.6 g, 10.84 mmol) was dissolved in THF (36 mL) to obtain a dark yellow solution. TBAF (8.5 g, 32.5 mmol) was added and the reaction mixture was stirred OVERNIGHT at room temperature. The solvent was removed under reduced pressure. The residue was dissolved in ethyl acetate and washed with aqueous HCl, then aqueous NaHCO$_3$ and finally brine. The organic solution was dried over Na$_2$SO$_4$ and evaporated to dryness and the residue was purified by flash chromatography on silica gel using cyclohexane to cyclohexane/ethyl acetate 95:5 as eluents affording the title compound (1.69 g) as colorless oil.

$^1$H NMR (400 MHz, DMSO-d$_6$) δ ppm 9.06 (1H, s), 6.65-6.69 (1H, m), 6.19 (1H, d), 4.11 (2H, s), 1.99 (3H, s), 1.33 (6H, s).

Intermediate 185

5-nitro-2-[(3,3,7-trimethyl-2,3-dihydro-1-benzofuran-4-yl)oxy]pyridine

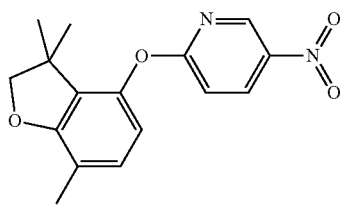 [SMILES: Cc1ccc(Oc2ccc([N+](=O)[O-])cn2)c2c1OCC2(C)C]

3,3,7-trimethyl-2,3-dihydro-1-benzofuran-4-ol (Intermediate 184, 0.9 g, 5.0 mmol) was dissolved in CH$_3$CN (5 mL) in the presence of 2-chloro-5-nitropyridine (790 mg, 5.0 mmol) and K$_2$CO$_3$ (1.72 g, 12.5 mmol) and the resulting suspension was heated to 60° C. for 1.5 hrs. The mixture was then cooled to room temperature and diluted with water and ethyl acetate. Two phases were separated and the organic layer was washed with brine, then dried over Na$_2$SO$_4$ and evaporated to dryness, The residue was purified by flash chromatography on silica gel using cyclohexane to cyclohexane/ethyl acetate 90:10 as eluents affording the title compound (0.92 g) as yellowish solid.

$^1$H-NMR (400 MHz, DMSO-d$_6$): δ ppm 9.04 (1H, d), 8.61 (1H, dd), 7.24 (1H, d), 7.02 (1H, d), 6.54 (1H, d), 4.21 (2H, s), 2.14 (3H, s), 1.21 (6H, s). $^{13}$C-NMR (200 MHz, DMSO-d$_6$): δ ppm 166.6, 158.7, 147.2, 144.8, 140.4, 135.8, 130.2, 126.1, 116.7, 114.5, 111.0, 83.6, 42.2, 26.0, 14.4.

Intermediate 186

6-[(3,3,7-trimethyl-2,3-dihydro-1-benzofuran-4-yl)oxy]-3-pyridinamine

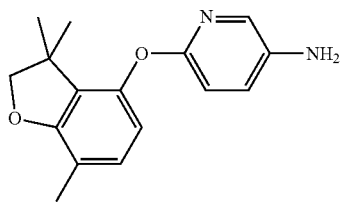 [SMILES: Cc1ccc(Oc2ccc(N)cn2)c2c1OCC2(C)C]

5-Nitro-2-[(3,3,7-trimethyl-2,3-dihydro-1-benzofuran-4-yl)oxy]pyridine (Intermediate 185, 920 mg, 3.0 mmol) was dissolved in EtOH (13.5 mL) and stirred under hydrogen atmosphere (2 bar) in the presence of Pd/C 10% w/w (46 mg, 5% w/w) at room temperature for 30 minutes. The catalyst was filtered off, washed with THF and the resulting solution evaporated to dryness to afford an orange solid. The crude product was crystallized from MeOH to the title compound (565 mg) as a beige solid.

$^1$H-NMR (400 MHz, DMSO-d$_6$): δ ppm 7.51 (1H, d), 7.05 (1H, dd), 6.85 (1H, d), 6.69 (1H, d), 6.21 (1H, d), 5.04 (2H, br.s), 4.19 (2H, s), 2.08 (3H, s), 1.30 (6H, s). $^{13}$C-NMR (200 MHz, DMSO-d$_6$): δ ppm 158.3, 154.2, 150.7, 141.5, 132.2, 129.6, 125.3, 124.7, 113.9, 112.2, 111.8, 83.7, 42.2, 26.0, 14.4.

Intermediate 187

1,1-dimethylethyl {(1R)-1-[({6-[(3,3,7-trimethyl-2,3-dihydro-1-benzofuran-4-yl)oxy]-3-pyridinyl}amino)carbonyl]propyl}carbamate

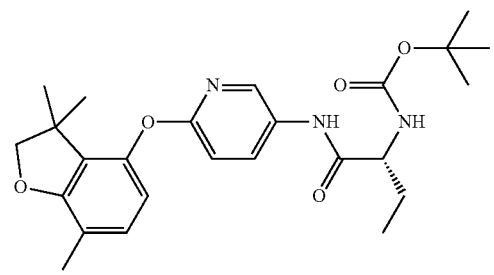 [SMILES: CC[C@@H](NC(=O)OC(C)(C)C)C(=O)Nc1ccc(Oc2ccc(C)c3c2C(C)(C)CO3)nc1]

6-{[3,3,7-Trimethyl-6-(trifluoromethoxy)-2,3-dihydro-1-benzofuran-4-yl]oxy}pyridin-3-amine (Intermediate 186, 405 mg, 1.27 mmol) was suspended in ethyl acetate (4 mL). Triethylamine (0.44 ml, 3.175 mmol) was added followed by the addition of (2R)-2-({[(1,1-dimethylethyl)oxy]carbonyl}amino)butanoic acid (258 mg, 1.27 mmol). The resulting suspension was cooled to 0° C. and T3P 50% w/w solution in ethyl acetate (1.4 mmol) was added drop wise. The reaction mixture was stirred at 0° C. for 1 hour and then warmed to room temperature and stirred for a further hour. An aqueous saturated solution of Na$_2$CO$_3$ was added and the mixture stirred for 10 min. Two phases were separated and the organic layer was washed with water and brine, dried over Na$_2$SO$_4$ and evaporated to dryness. The residue was purified by flash chromatography on silica gel using cyclohexane/ethyl acetate 80:20 to cyclohexane/ethyl acetate 70:30 as eluents affording the title compound (0.50 g) as white foam.

$^1$H-NMR (400 MHz, DMSO-d$_6$): δ ppm 10.08 and 10.03 (1H, br.s), 8.30 (1H, d), 8.03 (1H, dd), 7.00 (1H, d), 6.95-6.90 (2H, m), 6.36 (1H, d), 4.17 (2H, s), 3.98-3.92 (1H, m), 2.10 (3H, s), 1.73-1.52 (2H, m), 1.36 and 1.29 (9H, br.s), 1.23 (6H, s), 0.88 (3H, t). $^{13}$C-NMR (200 MHz, DMSO-d$_6$): δ ppm 171.4, 159.0, 158.5, 155.5, 148.9, 138.1, 131.4, 129.8, 125.8, 115.1, 113.9, 110.7, 83.6, 78.0, 56.3, 42.2, 28.9, 26.0, 25.0, 20.7, 14.4, 14.1, 10.5.

Intermediate 188

(2R)-2-amino-N-{6-[(3,3,7-trimethyl-2,3-dihydro-1-benzofuran-4-yl)oxy]-3-pyridinyl}butanamide

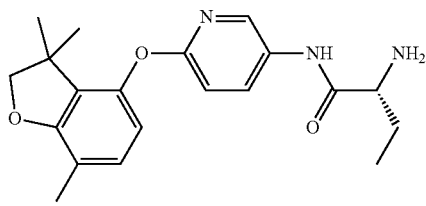 [SMILES: CC[C@@H](N)C(=O)Nc1ccc(Oc2ccc(C)c3c2C(C)(C)CO3)nc1]

The 1,1-dimethylethyl {(1R)-1-[({6-[(3,3,7-trimethyl-2,3-dihydro-1-benzofuran-4-yl)oxy]-3-pyridinyl}amino)carbonyl]propyl}carbamate (Intermediate 187, 480 mg, 1.05 mmol) was dissolved in iso-propyl acetate (5 mL) and HCl 5-6N in isopropanol (1 ml, 5.25 mmol) was added. The solution was stirred at room temperature for 1 hour and then heated to ~50-55° C. until complete conversion. The mixture was cooled to room temperature and treated with an aqueous saturated solution of NaHCO$_3$. Two phases were separated and the organic layer was washed with brine, dried over Na$_2$SO$_4$ and evaporated to dryness. The residue was purified by flash chromatography on silica gel using dichloromethane/methanol 95:5 as eluents affording the title compound (0.31 g) as yellowish foam.

$^1$H-NMR (400 MHz, DMSO-d$_6$): δ ppm 8.36 (1H, d), 8.11 (1H, dd), 6.96-6.92 (2H, m), 6.38 (1H, d), 4.19 (2H, s), 3.23 (1H, dd), 2.11 (3H, s), 1.72-1.61 (1H, m), 1.53-1.43 (1H, m), 1.25 (6H, s), 0.90 (3H, t). $^{13}$C-NMR (200 MHz, DMSO-d$_6$): δ ppm 174.5, 159.0, 158.5, 148.9, 138.2, 131.5, 131.4, 129.8, 125.7, 115.1, 113.9, 110.6, 83.6, 56.7, 42.2, 28.0, 26.0, 14.4, 10.2.

Intermediate 189

5-nitro-2-[(3,3,7-trimethyl-2,3-dihydro-1-benzofuran-4-yl)oxy]pyrimidine

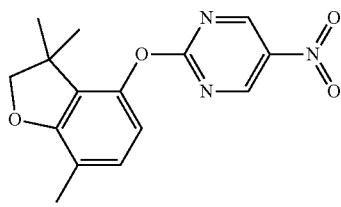 [SMILES: Cc1ccc(Oc2ncc([N+](=O)[O-])cn2)c2c1OCC2(C)C]

3,3,7-Trimethyl-2,3-dihydro-1-benzofuran-4-ol (Intermediate 184, 178 mg, 1.0 mmol) and 2-chloro-5-nitropyrimidine (191.5 mg, 1.2 mmol) were dissolved in CH$_3$CN (3.0 mL) and K$_2$CO$_3$ (345.5 mg, 2.5 mmol) was added. The resulting suspension was heated to 40° C. and stirred for 1 hour. The reaction mixture was then diluted with water (50 mL) and ethyl acetate (50 mL), The organic phase was collected, washed with brine (50 mL) and dried over Na$_2$SO$_4$. The residue was purified by flash chromatography on silica gel using cyclohexane/ethyl acetate 97:3 as eluents affording the title compound (243 mg).

Intermediate 190

2-[(3,3,7-trimethyl-2,3-dihydro-1-benzofuran-4-yl)oxy]-5-pyrimidinamine

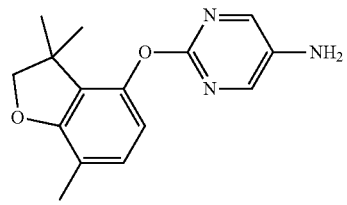 [SMILES: Cc1ccc(Oc2ncc(N)cn2)c2c1OCC2(C)C]

5-nitro-2-[(3,3,7-trimethyl-2,3-dihydro-1-benzofuran-4-yl)oxy]pyrimidine (Intermediate 189, 243 mg, 0.81 mmol) was dissolved in THF (4 mL) and Palladium on charcoal (5 mol %, 85 mg) was added. The reaction mixture was stirred under hydrogen atmosphere (3 bar) for 1 hour at room temperature. The catalyst was filtered on a pad of celite, washed with THF and the resulting solution was concentrated under vacuum. The residue was diluted with ethyl acetate and water, the organic phase collected, dried over Na$_2$SO$_4$ and evaporated to afford the title compound (220 mg) as colorless oil. The crude product, was used in the next step without further purification.

MS_2 (ESI): 272 [M+H]+

Intermediate 191

1,1-dimethylethyl {(1R)-1-[({2-[(3,3,7-trimethyl-2,3-dihydro-1-benzofuran-4-yl)oxy]-5-pyrimidinyl}amino)carbonyl]propyl}carbamate

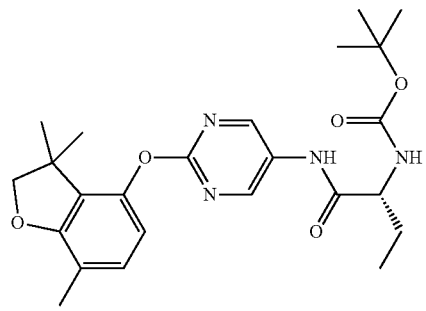 [SMILES: CC[C@@H](NC(=O)OC(C)(C)C)C(=O)Nc1cnc(Oc2ccc(C)c3c2C(C)(C)CO3)nc1]

2-[(3,3,7-trimethyl-2,3-dihydro-1-benzofuran-4-yl)oxy]-5-pyrimidinamine (Intermediate 190, 220 mg, 0.81 mmol) was dissolved in ethyl acetate (10 mL) and of (2R)-2-({[(1,1-dimethylethyl)oxy]carbonyl}amino)butanoic acid (181.1 mg, 0.89 mmol) was added followed by the addition of Et$_3$N (0.35 mL, 2.02 mmol). The resulting solution was cooled down to 5° C. and a solution of T3P 50% w/w in ethyl acetate (0.53 mL, 0.89 mmol) was added drop wise in 15 min. The reaction mixture was stirred for 30 min at 5° C. The reaction was quenched with water (50 mL) and ethyl acetate (50 mL), two phases were separated and the organic layer was dried over Na$_2$SO$_4$ and concentrated under vacuum. The residue was purified by flash chromatography on silica gel using cyclohexane/ethyl acetate 60:40 as eluent affording the title compound (213 mg).

MS_2 (ESI): 457 [M+H]+.

Intermediate 192

7-(methoxymethoxy)-3H-isobenzofuran-1-one

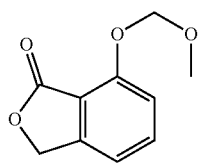

4-Hydroxy-1,3-dihydro-2-benzofuran-1,3-dione (685 mg, 4 mmol) was dissolved in dry THF (30 mL) at −78° C. K-Selectride 1M solution in THF (13 mL, 13 mmol) was added drop wise in 20 min then the mixture was warmed from −78° C. to −30° C. over 3 hrs. The final mixture was poured into ethyl acetate (100 mL), brine (25 mL) and a 3M hydrochloric acid solution (25 mL). The organic layer was collected, washed with brine and evaporated to dryness. The resulting compound was dissolved in MeOH (20 mL) and treated under stirring with a 3M hydrochloric acid solution (10 mL). The mixture was then diluted with ethyl acetate (100 mL) and brine (25 mL), the organic layer was collected and evaporated under vacuum. The residue was purified by flash chromatography on silica gel using dichloromethane as eluent affording the phenol intermediate (430 mg).

The phenol intermediate (430 mg, 2.9 mmol) was dissolved in dry dichloromethane (20 mL) at 0° C., DIPEA (5 mL, 5.5 mmol) was added followed by a drop wise addition of chloromethylmethylether (0.44 mL, 5.7 mmol) over 10 min. The resulting solution was stirred at 0° C. for 30 minutes then at room temperature for 15 minutes. Dichloromethane was partially evaporated and the obtained suspension was dissolved in ethyl acetate (20 mL), washed with a 50/50 mixture of water and brine (2×10 mL), dried over Na$_2$SO$_4$ and evaporated to give the title compound (549 mg) as a pale yellow solid.

$^1$H NMR (400 MHz, DMSO-d$_6$): δ ppm 7.68 (1H, m), 7.20 (2H, m), 5.36 (2H, s), 5.31 (2H, s), 3.41 (3H, s).

Intermediate 193

3,3-dimethyl-1H-isobenzofuran-4-ol

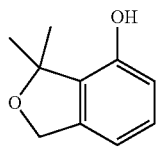

7-(methoxymethoxy)-3H-isobenzofuran-1-one (Intermediate 192, 550 mg, 2.8 mmol) was dissolved at −70° C. in dry THF (150 mL). A 3M solution of methylmagnesium bromide in diethyl ether (5.6 mL, 16.8 mmol) was added drop wise in 30 minutes and the obtained mixture stirred for 30 minutes at −70° C. and then 30 minutes at room temperature. The reaction mixture was poured into ethyl acetate (100 mL) and aqueous saturated solution of ammonium chloride (50 mL) at 0° C. The organic layer was collected, washed with an aqueous saturated solution of ammonium chloride (50 mL), brine (50 mL) and evaporated to give a yellow oil that was dissolved in acetonitrile (15 mL) and treated with sulphuric acid (0.15 mL). Acetonitrile was replaced with methyl alcohol (15 mL) and the resulting solution treated with p-toluensulfonic acid (100 mg). The solution was heated to 60° C. and stirred for 2 hours. The solvent was evaporated and the residue dissolved in ethyl acetate (30 mL), washed twice with an aqueous saturated solution of sodium bicarbonate (10 mL) and then with an aqueous diluted solution of hydrochloric acid, dried over Na$_2$SO$_4$, and evaporated to dryness. The residue was purified by flash chromatography on silica gel using cyclohexane/ethyl acetate 90:10 as eluent affording the title compound (210 mg) as white solid.

$^1$H NMR (DMSO-d$_6$, 400 MHz): δ ppm 9.51 (1H, s), 7.00-7.10 (1H, m), 6.60-6.70 (2H, m), 4.89 (2H, s), 1.45 (6H, s).

Intermediate 194

(5R)-3-(6-chloro-3-pyridinyl)-5-ethyl-5-methyl-2,4-imidazolidinedione

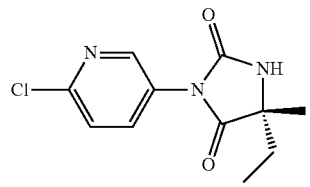 [SMILES: CC[C@@]1(C)NC(=O)N(c2ccc(Cl)nc2)C1=O]

6-Chloropyridin-3-amine (3.0 g, 23.3 mmol) was dissolved in a 3:1 v/v mixture of CH$_3$CN/ethyl acetate (20 mL) and (2R)-2-amino-2-methylbutanoic acid hydrochloride (3.97 g, 25.63 mmol) was added, followed by a 50% w/w solution in ethyl acetate of T3P (15.3 mL, 25.63). The mixture was heated to 60° C. for 2 hrs, then quenched with NaOH 3N while the pH was ~10 and then diluted with ethyl acetate (100 mL). The organic phase was collected, dried over Na$_2$SO$_4$ and concentrated under vacuum to a final volume of ~15 mL. The solution was cooled down to 0-5° C. and Et$_3$N (11.4 ml, 81.9 mmol) was added. A solution of triphosgene (2.76 g, 6.96 mmol) in 10 mL of ethyl acetate was added drop wise in 15 min, keeping the internal temperature below 5° C. The mixture was stirred at 5° C. for 30 minutes then quenched with water (100 mL) and finally diluted with additional ethyl acetate (100 mL). Two phases were separated and the organic layer was washed with water and brine, dried over Na$_2$SO$_4$ and concentrated under vacuum. The crude product was suspended in 15 mL of ethyl acetate followed by the drop wise addition of 65 mL of n-heptane. The resulting suspension was stirred at room temperature for 2 hrs, filtered, and the cake washed with a 2:8 v/v mixture of ethyl acetate/n-heptane (2×10 mL) before being dried at 40° C. for 18 hrs affording the title compound (3.5 g) as white solid.

$^1$H NMR (400 MHz, DMSO-d$_6$): δ ppm 8.68 (1H, s), 8.47 (1H, d), 7.95-7.89 (m, 1H), 7.68-7.63 (1H, m), 1.83-1.58 (2H, m), 1.38 (3H, s), 0.85 (3H, t).

Intermediate 195

(2,2-difluoro-1,3-benzodioxol-4-yl)boronic Acid

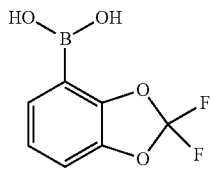 [SMILES: OB(O)c1cccc2c1OC(F)(F)O2]

2,2-Difluoro-1,3-benzodioxole (960 mg, 6.1 mmol) was dissolved in THF (8 mL) and cyclohexane (4 mL) and the resulting solution cooled to −78° C. sec-BuLi 1.4M solution in cyclohexane (4.3 mL, 6.1 mmol) was added dropwise and the reaction mixture stirred for 1.5 hours at −78° C. Trimethylborate (694 mg, 6.75 mmol) was added and the mixture was allowed to warm slowly to −30° C. The reaction mixture was quenched with a 2N solution of HCl and diluted with ethyl acetate. Two phases were separated and the organic layer was washed twice with brine, dried over $Na_2SO_4$ and evaporated to dryness affording the title compound as yellow oil which was used in the next step without further purification.

$^1$H-NMR (400 MHz, DMSO-$d_6$+$D_2O$): δ ppm 7.39 (1H, dd), 7.34 (1H, dd), 7.14 (t, 1H, J=7.90 Hz). $^{19}$F-NMR (376 MHz, DMSO-$d_6$+$D_2O$): δ ppm −48.92. $^{13}$C-NMR (200 MHz, DMSO-$d_6$+$D_2O$): δ ppm 147.3, 142.8, 131.6 (t, J=250.7 Hz), 130.1, 124.3, 112.0

Intermediate 196

(2,2-difluoro-7-methyl-1,3-benzodioxol-4-yl)boronic Acid

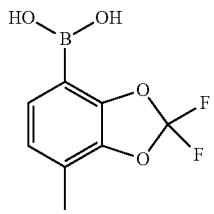

(2,2-difluoro-1,3-benzodioxol-4-yl)boronic acid (Intermediate 195, crude material) was dissolved in THF (20 mL) and the resulting solution cooled down to −78° C. sec-BuLi 1.4M solution in cyclohexane (17.4 ml, 24.36 mmol) was added dropwise and the reaction mixture was stirred for 1.5 hours at −78° C. Methyl iodide (4.6 ml, 73 mmol) was then added and the reaction mixture was stirred for 2 hours while the temperature was allowed to reach room temperature. The reaction was quenched by addition of an aqueous 2N solution of HCl and diluted with ethyl acetate. The organic layer was collected and then washed twice with brine, dried over $Na_2SO_4$ and evaporated to dryness. Crystallization from n-heptane afforded the title compound (150 mg) as white solid.

$^1$H-NMR (400 MHz, DMSO-$d_6$+$D_2O$): δ ppm 7.30 (1H, d), 6.68 (1H, d), 2.25 (s, 3H). $^{19}$F-NMR (376 MHz, DMSO-$d_6$+$D_2O$): δ ppm −48.55. $^{13}$C-NMR (200 MHz, DMSO-$d_6$+$D_2O$): δ ppm 152.5, 147.1, 141.5, 131.6 (t, J=250.0 Hz), 129.9, 125.8, 122.7, 110.1, 14.6.

Intermediate 197

2,2-difluoro-7-methyl-1,3-benzodioxol-4-ol

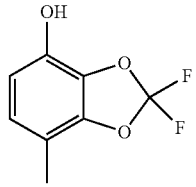

(2,2-difluoro-7-methyl-1,3-benzodioxol-4-yl)boronic acid (Intermediate 196, 150 mg, 1.28 mmol) was dissolved in THF (1.5 mL) and a 30% w/w aqueous solution of $H_2O_2$ (2.56 mmol) and NaOH (51 mg, 1.28 mmol) were added and the reaction mixture stirred for 2 days at room temperature. The reaction was quenched with a 2N aqueous solution of HCl and diluted with ethyl acetate. Two phases were separated and the organic layer was washed twice with brine, dried over $Na_2SO_4$ and evaporated to dryness, affording the title compound (140 mg) as yellow oil.

$^1$H-NMR (400 MHz, DMSO-$d_6$): δ ppm 10.31 (1H, s), 6.83 (1H, d), 6.63 (1H, d), 2.17 (3H, s). $^{19}$F-NMR (376 MHz, DMSO-$d_6$): δ ppm −48.68. $^{13}$C-NMR (200 MHz, DMSO-$d_6$): δ ppm 142.3, 139.1, 131.4 (t, J=251.9 Hz), 129.9, 125.6, 112.8, 110.0, 13.2.

Intermediate 198

2,2-difluoro-1,3-benzodioxol-4-ol

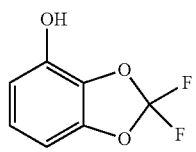 [SMILES: Oc1cccc2c1OC(F)(F)O2]

2,2-Difluoro-1,3-benzodioxole (320 mg, 2.05 mmol) was dissolved in THF (2.5 mL) and cyclohexane (1.2 mL) and the resulting solution cooled down to −78° C. sec-BuLi 2M solution in cyclohexane (1.025 ml, 2.05 mmol) was added drop wise and the reaction mixture stirred for 2 hours at −78° C. Trimethylborate (230 mg, 2.25 mmol) was added and the mixture was allowed to warm slowly to room temperature. A 30% w/w aqueous solution of $H_2O_2$ (4.1 mmol) and NaOH (82 mg, 2.05 mmol) were added and the reaction mixture stirred for 18 hours at room temperature. The reaction was quenched with a 2N aqueous solution of HCl and diluted with ethyl acetate. Two phases were separated and the organic layer was washed twice with brine, dried over $Na_2SO_4$ and evaporated to dryness, affording the title compound (340 mg).

$^1$H-NMR (400 MHz, CDCl$_3$): δ ppm 6.93 (1H, t), 6.69 (1H, d), 6.65 (1H, d). $^{19}$F-NMR (376 MHz, CDCl$_3$): δ ppm −49.86. $^{13}$C-NMR (200 MHz, CDCl$_3$): δ ppm 144.8, 139.6, 131.5 (t, J=255.1 Hz), 131.2, 123.9, 112.7, 101.8

Intermediate 199

2-[2-amino-6-(methyloxy)phenyl]-2-propanol

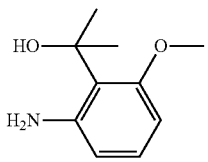

1-(2-Amino-6-methoxyphenyl)ethanone (500 mg, 3.03 mmol) was dissolved in THF (7.5 mL) and cooled to 0° C. A 3M solution of Methyl magnesium bromide in Et$_2$O (2.12 ml, 6.36 mmol) was added drop wise keeping the temperature below 10° C. The reaction was quenched with an aqueous saturated solution of NH$_4$Cl (7.5 mL) keeping the temperature below 15° C. The mixture was diluted with water and ethyl acetate, two phases separated and the organic layer was washed twice with brine, dried over Na$_2$SO$_4$ and evaporated to dryness affording the title compound (500 mg) as light orange solid.

$^1$H-NMR (400 MHz, DMSO-d$_6$): δ ppm 6.79 (1H, t), 6.19 (1H, dd), 6.14 (1H, dd), 5.76 (2H, br.s), 5.26 (1H, br.s), 3.64 (3H, s), 1.55 (6H, s). $^{13}$C-NMR (200 MHz, DMSO-d$_6$): δ ppm 157.4, 148.5, 126.8, 118.1, 110.5, 100.2, 74.2, 55.3, 30.7.

Intermediate 200

N-[2-(1-hydroxy-1-methylethyl)-3-(methyloxy)phenyl]acetamide

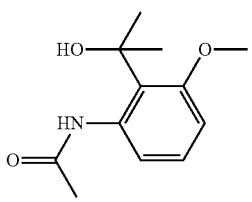 [SMILES: COc1cccc(NC(C)=O)c1C(C)(C)O]

2-(2-Amino-6-methoxyphenyl)propan-2-ol (Intermediate 199, 500 mg, 2.76 mmol) was dissolved in DCM (10 mL) and triethylamine (0.770 ml, 5.52 mmol) was added. The solution was cooled to 0° C. and treated with acetyl chloride (0.2 ml, 2.76 mmol) in a drop wise fashion. At the end of the addition, complete conversion was reached. The mixture was treated with an aqueous saturated solution of NH$_4$Cl, two phases were separated and the organic layer was washed with an aqueous saturated solution of NaHCO$_3$ and brine, then dried over Na$_2$SO$_4$ and evaporated to dryness. The crude was purified by re-slurry in tert-butyl methyl ether isolating 490 mg of the title compound as white solid.

$^1$H-NMR (400 MHz, DMSO-d$_6$): δ ppm 11.53 (1H, br.s), 7.91 (1H, d), 7.11 (1H, t), 6.71 (1H, d), 6.25 (1H, br.s), 3.74 (3H, s), 2.50 (1H, br.s), 2.00 (3H, s), 1.61 (6H, s). $^{13}$C-NMR (200 MHz, DMSO-d$_6$): δ ppm 167.0, 156.6, 138.5, 127.0, 123.1, 114.3, 107.6, 75.2, 55.7, 30.8, 25.2.

Intermediate 201

2,4,4-trimethyl-5-(methyloxy)-4H-3,1-benzoxazine

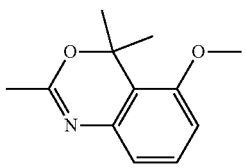

N-[2-(2-hydroxypropan-2-yl)-3-methoxyphenyl]acetamide (Intermediate 200, 470 mg, 2.10 mmol) was added to hot polyphosphoric acid and heated at 110° C. for 1 hour. The mixture was cooled to room temperature and quenched with water. Solid Na$_2$CO$_3$ was added while the pH was allowed to reach ~8-9. Water and DCM were added and two phases were separated. The combined organic layers were washed twice with brine, dried over Na$_2$SO$_4$ and evaporated to dryness, to obtain the title compound (342 mg) as an oil which was used in the next step without further purifications.

$^1$H-NMR (400 MHz, DMSO-d$_6$): δ ppm 7.17 (1H, t), 6.83 (1H, dd), 6.63 (1H, dd), 3.78 (3H, s), 1.98 (3H, s), 1.60 (6H, s). $^{13}$C-NMR (200 MHz, DMSO-d$_6$): δ ppm 158.4, 154.7, 139.0, 128.6, 117.0 (2C), 109.7, 77.8, 55.7, 28.5, 21.3.

Intermediate 202

2,4,4-trimethyl-4H-3,1-benzoxazin-5-ol

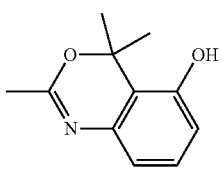

5-Methoxy-2,4,4-trimethyl-4H-3,1-benzoxazine (Intermediate 201, 342 mg, 1.67 mmol) was dissolved in DCM (7 mL) and 1M BBr$_3$ solution in DCM (1.67 ml, 1.67 mmol) was added. After 1.5 h at room temperature the mixture was heated to reflux and after 6 hours at reflux, some more 1M BBr$_3$ solution in DCM (1.67 ml, 1.67 mmol) was added leaving the mixture at reflux overnight. The reaction mixture was quenched with an aqueous saturated solution of NaHCO$_3$ while the pH was allowed to become basic. Two phases were separated and the organic layer was washed with brine, dried over Na$_2$SO$_4$ and evaporated to dryness, to obtain the title compound (330 mg) as foam.

$^1$H-NMR (400 MHz, DMSO-d$_6$): δ ppm 9.62 (1, s), 6.98 (1H, t), 6.62 (1H, dd), 6.46 (1H, dd), 1.96 (3H, s), 1.62 (6H, s). $^{13}$C-NMR (200 MHz, DMSO-d$_6$): δ ppm 157.9, 152.6, 139.2, 128.2, 115.4, 115.3, 113.9, 77.8, 28.3, 21.3.

Intermediate 203

2,4,4-trimethyl-5-[(5-nitro-2-pyridyl)oxy]-3,1-benzoxazine

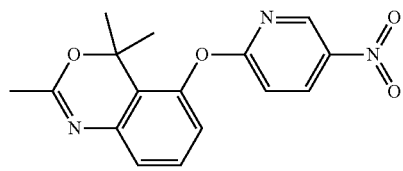 [SMILES: CC1=Nc2cccc(Oc3ccc([N+](=O)[O-])cn3)c2C(C)(C)O1]

To a suspension of 2,4,4-trimethyl-4H-3,1-benzoxazin-5-ol (Intermediate 202, 500 mg, 2.61 mmol) and 2-chloro-5-nitropyridine (410 mg, 2.58 mmol) in dry DMF (4 mL) potassium carbonate (400 mg, 2.89 mmol) was added and the resulting mixture was heated in a MW apparatus at 70° C. for 40 min. The mixture was diluted with water and ethyl acetate, phases were separated and the aqueous was back-extracted with ethyl acetate (2×20 mL). The combined organic layers were washed with brine (2×20 mL), dried over $Na_2SO_4$, filtered and concentrated and the residue was purified by flash chromatography on silica gel using cyclohexane/ethyl acetate from 70:30 to 50:50 as eluents affording the title compound (225 mg) as yellow foam.

$^1$H NMR (400 MHz, DMSO-$d_6$): δ ppm 9.05 (1H, d), 8.63 (1H, dd), 7.21-7.40 (2H, m), 6.84-7.02 (2H, m), 2.01 (3H, s), 1.50 (6H, s).

Intermediate 204

6-[(2,4,4-trimethyl-3,1-benzoxazin-5-yl)oxy]pyridin-3-amine

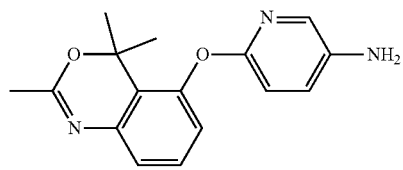 [SMILES: CC1=Nc2cccc(Oc3ccc(N)cn3)c2C(C)(C)O1]

To a solution of 2,4,4-trimethyl-5-[(5-nitro-2-pyridyl)oxy]-3,1-benzoxazine (Intermediate 203, 220 mg, 0.70 mmol) in EtOH (3 mL) palladium on carbon 10% w/w (25 mg) was added and the resulting mixture was stirred for 40 minutes under hydrogen atmosphere (2 bar) at room temperature. The catalyst was filtered off and washed with EtOH (3×10 mL). The filtrate was concentrated to the title compound (185 mg) as greenish solid.

$^1$H NMR (400 MHz, DMSO-$d_6$): δ ppm 7.51 (1H, d), 7.12 (1H, t), 7.05 (1H, dd), 6.75 (2H, d), 6.55 (1H, d), 5.07 (2H, s), 1.99 (3H, s), 1.58 (6H, s).

Intermediate 205

(2R)-2-amino-2-methyl-N-[6-[(2,4,4-trimethyl-3,1-benzoxazin-5-yl)oxy]-3-pyridyl]butanamide

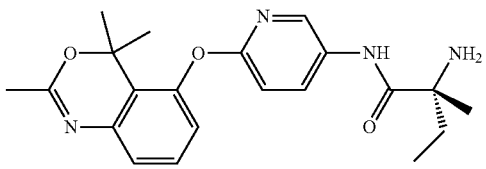 [SMILES: CC[C@@](C)(N)C(=O)Nc1ccc(Oc2cccc3c2C(C)(C)OC(C)=N3)nc1]

To a suspension of 6-[(2,4,4-trimethyl-3,1-benzoxazin-5-yl)oxy]pyridin-3-amine (Intermediate 204, 185 mg, 0.65 mmol) and (R)-2-amino-2-methyl-butanoic acid hydrochloride (100 mg, 0.67 mmol) in ethyl acetate/MeCN (2 mL, 1:3 v/v mixture), a 50% w/w solution in ethyl acetate of T3P (0.43 mL) was added drop wise at 0° C. The mixture was then heated at 60° C. for 3 hours and at 80° C. for 4.5 hours. The mixture was cooled to room temperature diluted with water (5 mL) and ethyl acetate (10 mL), Two phases were separated and the aqueous one was treated with a saturated solution of $NaHCO_3$ (pH=8) and back-extracted with ethyl acetate (2×10 mL). The combined organic layers were dried over $Na_2SO_4$, filtered and concentrated and the residue was purified by flash chromatography on silica gel using cyclohexane/ethyl acetate 20:80 as eluent affording the title compound (143 mg) as a yellow foam.

$^1$H NMR (400 MHz, DMSO-de): δ ppm 8.39 (1H, d), 8.17 (1H, dd), 7.20 (1H, t), 7.01 (1H, d), 6.84 (1H, d), 6.73 (1H, d), 2.00 (3H, s), 1.69 (1H, m), 1.43-1.57 (7H, m), 1.21 (3H, s), 0.80 (3H, t).

Intermediate 206

2-[(2,2-dimethyl-2,3-dihydro-1-benzofuran-4-yl)oxy]-5-nitropyridine

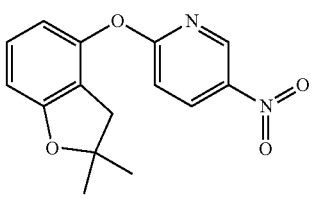 [SMILES: CC1(C)Cc2c(Oc3ccc([N+](=O)[O-])cn3)cccc2O1]

In a microwave vial, 2-chloro-5-nitropyridine (97 mg, 0.609 mmol) was dissolved in 3 mL of dimethylformamide. 2,2-dimethyl-2,3-dihydro-1-benzofuran-4-ol (100 mg, 0.609 mmol) and potassium carbonate (253 mg, 1.827 mmol) were added. The reaction mixture was heated under microwave irradiation for 1 hour at 110 C. The reaction mixture was filtered. The filtrated solid was washed with dichloromethane (5 ml). The volatiles were evaporated under vacuum. The crude compound was dissolved in dichloromethane (8 ml) and brine was added (8 ml). The compound was extracted 2 times with dichloromethane (2×8 ml) and 2 times with ethylacetate (2×8 ml). Combined organic layers were dried over sodium sulphate and evaporated. The residue was purified by silica gel chromatography (Companion system, 12 g Si cartridge) with cyclohexane/ethyl acetate from 100:0 to 80:20 as eluents affording the title compound (120 mg).

UPLC_ipqc: 1.20 min, 287 [M+H]+.

Intermediate 207

6-[(2,2-dimethyl-2,3-dihydro-1-benzofuran-4-yl)oxy]-3-pyridinamine

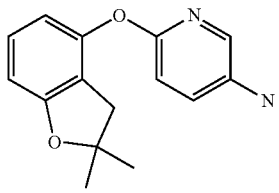

Fe powder (112 mg, 2.009 mmol) was added to a solution of 2-[(2,2-dimethyl-2,3-dihydro-1-benzofuran-4-yl)oxy]-5-nitropyridine (Intermediate 206, 115 mg 0.402 mmol) in a mixture THF/water (9 ml/3 ml) followed by the addition of ammonium chloride (107 mg 2.009 mmol). The reaction mixture was stirred overnight at room temperature. The catalyst was filtered off and the solution was diluted with an aqueous saturated aqueous solution of NaHCO$_3$ (10 ml) and ethyl acetate (15 ml). Two phases were separated and the aqueous layer was extracted twice with ethyl acetate (2×15 ml). Combined organic layers were dried over Na$_2$SO$_4$, filtered and evaporated. The residue was purified by flash chromatography (Companion system, 12 g silica gel cartridge) using cyclohexane/ethyl acetate from 80:20 to 50:50 as eluents affording the title compound (95 mg).

UPLC_ipqc: 0.87 min, 257 [M+H]+.

Intermediate 208

Tert-butyl N-[(1R)-1-[[6-[(2,2-dimethyl-3H-benzofuran-4-yl)oxy]-3-pyridyl]carbamoyl]propyl]carbamate

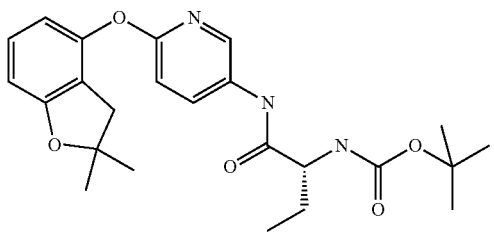

To a solution of (2R)-2-({[(1,1-dimethylethyl)oxy]carbonyl}amino)butanoic acid (17.84 mg, 0.088 mmol) in dry N,N dimethylformamide (DMF) (1 mL), DIPEA (25.6 µl, 0.146 mmol) and then HATU (37.8 mg, 0.099 mmol) were added and the reaction mixture was stirred for 15 minutes at room temperature under argon. Then 6-[(3,3-dimethyl-2,3-dihydro-1-benzofuran-4-yl)oxy]-3-pyridinamine (Intermediate 207, 15 mg, 0.059 mmol) was added and the reaction mixture was left overnight under stirring at 35° C. under argon. The reaction mixture was evaporated. Brine (4 ml) was added and it was extracted 3 times with ethyl acetate (3×5 ml). Combined organic layers were dried over Na$_2$SO$_4$, filtered and evaporated and the residue was purified by flash chromatography (Companion system, 12 g silica cartridge) with cyclohexane/ethyl acetate as eluents from 100:0 to 70:30 affording the title compound (18 mg).

UPLC_ipqc: 1.21 min, 442 [M+H]+.

Intermediate 209

(2R)-2-amino-N-{6-[(2,2-dimethyl-2,3-dihydro-1-benzofuran-4-yl)oxy]-3-pyridinyl}butanamide

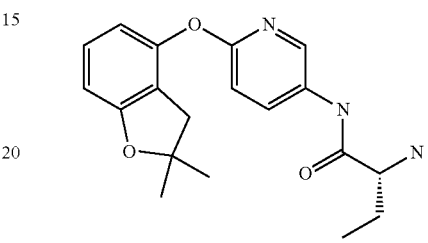

To a solution of tert-butyl N-[(1R)-1-[[6-[(2,2-dimethyl-3H-benzofuran-4-yl)oxy]-3-pyridyl]carbamoyl]propyl]carbamate (Intermediate 208, 14 mg, 0.032 mmol) in dry dichloromethane (1 ml) at 0° C., TFA (98 µl, 1.268 mmol) was slowly added and the reaction mixture was stirred for 4 hours at the same temperature. Some more dichloromethane (4 ml) was added to the reaction mixture. An aqueous saturated aqueous solution of NaHCO$_3$ was then added while the pH was allowed to reach ~8. Two phases were separated and the aqueous one was further extracted with DCM (3×3 ml). Combined organic layers were dried over Na$_2$SO$_4$, filtrated and evaporated affording the title compound (10 mg).

UPLC_ipqc: 0.73 min, 342 [M+H]+.

Intermediate 210

5-(methoxymethoxy)-4-methyl-chromane

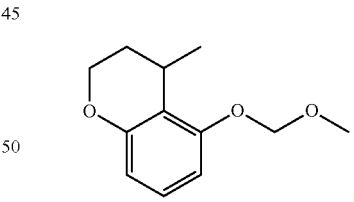

In a 50 mL round-bottomed flask 2-(3-hydroxy-1-methylpropyl)-3-(methoxymethoxy)phenol (56.3 mg, 0.249 mmol) was dissolved in Tetrahydrofuran (THF) to give a colourless solution. Triphenylphosphine (59.4 mg, 0.226 mmol) was added and the reaction mixture was stirred until complete solubilization of triphenylphosphine. DIAD (45.8 mg, 0.226 mmol) was added and the reaction mixture was stirred. Additional Triphenylphosphine (59.4 mg, 0.226 mmol) and DIAD (45.8 mg, 0.226 mmol) were added. The reaction mixture evaporated in vacuo and the residue was purified by flash chromatography (Biotage SP1) on silica gel using a 10 g SNAP silica cartridge as column and cyclohexane/ethyl acetate 10:1 as eluents affording the title compound (50.3 mg) as colorless oil.

$^1$H NMR (400 MHz, CDCl$_3$) δ ppm 7.03 (1H, t), 6.63 (1H, d), 6.52 (1H, d), 5.22 (2H, dd), 4.20-4.28 (1H, m), 4.09-4.19 (1H, m), 3.51 (3H, s), 3.09-3.23 (1H, m), 1.96-2.17 (1H, m), 1.61-1.74 (1H, m), 1.31 (3H, d).

Intermediate 211

4-methylchroman-5-ol

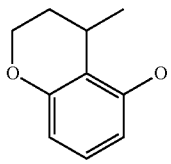

In a 50 mL round-bottomed flask 5-(methoxymethoxy)-4-methyl-chromane (Intermediate 210, 50.3 mg, 0.229 mmol) was dissolved in Methanol (4 mL) to give a pale yellow solution. A 2M aqueous solution of HCl (0.100 mL, 0.200 mmol) was added. The reaction mixture was stirred at 50° C. Sequential addition of 2M/H$_2$O solution of HCl (0.100 mL, 0.200 mmol) were added until completion of reaction. The reaction mixture was quenched with 10 mL of water and diluted with 25 mL of DCM. Phases were separated through a phase separator cartridge. The organic layer was evaporated in vacuo affording the title compound (38.7 mg) as orange oil.

$^1$H NMR (400 MHz, CDCl$_3$) δ ppm 6.95 (1H, t), 6.44 (1H, d), 6.32 (1H, dd), 4.87 (1H, br. s.), 4.20-4.31 (1H, m), 4.07-4.19 (1H, m), 3.05-3.15 (1H, m), 2.02-2.19 (1H, m), 1.66-1.74 (1H, m), 1.32 (3H, d).

Intermediate 212

2-(4-methylchroman-5-yl)oxy-5-nitro-pyridine

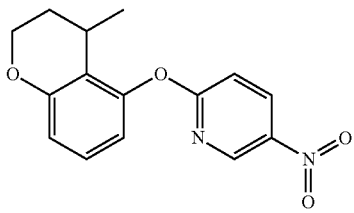 [SMILES: CC1CCOc2cccc(Oc3ccc([N+](=O)[O-])cn3)c21]

In a 0.5-2 ml Microwave vial 4-methylchroman-5-ol (Intermediate 211, 38.7 mg, 0.212 mmol) K$_2$CO$_3$ (88 mg, 0.636 mmol) and 2-chloro-5-nitropyridine (33.6 mg, 0.212 mmol) were dissolved in N,N-dimethylformamide (DMF) (2 mL) to give a light brown solution. The reaction vessel was sealed and heated under microwave irradiation at 110° C. for 1 hour. After cooling the reaction was quenched with 5 mL of water and diluted with 10 mL of ethyl acetate. Phases were separated by a separating funnel. The aqueous phase was extracted with 3×10 mL of ethyl acetate. The collected organic layer was dried using a hydrophobic frit and evaporated in vacuo to give the title compound (22.9 mg) as a colorless oil.

UPLC_B: 0.94 min, 287 [M+H]+.

Intermediate 213

6-(4-methylchroman-5-yl)oxypyridin-3-amine

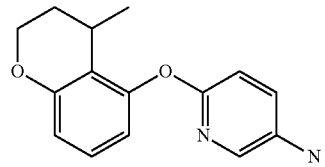

In a 50 mL round-bottomed flask 2-(4-methylchroman-5-yl)oxy-5-nitro-pyridine (Intermediate 212, 22.9 mg, 0.08 mmol) was dissolved in Ethanol (10 mL) to give a pale yellow solution. Pd/C (17.88 mg, 0.017 mmol) and hydrazine hydrate (0.4 mL, 4.15 mmol) were added. The reaction mixture was stirred at 90° C. The reaction mixture was filtered and evaporated in vacuo to give the title compound (22.9 mg) as a pale yellow oil.

UPLC_B: 0.65 min, 257 [M+H]+.

Intermediate 214

Tert-butyl N-[1,1-dimethyl-2-[[6-(4-methylchroman-5-yl)oxy-3-pyridyl]amino]-2-oxo-ethyl]carbamate

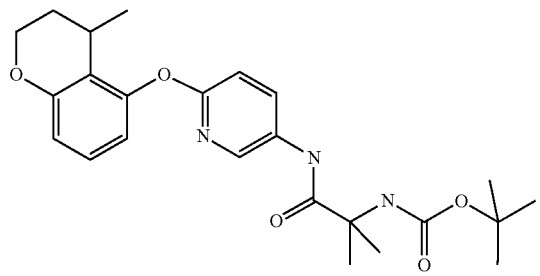

In a 8 mL vial the 6-(4-methylchroman-5-yl)oxypyridin-3-amine (Intermediate 213, 22.9 mg, 0.089 mmol) was dissolved in N,N-Dimethylformamide (3 mL) to give a pale yellow solution. DIPEA (0.069 mL, 0.394 mmol), N-{[(1,1-dimethylethyl)oxy]carbonyl}-2-methylalanine (60.0 mg, 0.295 mmol) and HATU (112 mg, 0.295 mmol) were added. The reaction mixture was shaken at 60° C. for 1 hour. The reaction mixture was evaporated in vacuo and the residue was purified by flash chromatography on silica gel using a column SNAP 25 g and cyclohexane/ethyl acetate from 3:1 to 1:2 as eluents affording the title compound (63.3 mg) as a colorless oil.

UPLC_B: 0.91 min, 442 [M+H]+.

Intermediate 215

2-amino-2-methyl-N-[6-(4-methylchroman-5-yl)oxy-3-pyridyl]propanamide

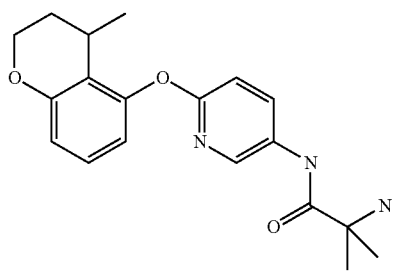 [SMILES: CC1CCOc2cccc(Oc3ccc(NC(=O)C(C)(C)N)cn3)c21]

In a 50 mL round-bottomed flask tert-butyl N-[1,1-dimethyl-2-[[6-(4-methylchroman-5-yl)oxy-3-pyridyl]amino]-2-oxo-ethyl]carbamate (Intermediate 214, 63.3 mg, 0.093 mmol), was dissolved in Dichloromethane (DCM) (3 mL) to give a pale yellow solution. The reaction mixture was cooled at 0° C. and TFA (3 mL, 38.9 mmol) was added. The reaction mixture was stirred at 0° C. for 2 hours. The reaction mixture was evaporated in vacuo to give the crude product as a pale yellow oil. The residue was charged on a 2 g SCX cartridge. It was then flushed with 40 mL of MeOH followed by 40 mL of 2M solution of ammonia in MeOH. The Ammonia eluate was evaporated in vacuo to give the title compound (22.9 mg) as a colourless oil.

UPLC_B: 0.77 min, 342 [M+H]+.

Intermediate 216

2-(4-methylchroman-5-yl)oxy-5-nitro-pyrimidine

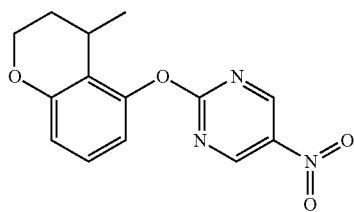 [SMILES: CC1CCOc2cccc(Oc3ncc([N+](=O)[O-])cn3)c21]

4-methyl-3,4-dihydro-2H-chromen-5-ol (Intermediate 211, 111 mg, 0.676 mmol) was dissolved in 5.0 mL of DMF. $K_2CO_3$ (140 mg, 1.01 mmol) and 2-chloro-5-nitropyrimidine (162 mg, 1.01 mmol) were added and the reaction mixture was stirred for 1 hour at room temperature. DMF was then evaporated under high vacuum and the residue was purified by flash chromatography on silica gel using cyclohexane/ethyl acetate from 1:0 to 7:3 as eluents affording the title compound (192 mg).

$^1$H NMR (400 MHz, CDCl$_3$) δ ppm 9.36 (2H, s), 7.21 (1H, t), 6.85 (1H, d), 6.68 (1H, d), 4.15-4.35 (2H, m), 2.90-3.02 (1H, m), 2.08-2.20 (1H, m), 1.65-1.75 (1H, m), 1.29 (3H, d).

Intermediate 217

2-[(4-methyl-3,4-dihydro-2H-chromen-5-yl)oxy]-5-pyrimidinamine

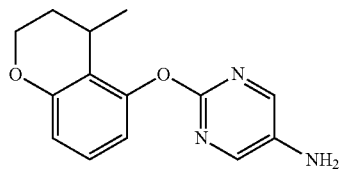 [SMILES: CC1CCOc2cccc(Oc3ncc(N)cn3)c21]

2-[(4-methyl-3,4-dihydro-2H-chromen-5-yl)oxy]-5-nitropyrimidine (Intermediate 216, 192 mg, 0.668 mmol) was dissolved in 9.0 mL of a 2/1 THF/water solution. Iron (187 mg, 3.34 mmol) and ammonium chloride (179 mg, 3.34 mmol) were added and the reaction mixture was stirred for 24 h at room temperature. After dilution with AcOEt and filtration over a celite pad (washing with AcOEt), the organic phase was washed (two times) with an aqueous saturated solution of NaHCO$_3$. The organic layer was dried over Na$_2$SO$_4$, filtered and evaporated and the residue was purified by flash chromatography on silica gel using cyclohexane/ethyl acetate from 1:0 to 0:1 as eluents affording the title compound (144 mg).

$^1$H NMR (400 MHz, CDCl$_3$) δ ppm 8.11 (2H, s), 7.13 (1H, t), 6.73 (1H, d), 6.60 (1H, d), 4.12-4.30 (2H, m), 3.52 (1H, br.s), 3.05-3.45 (1H, m), 2.08-2.18 (1H, m), 1.63-1.73 (1H, m), 1.31 (3H, d).

Intermediate 218

1,1-dimethylethyl {(1R)-1-methyl-1-[({2-[(4-methyl-3,4-dihydro-2H-chromen-5-yl)oxy]-5-pyrimidinyl}amino)carbonyl]propyl}carbamate

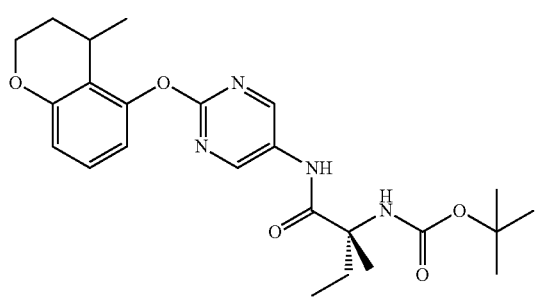 [SMILES: CC[C@@](C)(NC(=O)OC(C)(C)C)C(=O)Nc1cnc(Oc2cccc3c2C(C)CCO3)nc1]

2-[(4-methyl-3,4-dihydro-2H-chromen-5-yl)oxy]-5-pyrimidinamine (Intermediate 217, 144 mg, 0.56 mmol) was dissolved in toluene (8.0 mL) and S-2-pyridinyl (2R)-2-({[(1,1-dimethylethyl)oxy]carbonyl}amino)-2-methylbutanethioate (Intermediate 139, 86 mg, 0.28 mmol) was added. The reaction mixture was stirred at 140° C. for 20 minutes. Additional S-2-pyridinyl (2R)-2-({[(1,1-dimethylethyl)oxy]carbonyl}amino)-2-methylbutanethioate (Intermediate 139, 134 mg, 0.43 mmol) was added and the mixture was stirred at 140° C. for 15 minutes. Additional S-2-pyridinyl (2R)-2-({[(1,1-dimethylethyl)oxy]carbonyl}amino)-2-methylbutanethioate (Intermediate 139, 100 mg, 0.32 mmol) was added and the reaction mixture was stirred at 50° C. overnight and at 80° C. and for 4 hours. Additional S-2-pyridinyl (2R)-2-

({[(1,1-dimethylethyl)oxy]carbonyl}amino)-2-methylbutanethioate (Intermediate 139, 100 mg, 0.32 mmol) was added and the reaction mixture was stirred at 80° C. for 20 hours. Additional S-2-pyridinyl (2R)-2-({[(1,1-dimethylethyl)oxy]carbonyl}amino)-2-methylbutanethioate (Intermediate 139, 50 mg, 0.16 mmol) was added and the reaction mixture was stirred for additional 30 hours at 80° C. After cooling volatiles were removed and the residue was purified by flash chromatography (Biotage SP1) on silica gel using a 10 g SNAP silica cartridge as column and cyclohexane/ethyl acetate from 10:0 to 1:1 as eluents affording the title compound (100 mg).

UPLC_B: 1.13 min, 457 [M+H]+.

Intermediate 219

N1-{2-[(4-methyl-3,4-dihydro-2H-chromen-5-yl)oxy]-5-pyrimidinyl}-D-isovalinamide

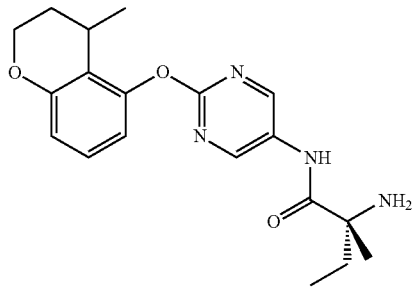 [SMILES: CC[C@@](C)(N)C(=O)Nc1cnc(Oc2cccc3c2C(C)CCO3)nc1]

To a solution of 1,1-dimethylethyl {(1R)-1-methyl-1-[({2-[(4-methyl-3,4-dihydro-2H-chromen-5-yl)oxy]-5-pyrimidinyl}amino)carbonyl]propyl}carbamate (Intermediate 218, 100 mg, 0.219 mmol) in dry Dichloromethane (5 mL), cooled to 0° C., TFA (1 mL, 12.98 mmol) was added dropwise. The reaction mixture was stirred at that temperature for 3 hours, then it was allowed to reach the room temperature and stirred at that temperature for 2 hours. Volatiles were evaporated and the residue was diluted with DCM (10 mL) and washed with an aqueous saturated solution of NaHCO3 (10 mL). The organic layer was separated, dried (Na$_2$SO$_4$), filtered and evaporated to afford the title compound (78 mg) as white solid that was used in the next step without further purification.

UPLC_B: 0.68 min, 357 [M+H]+.

Intermediate 220

5-{[(methyloxy)methyl]oxy}-2,3-dihydrospiro[chromene-4,1'-cyclopropane]

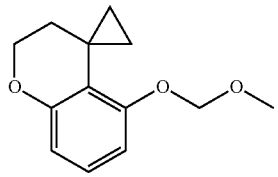 [SMILES: COCOc1cccc2c1C1(CCO2)CC1]

To a solution of 2,4,6-trichlorophenol (307 mg, 1.557 mmol) in 12.0 mL of DCM, at −40° C., 1M solution in hexane of diethylzinc (1.557 mL, 1.557 mmol) was added. After stirring at that temperature for 15 minutes, CH$_2$I$_2$ (0.126 mL, 1.557 mmol) was added. After stirring for additional 15 minutes, 4-methylidene-5-{[(methyloxy)methyl]oxy}-3,4-dihydro-2H-chromene (169 mg, 0.819 mmol) dissolved in 3.0 mL of DCM was added. The cold bath was removed and the mixture was stirred at room temperature for 2 hours. The mixture was diluted with DCM, washed with a 10% aqueous solution of HCl 2 times, then with an aqueous saturated solution of NaHCO$_3$ 2 times, an aqueous saturated solution of Na$_2$SO$_3$ 2 times and brine (2 times). The organic layer was then dried over Na$_2$OS$_4$, filtered and evaporated and the residue was purified by flash chromatography (Biotage SP1) on silica gel using cyclohexane/ethyl acetate from 100:0 to 95:5. Collected residue was dissolved in DCM and washed (two times) with KOH (30% aq sol). The organic layer was dried over sodium sulphate, filtered and evaporated to afford the title compound (145 mg).

$^1$H NMR (400 MHz, CDCl$_3$) δ ppm 6.96 (1H, t), 6.52-6.62 (2H, m), 5.05-5.15 (2H, m), 4.22 (2H, dd), 3.47 (3H, s), 1.80-1.86 (2H, m), 1.72-1.80 (2H, m), 0.51-0.61 (2H, m).

Intermediate 221

2,3-dihydrospiro[chromene-4,1'-cyclopropan]-5-ol

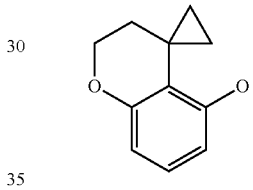

5-{[(methyloxy)methyl]oxy}-2,3-dihydrospiro[chromene-4,1'-cyclopropane] (Intermediate 220, 145 mg, 0.658 mmol) was dissolved in MeOH (6.0 mL) and a 2N aqueous solution of HCl (0.494 mL, 0.99 mmol) was added and the reaction mixture was stirred at 50° C. overnight. After addition of water, MeOH was removed under vacuum and the aqueous phase was extracted with ethyl acetate (three times). Combined organic layers were dried over Na$_2$SO$_4$, filtered and evaporated. The residue was purified by flash chromatography (Biotage system) on silica gel using cyclohexane to cyclohexane/ethyl acetate 9:1 as eluents affording the title compound (64 mg).

UPLC_B: 0.93 min, 177 [M+H]+.

Intermediate 222

2-(2,3-dihydrospiro[chromene-4,1'-cyclopropan]-5-yloxy)-5-nitropyrimidine

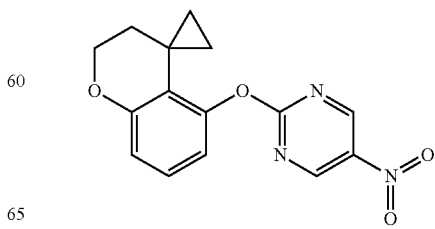

To a solution of 2,3-dihydrospiro[chromene-4,1'-cyclopropan]-5-ol (Intermediate 221, 63 mg, 0.358 mmol) in DMF (3 ml) K₂CO₃ (74.1 mg, 0.536 mmol) and 2-chloro-5-nitropyrimidine (86.0 mg, 0.536 mmol) were added and the reaction mixture was stirred at rt for 1 h. DMF was then evaporated under high vacuum, water was added and the reaction mixture was extracted with AcOEt (three times). Collected organic layers were dried over Na₂SO₄, filtered and evaporated. The residue was purified by flash chromatography (Biotage system) on silica gel using cyclohexane to cyclohexane/ethyl acetate 9:1 as eluents affording the title compound (91 mg).

UPLC_B: 1.10 min, 300 [M+H]+.

Intermediate 223

2-(2,3-dihydrospiro[chromene-4,1'-cyclopropan]-5-yloxy)-5-pyrimidinamine

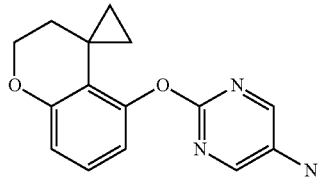 [SMILES: Nc1cnc(Oc2cccc3c2C2(CCO3)CC2)nc1]

2-(2,3-dihydrospiro[chromene-4,1'-cyclopropan]-5-yloxy)-5-nitropyrimidine (Intermediate 222, 91 mg, 0.304 mmol) was dissolved in 9.0 mL of a 2/1 THF/water solution. Then iron (85 mg, 1.52 mmol) and ammonium chloride (81 mg, 1.52 mmol) were added and the reaction mixture was stirred at room temperature for 10 h. After dilution with AcOEt and filtration over a celite pad (washing with AcOEt), the organic phase was washed (two times) with an aqueous saturated solution of NaHCO₃. The organic layer was dried over Na₂SO₄, filtered and evaporated. The residue was purified by flash chromatography (Biotage system) on silica gel using cyclohexane to cyclohexane/ethyl acetate 1:1 as eluents affording the title compound (52 mg).

UPLC_B: 0.82 min, 270 [M+H]+.

Intermediate 224

1,1-dimethylethyl [(1R)-1-({[2-(2,3-dihydrospiro[chromene-4,1'-cyclopropan]-5-yloxy)-5-pyrimidinyl]amino}carbonyl)-1-methylpropyl]carbamate

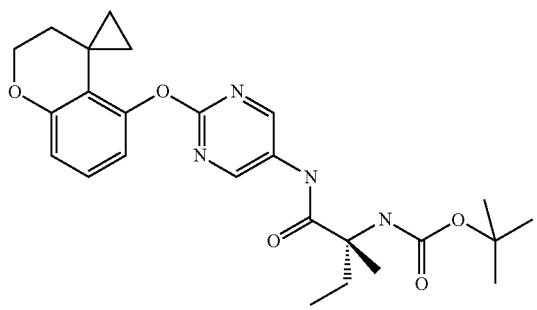 [SMILES: CC[C@@](C)(NC(=O)OC(C)(C)C)C(=O)Nc1cnc(Oc2cccc3c2C2(CCO3)CC2)nc1]

To a solution of (2R)-2-(tert-butoxycarbonylamino)-2-methyl-butanoic acid (105 mg, 0.483 mmol) in dry N,N-Dimethylformamide (2 mL) DIPEA (0.101 mL, 0.579 mmol) and HATU (184 mg, 0.483 mmol) were added. The reaction mixture was stirred at r.t. for 15 minutes, then it was added to a solution of 2-(2,3-dihydrospiro[chromene-4,1'-cyclopropan]-5-yloxy)-5-pyrimidinamine (Intermediate 223, 52 mg, 0.193 mmol) in dry DMF (0.5 mL). The mixture was heated at 40° C. overnight, it was then warmed to 60° C. and stirred at that temperature for 4 hours. After cooling the reaction was quenched with water (5 mL) and extracted with ethyl acetate (3×5 mL). Combined organic layers were washed with brine (3×5 mL), dried (Na₂SO₄), filtered and evaporated. The residue was purified by flash chromatography on silica gel using a column SNAP 25 g and toluene to toluene/ethyl acetate 60:40 as eluents affording the title compound (10 mg) as a white solid.

UPLC_B: 1.15 min, 469 [M+H]+.

Intermediate 225

N1-[2-(2,3-dihydrospiro[chromene-4,1'-cyclopropan]-5-yloxy)-5-pyrimidinyl]-D-isovalinamide

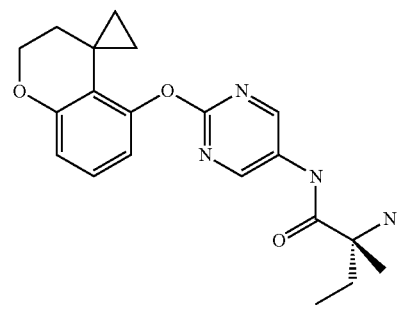 [SMILES: CC[C@@](C)(N)C(=O)Nc1cnc(Oc2cccc3c2C2(CCO3)CC2)nc1]

To a solution of 1,1-dimethylethyl [(1R)-1-({[2-(2,3-dihydrospiro[chromene-4,1'-cyclopropan]-5-yloxy)-5-pyrimidinyl]amino}carbonyl)-1-methylpropyl]carbamate (Intermediate 224, 5 mg, 10.67 μmol) in dry Dichloromethane (1 mL) cooled to 0° C. TFA (0.822 μL, 10.67 μmol) was added dropwise. The reaction mixture was stirred for 2 hours at the same temperature. The reaction was allowed to reach room temperature then the volatiles were evaporated. The residue was diluted with DCM (2 mL), and washed with NaHCO₃ sat. sol. (7 mL). The organic layer was dried (Na₂SO₄), filtered and evaporated to afford the title compound (4 mg) as a yellow oil that was used in the next step without further purification.

UPLC_B: 0.71 min, 369 [M+H]+.

Intermediate 226

6-(1,1a,2,7btetrahydrocyclopropa[c]chromen-7-yloxy)-3-pyridinamine

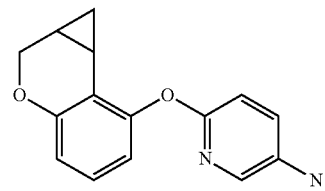 [SMILES: Nc1ccc(Oc2cccc3c2C2CC2CO3)nc1]

In a 8 mL vial 5-nitro-2-(1,1a,2,7b-tetrahydrocyclopropa[c]chromen-7-yloxy)pyridine (94.6 mg, 0.300 mmol) was dissolved in Tetrahydrofuran (THF) (3 mL) to give a pale yellow solution. Iron (84 mg, 1.498 mmol) and ammonium chloride (80 mg, 1.498 mmol) were added followed by Water (1.500 mL). The reaction mixture was stirred at room temperature overnight. Additional iron (44 mg, 0.75 mmol) and ammonium chloride (40 mg, 0.75 mmol) were added and the reaction mixture was stirred at room temperature for 6 hours. The reaction mixture was quenched with 10 mL of an aqueous saturated solution of sodium bicarbonate and diluted with 25 mL of EtOAc. The reaction mixture was filtered over a celite pad. Phases were separated by a separating funnel. The aqueous phase was extracted with DCM (3×10 mL). The combined organic layers were evaporated and the residue was purified by flash chromatography on silica gel using a column SNAP 25 g and Cyclohexane/ethyl acetate from 3:1 to 1:1 as eluents affording the title compound (82.9 mg) as colorless oil.

$^1$H-NMR (400 MHz, CDCl$_3$) δ ppm 7.76 (1H, d), 7.09 (1H, dd), 7.02 (1H, t), 6.75 (1H, d), 6.66 (1H, dd), 6.62 (1H, dd), 4.32 (1H, dd), 3.97 (1H, dd), 3.55 (2H, br. s.), 2.16-2.27 (1H, m), 1.61-1.76 (1H, m), 0.98-1.07 (2H, m). UPLC_B: 0.78 min, 255 [M+H]+.

Intermediate 227

Tert-butyl N-[(1R)-1-[[6-(1,1a,2,7b-tetrahydrocyclopropa[c]chromen-7-yloxy)-3-pyridyl]carbamoyl]-1-methyl-propyl]carbamate

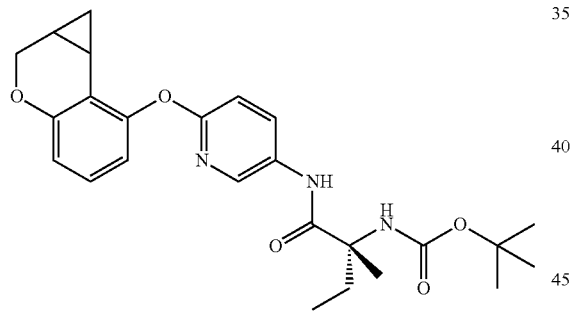

In a 8 mL vial tube 6-(1,1a,2,7btetrahydrocyclopropa[c]chromen-7-yloxy)-3-pyridinamine (Intermediate 226, 84 mg, 0.0305 mmol), (2R)-2-(tert-butoxycarbonylamino)-2-methyl-butanoic acid (59.7 mg, 0.275 mmol) and DIPEA (0.080 mL, 0.458 mmol) were dissolved in N,N-Dimethylformamide (DMF) (2 mL) to give a pale yellow solution. HATU (151 mg, 0.397 mmol) was added. The reaction mixture was stirred at room temperature over week-end. The reaction mixture was evaporated in vacuo and the residue was purified by flash chromatography on silica gel using a column SNAP 25 g and cyclohexane/ethyl acetate from 3:1 to 1:2 as eluents affording the title compound (74 mg) as white solid.

$^1$H NMR (400 MHz, CDCl$_3$) δ ppm 8.14-8.18 (1H, m), 8.09-8.14 (1H, m), 7.04 (1H, t), 6.85 (1H, d), 6.64-6.72 (2H, m), 6.30 (1H, br. s.), 4.91 (1H, br. s.), 4.31 (1H, dd), 3.94 (1H, dd), 1.83-2.17 (3H, m), 1.70-1.83 (1H, m), 1.51 (3H, s), 1.45 (9H, s), 0.91-1.05 (5H, m). UPLC_ipqc: 1.17 min, 454 [M+H]+.

Intermediate 228

(2R)—N-[6-(1,1a,2,7b-tetrahydrocyclopropa[c]chromen-7-yloxy)-3-pyridyl]-2-amino-2-methyl-butanamide

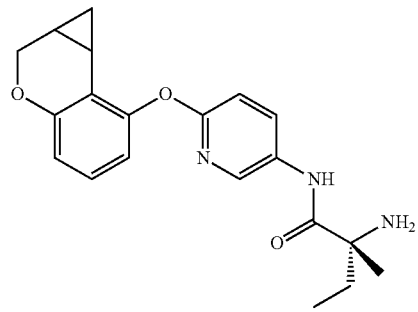 [SMILES: CC[C@@](C)(N)C(=O)Nc1ccc(Oc2cccc3c2C2CC2CO3)nc1]

In a 50 mL round-bottomed flask tert-butyl N-[(1R)-1-[[6-(1,1a,2,7b-tetrahydrocyclopropa[c]chromen-7-yloxy)-3-pyridyl]carbamoyl]-1-methyl-propyl]carbamate (Intermediate 227, 74 mg, 0.139 mmol) was dissolved in Dichloromethane (3 mL) to give a pale yellow solution. The reaction mixture was cooled at 0° C. and TFA (2 mL, 26.0 mmol) was added. The reaction mixture was stirred at 0° C. for 2 hours. The reaction mixture was evaporated in vacuo to give the crude product as a yellow oil. The sample was charged on a 2 g SCX cartridge. It was then flushed with 36 mL of MeOH followed by 25 mL of 2M solution of ammonia in MeOH. The ammonia eluate was evaporated in vacuo affording the title compound (46.2 mg) as a pale yellow oil.

$^1$H NMR (400 MHz, CDCl$_3$) δ ppm 9.89 (1H, br. s.), 8.17-8.28 (2H, m), 7.04 (1H, t), 6.81-6.88 (1H, m), 6.65-6.71 (2H, m), 4.31 (1H, dd), 3.95 (1H, dd), 2.06-2.14 (1H, m), 1.91-2.05 (1H, m), 1.53-1.77 (7H, m), 0.94 (3H, t), 0.90-1.05 (2H, m). LCMS UPLC/MS (method: IPQC2): rt=0.72 mins, MH+=354.

UPLC_ipqc: 0.72 min, 354 [M+H]+.

Example 1

(5R)-3-[4-(1,3-dihydro-2-benzofuran-4-yloxy)phenyl]-5-methyl-2,4-imidazolidinedione

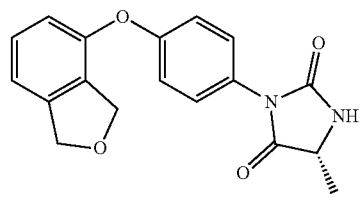 [SMILES: C[C@H]1NC(=O)N(c2ccc(Oc3cccc4c3COC4)cc2)C1=O]

A solution of N1-[4-(1,3-dihydro-2-benzofuran-4-yloxy)phenyl]-D-alaninamide (Intermediate 7, 80 mg) and TEA (0.187 ml, 1.341 mmol) in dichloromethane (10 ml) was stirred under argon at 0'C. Triphosgene (39.8 mg, 0.134 mmol) in dichloromethane (4 ml) was added and the mixture was left under stirring at 0° C. for 45 minutes. An aqueous saturated solution of NaHCO$_3$ was then added. The phases were separated and the aqueous one was extracted 3 times with dichloromethane. The gathered organic phases were dried over sodium sulphate and concentrated under vacuum. The crude was purified by flash chromatography (FlashMasterPersonal), using as eluents a gradient Cyclohexane/Ethyl acetate from 100:0 to 40:60. This afforded the title compound as a white solid (58.5 mg).

$^1$H NMR (400 MHz, DMSO-d$_6$): δ ppm 8.49-8.44 (1H, m), 7.39-7.32 (3H, m), 7.18-7.13 (1H, m), 7.11-7.06 (2H, m), 6.91-6.87 (1H, m), 5.09-5.03 (2H, m), 4.91-4.87 (2H, m), 4.29-4.22 (1H, m), 1.36 (3H, d); UPLC-MS: 0.69 min, 325 [M+1]+

Example 2

(5R)-5-methyl-3-{4-[(3-methyl-1,2-benzisoxazol-4-yl)oxy]phenyl}-2,4-imidazolidinedione

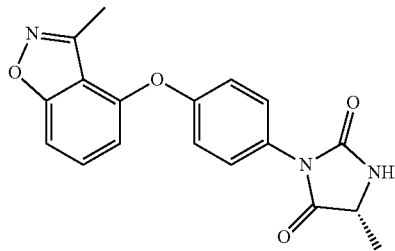 [SMILES: Cc1noc2cccc(Oc3ccc(N4C(=O)N[C@H](C)C4=O)cc3)c12]

N$^1$-{4-[(3-methyl-1,2-benzisoxazol-4-yl)oxy]phenyl}-D-alaninamide (Intermediate 14, 337 mg) was dissolved in 8.0 ml of ethyl acetate. Triethylamine (0.33 ml, 2.38 mmol) was added followed by a solution of triphosgene (161 mg, 0.54 mmol) in 2.0 ml of ethyl acetate. After 5 minutes stirring, DMAP (66 mg, 0.54 mmol) was added and the reaction mixture was stirred at room temperature for 10 minutes. After quenching with a saturated aqueous solution of NaHCO$_3$, the reaction mixture was extracted two times with ethyl acetate. The gathered organic layers were dried over sodium sulphate, filtered and evaporated. The residue was purified by silica gel chromatography eluting with a gradient Cy-Hex/EtOAc from 100/0% to 0/100%. This afforded the title compound (160 mg).

$^1$H NMR (400 MHz, DMSO-d$_6$): δ ppm 8.49 (1H, br. s), 7.64-7.58 (1H, m), 7.50-7.40 (3H, m), 7.34-7.25 (2H, m), 6.76 (1H, d), 4.34-4.18 (1H, m), 2.58 (3H, s), 1.38 (3H, d); UPLC-MS_B: 0.73 min, 338 [M+H]+.

Example 3

(5R)-3-{4-[(3,6-dimethyl-1,2-benzisoxazol-4-yl)oxy]phenyl}-5-methyl-2,4-imidazolidinedione

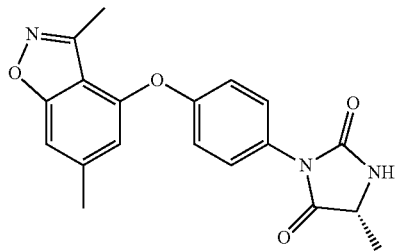 [SMILES: Cc1cc(Oc2ccc(N3C(=O)N[C@H](C)C3=O)cc2)c2c(C)noc2c1]

N$^1$-{4-[(3,6-dimethyl-1,2-benzisoxazol-4-yl)oxy]phenyl}-D-alaninamide (Intermediate 23, 54 mg) was dissolved in 7.0 ml of ethyl acetate. Then triethylamine (0.051 ml, 0.37 mmol) was added followed by a solution of triphosgene (24.6 mg, 0.083 mmol) in 2.0 ml of ethyl acetate. After stirring for 5 minutes, DMAP (10.1 mg, 0.083 mmol) was added and the reaction mixture was stirred at room temperature for 10 minutes. After quenching with an aqueous solution of NaHCO$_3$, the mixture was extracted two times with ethyl acetate and the collected organic layers were dried over sodium sulphate, filtered and evaporated. The residue was purified by silica gel chromatography eluting with a gradient c-Hex/EtOAc from 100/0 to 0/100 to afford the title compound (11 mg)

$^1$H-NMR (400 MHz, CD$_3$OD): δ ppm 7.50-7.45 (2H, m), 7.26-7.16 (3H, m), 6.63-6.57 (1H, m), 4.36-4.26 (1H, m), 2.57 (3H, s), 2.45 (3H, s), 1.52 (3H, d); UPLC-MS_B: 0.78 min, 352 [M+H]+.

Example 4

5,5-dimethyl-3-{4-[(3-methyl-1,2-benzisoxazol-4-yl)oxy]phenyl}-2,4-imidazolidinedione

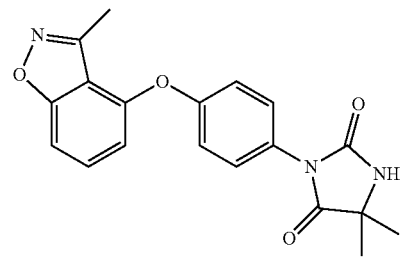 [SMILES: Cc1noc2cccc(Oc3ccc(N4C(=O)NC(C)(C)C4=O)cc3)c12]

2-methyl-N$^1$-{4-[(3-methyl-1,2-benzisoxazol-4-yl)oxy]phenyl}alaninamide (Intermediate 25, 18 mg) was dissolved in 4 ml of ethyl acetate. Triethylamine (0.017 ml, 0.12 mmol) was then added followed by a solution of triphosgene (8.21 mg, 0.028 mmol) in 1.0 ml of ethyl acetate. After stirring for 5 minutes, DMAP (3.4 mg, 0.028 mmol) was added and the reaction mixture was stirred at room temperature for 10 minutes. After quenching with a saturated aqueous solution of NaHCO$_3$, the mixture was extracted two times with ethyl acetate and the collected organic layers were dried over sodium sulphate, filtered and evaporated. The crude obtained was charged on a silica gel column and eluted with c-Hex/EtOAc as eluents (from all 100:0 to 0:100). This afforded 10 mg of the title compound.

$^1$H-NMR (400 MHz, DMSO-d$_6$): δ ppm 8.57 (1H, br. s), 7.66-7.57 (1H, m), 7.51-7.43 (3H, m), 7.27 (2H, d), 6.76 (1H, d), 2.57 (3H, s), 1.43 (6H, s); UPLC-MS: 0.72 min, 352 [M+H]+.

Example 5

(5R)-5-ethyl-3-{6-[(3-ethyl-1,2-benzisoxazol-4-yl)oxy]-3-pyridinyl}-2,4-imidazolidinedione

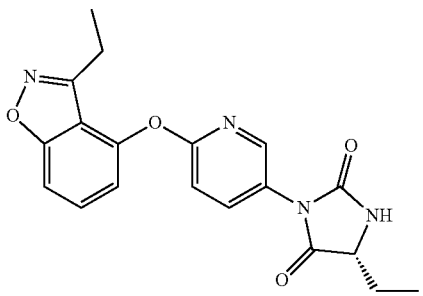 [SMILES: CCc1noc2cccc(Oc3ccc(N4C(=O)N[C@H](CC)C4=O)cn3)c12]

(2R)-2-amino-N-{6-[(3-ethyl-1,2-benzisoxazol-4-yl)oxy]-3-pyridinyl}butanamide (Intermediate 35) was dissolved in dichloromethane (1.0 ml) and TEA (0.004 ml, 0.03 mmol) was added. The reaction mixture was cooled down to 0° C. and triphosgene (1.3 mg, 4.49 µmol) dissolved in 0.1 ml of dichloromethane was added. The reaction mixture was stirred at that temperature for 30 minutes. The mixture was quenched with 0.5 ml of water and water was removed by addition of sodium sulphate. The organic phase was pipetted off and evaporated and the crude obtained was charged on a silica gel column (Biotage SP1 system) and eluted with Cyhexane/EtOAv (from 1/0 to 7/3, then 7/3, then from 7/3 to 1/1, the 1/1, then from 1/1 to 0/1) to afford the title compound (1.3 mg).

$^1$H-NMR (400 MHz, CDCl$_3$): δ ppm 8.35-8.31 (1H, m), 7.92-7.87 (1H, m), 7.60-7.52 (1H, m), 7.46-7.41 (1H, m), 7.19-7.13 (1H, m), 7.05-7.00 (1H, m), 5.57 (1H, br. s), 4.29-4.23 (1H, m), 2.94 (2H, q), 2.12-1.91 (2H, m), 1.39 (3H, t), 1.11 (3H, t). UPLC: 0.68 min, 367 [M+H]+.

Example 6

(5R)-5-ethyl-3-(6-{[3-(1-methylethyl)-1,2-benzisoxazol-4-yl]oxy}-3-pyridinyl)-2,4-imidazolidinedione

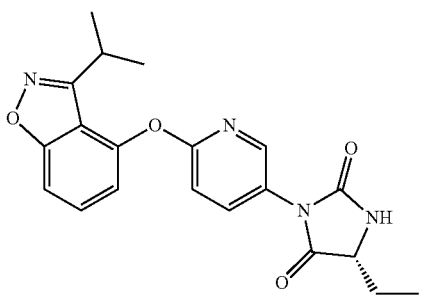 [SMILES: CC[C@H]1NC(=O)N(c2ccc(Oc3cccc4onc(C(C)C)c34)nc2)C1=O]

(2R)-2-amino-N-(6-{[3-(1-methylethyl)-1,2-benzisoxazol-4-yl]oxy}-3-pyridinyl)butanamide (Intermediate 44) was dissolved in dichloromethane (1.0 ml) and TEA (3 µL, 0.022 mmol) was added. The reaction mixture was cooled down to 0° C. and triphosgene (0.6 mg, 1.98 µmol) was added and the mixture was stirred at that temperature for 30 minutes. The reaction mixture was quenched with water and water was removed by addition of sodium sulphate. The organic phase was pipetted off and evaporated and the residue obtained was charged on a silica gel column (Biotage SP1 system) and eluted with Cyhexane/EtOAc (from all 1/0 to 7/3, then 7/3, then from 7/3 to 1/1, then 1/1, then 0/1) to afford the title compound (1 mg).

$^1$H-NMR (400 MHz, CDCl$_3$): δ ppm 8.39-8.34 (1H, m), 7.93-7.87 (1H, m), 7.59-7.51 (1H, m), 7.46-7.38 (1H, m), 7.20-7.14 (1H, m), 7.06-6.97 (1H, m), 5.50 (1H, br. s), 4.31-4.23 (1H, m), 3.42-3.32 (1H, m), 2.08-1.91 (2H, m), 1.45 (6H, d), 1.11 (3H, t). UPLC: 0.72 min, 381 [M+H]+.

Example 7

(5R)-3-{4-[(3,3-dimethyl-2,3-dihydro-1-benzofuran-4-yl)oxy]phenyl}-5-methyl-2,4-imidazolidinedione

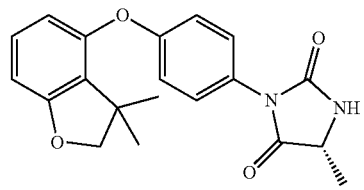 [SMILES: C[C@H]1NC(=O)N(c2ccc(Oc3cccc4c3C(C)(C)CO4)cc2)C1=O]

To a solution of N$^1$-{4-[(3,3-dimethyl-2,3-dihydro-1-benzofuran-4-yl)oxy]phenyl}-D-alaninamide (Intermediate 57, 66 mg) in dichloromethane (20 ml, SCRC) was added triethylamine (0.085 ml, 0.607 mmol, SCRC). Triphosgene (24.00 mg, 0.081 mmol, SCRC) was added dropwise at 0° C. and the reaction mixture was stirred at room temperature for 0.5 hours. The mixture was quenched with water (20 ml) and it was extracted with dichloromethane (3 times 50 ml, SCRC). The combined organic layers were dried, evaporated and purified by column chromatography on silica gel with EtAc/PE (1/30) as eluents to afford the title compound as a white solid (40 mg).

$^1$H NMR (CDCl$_3$): δ ppm 7.36-7.34 (2H, m), 7.09-7.03 (3H, m), 6.60-6.58 (1H, d), 6.41-6.39 (1H, d), 5.60 (1H, s), 4.27-4.25 (3H, m), 1.58-1.51 (3H, d), 1.42 (6H, s); MS_2 (ESI): 353 [M+H]+

Example 8

(5R)-3-{6-[(3,3-dimethyl-2,3-dihydro-1-benzofuran-4-yl)oxy]-3-pyridinyl}-5-methyl-2,4-imidazolidinedione

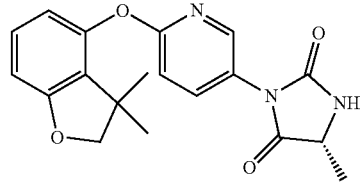 [SMILES: C[C@H]1NC(=O)N(c2ccc(Oc3cccc4c3C(C)(C)CO4)nc2)C1=O]

N$^1$-{6-[(3,3-dimethyl-2,3-dihydro-1-benzofuran-4-yl)oxy]-3-pyridinyl}-D-alaninamide (Intermediate 61, 28 mg) was dissolved in dry dichloromethane (3 ml). The reaction mixture was cooled down in an ice bath. Triethylamine (71.5 µl, 0.513 mmol) was added. Then a solution of triphosgene in dry dichloromethane (11.42 mg, 0.038 mmol dissolved in 1 ml of dichloromethane) was added dropwise.

The reaction mixture was stirred at 0° C., under argon, during 15 min. A saturated aqueous solution of NaHCO$_3$ was added (4 ml) and the aqueous layer was extracted with dichloromethane 4 times (4×5 ml). After drying over sodium sulphate, the solvents were removed under vacuum. The residue obtained was purified by silica gel chromatography (Companion system, 2×4 g silica cartridges) with a gradient cyclohexane/ethylacetate from 100/0 to 50/50. This afforded the title compound as a film (17.5 mg).

$^1$H NMR (400 MHz, CDCl$_3$): δ ppm 8.31 (1H, d), 7.77 (1H, dd), 7.13 (1H, t), 7.00 (1H, d), 6.66 (1H, d), 6.56 (1H, d), 5.81 (1H, br.s), 4.29 (1H, dd), 4.23 (2H, s), 1.58 (3H, d), 1.37 (6H, s); UPLC_B: 0.76 min, 354 [M+H]+

Example 9

(5R)-3-{6-[(3,3-dimethyl-2,3-dihydro-1-benzofuran-4-yl)oxy]-3-pyridinyl}-5-ethyl-2,4-imidazolidinedione

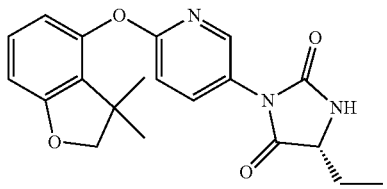 [SMILES: CC[C@H]1NC(=O)N(c2ccc(Oc3cccc4c3C(C)(C)CO4)nc2)C1=O]

The title compound was made in a similar fashion to the preparation of Example 8 replacing N$^1$-{6-[(3,3-dimethyl-2,3-dihydro-1-benzofuran-4-yl)oxy]-3-pyridinyl}-D-alaninamide (Intermediate 61) with (2R)-2-amino-N-{6-[(3,3-dimethyl-2,3-dihydro-1-benzofuran-4-yl)oxy]-3-pyridinyl}butanamide (Intermediate 63, 57 mg). This afforded the title compound as a white solid (40 mg).

$^1$H NMR (400 MHz, CDCl$_3$): δ ppm 8.30 (1H, d), 7.77 (1H, dd), 7.13 (1H, t), 7.01 (1H, d), 6.67 (1H, d), 6.57 (1H, d), 5.96 (1H, br.s), 4.23 (2H, s), 4.20 (1H, m), 2.03-1.97 (1H, m), 1.93-1.87 (1H, m), 1.38 (6H, s), 1.06 (3H, t); UPLC: 0.73 min, 368 [M+H]+

Example 10

(5R)-3-{2-[(3,3-dimethyl-2,3-dihydro-1-benzofuran-4-yl)oxy]-5-pyrimidinyl}-5-ethyl-2,4-imidazolidinedione

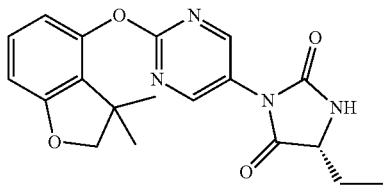 [SMILES: CC[C@H]1NC(=O)N(c2cnc(Oc3cccc4c3C(C)(C)CO4)nc2)C1=O]

To a solution of (2R)-2-amino-N-{2-[(3,3-dimethyl-2,3-dihydro-1-benzofuran-4-yl)oxy]-5-pyrimidinyl}butanamide (Intermediate 67, 3 mg) in dry dichloromethane (0.5 ml), TEA (6.11 µL, 0.044 mmol) was added and the reaction mixture was cooled to 0° C. A solution of triphosgene (1.170 mg, 3.94 µmol) in dry dichloromethane (0.125 ml) was then added dropwise and the reaction mixture was stirred at the 0° C. for 30 minutes. The reaction was quenched with water (3 ml), and the organic phase was separated, dried over sodium sulphate, filtered and evaporated. The residue was purified by flash chromatography on silica gel using a column Isolute (1 g) and dichloromethane/methanol from 99.5:0.5 to 9:10 as eluent to afford the title compound (0.7 mg) as a white solid.

$^1$H NMR (400 MHz, CDCl$_3$): δ ppm 8.73 (2H, s), 7.18 (1H, t), 6.72 (1H, d), 6.63 (1H, d), 5.58 (1H, bs), 4.28-4.23 (1H, m), 4.24 (2H, s), 2.09-1.89 (2H, m), 1.37 (6H, s). 1.09 (3H, t).

Example 11

7-{6-[(3,3-dimethyl-2,3-dihydro-1-benzofuran-4-yl)oxy]-3-pyridinyl}-5,7-diazaspiro[3.4]octane-6,8-dione

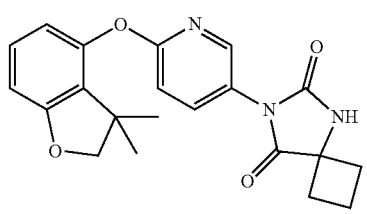 [SMILES: CC1(C)COc2cccc(Oc3ccc(N4C(=O)NC5(CCC5)C4=O)cn3)c21]

1-amino-N-{6-[(3,3-dimethyl-2,3-dihydro-1-benzofuran-4-yl)oxy]-3-pyridinyl}cyclobutanecarboxamide (Intermediate 70, 17 mg) was dissolved in dry dichloromethane (1.8 ml). The reaction mixture was cooled down in an ice bath. Triethylamine (39.48 µl, 0.283 mmol) was added at 0° C. Then 0.89 ml of a solution of triphosgene in dry dichloromethane was added dropwise (0.0135 mg, 4.00 mg). The reaction mixture was stirred under argon during 10 min at 0° C., then during 30 min at room temperature. Then an additional 0.25 equivalent of triphosgene in dichloromethane (0.26 M solution) was added at 0° C. and the reaction mixture was stirred under argon an additional 30 min at room temperature. The solvents were removed under vacuum. The residue obtained was purified by flash chromatography on silica gel (Companion system, 4 g silica cartridge) with cyclohexane/ethylacetate as eluents from 100/0 to 55/45. This afforded the title compound (12 mg).

$^1$H NMR (400 MHz, CDCl$_3$): δ ppm 8.31 (1H, d), 7.76 (1H, dd), 7.13 (1H, t), 7.11 (1H, d), 6.67 (1H, d), 6.65 (1H, d), 5.70 (1H, s), 2.50 (2H, s), 4.74 (2H, m), 2.43 (2H, m), 2.24 (1H, m), 1.94 (1H, m), 1.38 (6H, m); UPLC: 0.72 min, 380 [M+H]+

Example 12

6-{6-[(3,3-dimethyl-2,3-dihydro-1-benzofuran-4-yl)oxy]-3-pyridinyl}-4,6-diazaspiro[2.4]heptane-5,7-dione

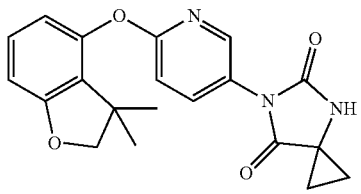 [SMILES: CC1(C)COc2cccc(Oc3ccc(N4C(=O)NC5(CC5)C4=O)cn3)c21]

The title compound (5 mg, 49% yield) was made in a similar fashion to the preparation of Example 11 replacing 1-amino-N-{6-[(3,3-dimethyl-2,3-dihydro-1-benzofuran-4-yl)oxy]-3-pyridinyl}cyclobutanecarboxamide (Intermediate 70) with 1-amino-N-{6-[(3,3-dimethyl-2,3-dihydro-1-benzofuran-4-yl)oxy]-3-pyridinyl}cyclopropanecarboxamide (Intermediate 73, 9 mg).

$^1$H NMR (400 MHz, MeOD): δ ppm 8.24 (1H, m), 7.93 (1H, m), 7.14 (1H, t), 7.07 (1H, d), 6.64 (1H, d), 6.54 (1H, d), 4.22 (2H, s), 1.51 (2H, m), 1.42 (2H, m), 1.35 (6H, s); UPLC: 0.78 min, 366 [M+H]+

Example 13

3-{6-[(3,3-dimethyl-2,3-dihydro-1-benzofuran-4-yl)oxy]-3-pyridinyl}-5,5-dimethyl-2,4-imidazolidinedione

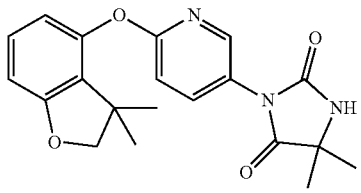 [SMILES: CC1(C)NC(=O)N(c2ccc(Oc3cccc4c3C(C)(C)CO4)nc2)C1=O]

N1-{6-[(3,3-dimethyl-2,3-dihydro-1-benzofuran-4-yl)oxy]-3-pyridinyl}-2-methylalaninamide (Intermediate 75, 7.5 mg) was dissolved in dry dichloromethane (1 ml). The reaction mixture was cooled down in an ice bath. Triethylamine (18.37 µl, 0.132 mmol) was added at 0° C. Then 0.5 ml of a solution of triphosgene in dry dichloromethane (0.012 mmol) was added dropwise. The solution was prepared with 7.18 mg of triphosgene dissolved in 1 ml of dichloromethane). The reaction mixture was stirred under argon during 10 min at 0° C., then during 30 min at room temperature. A saturated aqueous solution of NaHCO$_3$ was added and the aqueous layer was extracted with dichloromethane 4 times. After drying over sodium sulphate, the solvents were removed under vacuum.

The residue obtained was purified by flash chromatography on silica gel (Companion system, 4 g silica cartridge) with a gradient cyclohexane/ethylacetate from 100/0 to 55/45. This afforded the title compound (4.5 mg).

$^1$H NMR (400 MHz, CDCl$_3$): δ ppm 8.31 (1H, d), 7.77 (1H, dd), 7.12 (1H, t), 6.99 (1H, d), 6.66 (1H, d), 6.56 (1H, d), 5.47 (1H, br s), 4.22 (2H, s), 1.56 (6H, s), 1.36 (6H, s); UPLC: 0.70 min, 368 [M+H]+

Example 14

(5R)-3-{2-[(3,3-dimethyl-2,3-dihydro-1-benzofuran-4-yl)oxy]-5-pyrimidinyl}-5-(1,1-dimethylethyl)-2,4-imidazolidinedione

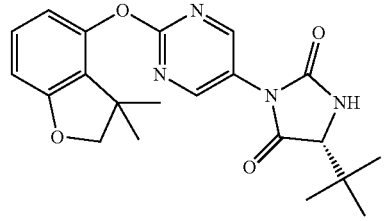 [SMILES: CC1(C)COc2cccc(Oc3ncc(N4C(=O)N[C@H](C(C)(C)C)C4=O)cn3)c21]

N1-{2-[(3,3-dimethyl-2,3-dihydro-1-benzofuran-4-yl)oxy]-5-pyrimidinyl}-3-methyl-D-valinamide (Intermediate 78, 9.9 mg) was dissolved in dry dichloromethane (1 ml). The reaction mixture was cooled down in an ice bath. Triethylamine (22.35 µl, 0.160 mmol) was added. The reaction mixture was cooled down at 0° C. Then 0.5 ml of a solution of triphosgene in dry dichloromethane (0.015 mmol) was added dropwise. The reaction mixture was stirred under argon during 20 min at 0° C. Some water (2 ml) was added and the aqueous layer was extracted with dichloromethane 4 times. After drying over sodium sulphate, the solvents were removed under vacuum. The residue obtained was purified by flash chromatography on silica gel (Companion system, 4 g silica cartridge) with cyclohexane/ethylacetate as eluents from 100/0 to 60/40. This afforded the title compound (7.7 mg).

$^1$H NMR (400 MHz, CDCl$_3$): δ ppm 8.68 (2H, s), 7.17 (1H, t), 6.71 (1H, d), 6.62 (1H, d), 6.19 (1H, s), 4.23 (2H, s) 3.92 (1H, s) 1.36 (6H, s) 1.12 (9H, s); UPLC: 0.75 min, 397 [M+H]+

Example 15

(5R)-5-ethyl-3-[6-(spiro[1-benzofuran-3,1'-cyclopropan]-4-yloxy)-3-pyridinyl]-2,4-imidazolidinedione

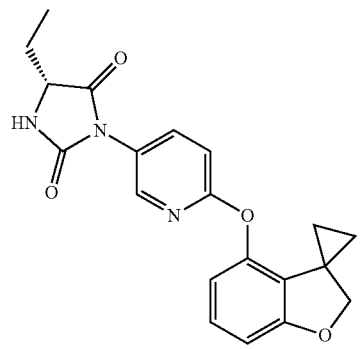 [SMILES: CC[C@H]1NC(=O)N(c2ccc(Oc3cccc4c3C3(CC3)CO4)nc2)C1=O]

To a solution of (2R)-2-amino-N-[6-(spiro[1-benzofuran-3,1'-cyclopropan]-4-yloxy)-3-pyridinyl]butanamide (Intermediate 89, 90 mg) in dry dichloromethane (15 ml) TEA (0.185 ml, 1.326 mmol) was added and the reaction mixture was cooled to 0° C. A solution of triphosgene (35.4 mg, 0.119 mmol) in dry dichloromethane (5 mL) was slowly added and the reaction mixture was stirred for 30 minutes at the same temperature. The reaction was quenched with water (10 ml) and two phases were separated. The organic layer was dried over sodium sulphate, filtered and evaporated. The residue was purified by flash chromatography (Biotage system) on silica gel using a 10 g SNAP column and cyclohexane/ethyl acetate 8:2 to cyclohexane/ethyl acetate 1:1 as eluents affording the title compound (65 mg, 0.178 mmol) as a white solid.

$^1$H NMR (400 MHz, DMSO-$d_6$): δ ppm 8.63 (1H, s), 8.14 (1H, d), 7.85 (1H, dd), 7.11 (1H, s), 7.09 (1H, t), 6.68 (1H, dd), 6.52 (1H, dd), 4.45 (2H, s), 4.18-1.24 (1H, m), 1.76-1.88 (1H, m), 1.64-1.76 (1H, m), 1.13-1.18 (2H, m), 0.96 (3H, t), 0.89-0.94 (2H, m); UPLC_B: 0.78 min, 366 [M+H]+.

Example 16

5,5-dimethyl-3-[6-(spiro[1-benzofuran-3,1'-cyclopropan]-4-yloxy)-3-pyridinyl]-2,4-imidazolidinedione

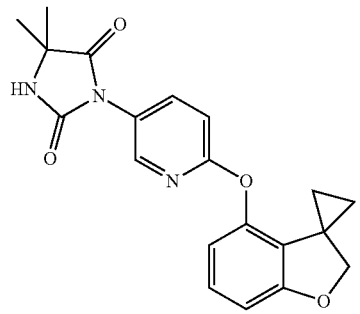 [SMILES: CC1(C)NC(=O)N(c2ccc(Oc3cccc4c3C3(CC3)CO4)nc2)C1=O]

To a solution of 2-methyl-N1-[6-(spiro[1-benzofuran-3,1'-cyclopropan]-4-yloxy)-3-pyridinyl]alaninamide (Intermediate 91, 34 mg) in dry dichloromethane (6 mL) TEA (0.070 mL, 0.501 mmol) was added and the mixture was cooled to 0° C. A solution of triphosgene (13.38 mg, 0.045 mmol) in dry dichloromethane (2 mL) was slowly added and the reaction mixture was stirred for 1 hour at the same temperature. The reaction was quenched with water (3 ml) and two phases were separated. The organic layer was dried over sodium sulphate, filtered and evaporated. The residue was purified by flash chromatography (Biotage system) on silica gel using a 10 g SNAP column SNAP and cyclohexane/ethyl acetate 7:3 to cyclohexane/ethyl acetate 3:7 as eluents affording the title as a white solid (23 mg).

$^1$H NMR (400 MHz, DMSO-$d_6$): δ ppm 8.63 (1H, s), 8.17 (1H, d), 7.88 (1H, d), 7.06-7.12 (2H, m), 6.67 (1H, d), 6.51 (1H, d), 4.45 (2H, s), 1.41 (6H, s), 1.12-1.17 (2H, m), 0.88-0.93 (2H, m); UPLC: 0.73 min, 366 [M+H]+.

Example 17

(5R)-5-ethyl-5-methyl-3-[6-(spiro[1-benzofuran-3,1'-cyclopropan]-4-yloxy)-3-pyridinyl]-2,4-imidazolidinedione

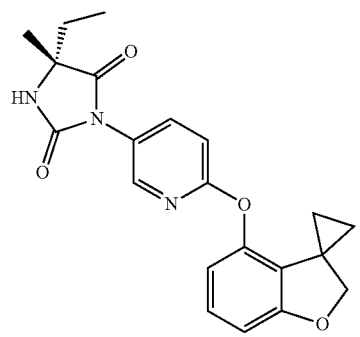 [SMILES: CC[C@@]1(C)NC(=O)N(c2ccc(Oc3cccc4c3C3(CC3)CO4)nc2)C1=O]

To a solution of N1-[6-(spiro[1-benzofuran-3,1'-cyclopropan]-4-yloxy)-3-pyridinyl]-D-isovalinamide (Intermediate 93, 68 mg) and TEA (0.134 mL, 0.962 mmol) in dry dichloromethane (11 ml) at 0° C. was added dropwise a solution of triphosgene (25.7 mg, 0.087 mmol) in dry dichloromethane (3.14 m) and the mixture thus obtained was stirred at the same temperature. After 1 hour a solution of triphosgene (25.7 mg, 0.087 mmol) in dry dichloromethane (3.14 ml) was added. After 3 hours UPLC/MS showed the absence of the starting material and the presence of the desired compound. Water was then added, the organic phase was separated and the aqueous one was extracted again with dichloromethane. The organic phase was washed with brine, dried over sodium sulphate and concentrated under vacuum to give 87 mg of crude. This was purified by flash chromatography (Biotage KP-Sil 10 g SNAP column, eluant cyclohexane/ethyl acetate from 88/12 to 0/100 in 10CV) to give 47 mg of the title compound as a white foam.

$^1$H NMR (400 MHz, DMSO-$d_6$): δ ppm 8.59 (1H, s), 8.14 (1H, d), 7.85 (1H, dd), 7.08 (2H, t), 6.66 (1H, d), 6.50 (1H, d), 4.44 (2H, s), 1.70-1.84 (1H, m), 1.57-1.70 (1H, m), 1.38 (3H, s), 1.08-1.19 (2H, m), 0.89-0.95 (2H, m), 0.85 (3H, t); UPLC: 1.04 min, 380 [M+H]+.

Example 18

(5R)-5-ethyl-3-(6-{[(3S/R)-3-methyl-1,3-dihydro-2-benzofuran-4-yl]oxy}-3-pyridinyl)-2,4-imidazolidinedione (Diastereoisomeric Mixture)

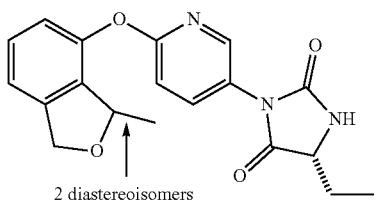 [SMILES: CC[C@H]1NC(=O)N(c2ccc(Oc3cccc4c3C(C)OC4)nc2)C1=O]

2 diastereoisomers

In a 50 ml round-bottomed flask (2R)-2-amino-N-{6-[(3-methyl-1,3-dihydro-2-benzofuran-4-yl)oxy]-3-pyridinyl}butanamide (Intermediate 102, 24.4 mg) was dissolved in dichloromethane (3 ml) to give a pale yellow solution which was cooled at 0° C. TEA (0.049 ml, 0.354 mmol) was added. A solution of triphosgene (9.46 mg, 0.032 mmol) in 0.7 ml of dichloromethane was added dropwise to the reaction mixture at 0° C. After 20 minutes, the reaction mixture was quenched with 5 ml of water and diluted with 5 ml of dichloromethane. Phases were separated through a phase separator cartridge. The organic phase was evaporated under vacuum to afford the crude product which was purified by silica gel chromatography (Biotage SP1 system, 10 g SNAP Silica column) with Cyclohexane/EtOAc as eluents (from 2/1 to 1/2 in 15 CV; then 1/2 for 10 CV). The collected fractions afforded the title compound as a 1:1 mixture of diastereoisomers (20.2 mg).

$^1$H NMR (400 MHz, CDCl$_3$): δ ppm 8.27 (1H, d), 7.78 (1H, dd), 7.33 (1H, t), 7.09 (1H, d), 7.06-6.96 (2H, m), 5.91 (1H, br. s.), 5.40-5.29 (1H, m), 5.20 (1H, dd), 5.09 (1H, d), 4.25-4.18 (1H, m), 2.08-1.84 (2H, m), 1.45 (3H, d), 1.07 (3H, t). UPLC_ipqc: 0.87 min, 354 [M+H]+

Example 19 and Example 20

(5R)-5-ethyl-3-{6-[(3-methyl-1,3-dihydro-2-benzo-furan-4-yl)oxy]-3-pyridinyl}-2,4-imidazolidinedione (Diastereoisomers 1 and 2)

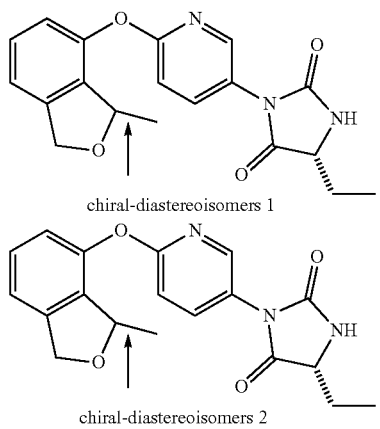

chiral-diastereoisomers 1 chiral-diastereoisomers 2

Both diastereoisomers of Example 18 were separated by preparative chiral chromatography.

Chiral preparative HPLC conditions were the following ones: Column: Chiralpak AS-H (25×2 cm), 5u; Mobile phase: n-Hexane/Ethanol 70:30% v/v; Flow rate: 15 ml/min; UV: 220 nm; Sample preparation: 20 mg dissolved in 1 ml of hexane/ethanol 1:1 v/v; Sample concentration: 20 mg/ml; Injection volume: 1000 uL.

Chiral Analytical Chromatography conditions were the following ones: Column: Chiralpak AS-H (25×0.46 cm); Mobile phase: n-Hexane/Ethanol 70:30% v/v; Flow rate: 0.8 ml/min; DAD: 210-340 nm; CD: 240 nm.

This chiral preparative HPLC afforded

Example 19 which was diastereoisomer 1 of (5R)-5-ethyl-3-{6-[(3-methyl-1,3-dihydro-2-benzofuran-4-yl)oxy]-3-pyridinyl}-2,4-imidazolidinedione (7.1 mg). $^1$H NMR (400 MHz, CDCl$_3$) δ ppm 8.27 (d, 1H), 7.78 (dd, 1H), 7.33 (t, 1H), 7.09 (d, 1H), 6.96-7.06 (m, 2H), 5.91 (br. s., 1H), 5.29-5.40 (m, 1H), 5.20 (dd, 1H), 5.09 (d, 1H), 4.18-4.25 (m, 1H), 1.84-2.08 (m, 2H), 1.45 (d, 3H), 1.07 (t, 3H). UPLC-MS_ipqc: 0.87 min, 354 [M+1]+. Chiral Analytical Chromatography HPLC: r.t.=12.327 min, 100% d.e.

Example 20 which was diastereoisomer 2 of (5R)-5-ethyl-3-{6-[(3-methyl-1,3-dihydro-2-benzofuran-4-yl)oxy]-3-pyridinyl}-2,4-imidazolidinedione (8.0 mg). $^1$H NMR (400 MHz, CDCl$_3$) δ ppm 8.27 (d, 1H), 7.78 (dd, 1H), 7.33 (t, 1H), 7.09 (d, 1H), 6.96-7.06 (m, 2H), 5.91 (br. s., 1H), 5.29-5.40 (m, 1H), 5.20 (dd, 1H), 5.09 (d, 1H), 4.18-4.25 (m, 1H), 1.84-2.08 (m, 2H), 1.45 (d, 3H), 1.07 (t, 3H). UPLC-MS_ipqc: 0.87 min, 354 [M+1]+. Chiral Analytical Chromatography HPLC: r.t.=16.579 min, 100% d.e.

Example 21

(5R)-5-ethyl-3-{6-[(3-ethyl-1,3-dihydro-2-benzo-furan-4-vi)oxy]-3-pyridinyl}-2,4-imidazolidinedione (Diastereoisomeric Mixture)

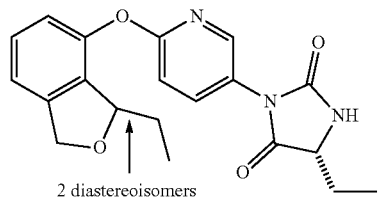 [SMILES: CCC1OCc2cccc(Oc3ccc(N4C(=O)N[C@H](CC)C4=O)cn3)c21]

2 diastereoisomers

In a 50 ml round-bottomed flask (2R)-2-amino-N-{6-[(3-ethyl-1,3-dihydro-2-benzofuran-4-yl)oxy]-3-pyridinyl}butanamide (Intermediate 110, 9 mg) was dissolved in dichloromethane (2 ml) to give a pale yellow solution that was cooled at 0° C. TEA (0.017 ml, 0.119 mmol) was added. 0.5 ml of a solution of triphosgene (14 mg in 2 ml of dichloromethane) was added dropwise to the reaction mixture at 0° C. The reaction mixture was stirred at 0° C. After 20 minutes, the reaction was completed. The reaction mixture was evaporated under vacuum to afford the crude product as a pale yellow oil which was purified via Biotage SP1 (with Cyclohexane/EtOAc as eluents from 2:1 to 1:2 in 15 CV; then 1:2 for 10 CV; 10 g SNAP Silica column). The collected fractions afforded the title compound (5R)-5-ethyl-3-{6-[(3-ethyl-1,3-dihydro-2-benzofuran-4-yl)oxy]-3-pyridinyl}-2,4-imidazolidinedione (6.9 mg) as a white solid.

$^1$H NMR (400 MHz, CDCl$_3$) δ ppm 8.29 (1H, d), 7.80 (1H, dd), 7.35 (1H, t), 7.11 (1H, d), 6.99-7.07 (2H, m), 5.91 (1H, br. s.), 5.25-5.33 (1H, m), 5.21 (1H, dd), 5.14 (1H, d), 4.21-4.26 (1H, m), 1.82-2.13 (3H, m), 1.69-1.81 (1H, m), 1.09 (3H, t), 0.93 (3H, t). UPLC_B: 0.78 min, 368 [M+H]+.

Example 22 and Example 23

(5R)-5-ethyl-3-{6-[(3-ethyl-1,3-dihydro-2-benzo-furan-4-yl)oxy]-3-pyridinyl}-2,4-imidazolidinedione (Diastereoisomers 1 and 2)

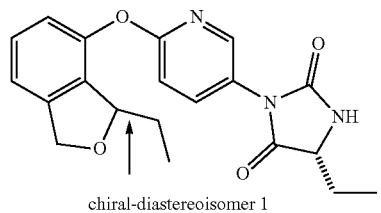

chiral-diastereoisomer 1

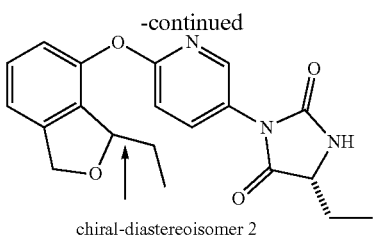

chiral-diastereoisomer 2

Both diastereoisomers of Example 21 were separated by preparative chiral chromatography affording two fractions.

Chiral preparative HPLC conditions were the following ones: Column Chiralpak AD-H (25×2 cm) 5 μm; Mobile phase n-Hexane/2-Propanol 85:15% v/v; Flow rate (ml/min) 15; UV detection 220 nm; Sample preparation 4 mg dissolved in 2 ml of methanol/ethanol 50:50% v/v; Sample concentration 2 mg/ml; Injection volume 2000 μl (equivalent to 4 mg)

Chiral Analytical Chromatography conditions were the following ones: Column: Chiralpak AD-H (25×0.46 cm); Mobile phase: n-Hexane/2-Propanol 85:15% v/v; Flow rate: 0.8 ml/min; DAD: 210-340 nm; CD: −.

This chiral preparative HPLC afforded:

Example 22 which was diastereoisomer 1 of (5R)-5-ethyl-3-{6-[(3-ethyl-1,3-dihydro-2-benzofuran-4-yl)oxy]-3-pyridinyl}-2,4-imidazolidinedione (2.3 mg). $^1$H NMR (400 MHz, MeOD) δ ppm 8.17 (1H, d), 7.89 (1H, dd), 7.37 (1H, t), 7.17 (1H, d), 7.10 (1H, d), 7.01 (1H, d), 5.13-5.23 (2H, m), 5.08 (1H, d), 4.25 (1H, dd), 1.78-2.01 (3H, m), 1.64-1.78 (1H, m), 1.05 (3H, t), 0.81-0.89 (3H, m). NH missed. UPLC_B: 0.76 min, 368 [M+1]+. Chiral Analytical Chromatography HPLC: 14.93 min, 98.6% d.e.

Example 23 which was diastereoisomer 2 of (5R)-5-ethyl-3-{6-[(3-ethyl-1,3-dihydro-2-benzofuran-4-yl)oxy]-3-pyridinyl}-2,4-imidazolidinedione (2.6 mg). $^1$H NMR (400 MHz, MeOD) δ ppm 8.18 (1H, d), 7.89 (1H, dd), 7.38 (1H, t), 7.17 (1H, d), 7.10 (1H, d), 7.02 (1H, d), 5.13-5.24 (2H, m), 5.09 (1H, d), 4.25 (1H, dd), 1.79-2.05 (3H, m), 1.65-1.78 (1H, m), 1.06 (3H, t), 0.85 (3H, t). NH missed. UPLC_B: 0.76 min, 368 [M+1]+. Chiral Analytical Chromatography HPLC: 17.51 min, 100% d.e.

Example 24

5,5-dimethyl-3-{6-[(3-methyl-3,4-dihydro-2H-chromen-5-yl)oxy]-3-pyridinyl}-2,4-imidazolidinedione (Racemic Mixture)

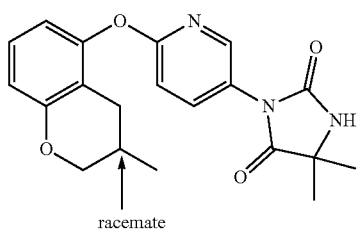 [SMILES: CC1COc2cccc(Oc3ccc(N4C(=O)NC(C)(C)C4=O)cn3)c2C1]

racemate

In a 50 ml round-bottomed flask 2-methyl-N1-{6-[(3-methyl-3,4-dihydro-2H-chromen-5-yl)oxy]-3-pyridinyl}alaninamide (Intermediate 121, 72.6 mg) was dissolved in dichloromethane (5 ml) to give a pale yellow solution. TEA (0.142 ml, 1.021 mmol) was added and the reaction mixture was cooled at 0° C. A solution of triphosgene (27.3 mg, 0.092 mmol) in 1 ml of dichloromethane was added to the reaction mixture which was stirred at 0° C. After 15 minutes, additional solution of triphosgene (27.3 mg, 0.092 mmol) in 1 ml of dichloromethane was added to the reaction mixture. After 15 minutes, the reaction mixture was evaporated under vacuum to give the crude product which was purified via Biotage SP1 (using Cyclohexane/EtOAc as eluents from 3:1 to 1:2 in 10 CV; then 1:2 for 5 CV; 10 g SNAP Silica column). The collected fractions afforded the title compound 5,5-dimethyl-3-{6-[(3-methyl-3,4-dihydro-2H-chromen-5-yl)oxy]-3-pyridinyl}-2,4-imidazolidinedione as a colourless oil (41.6 mg).

$^1$H NMR (400 MHz, CDCl$_3$) δ ppm 8.28 (1H, d), 7.75 (1H, dd), 7.13 (1H, t), 6.95 (1H, d), 6.74 (1H, dd), 6.65 (1H, dd), 5.76 (1H, br. s.), 4.15-4.20 (1H, m), 3.63-3.74 (1H, m), 2.72-2.82 (1H, m), 2.06-2.23 (2H, m), 1.57 (6H, s), 1.02 (3H, d). UPLC_B: 0.80 min, 368 [M+H]+.

Example 25 and Example 26

5,5-dimethyl-3-{6-[(3-methyl-3,4-dihydro-2H-chromen-5-yl)oxy]-3-pyridinyl}-2,4-imidazolidinedione (Enantiomers 1 and Enantiomer 2)

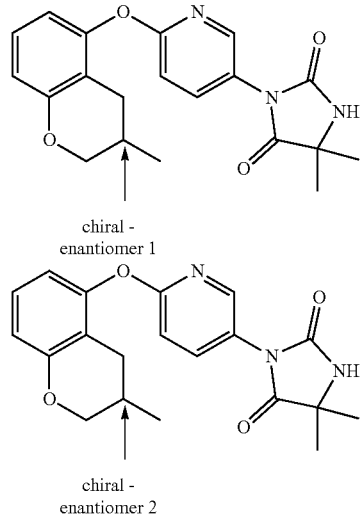

chiral - enantiomer 1 chiral - enantiomer 2

Both enantiomers of Example 24 were separated by preparative chiral chromatography.

Chiral preparative HPLC conditions were the following ones: Column: Chiralpak AD-H (25×2 cm), 5u; Mobile phase: n-Hexane/Ethanol 40/60 v/v; Flow rate: 15 ml/min; UV: 220 nm; Sample preparation: 50 mg dissolved in 2 ml of ethanol Added 1 ml n-Hexane; Sample concentration: 16.7 mg/ml; Injection volume: 1000 μL.

Chiral analytical chromatography conditions were the following ones: Column: Chiralpak AD-H (25×0.46 cm); Mobile phase: n-Hexane/Ethanol 40:60% v/v; Flow rate: 0.8 ml/min; DAD: 210-340 nm.

This preparative chiral chromatography afforded

Example 25 which was the enantiomer 1 of 5,5-dimethyl-3-{6-[(3-methyl-3,4-dihydro-2H-chromen-5-yl)oxy]-3-pyridinyl}-2,4-imidazolidinedione (16.6 mg). $^1$H NMR (400 MHz, CDCl$_3$) δ ppm 8.28 (1H, d), 7.75 (1H, dd), 7.13 (1H, t), 6.95 (1H, d), 6.74 (1H, dd), 6.65 (1H, dd), 5.76 (1H, br. s.), 4.15-4.20 (1H, m), 3.63-3.74 (1H, m), 2.72-2.82 (1H, m), 2.06-2.23 (2H, m), 1.57 (6H, s), 1.02 (3H, d). UPLC_B: 0.81 min, 368 [M+H]+. Chiral Analytical Chromatography HPLC: 12.48 min, 100.0% e.e.

Example 26 which was the enantiomer 2 of 5,5-dimethyl-3-{6-[(3-methyl-3,4-dihydro-2H-chromen-5-yl)oxy]-3-pyridinyl}-2,4-imidazolidinedione (17.0 mg). $^1$H NMR (400 MHz, CDCl$_3$) δ ppm 8.28 (1H, d), 7.75 (1H, dd), 7.13 (1H, t), 6.95 (1H, d), 6.74 (1H, dd), 6.65 (1H, dd), 5.76 (1H, br. s.), 4.15-4.20 (1H, m), 3.63-3.74 (1H, m), 2.72-2.82 (1H, m), 2.06-2.23 (2H, m), 1.57 (6H, s), 1.02 (3H, d). UPLC_B: 0.81 min, 368 [M+H]+. Chiral Analytical Chromatography HPLC: 14.68 min, 98.4% e.e.

Example 27

5,5-dimethyl-3-{6-[(1a-methyl-1,1a,2,7b-tetrahydro-cyclopropa[c]chromen-7-yl)oxy]-3-pyridinyl}-2,4-imidazolidinedione (Racemic Mixture)

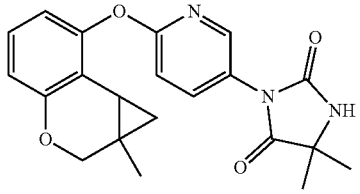 [SMILES: CC1(C)NC(=O)N(c2ccc(Oc3cccc4c3C3CC3(C)CO4)nc2)C1=O]

To a solution of 2-methyl-N1-{6-[(1a-methyl-1,1a,2,7b-tetrahydrocyclopropa[c]chromen-7-yl)oxy]-3-pyridinyl}alaninamide (Intermediate 129, 100 mg) in dry dichloromethane (10 ml) TEA (0.177 ml, 1.273 mmol) was added and the reaction mixture was cooled to 0° C. At this point a solution of triphosgene (37.8 mg, 0.127 mmol) in dry dichloromethane (2.5 ml) was slowly added (over 30 minutes) and the reaction mixture was stirred for 1 hour at the same temperature. The reaction was then quenched with water and the two phases were separated. The organic layer was dried over sodium sulphate, filtered and evaporated and the residue was purified by silica gel chromatography (Companion system, with a gradient from cyclohexane/ethyl acetate 8:2 to cyclohexane/ethyl acetate 1:1) to give the title compound as a white solid (40 mg, 0.103 mmol).

$^1$H NMR (400 MHz, CDCl$_3$): δ ppm 8.33 (1H, d), 7.77 (1H, dd), 7.07 (1H, t), 6.97 (1H, d), 6.74 (2H, dd), 5.60 (1H, br. s.), 4.19 (1H, d), 3.72 (1H, d), 1.88 (1H, dd), 1.59 (6H, s), 1.18-1.26 (4H, m), 0.87 (1H, dd); UPLC_ipqc: 1.03 min, 380 [M+H]+.

Example 28 and Example 29

5,5-dimethyl-3-{6-[(1a-methyl-1,1a,2,7b-tetrahydro-cyclopropa[c]chromen-7-yl)oxy]-3-pyridinyl}-2,4-imidazolidinedione (Enantiomer 1 and Enantiomer 2)

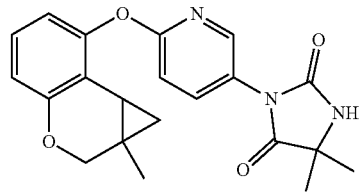 [SMILES: CC1(C)NC(=O)N(c2ccc(Oc3cccc4c3C3CC3(C)CO4)nc2)C1=O]

Both enantiomers of Example 27 were separated by semi-preparative chiral SFC chromatography. Chiral SFC conditions were the following ones: Column: Chiralpak IC (25×2.1 cm); Mobile phase: Ethanol+0.1% I-propylamine 20%; Flow rate: 45 ml/min; Pressure: 120 bar; UV: 220 nm; This semi-preparative chiral SFC chromatography on 30 mg of Example 27 afforded:

Example 28 which was the enantiomer 1 of 5,5-dimethyl-3-{6-[(1a-methyl-1,1a,2,7b-tetrahydrocyclopropa[c]chromen-7-yl)oxy]-3-pyridinyl}-2,4-imidazolidinedione (12 mg).

$^1$H NMR (400 MHz, CDCl$_3$): δ ppm 8.33 (1H, d), 7.77 (1H, dd), 7.07 (1H, t), 6.97 (1H, d), 6.74 (2H, dd), 5.81 (1H, s), 4.19 (1H, d), 3.72 (1H, d), 1.88 (1H, dd), 1.60 (6H, s), 1.16-1.24 (4H, m), 0.87 (1H, dd); Chiral Analytical SFC Chromatography: 7.51 min, 100.0% e.e.

and Example 29 which was the enantiomer 2 of 5,5-dimethyl-3-{6-[(1a-methyl-1,1a,2,7b-tetrahydrocyclopropa[c]chromen-7-yl)oxy]-3-pyridinyl}-2,4-imidazolidinedione (14 mg).

$^1$H NMR (400 MHz, CDCl$_3$): δ ppm 8.33 (1H, d), 7.77 (1H, dd), 7.07 (1H, t), 6.97 (1H, d), 6.74 (2H, dd), 5.87 (1H, s), 4.19 (1H, d), 3.72 (1H, d), 1.88 (1H, dd), 1.59 (6H, s), 1.19-1.23 (4H, m), 0.87 (1H, dd); Chiral Analytical SFC Chromatography: 9.40 min, 100.0% e.e.

Example 30

(5R)-5-ethyl-5-methyl-3-[6-(1H-spiro[2-benzopyran-4,1'-cyclopropan]-5-yloxy)-3-pyridinyl]-2,4-imidazolidinedione

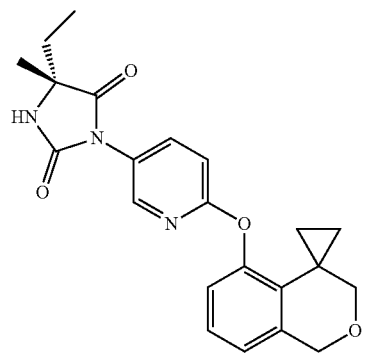 [SMILES: CC[C@@]1(C)NC(=O)N(c2ccc(Oc3cccc4c3C3(CC3)COC4)nc2)C1=O]

To a solution of N1-[6-(1H-spiro[2-benzopyran-4,1'-cyclopropan]-5-yloxy)-3-pyridinyl]-D-isovalinamide (Intermediate 141, 40 mg) in dry dichloromethane (8 mL) TEA (0.076 mL, 0.544 mmol) was added and the reaction mixture was cooled to 0° C. A solution of triphosgene (14.54 mg, 0.049 mmol) in dry dichloromethane (4 ml) was slowly added and the reaction mixture was stirred for 3 hours at the same temperature. The reaction was quenched with water (10 ml) and two phases separated. The organic layer was dried over sodium sulphate, filtered and evaporated and the residue was purified by flash chromatography (Biotage system) on silica gel using 10 g SNAP column and cyclohexane/ethyl acetate as eluents from 7:3 to 3:7 as eluent. This afforded the title compound (25 mg) as a white solid.

$^1$H NMR (400 MHz, DMSO-d$_6$): δ ppm 8.60 (1H, s), 8.15 (1H, d), 7.87 (1H, dd), 7.15 (1H, t), 7.10 (1H, d), 6.95 (1H, d), 6.79 (1H, d), 4.85 (2H, s), 3.54 (2H, s), 1.72-1.84 (1H, m), 1.60-1.72 (1H, m), 1.39 (3H, s), 1.33-1.38 (2H, m), 0.87 (3H, t), 0.62-0.67 (2H, m); UPLC_IPQC: 0.97 min, 394 [M+H]+.

Example 31

3-{2-[(3,3-dimethyl-2,3-dihydro-1-benzofuran-4-yl)oxy]-5-pyrimidinyl}-5,5-dimethyl-2,4-imidazolidinedione

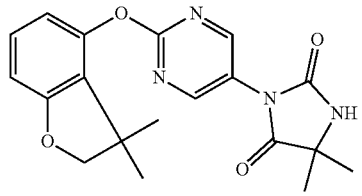 [SMILES: CC1(C)NC(=O)N(c2cnc(Oc3cccc4c3C(C)(C)CO4)nc2)C1=O]

To a solution of N1-{2-[(3,3-dimethyl-2,3-dihydro-1-benzofuran-4-yl)oxy]-5-pyrimidinyl}-2-methylalaninamide (Intermediate 143, 18 mg, 0.053 mmol) in dry Dichloromethane (DCM) (3 mL) TEA (0.037 ml, 0.263 mmol) was added and the reaction mixture was cooled to 0° C. A solution of triphosgene (7.02 mg, 0.024 mmol) in dry Dichloromethane (1 mL) was slowly added and the reaction mixture was stirred for 2 hours while the temperature was allowed to reach r.t. The reaction was quenched with water (3 ml) and two phases were separated. The organic layer was dried (Na$_2$SO$_4$), filtered and evaporated and the residue was purified by flash chromatography (Biotage system) on silica gel using a column SNAP 10 g and cyclohexane/ethyl acetate from 8:2 to 1:1 as eluents affording the title compound (13 mg) as a white solid.

$^1$H NMR (400 MHz, DMSO-d$_6$): δ ppm 8.72-8.77 (3H, m), 7.17 (1H, t), 6.65-6.75 (2H, m), 4.23 (2H, s), 1.43 (6H, s), 1.25 (6H, s). UPLC: 0.67 min, 369 [M+H]+.

Example 32

(5R)-3-{2-[(3,3-dimethyl-2,3-dihydro-1-benzofuran-4-yl)oxy]-5-pyrimidinyl}-5-(1-methylethyl)-2,4-imidazolidinedione

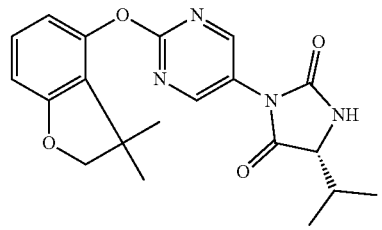 [SMILES: CC(C)[C@H]1NC(=O)N(c2cnc(Oc3cccc4c3C(C)(C)CO4)nc2)C1=O]

To a solution of N1-{2-[(3,3-dimethyl-2,3-dihydro-1-benzofuran-4-yl)oxy]-5-pyrimidinyl}-D-valinamide (Intermediate 145, 38 mg, 0.107 mmol) in dry Dichloromethane (DCM) (5 mL) TEA (0.074 mL, 0.533 mmol) was added and the reaction mixture was cooled to 0° C. A solution of triphosgene (14.24 mg, 0.048 mmol) in dry Dichloromethane (DCM) (1 mL) was slowly added and the reaction mixture was stirred for 30 minutes at the same temperature. The reaction was quenched with water (3 ml) and two phases were separated. The organic layer was dried (Na$_2$SO$_4$), filtered and evaporated and the residue was purified by flash chromatography (Biotage system) on silica gel using a column SNAP 25 g and cyclohexane/ethyl acetate from 8:2 to 1:1 as eluent affording the title compound (15 mg) as a white solid.

$^1$H NMR (400 MHz, DMSO-d$_6$): δ ppm 8.77 (1H, br.s), 8.62 (2H, s), 7.18 (1H, t), 6.65-6.75 (2H, m), 4.22 (2H, s), 4.15-4.20 (1H, m), 2.10-2.20 (1H, m), 1.25 (6H, s), 1.03 (3H, d), 0.90 (3H, d). UPLC: 0.71 min, 383 [M+H]+.

Example 33

(5R)-3-{6-[(2,2-dimethyl-2,3-dihydro-1-benzofuran-4-yl)oxy]-3-pyridinyl}-5-ethyl-2,4-imidazolidinedione

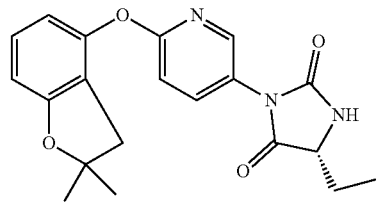 [SMILES: CC[C@H]1NC(=O)N(c2ccc(Oc3cccc4c3CC(C)(C)O4)nc2)C1=O]

((2R)-2-amino-N-{6-[(2,2-dimethyl-2,3-dihydro-1-benzofuran-4-yl)oxy]-3-pyridinyl}butanamide) (Intermediate 209, 10 mg, 0.029 mmol) was dissolved in dry dichloromethane (1 ml). The reaction mixture was cooled down in an ice bath. Triethylamine (0.024 ml, 0.176 mmol) was added at 0° C. Then 0.5 ml of a solution of triphosgene in dry dichloromethane (4.78 mg, 0.016 mmol in 0.5 ml) was added dropwise. The reaction mixture was stirred under argon during 20 min at 0° C. A saturated aqueous solution of NaHCO$_3$ was added (3 ml). The aqueous layer was extracted with dichloromethane 4 times (4×4 mL). Combined organic layers were dried over Na$_2$SO$_4$ and evaporated. the residue was purified by flash chromatography (Companion system) on silica gel using a 4 g silica cartridge and cyclohexane/ethyl acetate from 100:0 to 60:40 as eluents affording the title compound (7 mg).

$^1$H NMR (400 MHz, CDCl$_3$): δ ppm 8.29 (1H, d), 7.74 (1H, dd), 7.14 (1H, d), 7.00 (1H, d), 6.61 (1H, dd), 6.55 (1H, d), 5.91 (1H, br.s), 4.20-4.25 (1H, m), 3.02 (2H, s), 1.85-2.10 (2H, m), 1.51 (6H, s), 1.08 (3H, t).

UPLC_B: 1.02 min, 368 [M+H]+.

Example 34

5,5-dimethyl-3-[6-(1H-spiro[2-benzopyran-4,1'-cyclopropan]-5-yloxy)-3-pyridinyl]-2,4-imidazolidinedione

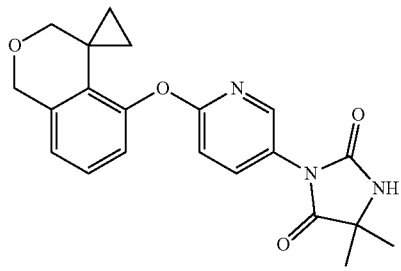 [SMILES: CC1(C)NC(=O)N(c2ccc(Oc3cccc4c3C3(CC3)COC4)nc2)C1=O]

To a solution of 2-methyl-N1-[6-(1H-spiro[2-benzopyran-4,1'-cyclopropan]-5-yloxy)-3-pyridinyl]alaninamide (34 mg, 0.096 mmol) in dry Dichloromethane (DCM) (5 mL) TEA (0.067 mL, 0.481 mmol) was added and the reaction mixture was cooled to 0° C. A solution of triphosgene (12.85 mg, 0.043 mmol) in dry Dichloromethane (DCM) (2 mL) was slowly added and the reaction mixture was stirred for 30 minutes at the same temperature. The reaction was quenched with water (5 ml) and two phases were separated. The organic layer was dried (Na$_2$SO$_4$), filtered and evaporated and the residue was purified by flash chromatography (Biotage system) on silica gel using a column SNAP 10 g and Dichloromethane/methanol 99:1 to Dichloromethane/methanol 95:5 as eluents affording the title compound (35 mg) as a white solid.

$^1$H NMR (400 MHz, DMSO-de): δ ppm 8.63 (1H, s), 8.18 (1H, d), 7.90 (1H, dd), 7.16 (1H, t), 7.10 (1H, d), 6.96 (1H, dd), 6.80 (1H, dd), 4.86 (2H, s), 3.55 (2H, s), 1.43 (6H, s), 1.34-1.39 (2H, m), 0.63-0.68 (2H, m). UPLC_B: 0.92 min, 380 [M+H]+.

Example 35

(5R)-3-[2-(2,3-dihydrospiro[chromene-4,1'-cyclopropan]-5-yloxy)-5-pyrimidinyl]-5-ethyl-5-methyl-2,4-imidazolidinedione

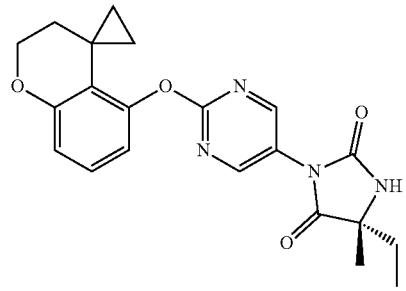 [SMILES: CC[C@@]1(C)NC(=O)N(c2cnc(Oc3cccc4c3C3(CCO4)CC3)nc2)C1=O]

To a solution of N1-[2-(2,3-dihydrospiro[chromene-4,1'-cyclopropan]-5-yloxy)-5-pyrimidinyl]-D-isovalinamide (Intermediate 225, 4 mg, 10.86 µmol) in dry Dichloromethane (1 mL) TEA (3.78 µL, 0.027 mmol) was added. The reaction was cooled in an ice-bath, then a solution of triphosgene (1.450 mg, 4.89 µmol) in dry Dichloromethane (0.250 mL) was added once then two other times with 10 minutes in between. The reaction was stirred at 0° C. for 40 minutes, then it was quenched with water (5 mL) maintaining the reaction in the ice-bath. The organic layer was separated, dried (Na$_2$SO$_4$), filtered and evaporated. The residue was purified by chromatography on silica gel using a column isolute 2 g and cyclohexane to cyclohexane/ethyl acetate 1:1 as eluent affording the title compound (3 mg) as a white solid.

$^1$H NMR (400 MHz, CDCl$_3$) δ ppm 8.73 (2H, s), 7.07 (1H, t), 6.78 (1H, dd) 6.52 (1H, dd) 5.69 (1H, br.s) 4.25-4.33 (2H, m) 1.95-2.05 (1H, m) 1.74-1.86 (3H, m) 1.54-1.62 (5H, s), 1.00 (3H, t) 0.60-0.67 (2H, m).

Examples 36, Example 37 and Example 38

5,5-dimethyl-3-{6-[(4-methyl-3,4-dihydro-2H-chromen-5-yl)oxy]-3-pyridinyl}-2,4-imidazolidinedione (Racemate Mixture, Enantiomer 1, Enantiomer 2)

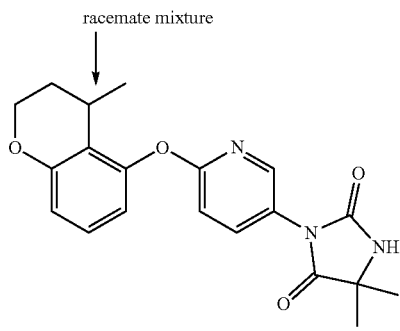

enantiomer 1

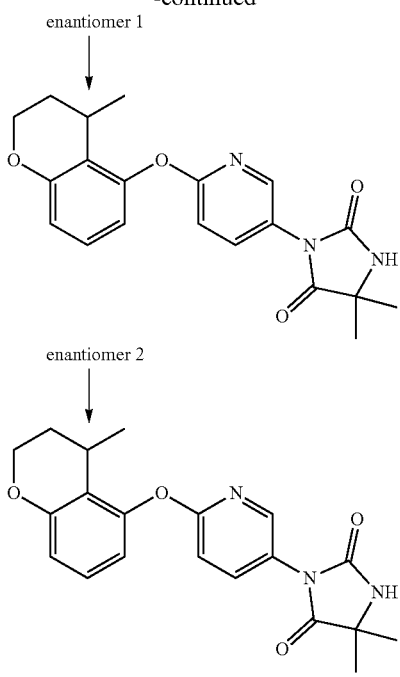

enantiomer 2

In a 50 mL round-bottomed flask the 2-amino-2-methyl-N-[6-(4-methylchroman-5-yl)oxy-3-pyridyl]propanamide (Intermediate 215, 22.9 mg, 0.064 mmol) was dissolved in Dichloromethane (3 mL) to give a colourless solution. TEA (0.051 mL, 0.369 mmol) was added and the obtained mixture was cooled at 0° C. Triphosgene (21.87 mg, 0.074 mmol) was dissolved in 1 ml of DCM and obtained solution was added to the reaction mixture. The reaction mixture was stirred at 0° C. for 15 minutes. Additional TEA (0.051 mL, 0.369 mmol) and triphosgene (21.87 mg, 0.074 mmol) dissolved in 1 ml of DCM were added to the reaction mixture at 0° C. and the reaction mixture was stirred for 15 minutes. The reaction mixture was quenched with 5 mL of saturated sodium bicarbonate solution and diluted with 10 mL of DCM. Phases were separated through a phase separator cartridge. The organic phase was evaporated in vacuo and the residue was purified by flash chromatography (Biotage system) on silica gel using a column SNAP 10 g and cyclohexane/ethyl acetate from 2:1 to 1:2 as eluents affording the title compound Example 36 (19.1 mg) as a colorless oil.

$^1$H NMR (400 MHz, CDCl$_3$) δ ppm 8.30 (1H, d), 7.76 (1H, dd), 7.12 (1H, t), 6.97 (1H, d), 6.72 (1H, dd), 6.61 (1H, dd), 5.74 (1H, br. s.), 4.23-4.32 (1H, m), 4.15-4.22 (1H, m), 2.97-3.11 (1H, m), 2.07-2.16 (1H, m), 1.62-1.70 (1H, m), 1.57 (6H, s), 1.28 (3H, d).

Both enantiomers of Example 36 were separated by preparative chiral chromatography.

Chiral preparative HPLC conditions were the following ones: Column: Chiralcel OD-H (25×2 cm), 5u; Mobile phase: n-Hexane/2-propanol 85:15% v/v; Flow rate: 18 ml/min; UV: 220 nm; Sample preparation: 18 mg dissolved in 1.2 ml of ethanol. Sample concentration: 15 mg/ml; Injection volume: 600 μL.

This preparative chiral chromatography afforded:

Example 37: 7.1 mg of a white solid (enantiomer 1); Rt (Chiral preparative HPLC)=21.018 minutes $^1$H NMR (400 MHz, CDCl$_3$) δ ppm 8.30 (1H, d), 7.76 (1H, dd), 7.12 (1H, t), 6.97 (1H, d), 6.72 (1H, dd), 6.61 (1H, dd), 5.74 (1H, br. s.), 4.23-4.32 (1H, m), 4.15-4.22 (1H, m), 2.97-3.11 (1H, m), 2.07-2.16 (1H, m), 1.62-1.70 (1H, m), 1.57 (6H, s), 1.28 (3H, d).

Example 38: 6.9 mg of a white solid (enantiomer 2); Rt (Chiral preparative HPLC)=25.752 minutes $^1$H NMR (400 MHz, CDCl$_3$) δ ppm 8.30 (1H, d), 7.76 (1H, dd), 7.12 (1H, t), 6.97 (1H, d), 6.72 (1H, dd), 6.61 (1H, dd), 5.74 (1H, br. s.), 4.23-4.32 (1H, m), 4.15-4.22 (1H, m), 2.97-3.11 (1H, m), 2.07-2.16 (1H, m), 1.62-1.70 (1H, m), 1.57 (6H, s), 1.28 (3H, d).

Examples 39, Example 40 and Example 41

(5R)-5-ethyl-5-methyl-3-{6-[(3-methyl-3,4-dihydro-2H-chromen-5-yl)oxy]-3-pyridinyl}-2,4-imidazolidinedione (Diastereoisomeric Mixture, Diastereoisomer 1, Diastereoisomer 2)

diastereoisomeric mixture

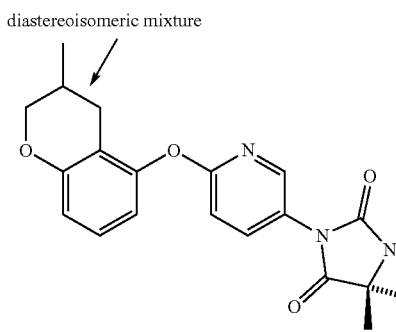

diastereoisomer 1

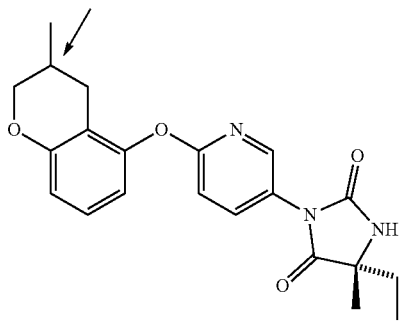

diastereoisomer 2

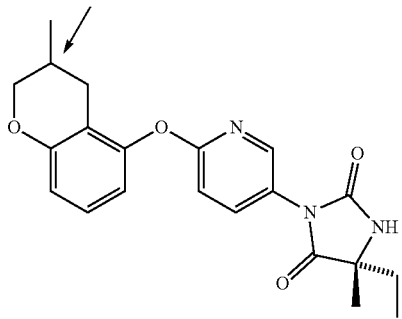

In a 25 mL round-bottomed flask (2R)-2-amino-2-methyl-N-[6-(3-methylchroman-5-yl)oxy-3-pyridyl]butanamide (Intermediate 147, 33 mg, 0.088 mmol) was dissolved in Dichloromethane (5 mL) to give a colourless solution. The reaction mixture was cooled at 0° C. TEA (0.061 mL, 0.441 mmol) and triphosgene (26.2 mg, 0.088 mmol) was added and the reaction mixture was stirred at 0° C. for 15 minutes. The reaction mixture was quenched with an aqueous saturated solution of sodium bicarbonate (5 mL) and diluted with 10 mL of dichloromethane. Phases were separated through a phase separator cartridge. The organic layer was evaporated in vacuo and the residue was purified by flash chromatography (Biotage system) on silica gel using a column SNAP 10 g and cyclohexane/ethyl acetate from 3:1 to 1:2 as eluents affording the title compound Example 39 (26.8 mg) as a yellow pale oil.

¹H NMR (400 MHz, CDCl₃) δ ppm 8.26 (1H, d), 7.73 (1H, dd), 7.13 (1H, t), 6.95 (1H, dd), 6.74 (1H, dd), 6.64 (1H, dd), 5.95 (1H, br. s.), 4.15-4.21 (1H, m), 3.57-3.75 (1H, m), 2.70-2.84 (1H, m), 2.17 (2H, d), 1.91-2.04 (1H, m), 1.70-1.82 (1H, m), 1.54 (3H, s), 1.01 (3H, d), 0.97 (3H, t).

Both diastereoisomers of Example 39 were separated by Semipreparative chiral SFC.

Semipreparative chiral SFC conditions were the following ones: Column: Chiralpack AD-H (25×3 cm), Sum; Modifier (Methanol+0.1% isopropylamine) 20%; Flow rate 50 ml/min; Pressure 120 bar; Temperature 38° C.; UV detection 220 nm; Loop 750 µL; Injection 13 mg (in Methanol).

This preparative chiral chromatography afforded:

Example 40: 5.9 mg (diastereoisomer 1); Rt (Semi-preparative chiral SFC)=13.48 minutes ¹H NMR (400 MHz, CDCl₃) δ ppm 8.26 (1H, d), 7.73 (1H, dd), 7.13 (1H, t), 6.95 (1H, dd), 6.74 (1H, dd), 6.64 (1H, dd), 5.95 (1H, br. s.), 4.15-4.21 (1H, m), 3.57-3.75 (1H, m), 2.70-2.84 (1H, m), 2.17 (2H, d), 1.91-2.04 (1H, m), 1.70-1.82 (1H, m), 1.54 (3H, s), 1.01 (3H, d), 0.97 (3H, t).

Example 41: 6.6 mg (diastereoisomer 1); Rt (Semi-preparative chiral SFC)=15.23 minutes ¹H NMR (400 MHz, CDCl₃) δ ppm 8.26 (1H, d), 7.73 (1H, dd), 7.13 (1H, t), 6.95 (1H, dd), 6.74 (1H, dd), 6.64 (1H, dd), 5.95 (1H, br. s.), 4.15-4.21 (1H, m), 3.57-3.75 (1H, m), 2.70-2.84 (1H, m), 2.17 (2H, d), 1.91-2.04 (1H, m), 1.70-1.82 (1H, m), 1.54 (3H, s), 1.01 (3H, d), 0.97 (3H, t).

Example 42 Example 43 and Example 44

(5R)-5-ethyl-5-methyl-3-[6-(1,1a,2,7b-tetrahydrocyclopropa[c]chromen-7-yloxy)-3-pyridinyl]-2,4-imidazolidinedione (Diastereoisomeric Mixture, Diastereoisomer 1, Diastereoisomer 2)

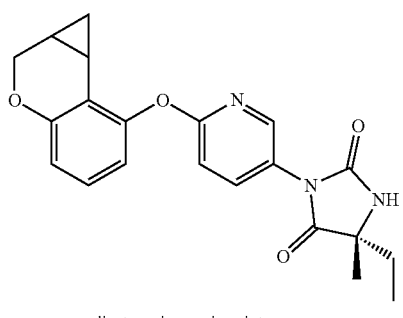

diastereoisomeric mixture

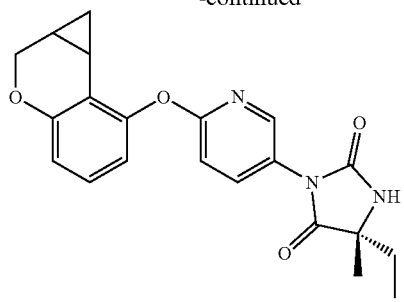

diastereoisomeric 1

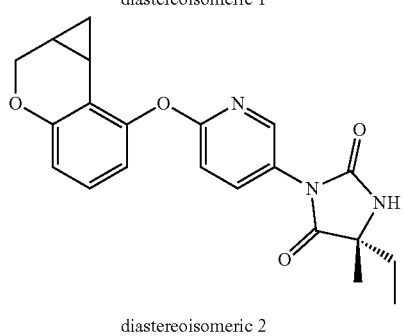

diastereoisomeric 2

In a 25 mL round-bottomed flask (2R)—N-[6-(1,1a,2,7b-tetrahydrocyclopropa[c]chromen-7-yloxy)-3-pyridyl]-2-amino-2-methyl-butanamide (Intermediate 228, 33 mg, 0.088 mmol) was dissolved in Dichloromethane (5 mL) to give a colourless solution. The reaction mixture was cooled at 0° C. TEA (0.091 mL, 0.66 mmol) and triphosgene (39 mg, 0.131 mmol) were added and the reaction mixture was stirred at 0° C. for 15 minutes. The reaction mixture was quenched with an aqueous saturated solution of sodium bicarbonate (5 mL) and diluted with 10 mL of dichloromethane. Phases were separated through a phase separator cartridge. The organic layer was evaporated in vacuo and the residue was purified by flash chromatography (Biotage system) on silica gel using a column SNAP 10 g and cyclohexane/ethyl acetate from 3:1 to 1:2 as eluents affording the title compound Example 42 (42.6 mg) as a yellow pale oil.

¹H NMR (400 MHz, CDCl₃) δ ppm 8.29 (1H, d), 7.73 (1H, dd), 7.07 (1H, t), 6.97 (1H, d), 6.72 (2H, d), 5.77 (1H, br. s.), 4.31 (1H, dd), 3.95 (1H, dd), 1.92-2.11 (2H, m), 1.72-1.83 (1H, m), 1.64-1.73 (1H, m), 1.54 (3H, s), 0.97 (3H, t), 0.93-1.06 (2H, m).

Both diastereoisomers of Example 42 were separated by preparative chiral chromatography.

Preparative HPLC chiral chromatography conditions were the following ones: Column: Chiralpack AD-H (25×3 cm), 5 um; Mobile phase: n-Hexane/2-Propanol 90/10% v/v; Flow rate: 40 ml/min; UV: 220 nm; Sample preparation: 41 mg dissolved in 4 ml of ethanol. Sample concentration: 10.3 mg/ml; Injection volume: 2000 µL.

This preparative chiral chromatography afforded:

Example 43: 14.1 mg as white solid (diastereoisomer 1); Rt (Chiral preparative HPLC)=17.95 minutes ¹H NMR (400 MHz, CDCl₃) δ ppm 8.29 (1H, d), 7.74 (1H, dd), 7.07 (1H, t), 6.97 (1H, d), 6.72 (2H, d), 5.51 (1H, br. s.), 4.32 (1H, dd), 3.96 (1H, dd), 2.01-2.09 (1H, m), 1.92-2.02 (1H, m), 1.72-1.82 (1H, m), 1.64-1.73 (1H, m), 1.55 (3H, s), 0.99-1.05 (2H, m), 0.95-1.01 (3H, m).

Example 44: 15 mg as white solid (diastereoisomer 2); Rt (Chiral preparative HPLC)=21.99 minutes $^1$H NMR (400 MHz, CDCl$_3$) δ ppm 8.29 (1H, d), 7.74 (1H, dd), 7.07 (1H, t), 6.97 (1H, d), 6.72 (2H, d), 5.51 (1H, br. s.), 4.32 (1H, dd), 3.96 (1H, dd), 2.01-2.09 (1H, m), 1.92-2.02 (1H, m), 1.72-1.82 (1H, m), 1.64-1.73 (1H, m), 1.55 (3H, s), 0.99-1.05 (2H, m), 0.95-1.01 (3H, m).

Example 45, Example 46 and Example 47

3-{6-[(3-ethyl-1,3-dihydro-2-benzofuran-4-yl)oxy]-3-pyridinyl}-5,5-dimethyl-2,4-imidazolidinedione (Racemate Mixture, Enantiomer 1, Enantiomer 2)

racemic mixture

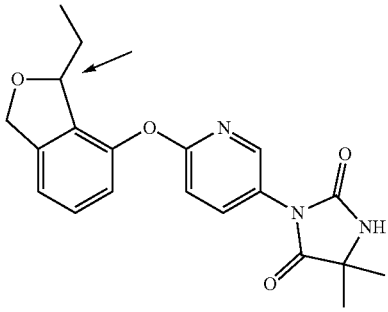

enantiomer 1

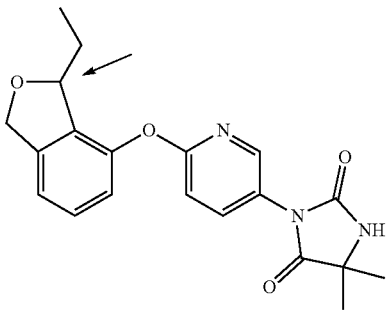

enantiomer 2

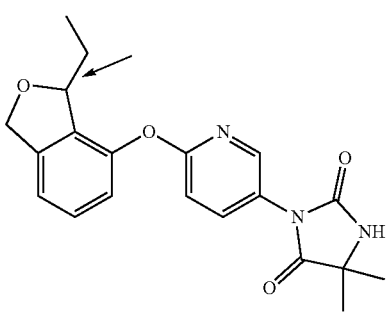

In a 50 mL round-bottomed flask N1-{6-[(3-ethyl-1,3-dihydro-2-benzofuran-4-yl)oxy]-3-pyridinyl}-2-methylalaninamide (Intermediate 149, 17.2 mg, 0.050 mmol) was dissolved in Dichloromethane (3 mL) to give a pale yellow solution that was cooled at 0° C. TEA (0.035 mL, 0.252 mmol) was added followed by a dropwise addition of a solution of triphosgene (6.43 mg, 0.023 mmol) in dichloromethane (0.5 ml) and the reaction mixture was stirred at 0° C. for 20 minutes. The reaction mixture was evaporated in vacuo and the residue was purified by flash chromatography (Biotage system) on silica gel using a column SNAP 10 g and cyclohexane/ethyl acetate from 2:1 to 1:2 as eluents affording the title compound Example 45 (15.3 mg) as a white solid.

$^1$H NMR (400 MHz, CDCl$_3$) δ ppm 8.29 (1H, d), 7.80 (1H, dd), 7.33 (1H, t), 7.09 (1H, d), 6.97-7.04 (2H, m), 5.70 (1H, br. s.), 5.23-5.30 (1H, m), 5.19 (1H, dd), 5.12 (1H, d), 1.85-1.98 (1H, m), 1.67-1.80 (1H, m), 1.57 (6H, s), 0.86-0.92 (3H, m).

Both enantiomers of Example 45 were separated by preparative chiral chromatography.

Chiral preparative HPLC conditions were the following ones: Column: Chiralpack AD-H (25×2 cm), 5u; Mobile phase: n-Hexane/2-propanol 85:15% v/v; Flow rate: 18 ml/min; UV: 220 nm; Sample preparation: 15 mg dissolved in 1.0 ml of ethanol (sample needs some drops of methanol for a complete solubilisation). Sample concentration: 15 mg/ml; Injection volume: 1000 IL.

This preparative chiral chromatography afforded:

Example 46: 5.6 mg (enantiomer 1); Rt (Chiral preparative HPLC)=9.877 minutes $^1$H NMR (400 MHz, MeOD) δ ppm 8.20 (1H, d), 7.92 (1H, dd), 7.38 (1H, t), 7.18 (1H, d), 7.10 (1H, d), 7.02 (1H, d), 5.14-5.24 (2H, m), 5.09 (1H, d), 1.81-1.96 (1H, m), 1.65-1.79 (1H, m), 1.52 (6H, s), 0.86 (3H, s).

Example 47: 5.5 mg (enantiomer 2); Rt (Chiral preparative HPLC)=13.203 minutes $^1$H NMR (400 MHz, MeOD) δ ppm 8.20 (1H, d), 7.92 (1H, dd), 7.38 (1H, t), 7.18 (1H, d), 7.10 (1H, d), 7.02 (1H, d), 5.14-5.24 (2H, m), 5.09 (1H, d), 1.81-1.96 (1H, m), 1.65-1.79 (1H, m), 1.52 (6H, s), 0.86 (3H, s).

Example 48, Example 49 and Example 50

(5R)-5-ethyl-5-methyl-3-[2-(4-methylchroman-5-yl)oxypyrimidin-5-yl]imidazolidine-2,4-dione (Diastereoisomeric Mixture, Diastereoisomer 1, Diastereoisomer 2)

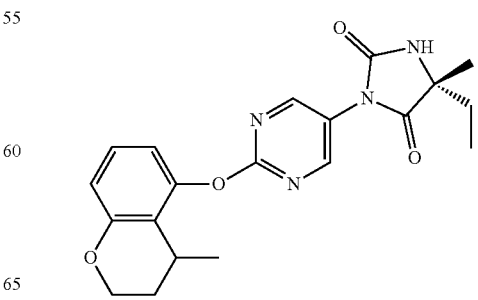

To a solution of N1-{2-[(4-methyl-3,4-dihydro-2H-chromen-5-yl)oxy]-5-pyrimidinyl}-Disovalinamide (Intermediate 219, 78 mg, 0.219 mmol) in dry Dichloromethane (4 mL) TEA (0.076 mL, 0.547 mmol) was added. The mixture was cooled to 0° C. then a solution of triphosgene (29.2 mg, 0.098 mmol) in dry Dichloromethane (1.0 mL) was added dropwise. The reaction mixture was stirred for 10 minutes at 0° C. then it was maintained in the ice-bath and quenched with water (10 mL). The organic layer was collected and the aqueous phase was extracted with DCM (2×5 mL). The combined organic layers were dried ($Na_2SO_4$), filtered and evaporated. The residue was purified by flash chromatography on silica gel using a column SNAP 25 g and cyclohexane/ethyl acetate from 8:2 to 1:1 as eluents affording the title compound (66 mg) as a white solid.

UPLC_IPQC: 0.99 min, 383 [M+H]+.

Both diastereoisomers of Example 48 were separated by Semipreparative chiral SFC.

Semipreparative chiral SFC conditions were the following ones: Column: Chiralpack AD-H (25×0.46 cm), 5 um; Modifier (Ethanol+0.1% isopropylamine) 20%; Flow rate 2.5 ml/min; Pressure 120 bar; Temperature 38° C.; UV detection 210-340 nm.

This preparative chiral chromatography afforded:

Example 49: 24 mg as white solid (diastereoisomer 1); Rt (Chiral preparative SFC)=7.583 min $^1$H NMR (400 MHz, $CDCl_3$) δ ppm 8.72 (2H, s), 7.17 (1H, t), 6.79 (1H, d), 6.68 (1H, d), 5.36 (1H, br.s), 4.25-4.35 (1H, m), 4.14-4.25 (1H, m), 2.98-3.09 (1H, m), 2.06-2.20 (1H, m), 1.95-2.06 (1H, m), 1.74-1.87 (1H, m), 1.70 (1H, d), 1.59 (3H, s), 1.31 (3H, s), 1.01 (3H, t).

Example 50: 25 mg as white solid (diastereoisomer 2); Rt (Chiral preparative SFC)=10.156 min $^1$H NMR (400 MHz, $CDCl_3$) δ ppm 8.72 (2H, s), 7.17 (1H, t), 6.78 (1H, d), 6.68 (1H, d), 5.38 (1H, br.s), 4.25-4.36 (1H, m), 4.12-4.25 (1H, m), 2.94-3.12 (1H, m), 2.05-2.20 (1H, m), 1.95-2.05 (1H, m), 1.75-1.87 (1H, m), 1.63-1.74 (1H, m), 1.58 (3H, s) 1.31 (3H, s), 1.01 (3H, t).

Example 51

(5R)-5-ethyl-5-methyl-3-[2-(7-methylspiro[2H-benzofuran-3,1'-cyclopropane]-4-yl)oxypyrimidin-5-yl]imidazolidine-2,4-dione

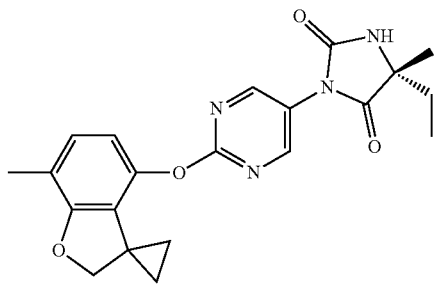

To a solution of 7-methylspiro[2H-benzofuran-3,1'-cyclopropane]-4-ol (Intermediate 156, 18 mg, 0.1 mmol) in dry DMF (1 ml) potassium carbonate (27.6 mg, 0.2 mmol) and then (5R)-3-(2-chloropyrimidin-5-yl)-5-ethyl-5-methyl-imidazolidine-2,4-dione (Intermediate 165, 20 mg, 0.08 mmol) were added and the reaction mixture was stirred for 2 hours at 80° C. After cooling the reaction mixture was quenched with water (1 ml), diluted with brine (5 ml) and extracted with ethyl acetate (2×10 ml). The organic layer was dried over sodium sulfate, filtered and evaporated and the residue was purified by flash chromatography (Biotage system) on silica gel using a 10 g SNAP column and cyclohexane/ethyl acetate 7:3 to cyclohexane/ethyl acetate 3:7 as eluents affording the title compound (21 mg) as a white solid.

$^1$H-NMR (400 MHz, DMSO-$d_6$) δ ppm: 8.69-8.74 (3H, m), 6.94 (1H, d), 6.52 (1H, d), 4.44 (2H, s), 2.15 (3H, s), 1.73-1.83 (1H, m), 1.63-1.73 (1H, m), 1.40 (3H, s), 1.02-1.06 (2H, m), 0.85-0.92 (5H, m). LC/MS: QC_3_MIN: Rt=2.007 min; 395 [M+H]+.

The following compounds were prepared using the foregoing methodology, replacing 7-methylspiro[2H-benzofuran-3,1'-cyclopropane]-4-ol (Intermediate 152) with the appropriate phenol. Final products were purified by flash-chromatography (Silica cartridge; Cyclohexane/EtOAc or other appropriate solvent system).

| Ex. | Structure | Name | Phenol | $^1$H-NMR | LCMS |
| --- | --- | --- | --- | --- | --- |
| 52 | 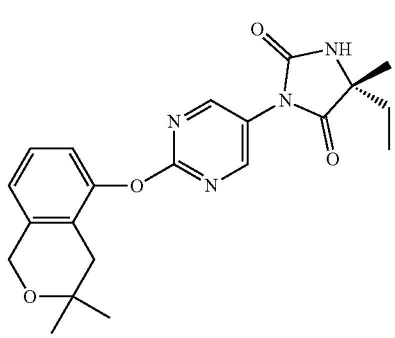 [SMILES: CC[C@@]1(C)NC(=O)N(c2cnc(Oc3cccc4c3CC(C)(C)OC4)nc2)C1=O] | (5R)-3-[2-(3,3-dimethylisochroman-5-yl)oxypyrimidin-5-yl]-5-ethyl-5-methyl-imidazolidine-2,4-dione | 3,3-dimethyl-isochroman-5-ol (Intermediate 170) | $^1$H-NMR (400 MHz, DMSO-$d_6$) δ ppm: 8.70-8.75 (3H, m), 7.27 (1H, t), 7.06 (2H, dd), 4.75 (2H, s), 2.42 (2H, s),1.63-1.75 (2H, m), 1.41 (3H, s), 1.18 (6H, s), 0.88 (3H, t). | LC/MS: QC_3_MIN: Rt = 1.894 min; 397 [M + H]+. |

-continued

| Ex. | Structure | Name | Phenol | ¹H-NMR | LCMS |
|---|---|---|---|---|---|
| 53 | 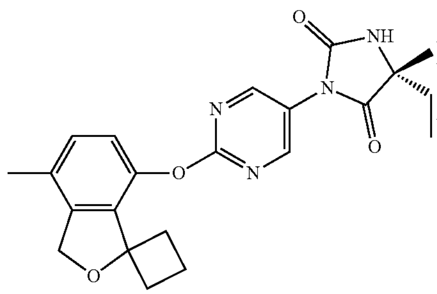 [SMILES: CC[C@@]1(C)NC(=O)N(c2cnc(Oc3ccc(C)c4c3C3(CCC3)OC4)nc2)C1=O] | (5R)-5-ethyl-5-methyl-3-[2-(7-methylspiro[1H-isobenzofuran-3,1'-cyclobutane]-4-yl)oxypyrimidin-5-yl]imidazolidine-2,4-dione | 7-methylspiro[1H-isobenzofuran-3,1'-cyclobutane]-4-ol (Intermediate 176) | ¹H-NMR (400 MHz, DMSO-$d_6$) δ ppm: 8.77-8.73 (3H, m), 7.16 (1H, d), 7.07 (1H, d), 4.98 (2H, s), 2.49-2.28 (4H, m), 2.21 (3H, s), 1.89-1.62 (4H, m), 1.41 (3H, s), 0.93-0.86 (3H, m). | LC/MS: QC_3_MIN: Rt = 1.997 min 409 [M + H]+. |
| 54 | 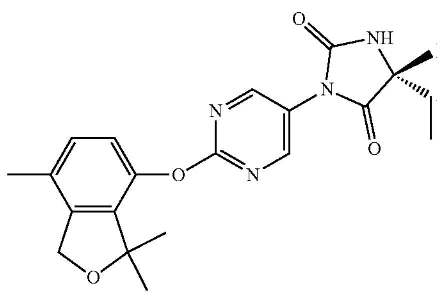 | (5R)-5-ethyl-5-methyl-3-{2-[(3,3,7-trimethyl-2,3-dihydro-1-benzofuran-4-yl)oxy]-5-pyrimidinyl}-2,4-imidazolidinedione | 3,3,7-trimethyl-2,3-dihydro-1-benzofuran-4-ol (Intermediate 184) | ¹H NMR (400 MHz, DMSO-$d_6$) δ ppm: 8.70 (1H, br.s), 8.69 (2H, s), 6.98 (1H, d), 6.55 (1H, d), 4.19 (2H, s), 2.12 (3H, s), 1.90-1.50 (1H, m), 1.38 (3H, s), 1.21 (6H, s), 0.86 (3H, t). | UPLC: 1.06 min, 397 [M + H]+ |
| 55 | 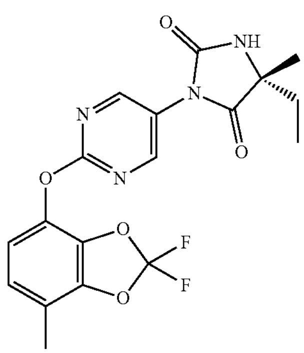 [SMILES: CC[C@@]1(C)NC(=O)N(c2cnc(Oc3ccc(C)c4c3OC(F)(F)O4)nc2)C1=O] | (5R)-3-{2-[(2,2-difluoro-7-methyl-1,3-benzodioxol-4-yl)oxy]-5-pyrimidinyl}-5-ethyl-5-methyl-2,4-imidazolidinedione | 2,2-difluoro-7-methyl-1,3-benzodioxol-4-ol (Intermediate 197) | ¹H-NMR (400 MHz, DMSO-$d_6$): δ ppm 8.78 (2H, s), 8.74 (1H, br.s), 7.18-7.13 (2H, m), 2.33 (3H, s), 1.84-1.75 (1H, m), 1.71-1.62 (1H, m), 1.40 (3H, s), 0.88 (3H, t. | UPLC: 1.11 min, 407 [M + H]+, |
| 56 | 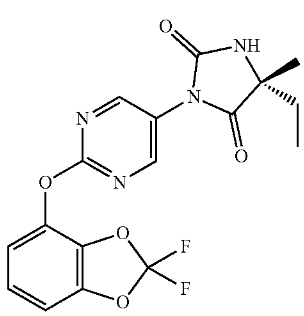 [SMILES: CC[C@@]1(C)NC(=O)N(c2cnc(Oc3cccc4c3OC(F)(F)O4)nc2)C1=O] | (5R)-3-{2-[(2,2-difluoro-1,3-benzodioxol-4-yl)oxy]-5-pyrimidinyl}-5-ethyl-5-methyl-2,4-imidazolidinedione | 2,2-difluoro-1,3-benzodioxol-4-ol (Intermediate 198) | ¹H-NMR (400 MHz, DMSO-$d_6$): δ ppm 8.80 (2H, s), 8.75 (1H, s), 7.39 (1H, d), 7.31 (1H, t), 7.27 (1H, d), 1.84-1.75 (1H, m), 1.72-1.62 (1H, m), 0.88 (3H, t). | UPLC: 1.04 min, 393 [M + H]+ |
| 57 | 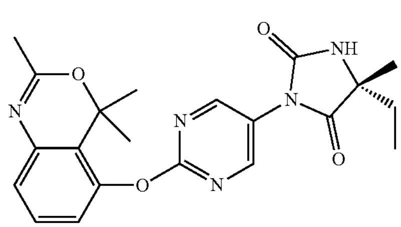 [SMILES: CC[C@@]1(C)NC(=O)N(c2cnc(Oc3cccc4c3C(C)(C)OC(C)=N4)nc2)C1=O] | (5R)-5-ethyl-5-methyl-3-{2-[(2,4,4-trimethyl-4H-3,1-benzoxazin-5-yl)oxy]-5-pyrimidinyl}-2,4-imidazolidinedione | 2,4,4-trimethyl-4H-3,1-benzoxazin-5-ol (Intermediate 202) | ¹H NMR (400 MHz, DMSO-$d_6$): δ ppm 8.73 (2H, s), 8.71 (1H, s), 7.30-7.25 (1H, m), 6.96 (2H, ddd), 2.01 (3H, s), 1.82-1.58 (2H, m), 1.51 (6H, s), 1.38 (3H, s), 0.85 (3H, t). | |

Example 58

5,5-dimethyl-3-[2-(7-methylspiro[2H-benzofuran-3,1'-cyclopropane]-4-yl)oxypyrimidin-5-yl]imidazolidine-2,4-dione

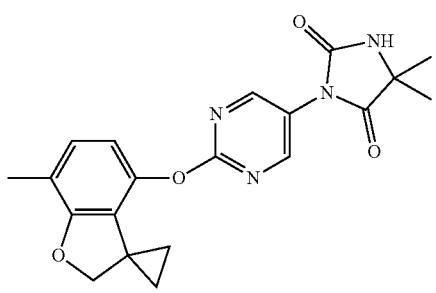

To a solution of 7-methylspiro[2H-benzofuran-3,1'-cyclopropane]-4-ol (Intermediate 156, 18 mg, 0.1 mmol) in dry DMF (1 ml) potassium carbonate (27.6 mg, 0.2 mmol) and then 3-(2-chloropyrimidin-5-yl)-5,5-dimethyl-imidazolidine-2,4-dione (Intermediate 166, 20 mg, 0.083 mmol) were added and the reaction mixture was stirred for 2 hours at 80° C. After cooling the reaction mixture was quenched with water (1 ml), diluted with brine (5 ml) and extracted with ethyl acetate (2×10 ml). The organic layer was dried over sodium sulfate, filtered and evaporated and the residue was purified by flash chromatography (Biotage system) on silica gel using a (Hg SNAP column and cyclohexane/ethyl acetate 7:3 to cyclohexane/ethyl acetate 3:7 as eluents affording the title compound (18 mg) as a light beige solid.

$^1$H-NMR (400 MHz, DMSO-$d_6$) δ ppm: 8.74 (1H, s), 8.70 (2H, s), 6.94 (1H, d), 6.52 (1H, d), 4.44 (2H, s), 2.14 (3H, s), 1.42 (6H, s), 1.01-1.06 (2H, n), 0.87-0.92 (2H, in). LC/MS: QC_3_MIN: Rt=1.946 m; 380 [M+H]+.

The following compounds were prepared using the foregoing methodology, replacing 7-methylspiro[2H-benzofuran-3,1'-cyclopropane]-4-ol (Intermediate 152) with the appropriate phenol. Final products were purified by flash-chromatography (Silica cartridge; Cyclohexane/EtOAc or other appropriate solvent system).

| Ex. | Structure | Name | Phenol | $^1$H-NMR | LCMS |
|---|---|---|---|---|---|
| 59 | 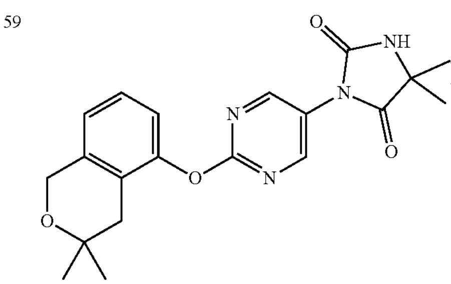 | 3-[2-(3,3-dimethylisochroman-5-yl)oxypyrimidin-5-yl]-5,5-dimethyl-imidazolidine-2,4-dione | 3,3-dimethylisochroman-5-ol (Intermediate 170) | $^1$H-NMR (400 MHz, DMSO-$d_6$) δ ppm: 8.75 (1H, s), 8.71 (1H, s), 7.28 (1H, t), 7.06 (1H, dd), 4.75 (2H, s), 2.41 (2H, s), 1.44 (6H, s), 1.18 (6H, s). | LC/MS: QC_3_MIN: Rt = 1.822min; 383 [M + H]+. |
| 60 | 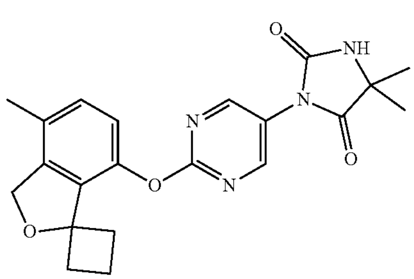 | 5,5-dimethyl-3-[2-(7-methylspiro[1H-isobenzofuran-3,1'-cyclobutane]-4-yl)oxypyrimidin-5-yl]imidazolidine-2,4-dione | 7-methylspiro[1H-isobenzofuran-3,1'-cyclobutane]-4-ol (Intermediate 176) | $^1$H-NMR (400 MHz, DMSO-$d_6$) δ ppm: 8.79-8.73 (3H, m), 7.17 (1H, d), 7.07 (1H, d),4.98 (2H, s), 2.49-2.28 (4H, m), 2.21 (3H, s), 1.89-1.67 (2H, m), 1.43 (6H, s). | LC/MS: QC_3_MIN: Rt = 1.936 min 395 [M + H]+. |

Example 61

(5R)-5-ethyl-3-[2-(7-methylspiro[2H-benzofuran-3,1'-cyclopropane]-4-yl)oxypyrimidin-5-yl]imidazolidine-2,4-dione

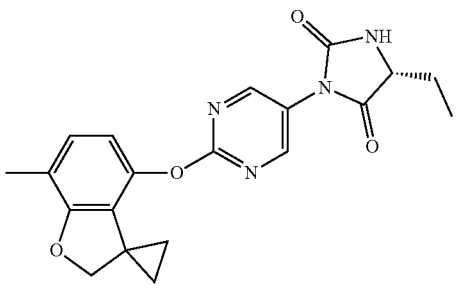 [SMILES: CC[C@H]1NC(=O)N(c2cnc(Oc3ccc(C)c4c3C3(CC3)CO4)nc2)C1=O]

To a solution of (2R)-2-amino-N-[2-(7-methylspiro[2H-benzofuran-3,1'-cyclopropane]-4-yl)oxypyrimidin-5-yl]butanamide (Intermediate 164, 24 mg, 0.068 mmol) in dry DCM (3 ml) TEA (0.028 ml, 0.2 mmol) was added and the reaction mixture was cooled to 0° C. A solution of triphosgene (15 mg, 0.05 mmol) in dry DCM (1.5 ml) was slowly added and the reaction mixture was stirred for 15 minutes at the same temperature. The reaction was quenched with water (10 ml) and two phases were separated. The organic layer was dried ($Na_2SO_4$), filtered and evaporated and the residue was purified by flash chromatography (Biotage system) on silica gel using a 10 g SNAP column and cyclohexane/ethyl acetate 75:25 to cyclohexane/ethyl acetate 25:75 as eluents affording the title compound (11 mg) as a white solid.

$^1$H-NMR (400 MHz, DMSO-de) δ ppm: 8.75 (1H, s), 8.68 (2H, s), 6.94 (1H, d), 6.52 (1H, d), 4.44 (2H, s), 4.20-4.25 (1H, m), 2.15 (3H, s), 1.77-1.88 (1H, m), 1.66-1.76 (1H, m), 1.02-1.06 (2H, m), 0.96 (3H, t), 0.87-0.92 (2H, m). LC/MS: QC_3_MIN: Rt=1.955 min; 381 [M+H]+.

Example 62

(5R)-5-ethyl-3-[6-(7-methylspiro[2H-benzofuran-3,1'-cyclopropane]-4-yl)oxy-3-pyridyl]imidazolidine-2,4-dione

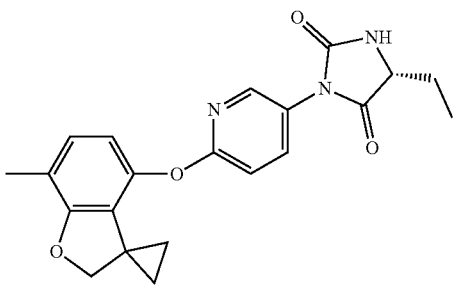 [SMILES: CC[C@H]1NC(=O)N(c2ccc(Oc3ccc(C)c4c3C3(CC3)CO4)nc2)C1=O]

To a solution of (2R)-2-amino-N-[6-(7-methylspiro[2H-benzofuran-3,1'-cyclopropane]-4-yl)oxy-3-pyridyl]butanamide (Intermediate 160, 40 mg, 0.11 mmol) in dry DCM (5 ml) TEA (0.042 ml, 0.3 mmol) was added and the reaction mixture was cooled to 0° C. A solution of triphosgene (23.7 mg, 0.08 mmol) in dry DCM (3 ml) was slowly added and the reaction mixture was stirred for 15 minutes at the same temperature. The reaction was quenched with water (10 ml) and two phases were separated. The organic layer was dried ($Na_2SO_4$), filtered and evaporated and the residue was purified by flash chromatography (Biotage system) on silica gel using a 10 g SNAP column and cyclohexane/ethyl acetate 75:25 to cyclohexane/ethyl acetate 25:75 as eluents affording the title compound (22 mg) as a white solid.

$^1$H-NMR (400 MHz, DMSO-$d_6$) δ ppm: 8.63 (1H, s), 8.13 (1H, d), 7.84 (1H, dd), 7.07 (1H, d), 6.94 (1H, d), 6.44 (1H, d), 4.46 (2H, s), 4.19-4.24 (1H, m), 2.15 (3H, s), 1.77-1.88 (1H, m), 1.65-1.75 (1H, m), 1.10-1.14 (2H, m), 0.96 (3H, t), 0.87-0.92 (2H, m). LC/MS: QC_3_MIN: Rt=2.025 min; 380 [M+H]+.

Example 63

(5R)-5-ethyl-3-{6-[(3,3,7-trimethyl-2,3-dihydro-1-benzofuran-4-yl)oxy]-3-pyridinyl}-2,4-imidazolidinedione

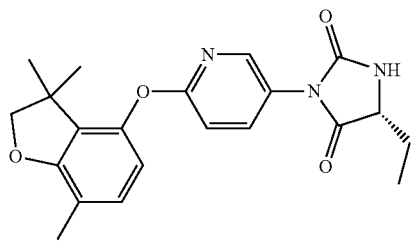 [SMILES: CC[C@H]1NC(=O)N(c2ccc(Oc3ccc(C)c4c3C(C)(C)CO4)nc2)C1=O]

(2R)-2-amino-N-{6-[(3,3,7-trimethyl-2,3-dihydro-1-benzofuran-4-yl)oxy]-3-pyridinyl}butanamide (Intermediate 188, 300 mg, 0.84 mmol) was dissolved in ethyl acetate (6 mL). Triethylamine (0.47 ml, 3.36 mmol) was added and the reaction mixture was cooled to 0° C. A solution of triphosgene (100 mg, 0.34 mmol) in ethyl acetate (6 mL) was slowly added. At the end of addition the mixture was treated with an aqueous saturated solution of $NaHCO_3$ and two phases were separated. The organic layer was washed with brine, dried over $Na_2SO_4$ and evaporated to dryness to obtain a waxy solid. The residue was purified by flash chromatography on silica gel using cyclohexane/ethyl acetate 70:30 to cyclohexane/ethyl acetate 50:50 as eluents affording the title compound (166 mg) as a white foam.

$^1$H-NMR (400 MHz, DMSO-$d_6$): δ ppm 8.61 (1H, br.s), 8.12 (1H, d), 7.82 (1H, dd), 7.10 (1H, d), 6.98 (1H, d), 6.47

(1H, d), 4.21 (2H, s), 4.18 (1H, br.s), 2.13 (3H, s), 1.86-176 (1H, m), 1.75-1.64 (1H, m), 1.25 (6H, s), 0.95 (3H, t). $^{13}$C-NMR (200 MHz, DMSO-d$_6$): δ ppm 173.2, 162.5, 158.6, 155.4, 148.2, 145.2, 138.5, 130.0, 126.1, 124.3, 115.7, 114.4, 110.6, 83.6, 57.5, 42.2, 26.0, 24.4, 14.4, 8.8.

Example 64

(5R)-5-ethyl-3-{2-[(3,3,7-trimethyl-2,3-dihydro-1-benzofuran-4-yl)oxy]-5-pyrimidinyl}-2,4-imidazolidinedione

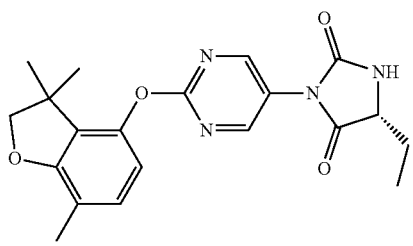 [SMILES: CC[C@H]1NC(=O)N(c2cnc(Oc3ccc(C)c4c3C(C)(C)CO4)nc2)C1=O]

1,1-dimethylethyl {(1R)-1-[({2-[(3,3,7-trimethyl-2,3-dihydro-1-benzofuran-4-yl)oxy]-5-pyrimidinyl}amino)carbonyl]propyl}carbamate (Intermediate 191, 213 mg, 0.47 mmol) was dissolved in HCl 5-6 N in isopropanol (1 mL) and the resulting solution was heated to 35° C. for 30 minutes. The reaction mixture was then concentrated under vacuum, the residue diluted with ethyl acetate (50 mL) and an aqueous 5% solution of K$_2$CO$_3$ (30 mL). Two phases were separated and the organic layer was washed with an aqueous saturated solution of ammonium chloride (30 mL), dried over Na$_2$SO$_4$ and concentrated under vacuum. The resulting crude was dissolved in ethyl acetate (10 mL) and triethylamine was added (0.23 mL, 1.64 mmol). The reaction mixture was cooled to 0-5° C. and a solution of triphosgene (55 mg, 0.185 mmol) in ethyl acetate (5 mL) was added drop wise in 10 minutes. The reaction was quenched with water (50 mL) and extracted with ethyl acetate (50 mL). The organic layer was washed with brine dried over Na$_2$SO$_4$ and concentrated under vacuum. The residue was purified purified by flash chromatography on silica gel using cyclohexane/ethyl acetate 50:50 as eluent affording the title compound (161 mg) as a white solid.

$^1$H NMR (400 MHz, DMSO-d$_6$): δ ppm 8.72 (1H, s), 8.66 (2H, s), 7.03-6.93 (1H, m), 6.55 (1H, d), 4.18 (2H, s), 2.12 (3H, s), 1.87-1.61 (2H, m), 1.2 (6H, s), 1.15 (1H, t), 0.94 (3H, t). MS_2 (ESI): 383 [M+H].

Example 65

(5R)-5-ethyl-5-methyl-3-[6-(7-methylspiro[2H-benzofuran-3,1'-cyclopropane]-4-yl)oxy-3-pyridyl]imidazolidine-2,4-dione

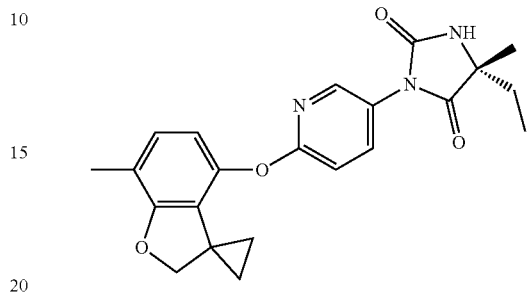

To a solution of triphosgene (30 mg, 0.1 mmol) in dry DCM (1 ml) at 0° C., under nitrogen atmosphere, DIPEA (0.175 ml, 1.0 mmol) was added followed by the addition (slowly added) of a solution of 6-(7-methylspiro[2H-benzofuran-3,1'-cyclopropane]-4-yl)oxypyridin-3-amine (Intermediate 158, 27 mg, 0.1 mmol) in dry DCM (2 ml) and the reaction mixture was stirred for 15 minutes at the same temperature. After that a solution of Methyl (R)-2-amino-2-methyl-butyrate hydrochloride (33 mg, 0.2 mmol) in dry DCM (2 ml) was added and the reaction mixture was stirred for 30 minutes at 0° C. The reaction was quenched with a 1M aqueous solution of HCl (5 ml), diluted with DCM (10 ml) and two phases were separated. The organic layer was washed with brine (10 ml), dried (Na$_2$SO$_4$), filtered and evaporated affording the urea intermediate as yellow foam.

The urea was dissolved in MeOH (5 ml), NaOMe (10 mg) was added and the reaction mixture was stirred for 15 minutes at room temperature. The reaction was quenched with an aqueous saturated solution of ammonium chloride (20 ml) and diluted with ethyl acetate (40 ml). Two phases were separated and the organic layer was dried (Na$_2$SO$_4$), filtered and evaporated and the residue was purified by flash chromatography (Biotage system) on silica gel using a 10 g SNAP column and cyclohexane/ethyl acetate 75:25 to cyclohexane/ethyl acetate 25:75 as eluents affording the title compound (29 mg) as a white solid.

$^1$H-NMR (400 MHz, DMSO-d$_6$) δ ppm: 8.60 (1H, s), 8.15 (1H, d), 7.85 (1H, dd), 7.06 (1H, d), 6.94 (1H, d), 6.44 (1H, d), 4.46 (2H, s), 2.15 (3H, s), 1.73-1.83 (1H, m), 1.62-1.72 (1H, m), 1.40 (3H, s), 1.10-1.14 (2H, m), 0.84-0.92 (5H, m). LC/MS: QC_3_MIN: Rt=2.076 min; 394 [M+H]+.

The following compounds were prepared using the foregoing methodology, replacing 6-(7-methylspiro[2H-benzofuran-3,1'-cyclopropane]-4-yl)oxypyridin-3-amine (Intermediate 154) with the appropriate aniline. Final products were purified by flash-chromatography (Silica cartridge; Cyclohexane/EtOAc or other appropriate solvent system).

| Ex. | Structure | Name | Aniline | ¹H-NMR | LCMS |
|---|---|---|---|---|---|
| 66 | 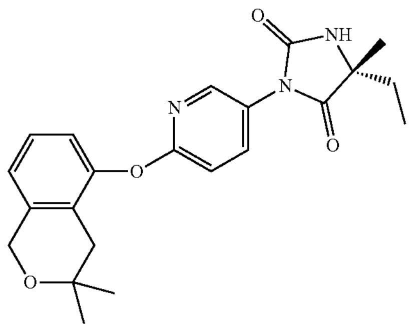 [SMILES: CC[C@@]1(C)NC(=O)N(c2ccc(Oc3cccc4c3CC(C)(C)OC4)nc2)C1=O] | (5R)-3-[6-(3,3-dimethylisochroman-5-yl)oxy-3-pyridyl]-5-ethyl-5-methyl-imidazolidine-2,4-dione | 6-(3,3-dimethylisochroman-5-yl)oxypyridin-3-amine (Intermediate 172) | ¹H-NMR (400 MHz, DMSO-d₆) δ ppm: 8.11 (1H, d), 7.86 (1H, dd), 7.25 (1H, t), 7.13 (1H, d), 7.00 (2H, dd), 4.75 (2H, s), 2.44 (2H, s), 1.61-1.84 (2H, m), 1.40 (3H, s), 1.18 (6H, s) 0.87 (3H, t). | LC/MS: QC_3_MIN: Rt = 1.962 min; 396 [M + H]+. |
| 67 | 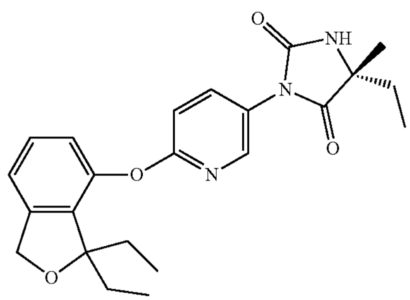 [SMILES: CCC1(CC)OCc2cccc(Oc3ccc(N4C(=O)N[C@](C)(CC)C4=O)cn3)c21] | (5R)-3-[6-[(3,3-diethyl-1H-isobenzofuran-4-yl)oxy]-3-pyridyl]-5-ethyl-5-methyl-imidazolidine-2,4-dione | 6-[(3,3-diethyl-1H-isobenzofuran-4-yl)oxy]pyridin-3-amine (Intermediate 180) | ¹H-NMR (400 MHz, DMSO-d₆) δ ppm: 8.61 (1H, s), 8.16 (1H, d), 7.89-7.87 (1H, dd), 7.35 (1H, t), 7.18 (1H, d), 7.14 (1H, d), 7.10 (1H, d), 5.08 (2H, s), 1.85-1.61 (6H, m), 1.40 (3H, s), 0.88 (3H,t),0.67 (6H, t). | LC/MS: QC_3_MIN: Rt 2.067 min, 410 [M + H]+. |

Example 68

(5R)-5-ethyl-5-methyl-3-[6-[(2,4,4-trimethyl-3,1-benzoxazin-5-yl)oxy]-3-pyridyl]imidazolidine-2,4-dione

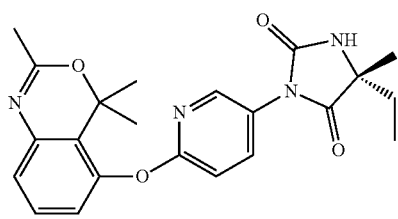 [SMILES: CC[C@@]1(C)NC(=O)N(c2ccc(Oc3cccc4c3C(C)(C)OC(C)=N4)nc2)C1=O]

Example 69

(5R)-3-{6-[(3,3-dimethyl-1,3-dihydro-2-benzofuran-4-yl)oxy]-3-pyridinyl}-5-ethyl-5-methyl-2,4-imidazolidinedione

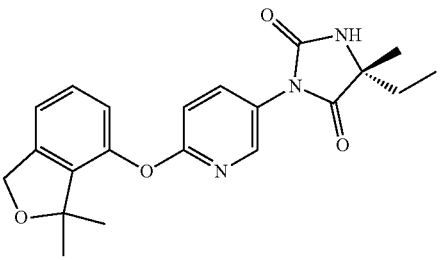 [SMILES: CC[C@@]1(C)NC(=O)N(c2ccc(Oc3cccc4c3C(C)(C)OC4)nc2)C1=O]

To a solution of (2R)-2-amino-2-methyl-N-[6-[(2,4,4-trimethyl-3,1-benzoxazin-5-yl)oxy]-3-pyridyl]butanamide (Intermediate 205, 143 mg, 0.37 mmol) and TEA (0.21 mL) in ethyl acetate (2.5 mL) at 0° C., triphosgene (44 mg, 0.15 mmol) dissolved in ethyl acetate (2.5 mL) was added drop wise in 10 min. The reaction mixture was stirred at 0° C. for 40 min. The reaction mixture was diluted with water (5 mL) and ethyl acetate (10 mL). Phases were separated and the aqueous was back-extracted with ethyl acetate (2×10 mL). The combined organic layers were washed with brine (15 mL), dried over Na₂SO₄, filtered and concentrated and the residue was purified by flash chromatography on silica gel using ethyl acetate as eluent affording the title compound (115 mg) as white solid.

¹H NMR (400 MHz, DMSO-d₆): δ ppm 8.58 (1H, s), 8.15 (1H, d), 7.87 (1H, dd), 7.24 (1H, t), 7.17 (1H, d), 6.89 (1H, d), 6.84 (1H, d), 2.01 (3H, s), 1.81-1.70 (1H, m), 1.69-1.59 (1H, m), 1.54 (6H, s), 1.37 (3H, s), 0.84 (3H, t).

3,3-Dimethyl-1,3-dihydro-2-benzofuran-4-ol (Intermediate 193, 68 mg, 0.4 mmol) and (5R)-3-(6-chloropyridin-3-yl)-5-ethyl-5-methylimidazolidine-2,4-dione (Intermediate 194, 126 mg, 0.48 mmol) were dissolved in DMF (1.0 mL) and K₂CO₃ (143 mg, 1.03 mmol) was added. The resulting suspension was heated to 130° C. under microwave irradiation for 40 minutes. The reaction mixture was diluted with water (25 mL) and ethyl acetate (25 mL), and then two phases were separated. The organic layer was washed with water and brine, dried over Na₂SO₄ and concentrated under vacuum. The residue was purified by flash chromatography (Biotage system) on silica gel using cyclohexane/ethyl acetate 50:50 as eluent affording the title compound (70 mg) as a white solid.

¹H NMR (400 MHz, DMSO-d₆): δ ppm 8.57 (1H, s), 8.12 (1H, d), 7.86 (1H, dd), 7.30 (1H, t), 7.22-7.03 (2H, m), 6.96 (1H, d), 4.99 (2H, s), 1.80-1.57 (2H, m), 1.37 (6H, s), 1.36 (3H, s), 0.84 (3H, s). MS_2 (ESI): 382 [M+H]+.

Example 70

5,5-dimethyl-3-[6-(7-methylspiro[2H-benzofuran-3,1'-cyclopropane]-4-yl)oxy-3-pyridyl]imidazolidine-2,4-dione

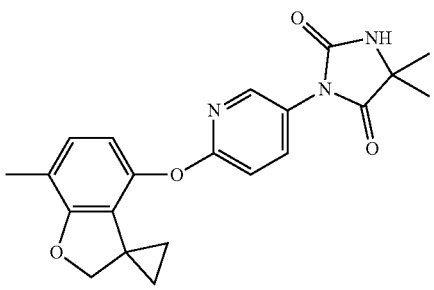

To a solution of triphosgene (30 mg, 0.1 mmol) in dry DCM (1 ml) at 0° C., under nitrogen atmosphere, DIPEA (0.175 ml, 1.0 mmol) was added followed by the addition (slowly added) of a solution of 6-(7-methylspiro[2H-benzofuran-3,1'-cyclopropane]-4-yl)oxypyridin-3-amine (Intermediate 158, 27 mg, 0.1 mmol) in dry DCM (2 ml) and the reaction mixture was stirred for 15 minutes at the same temperature. After that a solution of Methyl 2-amino-2-methylpropanoate hydrochloride (30 mg, 0.2 mmol) in dry DCM (2 ml) was added and the reaction mixture was stirred for 30 minutes at 0° C. The reaction was quenched with a 1M aqueous solution of HCl (5 ml), diluted with DCM (10 ml) and two phases were separated. The organic layer was washed with brine (10 ml), dried (Na$_2$SO$_4$), filtered and evaporated affording the urea intermediate as yellow foam.

The urea was dissolved in MeOH (5 ml), NaOMe (10 mg, 0.19 mmol) was added and the reaction mixture was stirred for 15 minutes at room temperature. The reaction was quenched with an aqueous saturated solution of ammonium chloride (20 ml) and diluted with ethyl acetate (40 ml). Two phases were separated and the organic layer was dried (Na$_2$SO$_4$), filtered and evaporated and the residue was purified by flash chromatography (Biotage system) on silica gel using a 10 g SNAP column and cyclohexane/ethyl acetate 75:25 to cyclohexane/ethyl acetate 25:75 as eluents affording the title compound (23 mg) as a white solid.

$^1$H-NMR (400 MHz, DMSO-d$_6$) δ ppm: 8.62 (1H, s), 8.14 (1H, d), 7.86 (1H, dd), 7.05 (1H, d), 6.92 (1H, d), 6.43 (1H, d), 4.44 (2H, s), 2.14 (3H, s), 1.40 (6H, s), 1.08-1.13 (2H, m), 0.96 (3H, t), 0.85-0.90 (2H, m). LC/MS: QC_3_MIN: Rt=2.016 min; 380 [M+H]+.

The following Reference Intermediates and Examples describe the preparation of compounds for use in assays.

Reference Intermediate R1

4-methyl-3-(methyloxy)aniline

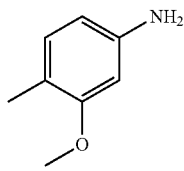

To a solution of 1-methyl-2-(methyloxy)-4-nitrobenzene (2.5 g, 14.96 mmol) in methanol (50 mL) Ni-Raney (~2 g) was added and the reaction mixture was stirred overnight at room temperature under H$_2$ atmosphere (1 atm). The catalyst was filtered off and the residue was purified by SCX cartridge (50 g) to afford the title compound (1.86 g) as a colourless oil.

$^1$H-NMR (400 MHz, DMSO-d$_6$) δ ppm: 6.73 (1H, d), 6.19 (1H, d), 6.05 (1H, dd), 4.85 (2H, s), 3.68 (3H, s), 1.97 (3H, s); UPLC_B: 0.62 min, 138 [M+H]+.

Reference Intermediate R2

4-methyl-3-(methyloxy)phenol

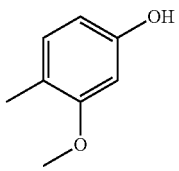

To a suspension of 4-methyl-3-(methyloxy)aniline (Reference Intermediate R1, 1.86 g) in water (100 mL)/H$_2$SO$_4$ (30 mL, 563 mmol) at 0° C. a solution of sodium nitrite (1.029 g, 14.91 mmol) in water (10 mL) was slowly added and the reaction mixture was stirred for 30 minutes at 0° C. The reaction mixture was slowly added to a solution of H$_2$SO$_4$ 98% (20 mL) in Water (80 mL) pre-heated at 90° C. and stirred at this temperature for 1 h. After cooling the mixture was extracted with Et$_2$O (2×200 mL), the organic layer was dried on sodium sulphate, filtered and evaporated to afford the title compound (1.86 g) as a red/brown oil.

$^1$H-NMR (400 MHz, DMSO-d$_6$) δ ppm: 9.14 (1H, br.s), 6.87 (1H, d), 6.35 (1H, d), 6.24 (1H, dd), 3.71 (3H, s), 2.01 (3H, s); UPLC_B: 0.63 min, 137 [M−H]−.

Reference Intermediate R3

2-{[4-methyl-3-(methyloxy)phenyl]oxy}-5-nitropyridine

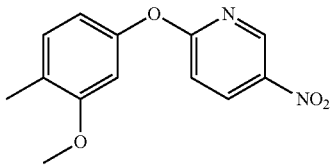 [SMILES: COc1cc(Oc2ccc([N+](=O)[O-])cn2)ccc1C]

To a solution of 4-methyl-3-(methyloxy)phenol (Reference Intermediate R2, 400 mg) in dry N,N-dimethylformamide (15 mL), potassium carbonate (1200 mg, 8.69 mmol) and then 2-chloro-5-nitropyridine (551 mg, 3.47 mmol) were added and the reaction mixture was stirred for 2 hours at 115° C. The reaction was quenched with water (10 mL), diluted with brine (20 mL) and extracted with ethyl acetate (3 times 30 mL). The organic layer was washed with ice cold brine (2 times 30 mL), dried over sodium sulphate, filtered and evaporated. The residue was purified by silica gel chromatography (Biotage system, 100 g SNAP column) with a gradient cyclohexane/ethyl acetate from 10/0 to 8/2. Evaporation afforded the to title compound as a light yellow oil (570 mg).

¹H-NMR (400 MHz, DMSO-d₆) δ ppm: 2.16 (3H, s), 3.76 (3H, s), 6.68-6.73 (1H, m), 6.83-6.86 (1H, m), 7.24-7.18 (2H, m), 8.64-8.58 (1H, m), 9.08-9.02 (1H, m); UPLC_B: 0.93 min, 261 [M+H]+.

Reference Intermediate R4

6-{[4-methyl-3-(methyloxy)phenyl]oxy}-3-pyridinamine

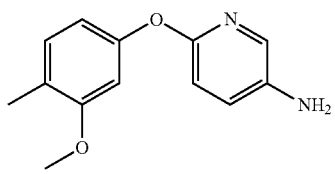

To a solution of 2-{[4-methyl-3-(methyloxy)phenyl]oxy}-5-nitropyridine (Reference Intermediate R3, 568 mg) in tetrahydrofuran (25 mL)/water (12.50 mL), iron (609 mg, 10.91 mmol) and then ammonium chloride (584 mg, 10.91 mmol) were added and the reaction mixture was stirred for 8 hours at room temperature. The catalyst was filtered off and the solution was diluted with an aqueous saturated solution of Na₂CO₃ (5 mL) and extracted with ethyl acetate (2 times 40 mL). Combined organic layers were dried over sodium sulphate, filtered and evaporated and the residue was purified by silica gel chromatography (Biotage system with a 50 g SNAP column) using a as eluent a gradient cyclohexane/ethyl acetate from 8/2 to 1/1. Evaporation afforded the title compound as light yellow oil (465 mg).

¹H-NMR (400 MHz, DMSO-d₆) δ ppm: 7.54 (1H, d), 7.06 (2H, ddd), 6.72 (1H, d), 6.59 (1H, d), 6.38 (1H, dd), 5.07 (2H, s), 3.73 (3H, s), 2.10 (3H, s); UPLC_B: 0.72 min, 231 [M+H]+.

Reference Intermediate R5

1,1-dimethylethyl((1R)-1-{[(6-{[4-methyl-3-(methyloxy)phenyl]oxy}-3-pyridinyl)amino]carbonyl}propyl)carbamate

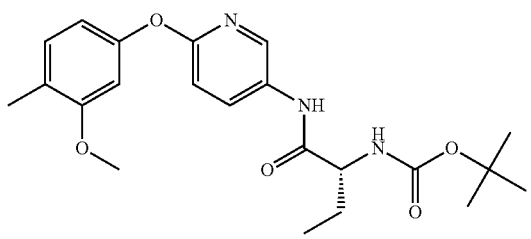 [SMILES: CC[C@@H](NC(=O)OC(C)(C)C)C(=O)Nc1ccc(Oc2ccc(C)c(OC)c2)nc1]

To a solution of (2R)-2-({[(1,1-dimethylethyl)oxy]carbonyl}amino)butanoic acid (106 mg, 0.521 mmol) in dry N,N-dimethylformamide (2 mL) DIPEA (0.152 mL, 0.869 mmol) and then TBTU (181 mg, 0.565 mmol) were added and the reaction mixture was stirred for 15 minutes at room temperature. 6-{[4-methyl-3-(methyloxy)phenyl]oxy}-3-pyridinamine (Reference Intermediate R4, 100 mg) was then added and the reaction mixture was stirred overnight at the same temperature. The reaction was quenched with water (1 mL), diluted with brine (1 mL) and extracted with ethyl acetate (3 times 5 mL). The organic layer was dried over sodium sulphate, filtered and evaporated and the residue was purified by silica gel chromatography (Biotage system, 10 g SNAP column) using as eluent a gradient cyclohexane/ethyl acetate from 100/0 to 70/30 to afford the title compound as a white solid (180 mg).

¹H NMR (400 MHz, DMSO-d₆) δ ppm: 10.13 (1H, br. s), 8.31-8.37 (1H, m), 8.02-8.10 (1H, m), 7.09-7.16 (1H, m), 7.01-7.08 (1H, m), 6.96 (1H, d), 6.70 (1H, d), 6.51-6.58 (1H, m), 3.91-4.03 (1H, m), 3.75 (3H, s), 2.13 (3H, s), 1.50-1.76 (2H, m), 1.39 (9H, s), 0.90 (3H, t); UPLC_B: 0.91 min, 416 [M+H]+.

Reference Intermediate R6

(2R)-2-amino-N-(6-{[4-methyl-3-(methyloxy)phenyl]oxy}-3-pyridinyl)butanamide

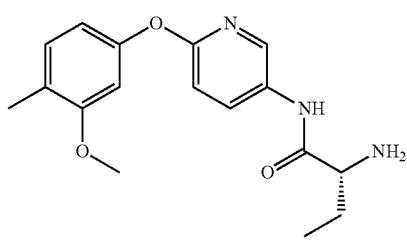 [SMILES: CC[C@@H](N)C(=O)Nc1ccc(Oc2ccc(C)c(OC)c2)nc1]

To a solution of 1,1-dimethylethyl ((1R)-1-{[(6-{[4-methyl-3-(methyloxy)phenyl]oxy}-3-pyridinyl)amino]carbonyl}propyl)carbamate (Reference Intermediate R5, 175 mg) in dry dichloromethane (DCM) (6 mL) TFA (2 mL, 26.0 mmol) was slowly added and the reaction mixture was stirred for 1 h at room temperature. The solvent and the excess of TFA were evaporated and the residue was purified by SCX cartridge (5 g) to afford the title compound as a colourless solid (122 mg).

¹H-NMR (400 MHz, DMSO-d₆) δ ppm: 8.36-8.42 (1H, m), 8.11 (1H, dd), 7.12 (1H, d), 6.95 (1H, d), 6.67-6.73 (1H, m), 6.54 (1H, dd), 3.75 (3H, s), 3.24 (1H, m), 2.13 (3H, s), 1.59-1.73 (1H, m), 1.42-1.56 (1H, m), 0.90 (3H, t); UPLC_B: 0.74 min, 316 [M+H]+.

Reference Intermediate R7

1,1-dimethylethyl((1R)-1-methyl-1-{[(6-{[4-methyl-3-(methyloxy)phenyl]oxy}-3-pyridinyl)amino]carbonyl}propyl)carbamate

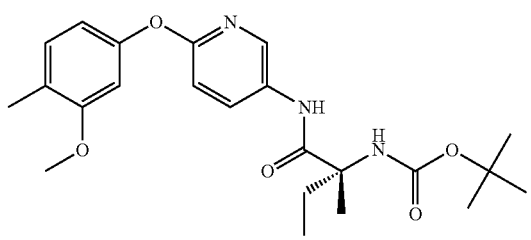 [SMILES: CC[C@@](C)(NC(=O)OC(C)(C)C)C(=O)Nc1ccc(Oc2ccc(C)c(OC)c2)nc1]

To a solution of N-{[(1,1-dimethylethyl)oxy]carbonyl}-D-isovaline (94 mg, 0.434 mmol) in dry N,N-Dimethylformamide (1 mL) DIPEA (0.114 mL, 0.651 mmol) and HATU (165 mg, 0.434 mmol) were added. The reaction was stirred at room temperature for 15 minutes. 6-{[4-methyl-3-(methyloxy)phenyl]oxy}-3-pyridinamine (Reference Intermediate R4, 50 mg) was then added. After 1 hour of stirring at room temperature the mixture was heated at 50° C. and stirred at that temperature for 4 hours, it was then cooled down to room temperature and stirred overnight at that temperature. The mixture was quenched with brine (2 mL) and extracted with ethyl acetate (3×2 mL). Combined organic layers were dried over sodium sulphate, filtered and evaporated. The residue was purified by flash chromatography on silica gel using a 10 g SNAP column and cyclohexane/ethyl acetate as eluents from 100/0 to 60/40 (Biotage system) to afford the title compound as a white solid (65 mg).

$^1$H NMR (400 MHz, DMSO-$d_6$): δ ppm 9.60 (1H, br s), 9.10 (1H, br s), 8.31 (1H, br. s.), 8.03 (1H, br s), 7.12 (1H, d), 6.93 (1H, d), 6.69 (1H, d), 6.53 (1H, dd), 3.74 (3H, s), 2.11 (3H, s), 1.72-1.86 (1H, m), 1.60-1.72 (1H, m), 1.41 (9H, s), 1.33 (3H, s), 0.78 (3H, t); UPLC: 0.87 min, 430 [M+H]+

Reference Intermediate R8

N$^1$-(6-{[4-methyl-3-(methyloxy)phenyl]oxy}-3-pyridinyl)-D-isovalinamide

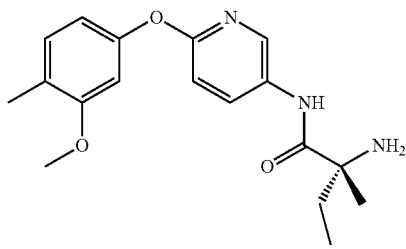 [SMILES: CC[C@@](C)(N)C(=O)Nc1ccc(Oc2ccc(C)c(OC)c2)nc1]

To a solution of 1,1-dimethylethyl ((1R)-1-methyl-1-{[(6-{[4-methyl-3-(methyloxy)phenyl]oxy}-3-pyridinyl)amino]carbonyl}propyl)carbamate (Reference Intermediate R7, 65 mg) in dry dichloromethane (3 mL) cooled to 0° C., TFA (0.700 mL, 9.08 mmol) was added dropwise. The reaction was stirred at that temperature for 2 hours. The reaction was quenched with a saturated aqueous solution of NaHCO$_3$ (20 mL) added at 0° C., and extracted with dichloromethane (3×7 mL). The combined organic layers were dried over sodium sulphate, filtered and evaporated to afford the title compound as a white solid (44 mg).

Reference Intermediate R9

3-(1,1-dimethylethyl)-4-hydroxybenzaldehyde

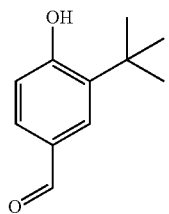

2-(1,1-dimethylethyl)phenol (10 g, 66.67 mmol) was dissolved in 40 mL of MeOH and NaOH (40 g, 1 mol) dissolved in 40 mL of water was added dropwise. Then 40 mL of CHCl$_3$ was added (during the course of 1 h) at 60° C. The reaction mixture was stirred at that temperature for 3 h. After cooling down to r.t., the mixture was cooled to 0° C. and 4M HCl was added until the solution reached pH 5-6. The mixture was extracted with DCM (three times) and the collected organic were dried over Na$_2$SO$_4$, filtered and evaporated. The crude was charged on a silica gel column and eluted with Cyclohexane/EtOAc (from 100:0 to 80:20 Cyclohexane/EtOAc, then plateau at 80:20) affording 766 mg of the of the title compound.

$^1$H-NMR (400 MHz, DMSO-$d_6$): δ ppm 10.62 (1H, s), 9.79 (1H, s), 7.73 (1H, br. s), 7.67-7.57 (1H, m), 7.01-6.90 (1H, m), 1.38 (9H, s); UPLC_ipqc: 0.97 min, 177 [M−H]−.

Reference Intermediate R10

3-(1,1-dimethylethyl)-4-hydroxybenzonitrile

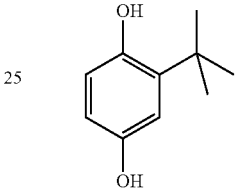

3-(1,1-dimethylethyl)-4-hydroxybenzaldehyde (Reference Intermediate R9, 550 mg) and hydroxylamine hydrochloride (322 mg, 4.63 mmol) were stirred in 8.0 mL of acetic acid at reflux for 1 h. After cooling down to 0° C., the mixture was poured into Et$_2$O and washed once with water and once with NaOH (5% aqueous solution). The collected aqueous phases were extracted with Et$_2$O (two times) and the combined organic phases were dried over Na$_2$SO$_4$, filtered, evaporated and triturated with pentane affording 540 mg of the title compound.

$^1$H-NMR (400 MHz, DMSO-$d_6$): δ ppm 10.92 (1H, br. s), 7.53-7.45 (2H, m), 6.92 (1H, d), 1.34 (9H, s); UPLC_ipqc: 1.03 min, 174 [M−H]−.

Reference Intermediate R11

4-hydroxy-2-iodobenzonitrile

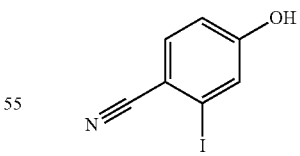

To a solution of 2-fluoro-4-iodobenzonitrile (5.0 g, 20.24 mmol) in dry acetonitrile (100 mL) potassium trimethylsilanolate (1.18 g) was added and the reaction mixture was stirred overnight at 50° C. The solvent was removed under reduced pressure and the residue was dissolved in ethyl acetate (100 mL) and an aqueous pH 3 buffer solution was added up to pH ~5. Two phases were separated and the organic layer was dried (Na$_2$SO$_4$), filtered and evaporated to afford the title compound (4.90 g) as brown solid.

¹H NMR (400 MHz, DMSO-d₆): δ ppm 10.92 (1H, s), 7.65 (1H, d), 7.39 (1H, d), 6.93 (1H, dd); UPLC_ipqc: 0.81 min, 244 [M−H]−.

Reference Intermediate R12

4-hydroxy-2-[(trifluoromethyl)oxy]benzonitrile

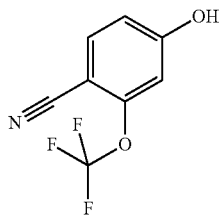 [SMILES: N#Cc1ccc(O)cc1OC(F)(F)F]

Two reactions were carried out in parallel (A and B) and then the two reaction mixtures were combined to run work-up and purification.

Reaction A: To a solution of 4-Methoxy-2-(trifluoromethoxy)benzonitrile (50 mg, 0.23 mmol) in 1,2-dichloroethane (1 mL) was added 1M BBr₃ solution in DCM (0.69 mL, 0.69 mmol) dropwise. The resulting reaction mixture was stirred under microwave irradiation five times (set parameters: T=100° C., t=1 hour) adding further 1M BBr₃ solution in DCM (1 mL) each time. The total amount of 1M BBr₃ solution in DCM used was 4.69 mL.

Reaction B: In a vial were added 4-Methoxy-2-(trifluoromethoxy)benzonitrile (750 mg, 3.45 mmol), 1,2-dichloroethane (5 mL) and then 1M BBr₃ solution in DCM (10.36 mL, 10.36 mmol) dropwise. The resulting reaction mixture was stirred under microwave irradiation for 1 hour (set T=100° C.). To the reaction mixture further 1M BBr₃ solution in DCM (1 mL) was added and the resulting reaction mixture was stirred under microwave irradiation three more times (set parameters: T=100° C., t=1.5 hours), adding further 1M BBr₃ solution in DCM (0.8 mL) each time. The total amount of 1M BBr₃ solution in DCM used was 13.76 mL.

The two reactions mixtures A and B were added dropwise to a NaHCO₃ saturated aqueous solution and the pH was adjusted to 7 with the addition of solid NaHCO₃. The two phases were separated and the aqueous phase was extracted with DCM (1×) and with EtOAc (2×). The combined organic phases were dried and evaporated to dryness to give the title compound in mixture with unreacted starting material (1.48 g) as a black oil. This mixture was used in the next step without further purification.

¹H NMR (400 MHz, DMSO-d₆): δ ppm 11.35 (1H, s), 7.82 (1H, d), 6.91-6.98 (2H, m); UPLC_ipqc: 0.88 min, 204 [M+H]+, 202 [M−H]−.

Reference Intermediate R13

4-[(5-nitro-2-pyridinyl)oxy]-3-(trifluoromethyl)benzonitrile

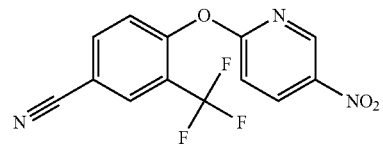 [SMILES: N#Cc1ccc(Oc2ccc([N+](=O)[O-])cn2)c(C(F)(F)F)c1]

A mixture of 2-chloro-5-nitropyridine (70 mg, 0.44 mmol), 4-hydroxy-3-(trifluoromethyl)benzonitrile (91 mg, 0.49 mmol), K₂CO₃ (92 mg, 0.66 mmol) in DMF (2 mL) was stirred at 50° C. overnight. Water (4 mL) was added and a precipitate was formed. The solid was filtered-off and it was triturated with MeOH to give the title compound (85 mg) as a brownish solid.

¹H NMR (400 MHz, CDCl₃): δ ppm 8.99 (1H, d), 8.60 (1H, dd), 8.07 (1H, s), 7.95 (1H, d), 7.48 (1H, d), 7.19-7.32 (1H, in); UPLC_ipqc: 1.1 min, 310 [M+H]+.

The following compounds were prepared using the foregoing methodology, reacting the appropriate halo nitroaryl such as 2-chloro-5-nitropyridine, 2-chloro-5-nitropyrimidine, 1-fluoro-4-nitrobenzene etc. with the appropriately substituted phenol at a suitable temperature, optionally under microwave irradiation. Some final products were purified by flash-chromatography (Silica; Cyclohexane/EtOAc or other appropriate solvent system).

| | Structure | Name | Reagent 1 | Reagent 2 | NMR | UPLC |
|---|---|---|---|---|---|---|
| R14 | 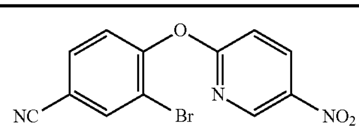 | 3-bromo-4-[(5-nitro-2-pyridinyl)oxy]benzonitrile | 2-chloro-5-nitropyridine | 3-bromo-4-hydroxybenzonitrile | ¹H-NMR (400 MHz, CDCl₃): δ ppm 9.01 (1H, br. s), 8.65-8.56 (1 H, m), 8.02 (1H, s), 7.75 (1H, d), 7.38 (1H, d), 7.25 (1H, d) | 1.08 min, 320 [M]+, Br pattern |
| R15 | 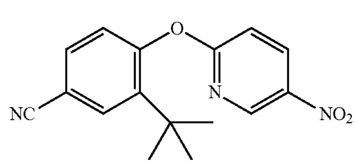 | 3-(1,1-dimethylethyl)-4-[(5-nitro-2-pyridinyl)oxy]benzonitrile | 2-chloro-5-nitropyridine | 3-(1,1-dimethylethyl)-4-hydroxybenzonitrile (Reference Intermediate R10) | ¹HNMR (400 MHz, DMSO-d₆): δ ppm 9.09-9.04 (1H, m), 8.74-8.64 (1H, m), 7.87 (1H, br. s), 7.83-7.77 (1H, m), 7.44 (1H, d), 7.33 (1H, d), 1.32 (9H, s) | 1.23 min, 298 [M + H]+ |
| R16 | 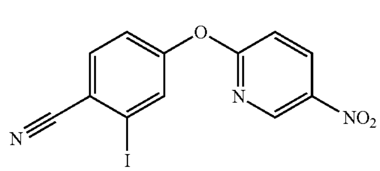 | 2-iodo-4-[(5-nitro-2-pyridinyl)oxy]benzonitrile | 2-chloro-5-nitropyridine | 4-hydroxy-2-iodobenzonitrile (Reference Intermediate 11) | ¹H NMR (400 MHz, DMSO-d₆): δ ppm 9.08 (1H, d), 8.70 (1H, dd), 8.03 (1H, d), 7.98 (1H, d), 7.52 (1H, dd), 7.41 (1H, d) | 1.10 min |

| | | | | | |
|---|---|---|---|---|---|
| R17 | ![structure] | 4-[(5-nitro-2-pyridinyl)oxy]-2-[(trifluoromethyl)oxy]benzonitrile | 2-chloro-5-nitropyridine | 4-hydroxy-2-[(trifluoromethyl)oxy]benzonitrile (Reference Intermediate 12) | $^1$H NMR (400 MHz, CDCl$_3$): δ ppm 9.02-9.11 (1H, m), 8.55-8.65 (1H, m), 7.82 (1H, d), 7.25-7.35 (2H, m), 7.20 (1H, d) | 1.14 min, 326 [M + H]+ |

Reference Intermediate R18

2-cyclopropyl-4-[(5-nitro-2-pyridinyl)oxy]benzonitrile

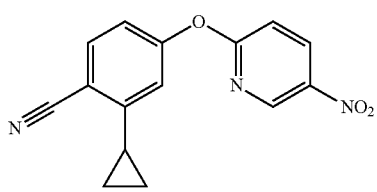 [SMILES: N#Cc1ccc(Oc2ccc([N+](=O)[O-])cn2)cc1C1CC1]

Preparation of organometallic solution: to a solution of 0.5M ZnCl$_2$ in THE (9 mL) a solution of 0.5M Cyclopropyl Magnesium bromide in THE (9 mL) was slowly added at r.t. and the reaction mixture was stirred for 20 minutes at r.t.

To a solution of 2-iodo-4-[(5-nitro-2-pyridinyl)oxy]benzonitrile (Reference Intermediate R16, 550 mg) and Pd(tBu$_3$P)$_2$ (76 mg, 0.15 mmol), warmed at 60° C., were added 6 mL of the organometallic solution previously formed and the reaction mixture was stirred for 1 hour at 60° C. Further 6 mL of the organometallic solution were added and the reaction mixture was stirred for additional 1 hour at 60° C. Further 6 mL of the organometallic solution were added and the reaction mixture was stirred for additional 1 hour at 60° C. After cooling the reaction was quenched with water (1 mL), diluted with an aqueous saturated solution of ammonium chloride (20 mL) and extracted with ethyl acetate (2×50 mL).

The organic layer was washed with brine (2×20 mL), dried (Na$_2$SO$_4$), filtered and evaporated and the residue was purified by flash chromatography on silica gel (SNAP 50 g), eluting from 100:0 to 80:20 n-hexane/ethyl acetate affording the title compound (400 mg) as white solid.

$^1$H NMR (400 MHz, DMSO-d$_6$): δ ppm 9.06 (1H, d), 8.67 (1H, dd), 7.88 (1H, d), 7.35 (1H, d), 7.23 (1H, dd), 7.01 (1H, dd), 2.17-2.27 (1H, m), 1.10-1.19 (2H, m), 0.82-0.90 (2H, m); UPLC_ipqc: 1.13 min, 282 [M+H]+.

The following compounds were prepared using the foregoing methodology, replacing Cyclopropyl Magnesium bromide with the appropriate Grignard reagent to form the organozinc reagent.

Reference Intermediate R20

3-cyclopropyl-4-[(5-nitro-2-pyridinyl)oxy]benzonitrile

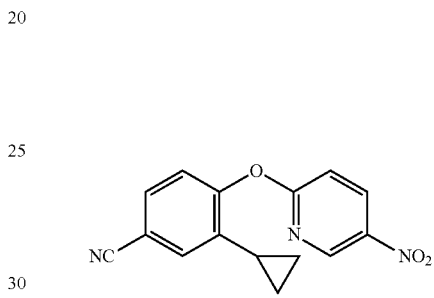

In a vial 3-bromo-4-[(5-nitro-2-pyridinyl)oxy]benzonitrile (Reference Intermediate R14, 800 mg) was dissolved in 16.0 mL of toluene. Cyclopropylboronic acid (1073.8 mg, 12.5 mmol) was added, followed by Pd(OAc)$_2$ (56.1 mg, 0.25 mmol) and (Cy)$_3$P (70.0 mg 0.25 mmol). Then, an aqueous solution (8.0 mL of water) of K$_3$PO$_4$ (1855.0 mg, 8.75 mmol) was added. The reaction mixture was heated at 80° C. overnight. After cooling down to r.t., the mixture was partitioned between brine and EtOAc and the separated aqueous phase was extracted with EtOAc (three times). The collected organic were dried over Na$_2$SO$_4$, filtered and evaporated. The crude obtained was charged on a silica gel column and eluted with Cyclohexane/EtOAc (from 100:0 to 80:20 Cyclohexane/EtOAc) affording 634 mg of the title compound.

$^1$H NMR (400 MHz, DMSO-d$_6$): δ ppm 9.04 (1H, br. s), 8.69 (1H, dd), 7.75 (1H, d), 7.58 (1H, s), 7.41 (2H, t), 1.90-1.80 (1H, m), 0.90-0.73 (4H, m); UPLC_ipqc: 1.12 min, 282 [M+H]+.

| | | | | | |
|---|---|---|---|---|---|
| R19 | ![structure] | 2-ethyl-4-[(5-nitro-2-pyridinyl)oxy]benzonitrile | Ethyl magnesium bromide | $^1$H-NMR (400 MHz, CDCl$_3$): δ ppm 9.06 (1H, d) 8.56 (1H, dd) 7.72 (1H, d) 7.18 (1H, d) 7.10-7.17 (2H, m) 2.95 (2H, q) 1.35 (3H, t) | 1.12 min, 270 [M + H]+ |

Reference Intermediate R21

2-(1-methylethenyl)-4-[(5-nitro-2-pyridinyl)oxy]benzonitrile

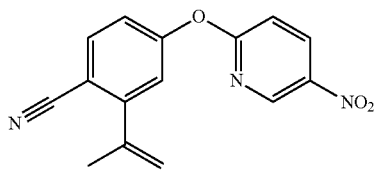 [SMILES: C=C(C)c1cc(Oc2ccc([N+](=O)[O-])cn2)ccc1C#N]

To a solution of 2-iodo-4-[(5-nitro-2-pyridinyl)oxy]benzonitrile (Reference Intermediate R16, 5.0 g) in DMF (50 mL) were added $K_3PO_4$ (5.77 g, 27.24 mmol), $Pd(tBu_3)_2$ (696 mg, 1.36 mmol) and 4,4,5,5-tetramethyl-2-(1-methylethenyl)-1,3,2-dioxaborolane (3.84 mL, 20.43 mmol) and the reaction mixture was stirred for 4 hours at 110° C. After cooling the reaction was diluted with water (100 mL) and extracted with ethyl acetate (3×100 mL). The organic layer was washed with ice cold brine (3×50 mL), dried ($Na_2SO_4$), filtered and evaporated and the residue was purified by flash chromatography on silica gel (SNAP 100 g) eluting from 100:0 to 80:20 cyclohexane/ethyl acetate to afford the title compound (1.8 g) as white solid.

$^1$H-NMR (400 MHz, DMSO-$d_6$): δ ppm 9.08 (1H, d), 8.69 (1H, dd), 7.97 (1H, d), 7.47 (1H, d), 7.40 (2H, d), 5.46 (1H, s), 5.32 (1H, s), 2.16 (3H, s); UPLC_ipqc: 1.14 min, 282 [M+H]+.

Reference Intermediate R22

2-[(1-methylethyl)oxy]-4-[(5-nitro-2-pyridinyl)oxy]benzonitrile

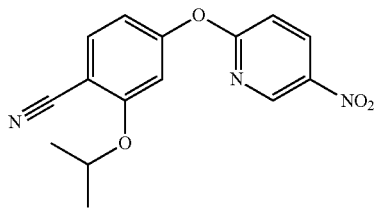 [SMILES: CC(C)Oc1cc(Oc2ccc([N+](=O)[O-])cn2)ccc1C#N]

In a vial 2,4-dihydroxybenzonitrile (300 mg, 2.2 mmol), 2-chloro-5-nitropyridine (351.96 mg, 2.22 mmol) and $K_2CO_3$ (920 mg, 6.62 mmol) were dissolved in DMF (5 mL). The reaction was heated for 1 hour under microwave irradiations (Set Temperature: 110° C.). The reaction mixture was diluted with $Et_2O$ and water, acidified with aqueous 1N HCl until pH=2, the phases were separated and the organics were dried over $Na_2SO_4$. The solid was filtered out and the solvent was removed affording crude 2-hydroxy-4-[(5-nitro-2-pyridinyl)oxy]benzonitrile (664 mg) as a brown solid. To a solution of this crude in dry DMF (5 mL) potassium carbonate (460 mg, 3.33 mmol) and isopropyl bromide (313 μL, 3.33 mmol) were added and the reaction mixture was stirred overnight at 50° C. The reaction was diluted with brine (10 mL) and extracted with ethyl acetate (2×20 mL). The organic layer was dried ($Na_2SO_4$), filtered and evaporated and the residue was purified by flash chromatography on silica gel (SNAP 25 g) eluting from 100:0 to 75:25 cyclohexane/ethyl acetate affording the title compound (260 mg) as white solid.

$^1$H-NMR (400 MHz, CDCl$_3$): δ ppm 9.06 (1H, d), 8.56 (1H, dd), 7.61-7.67 (1H, m), 7.15 (1H, d), 6.76-6.84 (2H, m), 4.56-4.68 (1H, m), 1.44 (6H, d).

Reference Intermediate R23

4-[(5-amino-2-pyridinyl)oxy]-3-(trifluoromethyl)benzonitrile

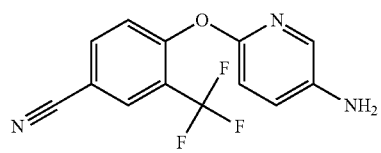

To a solution of 4-[(5-nitro-2-pyridinyl)oxy]-3-(trifluoromethyl)benzonitrile (Reference Intermediate R13, 83 mg) in THF (3 mL)/water (1.5 mL) was added at room temperature, iron (75 mg, 1.34 mmol) and $NH_4Cl$ (72 mg, 1.34 mmol) and the resulting reaction mixture was stirred overnight. The mixture was filtered through a small pad of celite washing with EtOAc and water. To the filtered mixture was added an aqueous $NaHCO_3$ saturated solution and the two phases were separated. The aqueous phase was extracted with EtOAc and the combined organic phases were dried and evaporated to dryness. The crude was purified by flash chromatography (companion system, 2×12 g Si cartridge, from 100:0 to 70:30 Cyclohexane/EtOAc) to afford the title compound (72 mg).

$^1$H NMR (400 MHz, CDCl$_3$): δ ppm 7.97 (1H, s), 7.69-7.79 (2H, m), 7.23 (1H, d), 7.16 (1H, dd), 6.93 (1H, d); UPLC_ipqc: 0.91 min, 280 [M+H]+.

The following compounds were prepared using the foregoing methodology, replacing 4-[(5-nitro-2-pyridinyl)oxy]-3-(trifluoromethyl)benzonitrile (Reference Intermediate R13) with the appropriate nitro derivative. Some final products were purified by flash-chromatography (Silica or NH cartridge; Cyclohexane/EtOAc or other appropriate solvent system). In some cases purification by SCX (MeOH and then 2M ammonia solution in MeOH) was run before the usual flash-chromatography.

| | | | | |
|---|---|---|---|---|
| R24 | 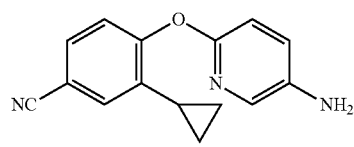 | 4-[(5-amino-2-pyridinyl)oxy]-3-cyclopropyl-benzonitrile | 3-cyclopropyl-4-[(5-nitro-2-pyridinyl)oxy] benzonitrile (Reference Intermediate R20) | $^1$H NMR (400 MHz, DMSO-$d_6$): δ ppm 7.61-7.52 (2H, m), 7.42 (1H, s), 7.16-7.09 (1H, m), 6.89 (2H, t), 5.19 (2H, br. s), 2.14-2.04 (1H, m), 0.97-0.89 (2H, m), 0.82-0.75 (2H, m) | 0.86 min, 252 [M + H]+ |

| | | | | | |
|---|---|---|---|---|---|
| R25 | ![structure] | 4-[(5-amino-2-pyridinyl)oxy]-3-(1,1-dimethylethyl)benzonitrile | 3-(1,1-dimethylethyl)-4-[(5-nitro-2-pyridinyl)oxy]benzonitrile (Reference Intermediate R15) | $^1$H NMR (400 MHz, DMSO-$d_6$): δ ppm 7.72 (1H, br. s), 7.65-7.57 (2H, m), 7.16-7.08 (1H, m), 6.89-6.78 (2H, m), 5.28-5.19 (2H, m), 1.39 (9H, s) | 1.02 min, 268 [M + H]$^+$ |
| R26 | ![structure] | 4-[(5-amino-2-pyridinyl)oxy]-2-1-methylethenyl)benzonitrile | 2-(1-methylethenyl)-4-[(5-nitro-2-pyridinyl)oxy]benzonitrile (Reference Intermediate R21) | $^1$H-NMR (400 MHz, DMSO-$d_6$): δ ppm 7.79 (1H, d), 7.62 (1H, d), 7.12 (1H, dd), 7.05 (1H, d), 6.98 (1H, dd), 6.89 (1H, d), 5.40 (1H, s), 5.28 (2H, br. s.), 5.23 (1H, s), 2.12 (3H, s) | 0.90 min, 252 [M + H]+ |
| R27 | ![structure] | 4-[(5-amino-2-pyridinyl)oxy]-2-ethylbenzonitrile | 2-ethyl-4-[(5-nitro-2-pyridinyl)oxy]benzonitrile (Reference Intermediate R19) | $^1$H-NMR (400 MHz, CDCl$_3$): δ ppm 7.77 (1H, d) 7.58 (1H, d) 7.15 (1H, dd) 7.00 (1H, d) 6.92 (1H, dd) 6.86 (1H, d) 3.62 (2H, br. s.) 2.86 (2H, q) 1.29 (3H, t) | 0.86 min, 240 [M + H]+ |
| R28 | ![structure] | 4-[(5-amino-2-pyridinyl)oxy]-2-[(1-methylethyl)oxy]benzonitrile | 2-[(1-methylethyl)oxy]-4-[(5-nitro-2-pyridinyl)oxy]benzonitrile (Reference Intermediate R22) | $^1$H-NMR(400 MHz, DMSO-$d_6$): δ ppm 7.63 (1H, d), 7.61 (1H, d), 7.12 (1H, dd), 6.88 (1H, d), 6.84 (1H, d), 6.51 (1H, dd), 5.29 (2H, br. s.), 4.66-4.77 (1H, m), 1.29 (6H, d) | 0.89 min, 270 [M + H]+ |
| R29 | ![structure] | 4-[(5-amino-2-pyridinyl)oxy]-2-[(trifluoromethyl)oxy]benzonitrile | 4-[(5-nitro-2-pyridinyl)oxy]-2-[(trifluoromethyl)oxy]benzonitrile (Reference Intermediate R16) | $^1$H NMR (400 MHz, CDCl$_3$): δ ppm 7.77 (1H, d), 7.66 (1H, d), 7.17 (1 H, dd), 7.11 (1H, s), 7.06 (1 H, dd), 6.89 (1H, d) | 0.94 min, 296 [M + H]+ |

Reference Intermediate R30

1,1-dimethylethyl {(1R)-1-[({6-[(4-cyano-2-cyclopropylphenyl)oxy]-3-pyridinyl}amino)carbonyl]propyl}carbamate

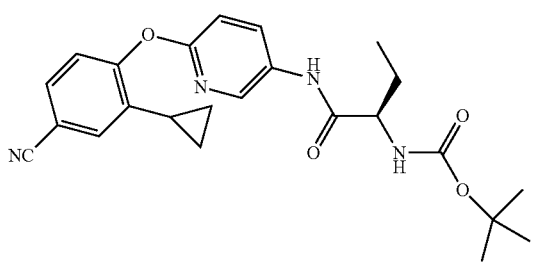 [SMILES: CC[C@@H](NC(=O)OC(C)(C)C)C(=O)Nc1ccc(Oc2ccc(C#N)cc2C2CC2)nc1]

(2R)-2-({[(1,1-dimethylethyl)oxy]carbonyl}amino)butanoic acid (121.4 mg, 0.60 mmol) was dissolved in N,N-Dimethylformamide (1 mL). N,N-Diisopropylethylamine (0.126 mL, 0.72 mmol) and O-(7-Azabenzotriazol-1-yl)-N,N,N',N'-tetramethyluronium hexafluorophosphate (227.2 mg, 0.60 mmol) were added. The reaction mixture was stirred at r.t. for 30 min. 4-[(5-amino-2-pyridinyl)oxy]-3-cyclopropylbenzonitrile (Reference Intermediate R24, 100 mg) was dissolved in 1.0 mL of DMF and the obtained solution was added to the reaction mixture. The reaction mixture was stirred and heated at 60° C. for 2 h. After cooling down to r.t., the reaction mixture was evaporated under vacuum and the crude obtained was charged on a silica gel column and eluted with Cyclohexane/EtOAc (from 100:0 to 50:50 Cyclohexane/EtOAc, then plateau at 50:50) affording 133 mg of the title compound.

$^1$H-NMR (400 MHz, CDCl$_3$): δ ppm 8.42 (1H, br. s), 8.20-8.10 (2H, m), 7.51-7.44 (1H, m), 7.32-7.23 (1H, m), 7.08 (1H, d), 7.03-6.95 (1H, m), 4.95 (1H, br. s), 4.16-4.05 (1H, m), 2.07-1.95 (2H, m), 1.77-1.68 (1H, m), 1.47 (9H, s), 1.04 (3H, t), 0.95-0.88 (2H, m), 0.71-0.64 (2H, m); UPLC_ipqc: 1.14 min, 437 [M+H]+.

The following compounds were prepared using the foregoing methodology, replacing (2R)-2-({[(1,1-dimethylethyl)oxy]carbonyl}amino)butanoic acid with the appropriate aminoacid and 4-[(5-amino-2-pyridinyl)oxy]-3-cyclopropylbenzonitrile (Intermediate 165) with the appropriate anilin. The reaction was carried out at a suitable temperature ranging from r.t. to high temperature. Final products were purified by flash-chromatography (Silica; Cyclohexane/EtOAc or other appropriate solvent system).

| | | | | | | |
|---|---|---|---|---|---|---|
| R31 | 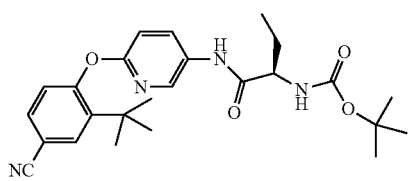 | 1,1-dimethylethyl ((1R)-1-{[(6-{[4-cyano-2-(1,1-dimethylethyl)phenyl]oxy}-3-pyridinyl)amino]carbonyl}propyl)carbamate | (2R)-2-({[(1,1-dimethylethyl)oxy]carbonyl}amino)butanoic acid | 4-[(5-amino-2-pyridinyl)oxy]-3-(1,1-dimethylethyl)benzonitrile (Reference Intermediate R25) | ¹H NMR (400 MHz, DMSO-d₆): δ ppm 10.20 (1H, br.s), 8.38 (1H, br. s), 8.20-8.11 (1H, m), 7.77 (1H, br.s), 7.70-7.64 (1H, m), 7.15 (1H, d), 7.05 (2H, d), 4.04-3.91 (1H, m), 1.77-1.55 (2H, m), 1.41-1.34 (18H, m), 0.93-0.87 (3H, m) | 1.25 min, 453 [M + H]⁺. |
| R32 | 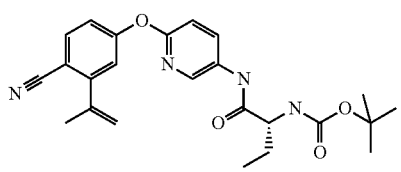 | 1,1-dimethylethyl ((1R)-1-{[(6-{[4-cyano-3-(1-methylethenyl)phenyl]oxy}-3-pyridinyl)amino]carbonyl}propyl)carbamate | (2R)-2-({[(1,1-dimethylethyl)oxy]carbonyl}amino)butanoic acid | 4-[(5-amino-2-pyridinyl)oxy]-2-(1-methylethenyl)benzonitrile (Reference Intermediate R26) | 1H-NMR (400 MHz, DMSO-d₆): δ ppm 10.21 (1H, br. s), 8.39-8.47(1H, m), 8.17(1H, dd), 7.86 (1H, d), 7.24 (1H, d), 7.17 (2H, d), 7.01-7.10 (1H, m), 5.43 (1H, s), 5.27 (1H, s), 3.95-4.05 (1H, m), 2.14 (3H, s), 1.57-1.79 (2H, m), 1.40 (9H, s), 0.92 (3H, t) | 1.16 min, 437 [M + H]+. |
| R33 | 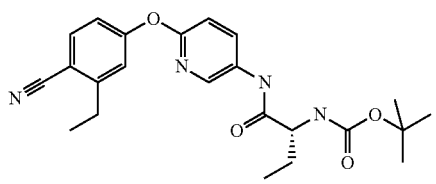 | 1,1-dimethylethyl {(1R)-1-[({6-[(4-cyano-3-ethyl-phenyl)oxy]-3-pyridinyl}amino)carbonyl]propyl}carbamate | (2R)-2-({[(1,1-dimethylethyl)oxy]carbonyl}amino)butanoic acid | 4-[(5-amino-2-pyridinyl)oxy]-2-ethylbenzonitrile (Reference Intermediate R27) | ¹H-NMR (400 MHz, DMSO-d₆): δ ppm 10.25 (1H, s) 8.43 (1H, d) 8.16 (1H, dd) 7.80 (1H, d) 7.20 (1H, d) 7.15 (1H, d) 7.05-7.11 (2H, m) 3.94-4.02 (1H, m) 2.79 (2H, q) 1.53-1.76 (2H, m) 1.39 (9H, s) 1.21 (3H, t) 0.91 (3H, t) | |
| R34 | 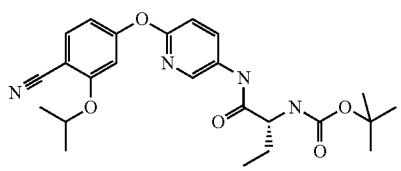 | 1,1-dimethylethyl [(1R)-1-({[6-({4-cyano-3-[(1-methylethyl)oxy]phenyl}oxy)-3-pyridinyl]amino}carbonyl)propyl]carbamate | (2R)-2-({[(1,1-dimethylethyl)oxy]carbonyl}amino)butanoic acid | 4-[(5-amino-2-pyridinyl)oxy]-2-[(1-methylethyl)oxy]benzonitrile (Reference Intermediate R28) | 1H-NMR (400 MHz, DMSO-d₆): δ ppm 10.24 (1H, br. s.), 8.42 (1H, d), 8.16 (1H, dd), 7.70 (1H, d), 7.15 (1H, d), 7.09 (1H, d), 7.02 (1H, d), 6.72 (1H, dd), 4.70-4.81 (1H, m), 3.94-4.02 (1H, m), 1.54- 1.77 (2H, m), 1.39 (9H, s), 1.30 (6H, d), 0.91 (3H, t) | 1.15 min, 455 [M + H]+ |
| R35 | 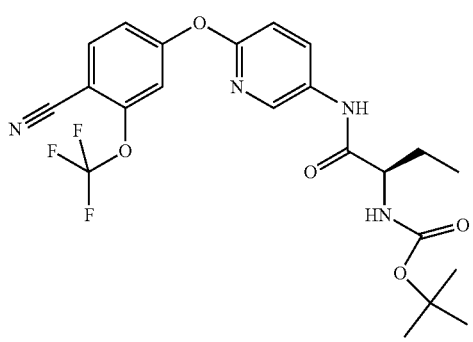 | 1,1-dimethylethyl [(1R)-1-({[6-(4-cyano-3-[(trifluoromethyl)oxy]phenyl}oxy)-3-pyridinyl]amino}carbonyl)propyl]carbamate | (2R)-2-({[(1,1-dimethylethyl)oxy]carbonyl}amino)butanoic acid | 4-[(5-amino-2-pyridinyl)oxy]-2-[(trifluoromethyl)oxy]benzonitrile (Reference Intermediate R29) | ¹H NMR (400 MHz, CDCl₃): δ ppm 8.64 (1H, br. s.), 8.26 (1H, d), 8.15-8.23 (1H, m), 7.70 (1H, d), 7.20 (1H, s), 7.12-7.18 (1H, m), 7.02 (1H, d), 4.93-5.06 (1H, m), 4.10-4.21 (1H, m), 1.93-2.12 (1H, m), 1.67-1.83 (1H, m), 1.49 (9H,s), 1.06 (3H, t) | 1.18 min, 481 [M + H]+, 479 [M − H]− |

Reference Intermediate R36

1,1-dimethylethyl ((1R)-1-{[(6-{[4-cyano-3-(1-methylethyl)phenyl]oxy}-3-pyridinyl)amino]carbonyl}propyl)carbamate

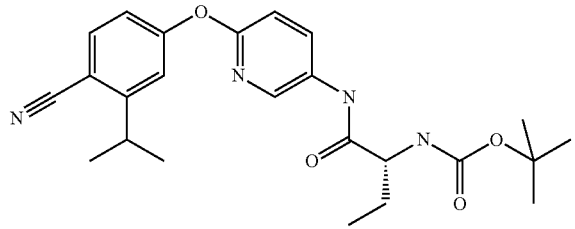

To a solution of 1,1-dimethylethyl((1R)-1-{[(6-{[4-cyano-3-(1-methylethenyl)phenyl]oxy}-3-pyridinyl)amino]carbonyl}propyl)carbamate (Reference Intermediate R32, 73 mg) in MeOH (10 mL) was added Pd 10% w/w on activated carbon (14 mg) and the reaction mixture was stirred for 30 minutes under H$_2$ atmosphere (P=1 atm). The catalyst was filtered off and the solvent removed under reduced pressure. The residue was purified by flash chromatography on silica gel (SNAP 10 g) eluting from 75:25 to 40:60 cyclohexane/ethyl acetate affording the title compound (62 mg) as white solid.

$^1$H-NMR (400 MHz, DMSO-d$_6$): δ ppm 10.24 (1H, br. s.), 8.42 (1H, d), 8.16 (1H, dd), 7.78 (1H, d), 7.24 (1H, d), 7.15 (1H, d), 7.07-7.11 (1H, m), 7.05 (1H, dd), 3.95-4.02 (1H, m), 3.19-3.27 (1H, m), 1.57-1.76 (2H, m), 1.39 (9H, s), 1.26 (6H, d), 0.91 (3H, t); UPLC_ipqc: 1.20 min, 439 [M+H]+.

Reference Intermediate R37

(2R)-2-amino-N-{6-[(4-cyano-2-cyclopropylphenyl)oxy]-3-pyridinyl}butanamide

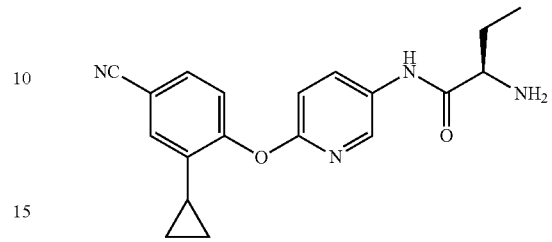

1,1-dimethylethyl {(1R)-1-[({6-[(4-cyano-2-cyclopropylphenyl)oxy]-3-pyridinyl}amino)carbonyl]propyl}carbamate (Reference Intermediate R30, 133 mg) was dissolved in DCM (6 mL) and, at 0° C., TFA (3.0 mL) was slowly added. The reaction mixture was stirred at that temperature for 2 h. After the removal of the volatiles, the crude obtained was charged on a SCX cartridge and eluted with MeOH and then 2M NH$_3$ in MeOH affording 102 mg of the title compound.

$^1$H-NMR (400 MHz, CDCl$_3$): δ ppm 9.68 (1H, br. s), 8.32-8.18 (2H, m), 7.51-7.43 (1H, m), 7.25-7.31 (1H, m), 7.08 (1H, d), 6.99 (1H, d), 3.59-3.51 (1H, m), 2.06-1.95 (2H, m), 1.73-1.63 (1H, m), 1.03 (3H, t), 0.95-0.89 (2H, m), 0.74-0.63 (2H, m); UPLC_ipqc: 0.68 min, 337 [M+H]+.

The following compounds were prepared using the foregoing methodology, replacing 1,1-dimethylethyl {(1R)-1-[({6-[(4-cyano-2-cyclopropylphenyl)oxy]-3-pyridinyl}amino)carbonyl]propyl}carbamate (Reference Intermediate R30) with the appropriate N—BOC protected amine. Final products were purified by SCX (MeOH and then 2M ammonia solution in MeOH) and fractions eluted with ammonia, containing the product, were concentrated to provide the free-base. Alternatively, after removing the volatiles, to the crude taken up with an appropriate organic solvent was added NaHCO$_3$ saturated aqueous solution, the two phases were separated and the organic layer was dried, filtered and evaporated affording the final compound as the free-base.

| | | | | | |
|---|---|---|---|---|---|
| R38 | 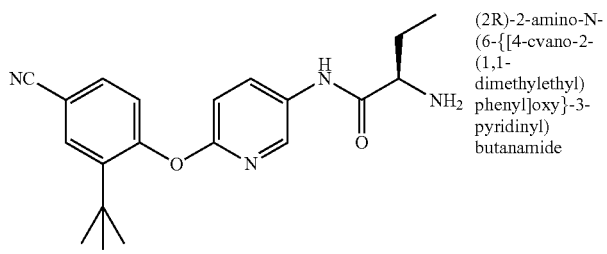 | (2R)-2-amino-N-(6-{[4-cyano-2-(1,1-dimethylethyl)phenyl]oxy}-3-pyridinyl)butanamide | 1,1-dimethylethyl ((1R)-1-({[(6-{[4-cyano-2-(1,1-dimethylethyl)phenyl]oxy}-3-pyridinyl)amino]carbonyl}propyl)carbamate (Reference Intermediate R31) | $^1$H NMR (400 MHz, DMSO-d$_6$): δ ppm 8.43 (1H, br.s), 8.25-8.15 (1H, m), 7.78 (1H, br.s), 7.70-7.65 (1H, m), 7.14 (1H, d), 7.05 (1H, d), 3.20-3.15 (1H, m), 1.74-1.61 (1H, m), 1.57-1.45 (1H, m), 1.36 (9H, s), 0.93 (3H, t) | 0.79 min, 353 [M + H]$^+$ |
| R39 | 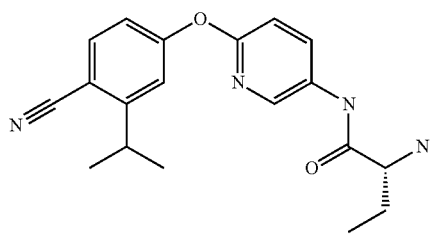 | (2R)-2-amino-N-(6-{[4-cyano-3-(1-methylethyl)phenyl]oxy}-3-pyridinyl)butanamide | 1,1-dimethylethyl ((1R)-1-{[(6-{[4-cyano-3-(1-methylethyl)phenyl]oxy}-3-pyridinyl)amino]carbonyl}propyl)carbamate (Reference Intermediate R36) | $^1$H-NMR(400 MHz, DMSO-d$_6$): δ ppm 8.48 (1H, d) 8.22 (1H, dd) 7.79 (1H, d) 7.24 (1H, d) 7.15 (1H, d) 7.05 (1H, dd) 3.19-3.30 (2H, m) 1.61-1.74 (1H, m) 1.45-1.56 (1H, m) 1.26 (6H, d) 0.91 (3H, t) | 0.76 min, 339 [M + H]+ |

| | | | | |
|---|---|---|---|---|
| R40 | ![structure] | (2R)-2-amino-N-{6-[(4-cyano-3-ethylphenyl)oxy]-3-pyridinyl}butanamide | 1,1-dimethylethyl {(1R)-1-[({6-[(4-cyano-3-ethylphenyl)oxy]-3-pyridinyl}amino)carbonyl]propyl}carbamate (Reference Intermediate R33) | $^1$H-NMR (400 MHz, DMSO-d$_6$): δ ppm 8.48 (1H, d) 8.22 (1H, dd) 7.80 (1H, d) 7.19 (1H, d) 7.15 (1H, d) 7.07 (1H, dd) 3.22-3.29 (1H,m) 2.79 (2H, q) 1.60-1.74 (1H, m) 1.44-1.56 (1H, m) 1.21 (3H, t) 0.91 (3H, t) |
| R41 | ![structure] | (2R)-2-amino-N-[6-({4-cyano-3-[(1-methylethyl)oxy]phenyl}oxy)-3-pyridinyl]butanamide | 1,1-dimethylethyl [(1R)-1-({[6-({4-cyano-3-[(1-methylethyl)oxy]phenyl}oxy)-3-pyridinyl]amino}carbonyl)propyl]carbamate (Reference Intermediate R34) | $^1$H-NMR (400 MHz, CDCl$_3$): δ ppm 9.70 (1H, br.s.), 8.26-8.38 (2H, m), 7.54 (1H, d), 7.01 (1H, d), 6.74 (1H, d), 6.68(1H, dd), 4.52-4.66 (1H, m), 3.45-3.54 (1H, m), 1.97-2.10 (1H, m), 1.65-1.76 (1H, m), 1.41 (6H, d), 1.06 (3H, t) |
| R42 | ![structure] | (2R)-2-amino-N-[6-({4-cyano-3-[(trifluoromethyl)oxy]phenyl}oxy)-3-pyridinyl]butanamide | 1,1-dimethylethyl [(1R)-1-({[6-({4-cyano-3-[(trifluoromethyl)oxy]phenyl}oxy)-3-pyridinyl]amino}carbonyl)propyl]carbamate (Reference Intermediate R35) | $^1$H NMR (400 MHz, CDCl$_3$): δ ppm 9.76 (1H, s), 8.25-8.43 (2H, m), 7.70 (1H, d), 7.20 (1H, s), 7.16 (1H, dd), 7.06 (1H, d), 3.44-3.59 (1H, m), 1.53-2.12 (2H, m), 1.07 (3H, t) | 0.72 min, 381 [M + H]+, 379 [M − H]−. |

Reference Example RE1

(5R)-5-ethyl-3-(6-{[4-methyl-3-(methyloxy)phenyl]oxy}-3-pyridinyl)-2,4-imidazolidinedione

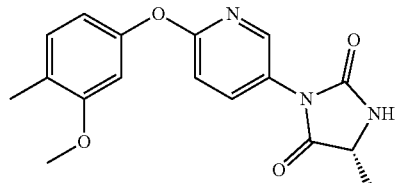

Method A

To a solution of (2R)-2-amino-N-(6-{[4-methyl-3-(methyloxy)phenyl]oxy}-3-pyridinyl)butanamide (Reference Intermediate R6, 120 mg) in dry dichloromethane (8 mL) TEA (0.265 mL, 1.903 mmol) was added and the reaction mixture was cooled to 0° C. A solution of triphosgene (50.8 mg, 0.171 mmol) in dry dichloromethane (DCM) (2 mL) was slowly added and the reaction mixture was stirred for 30 minutes at the same temperature. The reaction was quenched with water (2 mL) and two phases were separated. The organic layer was dried over sodium sulphate, filtered and evaporated and the residue was purified by silica gel chromatography (Biotage system, 10 g SNAP column) with as eluent a gradient cyclohexane/ethyl acetate 80/20 to cyclohexane/ethyl acetate 50/50 to afford the title compound as a white solid (108 mg).

$^1$H NMR (400 MHz, DMSO-d$_6$): δ ppm 8.61 (1H, s), 8.12 (1H, d), 7.82 (1H, dd), 7.17 (1H, d), 7.08 (1H, d), 6.79 (1H, d), 6.63 (1H, dd), 4.25-4.18 (1H, m), 3.77 (3H, s), 2.15 (3H, s), 1.89-1.62 (2H, m), 0.95 (3H, t): UPLC_B: 0.79 min, 342 [M+H]+.

Reference RE2

(5R)-5-ethyl-5-methyl-3-(6-{[4-methyl-3-(methyloxy)phenyl]oxy}-3-pyridinyl)-2,4-imidazolidinedione

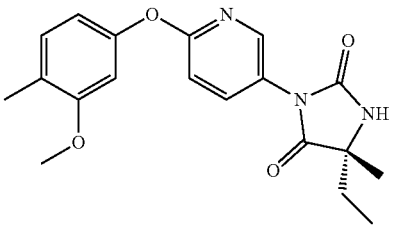

To a solution of N1-(6-{[4-methyl-3-(methyloxy)phenyl]oxy}-3-pyridinyl)-D-isovalinamide (Reference Intermediate R8 42 mg) in dry dichloromethane (6 mL), TEA (0.089 mL, 0.638 mmol) was added. The mixture was cooled down to 0° C. and a solution of triphosgene (17.03 mg, 0.057 mmol) in dry dichloromethane (1.500 mL) was added dropwise. The mixture was stirred at that temperature for 1 hour, then a solution of triphosgene (17.03 mg, 0.057 mmol) in dry dichloromethane (DCM) (1.500 mL) was added dropwise again. The reaction was stirred for 30 minutes, it was maintained in the ice-bath and quenched with water (10 mL). The mixture was allowed to reach the room temperature then it was extracted with dichloromethane (3×7 mL).

The combined organic layers were dried over sodium sulphate, filtered and evaporated. The residue obtained was purified by flash chromatography on silica gel using a 10 g SNAP column and cyclohexane/ethyl acetate as eluents from 80/20 to 50/50 (Biotage system). This afforded the title compound as a white solid (24 mg).

$^1$H NMR (400 MHz, DMSO-$d_6$): δ ppm 8.57 (1H, s), 8.13 (1H, d), 7.83 (1H, dd), 7.17 (1H, d), 7.07 (1H, d), 6.79 (1H, d), 6.62 (1H, dd), 3.76 (3H, s), 2.14 (3H, s), 1.57-1.86 (2H, m), 1.39 (3H, s), 0.86 (3H, t); UPLC_B: 0.83 min, 354 [M−H]+.

Method for Reference Examples RE3 to RE8

4-{[4-(4,4-dimethyl-2,5-dioxo-1-imidazolidinyl)phenyl]oxy}-2-(methyloxy)benzonitrile

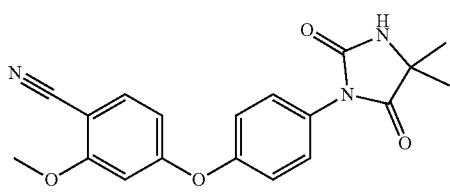 [SMILES: COc1cc(Oc2ccc(N3C(=O)NC(C)(C)C3=O)cc2)ccc1C#N]

$N^1$-(4-{[4-cyano-3-(methyloxy)phenyl]oxy}phenyl)-2-methylalaninamide (77.0 mg) was dissolved in DCM (10 mL). Triethylamine (0.218 mL, 1.57 mmol) was added and the obtained mixture was cooled at 0° C. Bis(trichloromethyl) carbonate (68.1 mg, 0.22 mmol) was dissolved in 5 mL of DCM and the obtained solution was added dropwise to the reaction mixture. The reaction mixture was stirred at 0° C. After 15 min, the reaction mixture was evaporated in vacuo to obtain the crude product that was purified by silica gel chromatography (from 100:0 to 50:50 Cyclohexane/EtOAc in 10 CV; then 50:50 Cyclohexane/EtOAc for 10 CV) to obtain 65.1 mg of the title compound as a white solid.

$^1$H NMR (400 MHz, DMSO-$d_6$): δ ppm 8.56 (1H, br. s.) 7.72 (1H, d) 7.42-7.49 (2H, m) 7.19-7.29 (2H, m) 6.97 (1H, d) 6.57 (1H, dd) 3.89 (3H, s) 1.41 (6H, s); UPLC_ipqc: 0.93 min, 352 [M+H]+.

The following compounds were prepared using the foregoing methodology, replacing $N^1$-(4-{[4-cyano-3-(methyloxy)phenyl]oxy}phenyl)-2-methylalaninamide with the appropriate amine. Final products were purified by flash-chromatography (Silica cartridge; Cyclohexane/EtOAc or other appropriate solvent system).

| | | | | | |
|---|---|---|---|---|---|
| RE3 | 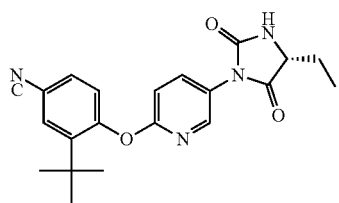 | 3-(1,1-dimethylethyl)-4-((5-[(4R)-4-ethyl-2,5-dioxo-1-imidazolidinyl]-2-pyridinyl}oxy)benzonitrile | (2R)-2-amino-N-(6-{[4-cyano-2-(1,1-dimethylethyl)phenyl]oxy}-3-pyridinyl)butanamide (Reference Intermediate R38) | $^1$H NMR (400 MHz, DMSO-$d_6$): δ ppm 8.64 (1H, br.s), 8.19 (1H, br. s), 7.96-7.90 (1H, m), 7.82 (1H, br.s), 7.76-7.68 (1H, m), 7.30 (1H, d), 7.19 (1H, d), 4.25-4.17 (1H, m), 1.86-1.77 (1H, m), 1.76-1.66 (1H, m), 1.35 (9H, s), 0.95 (3H, t) | |
| RE4 | 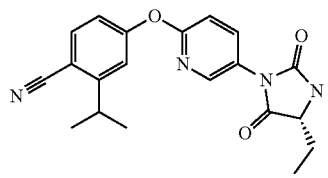 | 4-({5-[(4R)-4-ethyl-2,5-dioxo-1-imidazolidiniy]-2-pyridinyl}oxy)-2-(1-methylethyl)benzonitrile | (2R)-2-amino-N-(6-{[4-cyano-3-1-methylethyl)phenyl]oxy}-3-pyridinyl)butanamide (Reference Intermediate R39) | $^1$H-NMR (400 MHz, DMSO-$d_6$): δ ppm 8.66 (1H, s) 8.19 (1H, d) 7.93 (1H, dd) 7.84 (1H, d) 7.36 (1H, d) 7.28 (1H, d) 7.18 (1H, dd) 4.19-4.25 (1H, m) 3.21-3.30 (1H, m) 1.77-1.87 (1H, m) 1.65-1.76 (1H, m) 1.27 (6H, d) 0.96 (3H, t) | 1.03 min, 365 [M + H]+ |
| RE5 | 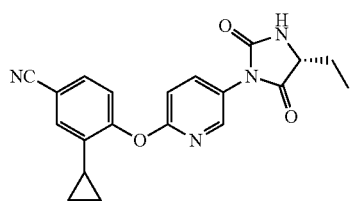 | 3-cyclopropyl-4-({5-[(4R)-4-ethyl-2,5-dioxo-1-imidazolidinyl]-2-pyridinyl}oxy)benzonitrile | (2R)-2-amino-N-{6-[(4-cyano-2-cyclopropyl-phenyl)oxy]-3-pyridinyl}butanamide (Reference Intermediate R37) | $^1$H NMR (400 MHz, DMSO-$d_6$): δ ppm 8.64 (1H, br.s), 8.14-8.11 (1H, m), 7.96-7.84 (1H, m), 7.71-7.66 (1H, m), 7.52 (1H, br.s), 7.29 (2H, d), 4.24-4.18 (1H, m), 1.97-1.89 (1H, m), 1.86-1.78 (1H, m), 1.75-1.67 (1H, m), 0.95 (3H, t), 0.91-0.85 (2H, m), 0.81-0.75 (2H, m) | 0.98 min, 363 [M + H]+. |

| | | | | |
|---|---|---|---|---|
| RE6 | 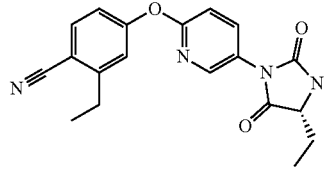 | 4-({5-[(4R)-4-ethyl-2,5-dioxo-1-imidazolidinyl]-2-pyridinyl}oxy)-2-(1-methylethyl)benzonitrile | (2R)-2-amino-N-{6-[(4-cyano-3-ethylphenyl)oxy]-3-pyridinyl}butanamide (Reference Intermediate R40) | $^1$H-NMR (400 MHz, DMSO-$d_6$): δ ppm 8.66 (1H, s) 8.19 (1H, dd) 7.93 (1H, dd) 7.85 (1H, d) 7.32 (1H, d) 7.28 (1H, dd) 7.19 (1H, dd) 4.19-4.25 (1H, m) 2.82 (2H, q) 1.77-1.88 (1H, m) 1.65-1.77 (1H, m) 1.23 (3H, t) 0.96 (3H, t) | 0.98 min, 351 [M + H]+ |
| RE7 | 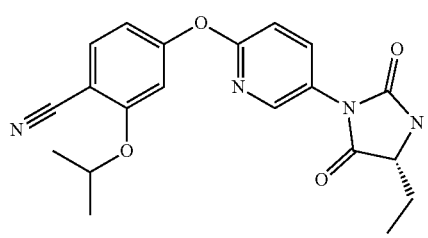 | 4-({5-[(4R)-4-ethyl-2,5-dioxo-1-imidazolidinyl]-2-pyridinyl}oxy)-2-[(trifluoromethyl)oxy]benzonitrile | (2R)-2-amino-N-[6-({4-cyano-3-[(trifluoromethyl)oxy]phenyl}oxy)-3-pyridinyl]butanamide (Reference Intermediate R42) | $^1$H NMR (400 MHz, DMSO-$d_6$): δ ppm 8.67 (1H, s), 8.19-8.26 (1H, m), 8.14 (1H, d), 7.94-8.02 (1H, m), 7.66 (1H, s), 7.43-7.51 (1H, m), 7.36 (1H, d), 4.18-4.27 (1H, m), 1.63 -1.91 (2H, m), 0.96 (3H, t) | 1.02 min, 407 [M + H]+, 405 [M − H]− |
| RE8 | 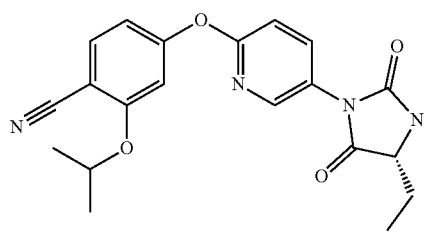 | 4-({5-[(4R)-4-ethyl-2,5-dioxo-1-imidazolidinyl]-2-pyridinyl}oxy)-2-[1-methylethyl)oxy]benzonitrile | (2R)-2-amino-N-[6-({4-cyano-3-[(1-methylethyl)oxy]phenyl}oxy)-3-pyridinyl]butanamide (Reference Intermediate R41) | $^1$H-NMR (400 MHz, DMSO-$d_6$): δ ppm 8.65 (1H, s), 8.20 (1H, d), 7.93 (1H, dd), 7.76 (1H, d), 7.27 (1H, d), 7.16 (1H, d), 6.84 (1H, dd), 4.74-4.85 (1H, m), 4.17-4.26 (1H, m), 1.76-1.89 (1H, m), 1.65-1.76 (1H, m), 1.31 (6H, d), 0.96 (3H, t) | 1.00 min, 381 [M + H]+. |

Biological Example 1

The ability of the compounds of the disclosure to modulate the voltage-gated potassium channel subtypes Kv3.2/3.1 may be determined using the following assay.

Cell Biology

To assess compound effects on human Kv3.2 channels (hKv3.2), a stable cell line expressing hKv3.2 was created by transfecting Chinese Hamster Ovary (CHO)-K1 cells with a pClH5-hKv3.2 vector. Cells were cultured in DMEM/F12 medium supplemented by 10% Foetal Bovine Serum, 1× non-essential amino acids (Invitrogen) and 500 ug/ml of Hygromycin-B (Invitrogen). Cells were grown and maintained at 37° C. in a humidified environment containing 5% $CO_2$ in air.

To assess compound effects on human Kv3.1 channels (hKv3.1), CHO/Gam/E1A-clone22 alias CGE22 cells were transduced using a hKv3.1 BacMam reagent. This cell line was designed to be an improved CHO-K1-based host for enhanced recombinant protein expression as compared to wild type CHO-K1. The cell line was generated following the transduction of CHO-K1 cells with a BacMam virus expressing the Adenovirus-Gam1 protein and selection with Geneticin-G418, to generate a stable cell line, CHO/Gam-A3. CHO/Gam-A3 cells were transfected with pCDNA3-E1A-Hygro, followed by hygromycin-B selection and FACS sorting to obtain single-cell clones. BacMam-Luciferase and BacMam-GFP viruses were then used in transient transduction studies to select the clone based on highest BacMam transduction and recombinant protein expression. CGE22 cells were cultured in the same medium used for the hKv3.2 CHO-K1 stable cell line with the addition of 300 ug/ml hygromycin-B and 300 ug/ml G418. All other conditions were identical to those for hKv3.2 CHO-K1 cells. The day before an experiment 10 million CGE22 cells were plated in a T175 culture flask and the hKv3.1 BacMam reagent (pFBM/human Kv3.1) was added (MOI of 50). Transduced cells were used 24 hours later.

Cell Preparation for IonWorks Quattro™ Experiments

The day of the experiment, cells were removed from the incubator and the culture medium removed. Cells were washed with 5 ml of Dulbecco's PBS (DPBS) calcium and magnesium free and detached by the addition of 3 ml Versene (Invitrogen, Italy) followed by a brief incubation at 37° C. for 5 minutes. The flask was tapped to dislodge cells and 10 ml of DPBS containing calcium and magnesium was added to prepare a cell suspension. The cell suspension was then placed into a 15 ml centrifuge tube and centrifuged for 2 min at 1200 rpm. After centrifugation, the supernatant was removed and the cell pellet re-suspended in 4 ml of DPBS containing calcium and magnesium using a 5 ml pipette to break up the pellet. Cell suspension volume was then corrected to give a cell concentration for the assay of approximately 3 million cells per ml.

All the solutions added to the cells were pre-warmed to 37° C.

Electrophysiology

Experiments were conducted at room temperature using IonWorks Quattro™ planar array electrophysiology technology (Molecular Devices Corp.) with PatchPlate™ PPC. Stimulation protocols and data acquisition were carried out using a microcomputer (Dell Pentium 4). Planar electrode hole resistances (Rp) were determined by applying a 10 mV voltage step across each well. These measurements were performed before cell addition. After cell addition and seal formation, a seal test was performed by applying a voltage step from −80 mV to −70 mV for 160 ms. Following this, amphotericin-B solution was added to the intracellular face of the electrode to achieve intracellular access. Cells were held at −70 mV. Leak subtraction was conducted in all experiments by applying 50 ms hyperpolarizing (10 mV) prepulses to evoke leak currents followed by a 20 ms period at the holding potential before test pulses. From the holding potential of −70 mV, a first test pulse to −15 mV was applied for 100 ms and following a further 100 ms at −70 mV, a second pulse to 40 mV was applied for 50 ms. Cells were then maintained for a further 100 ms at −100 mV and then a voltage ramp from −100 mV to 40 mV was applied over 200 ms. In all experiments, the test pulses protocol was performed in the absence (pre-read) and presence (post-read) of the test compound. Pre- and post-reads were separated by the compound addition followed by a 3 minute incubation.

Solutions and Drugs

The intracellular solution contained the following (in mM): K-gluconate 100, KCl 54, $MgCl_2$ 3.2, HEPES 5, adjusted to pH 7.3 with KOH. Amphotericin-B solution was prepared as 50 mg/ml stock solution in DMSO and diluted to a final working concentration of 0.1 mg/ml in intracellular solution. The external solution was Dulbecco's Phosphate Buffered Saline (DPBS) and contained the following (in mM): $CaCl_2$ 0.90, KCl 2.67, $KH_2PO_4$ 1.47, $MgCl.6H_2O$ 0.493, NaCl 136.9, $Na_3PO_4$ 8.06, with a pH of 7.4.

Compounds of the disclosure (or reference compounds such as N-cyclohexyl-N-[(7,8-dimethyl-2-oxo-1,2-dihydro-3-quinolinyl)methyl]-N'-phenylurea were dissolved in dimethylsulfoxide (DMSO) at a stock concentration of 10 mM. These solutions were further diluted with DMSO using a Biomek FX (Beckman Coulter) in a 384 compound plate. Each dilution (1 μL) was transferred to another compound plate and external solution containing 0.05% pluronic acid (66 μL) was added. 3.5 μL from each plate containing a compound of the disclosure was added and incubated with the cells during the IonWorks Quattro™ experiment. The final assay dilution was 200 and the final compound concentrations were in the range 50 μM to 50 nM.

Data Analysis

The recordings were analysed and filtered using both seal resistance (>20 MΩ) and peak current amplitude (>500 pA at the voltage step of 40 mV) in the absence of compound to eliminate unsuitable cells from further analysis. Kv3 channel-mediated outward currents were measured determined from the mean amplitude of the current over the final 10 ms of the −15 mV voltage pulse minus the mean baseline current at −70 mV over a 10 ms period just prior to the −15 mV step. This Kv3 channel currents following addition of the test compound were then compared with the currents recorded prior to compound addition. Data were normalised to the maximum effect of the reference compound (50 microM of N-cyclohexyl-N-[(7,8-dimethyl-2-oxo-1,2-dihydro-3-quinolinyl)methyl]-N'-phenylurea) and to the effect of a vehicle control (0.5% DMSO). The normalised data were analysed using ActivityBase or Excel software. The concentration of compound required to increase currents by 50% of the maximum increase produced by the reference compound (pEC50) was determined by fitting of the concentration-response data using a four parameter logistic function.

N-cyclohexyl-N-[(7,8-dimethyl-2-oxo-1,2-dihydro-3-quinolinyl)methyl]-N'-phenylurea was obtained from ASINEX (Registry Number: 552311-06-5).

All the Example compounds were tested in the above assay and demonstrated potentiation of Kv3.1 or Kv3.2 or Kv3.1 and Kv3.2 (herein after "Kv3.1 and/or Kv3.2") whole-cell currents of, on average, at least 20% of that observed with 50 microM N-cyclohexyl-N-[(7,8-dimethyl-2-oxo-1,2-dihydro-3-quinolinyl)methyl]-N'-phenylurea.

Thus, in the recombinant cell assays of Biological Example 1, all of the Example compounds act as positive modulators. As used herein, a Kv3.1 and/or Kv3.2 positive modulator is a compound which has been shown to produce at least 20% potentiation of whole-cell currents mediated by human Kv3.1 and/or human Kv3.2 channels recombinantly expressed in mammalian cells, as determined using the assays described in Biological Example 1 (Biological Assays).

A secondary analysis of the data from the assays described in Biological Example 1 investigates the effect of the compounds on rate of rise of the current from the start of the depolarising voltage pulses. The magnitude of the effect of a compound can be determined from the time constant ($Tau_{act}$) obtained from a non-linear fit, using the equation given below, of the rise in Kv3.1 or Kv3.2 currents following the start of the −15 mV depolarising voltage pulse.

$$Y=(Y0-Y\max)*\exp(-K*X)+Y\max$$

where:
Y0 is the current value at the start of the depolarising voltage pulse;
Ymax is the plateau current;
K is the rate constant, and $Tau_{act}$ is the activation time constant, which is the reciprocal of K.

Similarly, the effect of the compounds on the time taken for Kv3.1 and Kv3.2 currents to decay on closing of the channels at the end of the −15 mV depolarising voltage pulses can also be investigated. In this latter case, the magnitude of the effect of a compound on channel closing can be determined from the time constant ($Tau_{deact}$) of a non-linear fit of the decay of the current ("tail current") immediately following the end of the depolarising voltage pulse.

The time constant for activation ($Tau_{act}$) has been determined for several of the compounds of the Examples. FIG. 1 shows the data for two compounds of the disclosure. Table 1 provides the $Tau_{act}$ data for all of the Examples analysed in this way.

FIG. 1a shows hKv3.2 currents recorded using the assay described in Biological Example 1. Data shown are the individual currents over the period of the depolarising voltage step to −15 mV recorded from 4 different cells at two concentrations of compound (Reference Example RE1). The data are fitted by a single exponential curve (solid lines) using the fitting procedure in Prism version 5 (Graphpad Software Inc).

Figure 1B:
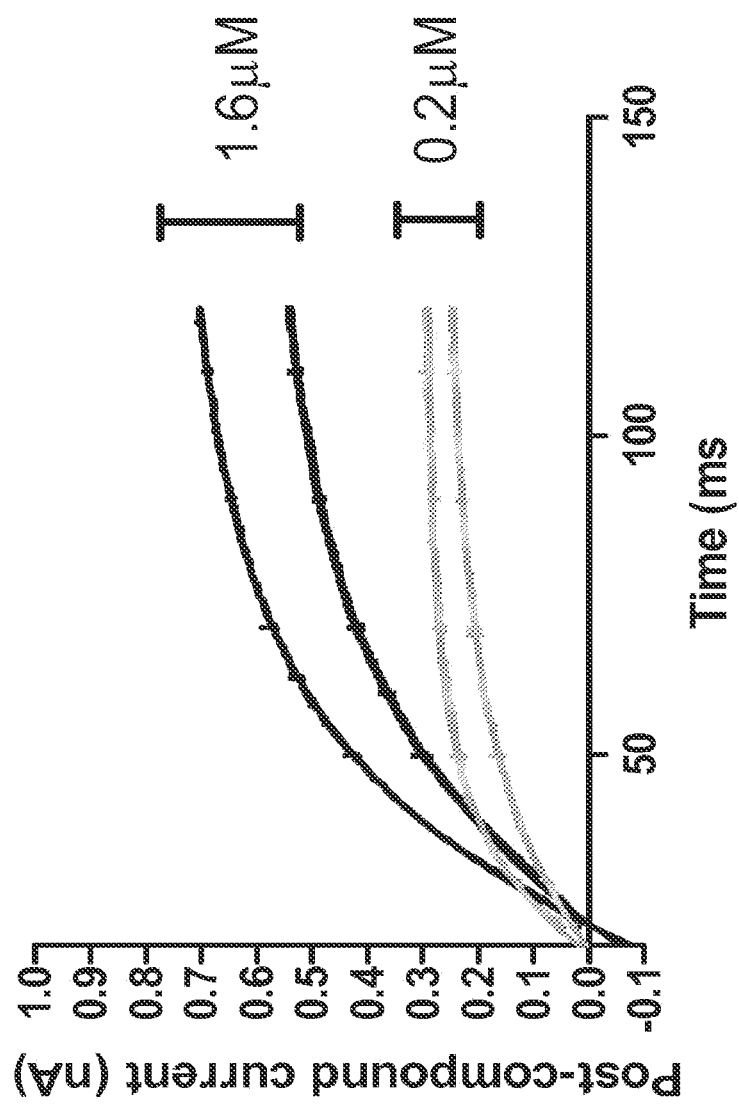
FIG. 1b hKv3.2 currents recorded using the assay described in Biological Example 1. Data shown are the individual currents over the period of the depolarising voltage step to −15 mV recorded from 2 different cells at two concentrations of compound of Reference Example RE3. The data are fitted by a single exponential curve (solid lines) using the fitting procedure in Prism version 5 (Graphpad Software Inc).

FIG. 1b shows hKv3.2 currents recorded using the assay described in Biological Example 1. Data shown are the individual currents over the period of the depolarising voltage step to −15 mV recorded from 2 different cells at two concentrations of the compound of Reference Example RE3. The data are fitted by a single exponential curve (solid lines) using the fitting procedure in Prism version 5 (Graphpad Software Inc).

TABLE 1

Summary hKv3.2 data from the analysis of activation time (Tau$_{act}$).
To allow for comparison between compounds, the compound
concentration chosen was that which produced a similar current
(~0.3 nA) at the end of the voltage pulse, with the exception of
the vehicle, where maximum currents were < 0.1 nA.

| Example | Concentration (µM) | Tau$_{act}$ mean (ms) | Standard Deviation | Number of experiments |
|---|---|---|---|---|
| Vehicle | — | 7.1 | 1.7 | 6 (cells) |
| RE1 | 6.25 | 9.9 | 2.2 | 5 |
| RE2 | 12.5 | 7.3 | 1.8 | 4 |
| Example 15 | 0.2 | 50.1 | 7.5 | 5 |
| Example 16 | 0.4 | 19.3 | 1.0 | 4 |
| Example 25 | 6.25 | 7.87 | 3.24 | 4 |
| RE3 | 0.2 | 23.0 | 6.2 | 4 |
| RE4 | 0.8 | 9.2 | 2.3 | 2 |
| RE5 | 3.1 | 13.0 | 2.3 | 2 |
| RE6 | 3.1 | 8.2 | 2.0 | 2 |
| RE7 | 3.1 | 10.4 | 2.8 | 2 |
| RE8 | 3.1 | 9.7 | 1.0 | 2 |
| Example 65 | 0.8 | 24.0 | 3.6 | 2 |
| Example 62 | 0.4 | 34.8 | 4.9 | 2 |
| Example 61 | 0.8 | 31.5 | 4.0 | 2 |
| Example 51 | 1.6 | 21.3 | 0.1 | 2 |
| Example 54 | 1.6 | 14.8 | 1.9 | 2 |
| Example 63 | 0.4 | 28.0 | 0.4 | 2 |
| Example 64 | 1.6 | 25.0 | 2.1 | 2 |

As can be seen from Table 1, in the absence of compound and presence of vehicle the Tau$_{act}$ was 7.1±1.7 msec. A range of Tau$_{act}$ values (7.3-50.1 msec) was observed in the presence of the test compounds when each was tested at a concentration that increased the Kv3.2 current to a similar level (~0.3 nA).

Kv3.1 and Kv3.2 channels must activate and deactivate very rapidly in order to allow neurons to fire actions potentials at high frequency (Rudy and McBain, 2001, Trends in Neurosciences 24, 517-526). Slowing of activation is likely to delay the onset of action potential repolarisation; slowing of deactivation could lead to hyperpolarising currents that reduce the excitability of the neuron and delay the time before the neuron can fire a further action potential. Together these slowing effects on channel activation and deactivation are likely to lead to a reduction rather than a facilitation of the neurons ability to fire at high frequencies. Thus compounds that have this slowing effect on the Kv3.1 and/or Kv3.2 channels may slow neuronal firing. This slowing of neuronal firing by a compound of the disclosure, specifically Example 15 which markedly increases Tau$_{act}$ to 50.1±7.5 msec (Table 1), can be observed from recordings made from "fast-firing" interneurons in the cortex of rat brain, using electrophysiological techniques, in vitro. As can be observed in FIG. 2, the addition of Example 15 reduces the ability of the neurons to fire in response to trains of depolarising pulses at 300 Hz.

Figure 2:
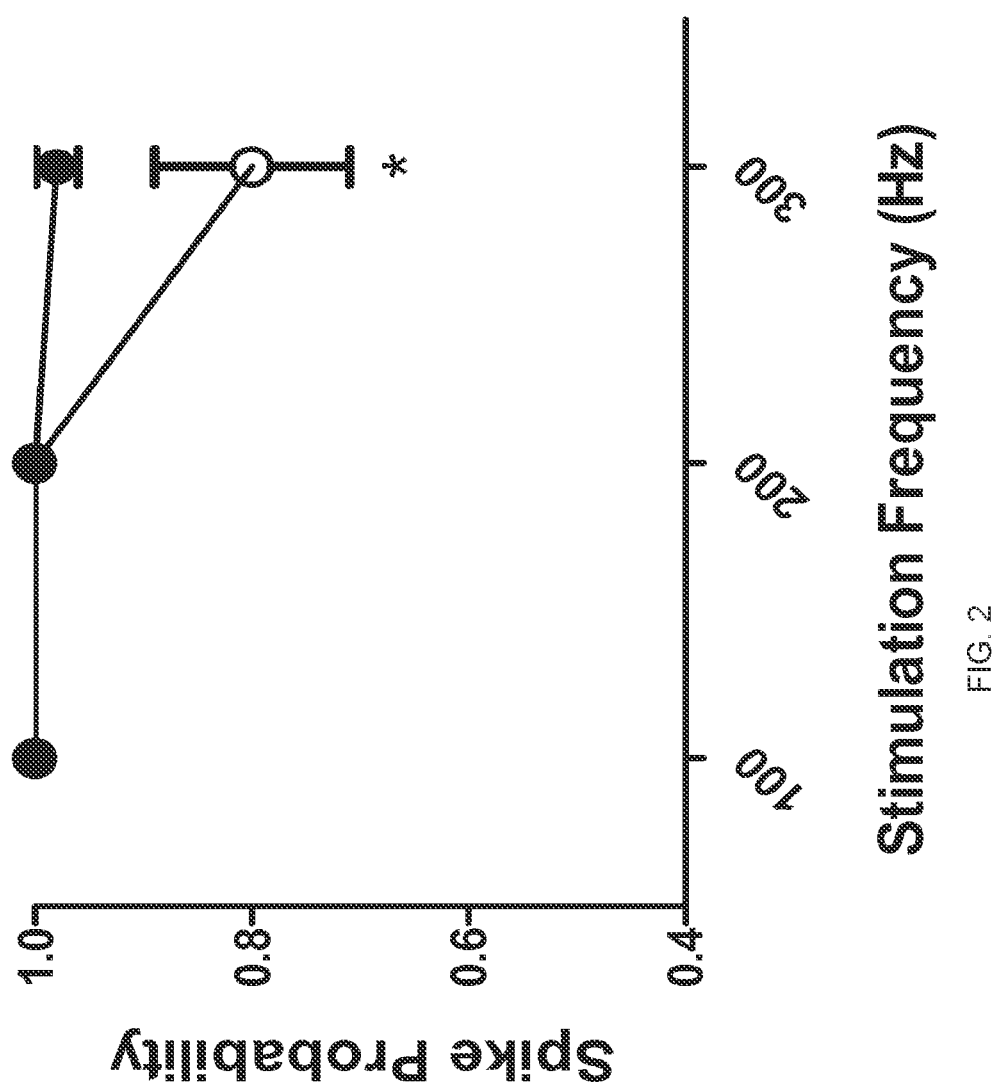
FIG. 2 Recordings made from identified "fast-firing" interneurons in the somatosensory cortex of the mouse.

FIG. 2 shows recordings made from identified "fast-firing" interneurons in the somatosensory cortex of the mouse. The neurons are induced to fire at high frequencies by trains of high frequency depolarising current pulses at 100, 200, and 300 Hz. The ability of the neuron to fire an action potential on each pulse is determined. A spike probability of 1 on the y-axis of the graph indicates that an action potential is generated by the neuron on each of the depolarising current pulses. In the absence of drug (closed circles, n=9), the neurons maintained a spike probability of 1 up to 300 Hz. However, in the presence of Example 15 (1 microM; open circles, n=6), the neurons were unable to follow trains at the highest frequency. *$p<0.05$, ANOVA for repeated measures.

Therefore, although all the Examples herein identified act as positive modulators in the recombinant cell assay of Biological Example 1, those compounds which markedly increase the value of Tau$_{act}$, such as Example 15, may reduce the ability of neurons in native tissues to fire at high frequency.

In one aspect of the disclosure, there is provided a Kv3 potentiating compound which is associated with a mean tau value that is not more that 2 standard deviations greater than the mean value obtained in the presence of vehicle (DMSO 0.5%), for use in the treatment of disorders where positive modulation of Kv3.1 and/or Kv3.2 channel function is beneficial, including schizophrenia, bipolar disorder, hearing disorders, sleep disorders, substance-related disorders, and epilepsy.

In one aspect of the disclosure, there is provided a Kv3 potentiating compound which is associated with a mean tau value that is more that 2 standard deviations greater than the mean value obtained in the presence of vehicle (DMSO 0.5%), for use in the treatment of disorders where inhibition of Kv3.1 and/or Kv3.2 channel function is beneficial, including hyperacusis, Fragile-X, and autism.

Preclinical Experiments

All in vivo studies were conducted in compliance with Project Licences obtained according to Italian law (art. 7, Legislative Decree no. 116, 27 Jan. 1992), which acknowledged the European Directive 86/609/EEC, and with the GlaxoSmithKline company policy on the care and use of laboratory animals and related codes of practice.

In the studies that follow, Compound 48 is the compound of Reference Example RE1.

Biological Example 2

Evaluation of Compound Effects on the Firing of Interneurons in the Somatosensory Cortex of Mice, In Vitro Animals Transgenic mice [CB6-Tg (Gad1-EGFP) G42Zjh/J] were purchased from The Jackson Laboratory (Maine, USA). These mice selectively express enhanced green fluorescent protein (EGFP) in the calcium-binding protein parvalbumin (Pv)-expressing subclass of basket interneurons. EGFP expression is not reported in other interneuron classes positive for somatostatin (SOM), cholecystokinin (CCK), calretinin (CR), and VIP. These mice are therefore useful for the identification of the Pv-expressing subset of GABAergic neurons that express Kv3.1 and Kv3.2 channels and are able to fire at high frequency.

Slice Preparation

Experiments were performed on 250-µm-thick brain slices containing the somatosensory cortex. Briefly, brains were removed from deeply anaesthetized (isofluorane) 25-35 day-old Gad1-EGFP mice. Slices were cut using a DTK 1000 microslicer (DSK, Japan) in the following solution (in mM): KCl (2.5), CaCl$_2$ (0.1), NaH$_2$PO$_4$ (1.2), MgCl$_2$ (5), NaHCO$_3$ (26), sucrose (189) and glucose (10), kept at 2-6° C. and gassed with 95% O$_2$-5% CO$_2$. After cutting, the slices were left to equilibrate in a recovery chamber for at least one hour in an artificial cerebrospinal fluid (ACSF) containing (in mM): NaCl (120), KCl (2.5), CaCl$_2$ (2), NaH$_2$PO$_4$ (2.5), MgCl$_2$ (1.5), NaHCO$_3$ (26), and glucose (10), at room temperature and saturated with 95% O$_2$-5% CO$_2$.

Electrophysiological Recordings

For electrophysiological recordings, a slice was transferred to a submersion chamber mounted on the stage of an upright microscope (Axioskop, Carl Zeiss, Germany) and superfused with oxygenated ACSF. Visualization of neurons in the slices was accomplished with a 40× objective using infrared-differential interference contrast (IR-DIC) video microscopy (Hamamatsu C5985, Hamamatsu City, Japan). Parvalbumin-positive interneurons were identified by illuminating the preparation with a fluorescence lamp with a GFP-filter and switching between fluorescence and IR-DIC video microscopy. Only GFP-positive neurons were recorded. Whole-cell recordings were made using borosilicate-glass patch pipettes pulled using a Sutter P-97 electrode puller and filled with an internal solution containing (in mM): KGluconate (125), EGTA (10), HEPES (10), $MgCl_2$ (1), KCl (10) and MgATP (2); pH 7.3 adjusted with KOH. When filled with this internal solution, patch electrodes had a tip resistance of 4-7 MΩ. Recordings were carried out at room temperature (20-22° C.) using a Multiclamp 700B amplifier (Axon Instruments, Foster City, Calif., USA). Current-command protocols (indicated below) and data acquisition were performed using pClamp 10.0 software and a Digidata 1320A interface (Axon Instruments, Foster City, Calif., USA). Capacitive transients were neutralised and series-resistance was monitored continuously throughout the experiment. If it changed by >20% the cell was discarded. Data were filtered at 3 kHz and sampled at 10 kHz.

Drugs

Compounds of the disclosure were dissolved in DMSO (100%), tetraethylammonium (TEA) and tetrodotoxin (TTX), (both from Sigma, Italy) were dissolved in distilled water and stored at −20° C. until use. Drugs were diluted to the final concentration on the day of the experiment. The highest final concentration of DMSO used was 0.1%.

Experimental Procedure

The firing activity of the recorded interneurons was evaluated by applying long current steps at different intensities. Thus, after the formation of a giga-seal, the amplifier was switched to current-clamp mode, allowing the neuron to reach its resting membrane potential. A negative current was then injected into the cell in order to obtain a resting potential close to −80 mV. From this condition, step current injections (50 pA increments, 600 ms) were applied to elicit action potentials. This protocol was repeated at least 2 times for each cell.

Online bridge-balance compensation was carried out and $R_m$ value was monitored continuously throughout the experiment.

Drug Application

Slices were incubated in the recovery chamber for at least 1 hour in the presence of either vehicle (0.1% DMSO), TEA (0.5 mM)+0.1% DMSO, or TEA (0.5 mM)+Reference Example RE1 (1 or 10 microM). After transfer of a slice to the recording chamber, the same drug condition was maintained by superfusion of the appropriate drugs in the circulating ACSF.

Data Acquisition and Analysis

Raw data were acquired using Clampex 10.0 (Molecular Devices, USA). Data were analyzed using Clampfit 10.0 software (Molecular Devices, USA). The frequency of action potential firing (expressed in Hz) in response to step current injections was calculated from the number of action potentials detected over the 600 ms step current. Values of frequency obtained for each current step in the same experimental condition and in the same cell were averaged. Since the threshold to evoke action potentials differed from one cell to another, current step intensity was expressed as pA from the current threshold for action potential generation, rather than in absolute values.

Action potential half-width was calculated for each action potential using Clampfit. The values of the $2^{nd}$-$5^{th}$ or the last ten action potentials evoked by a non-saturating current step (typically 100-150 pA from threshold) were averaged for each experimental condition in each analyzed cell.

Statistical Analysis

Statistical differences between the effect of treatments on action firing frequency were evaluated using a two-way ANOVA for repetitive measurements and, if necessary, post hoc planned comparisons (differences were considered significant where $p<0.05$). The effect of drug treatment on action potential half-width and on the first derivative amplitude was evaluated using an ANOVA. All statistical analyses were conducted using Statistica Software (StatSoft version 8). When appropriate, results were reported as mean±SEM.

Criteria for Data Inclusion/Exclusion

The criteria used to include or exclude a cell from the analysis were based on accurate current-clamp conditions and the stability of the recording throughout the experiment. Online evaluation allowed the exclusion of a cell when the $R_s$ and/or $R_m$ values changed by >20%.

Results

Figure 3:
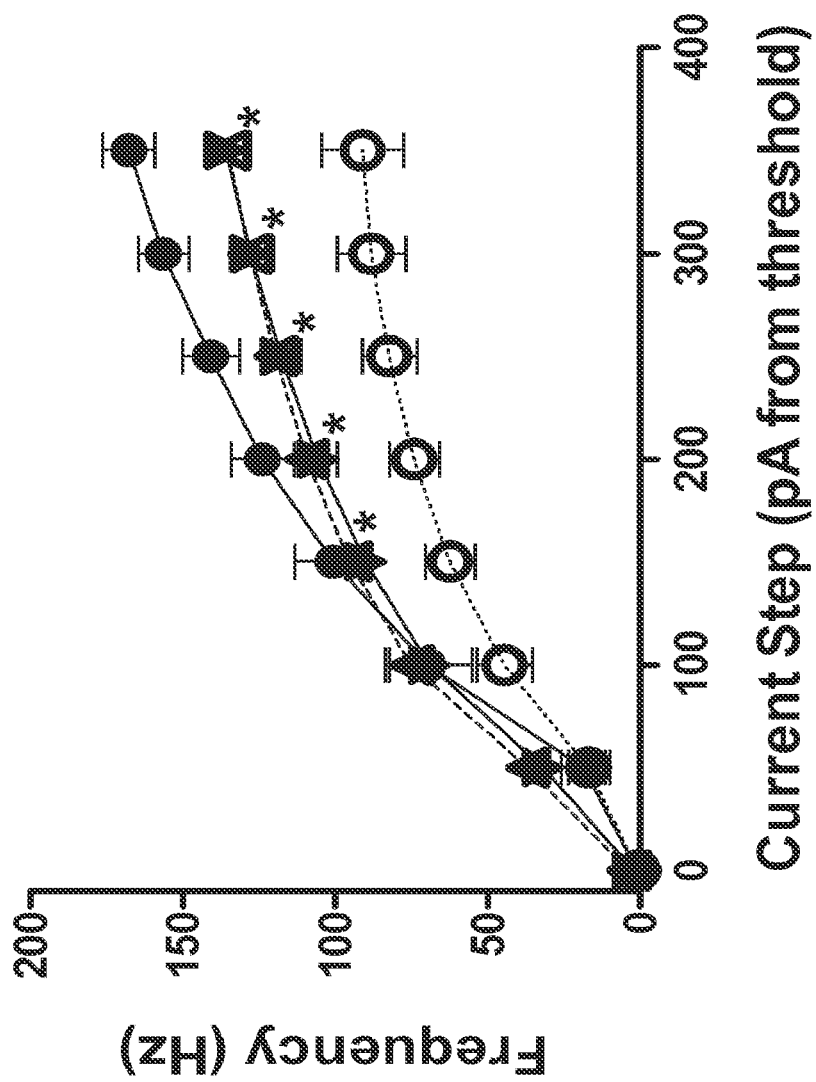
FIG. 3 The frequency of action potentials recorded from parvalbumin-positive interneurons in the somatosensory cortex of the mouse, evoked by depolarizing current steps FIG. 4 The half-width of evoked action potentials from parvalbumin-positive interneurons in the somatosensory cortex of the mouse FIG. 5 High-voltage activated potassium currents recorded from visually identified MNTB neurons in the mouse, in vitro FIG. 6a Expression of Kv3.1b mRNA in the suprachiasmatic nucleus of mice sacrificed during at different Circadian times over a 24-hour light-dark cycle.

Interneurons recorded from slices incubated with 0.5 mM TEA fired at a lower maximal frequency in response to step currents compared to neurons recorded from control slices (FIG. 3). This effect was significantly reversed in slices incubated with TEA (0.5 mM) plus Reference Example RE1 at 1 μM or 10 μM (one-way ANOVA for repeated measurements, *$p<0.05$ with respect to TEA alone).

FIG. 3. The frequency of action potentials recorded from parvalbumin-positive interneurons in the somatosensory cortex of the mouse, evoked by depolarizing current steps (600 ms duration and Δ-increment of 50 pA) after at least 1 hour with either vehicle (0.1% DMSO; filled circles, n=6), TEA (0.5 mM)+0.1% DMSO (open circles, n=7), TEA (0.5 mM)+Reference Example RE1 (1 μM; filled triangles, n=9), or TEA (0.5 mM)+Reference Example RE1 (10 μM; open triangles, n=5). *$p<0.05$; One-way ANOVA for repeated measurements.

Figure 4:
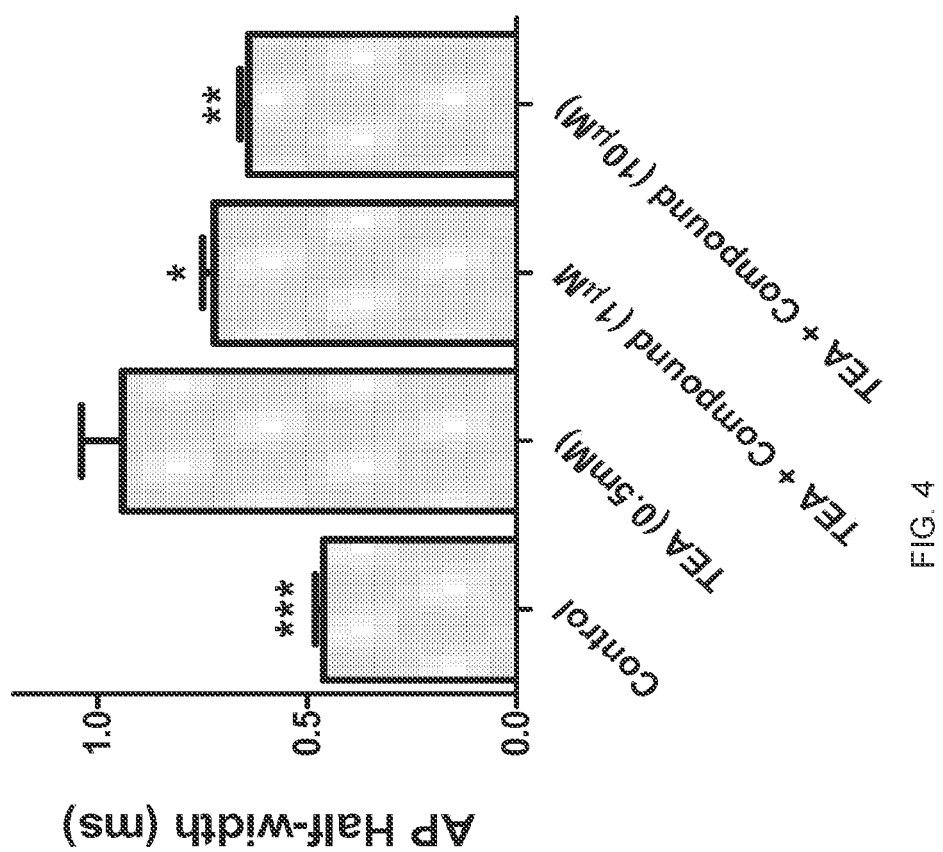

Furthermore, the action potential half-width and was significantly increased in cells recorded from slices incubated with TEA (0.5 mM) compared to control slices (0.1% DMSO) (FIG. 4). In slices incubated with TEA (0.5 mM) plus Reference Example RE1 at 1 μM or 10 μM, the mean action potential half-width was significantly decreased by 24% and 36%, respectively, compared to slices incubated with TEA (0.5 mM) only (ANOVA and Dunnett test, *$p<0.05$, n=9; **$p<0.01$, n=5, respectively).

FIG. 4. The half-width of evoked action potentials from parvalbumin-positive interneurons in the somatosensory cortex of the mouse. Prior to recordings, slices were incubated for at least 1 hour with either vehicle (Control; 0.1% DMSO, n=6), TEA (0.5 mM)+0.1% DMSO (n=7), TEA (0.5 mM)+Reference Example RE1 (1 μM; n=9), or TEA (0.5 mM)+Reference Example RE1 (10 μM; n=5). *$p<0.05$; $p<0.01$, *$p<0.001$, ANOVA followed by Dunnett test.

These results demonstrate the ability of compounds which have activity in the assays of Biological Example 1 to modulate the behaviour of fast-firing interneurons in the mouse brain in a manner consistent with positive modulation of Kv3.1 and/or Kv3.2 channels. The ability to enhance Kv3 function in cortical brain areas is also consistent with the potential of these compounds to treat a range of central nervous system, disorders, including schizophrenia, bipolar disorder, and epilepsy.

Biological Example 3

Evaluation of compound effects on potassium currents recorded from neurons in the medial nucleus of the trapezoid body in mice, in vitro Animals Male CBA/Ca mice (aged 12-16 days) were used in these experiments (in accordance with the UK Animals Scientific Procedures Act, 1986). Brain slices containing the medial nucleus of the trapezoid body (MNTB) were prepared as described previously (Brew and Forsythe, 2005).

Drugs

Chemicals and reagents were purchased from Sigma, (Poole, UK) unless otherwise noted. Reference Example RE1 was dissolved in DMSO and diluted in ACSF to the required concentration.

Electrophysiological Recording

Recordings from identified MNTB neurons were conducted as previously described (Brew and Forsythe, 2005). Slices was placed in a superfusion chamber on an inverted microscope stage and continuously perfused with gassed (95% $O_2$-5% $CO_2$) ACSF at a rate of 1 ml min$^{-1}$ at room temperature. Whole-cell recordings were made from visually identified MNTB neurons using an Axopatch 700B amplifier (Molecular Devices, Union City, Calif., USA). Patch solution comprised (in mM) potassium gluconate (97.5), KCl (32.5), Hepes (40), EGTA (5), $MgCl_2$ (1), $Na_2$ phosphocreatin (5), pH 7.2 with KOH. Pipettes had resistances of 3-5 MΩ and series resistances were 6-10 MΩ (compensated by 70%, 10 µs lag). Access resistance was frequently monitored and the recording discarded if increases were more than 2 MΩ.

Once a whole-cell configuration had been obtained, cells were held at −60 mV prior to application of voltage protocols as follows: cells were stepped from the holding potential to −90 for 700 ms and stepped to −40 mV for 25 ms and then a voltage pulse to a range of voltages from −100 to +40 mV (10 mV increments) was applied for 220 ms before returning to the holding potential. Following completion of this protocol, TEA (1 mM) was added to the superfusion medium. After 5 minutes, a second set of recordings using the same voltage protocol was carried out. Following this, Reference Example RE1 (10 microM) was added to the ACSF, in the continuing presence of TEA (1 mM), and after a further 5 minutes, a final set of recordings with the voltage protocol was made.

Statistical Analysis

Currents evoked by the voltage step to +40 mV were compared across drug treatments for each cell using an unpaired t-test.

Results

Figure 5:
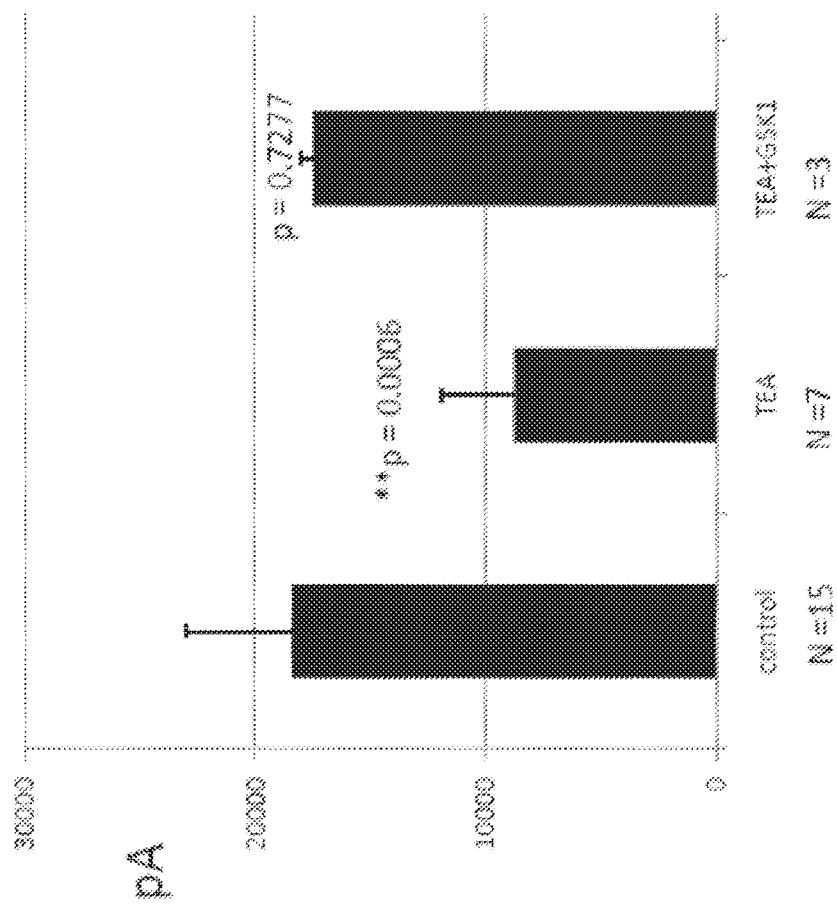

TEA (1 mM) significantly reduced the amplitude of outward, high voltage-activated potassium currents evoked by voltage steps to +40 mV (FIG. 5). This effect was reversed by the subsequent application of Reference Example RE1 (10 microM).

FIG. 5. High-voltage activated potassium currents recorded from visually identified MNTB neurons in the mouse, in vitro. Data shown are the mean (+/−s.d.) of the current amplitude evoked by voltage steps to +40 mV under different drug conditions. TEA (1 mM), TEA (1 mM)+ Reference Example RE1 (10 microM). Statistical analysis was conducted using an unpaired t-test.

These data indicate that compounds which have activity in the assays of Biological Example 1 can modulate high voltage-activated potassium currents (presumed to be mediated by Kv3.1 channels; Brew and Forsythe, 2005) in neurons of the MNTB, a region of the brainstem that processes auditory information. This result supports the utility of compounds of the disclosure for the treatment of hearing disorders.

Biological Example 4

Electroshock Seizure Model in Rats

Experimental Preparation

Male CD rats (85-130 g) were supplied by Charles River, Italy. Animals were group housed with free access to food (Standard rodent chow) and water under a 12 h light/dark cycle (lights on at 0600 h). A period of at least 5 days between arrival at GSK and the study was allowed in all cases.

Experimental Protocol

Animals were administered a test compound at the appropriate dose, route and pre-treatment time and returned to their home cage. Testing occurred in a separate room from that used for housing. Testing involved determining the threshold for tonic hindlimb extensor seizures using a Hugo Sachs Electronik stimulator which delivers a constant current of 0.3 second duration, 50 Hz, sinewave form, fully adjustable between 1 and 300 mA. Stimuli were delivered via corneal electrodes (Stean T O, Atkins A R, Heidbreder C A, Quinn L P, Trail B K, Upton N. (2005) Br J Pharmacol. 144(5):628-35). Seizure threshold was determined using the 'up and down' method of Kimball et al. (1957)(Kimball A W, Burnett W T Jr, Doherty D G. (1957) Radiat Res. 7(1):1-12). The first animal tested in each group was stimulated with a current that might be expected to be close to the threshold for induction of a seizure. If a tonic seizure was not induced, then the next animal in the group received a stimulus 5 mA higher. If a tonic seizure was induced, then the next animal received a stimulus 5 mA lower. This is repeated for all animals within the control (vehicle) group. In the case of groups treated with a test compound steps of 5 to 10 mA were used. At the end of the study, blood samples were taken for analysis of the drug concentrations in this compartment (n=4/group).

Drugs and Materials

All doses were calculated as base. Sodium valproate was suspended in Methocell 1% (w/v) and dosed via the oral (p.o.) route at 5 mL/kg 1 hour before test. Reference Example RE1 was dissolved in DMSO and then suspended in Methocell 1% (w/v) to a final DMSO concentration of 5% (v/v). Reference Example RE1 was then dosed p.o. at 5 mL/kg 2 hours before test.

Data Analysis

Induction of seizure is measured as an all-or-nothing effect scored as either present (+) or absent (0) for each animal. The data for each treatment group were recorded as the number of +'s and 0's at each current level employed and this information was then used to calculate the CC50 value (current required for 50% of animals to show seizure behaviour)+standard error of the mean according to the method of Kimball et al. (1957). Drug effects were calculated as the % change in CC50. Significant differences between drug-treated animals and appropriate vehicle treated groups were assessed according to the methods of Litchfield and Wilcoxon (1949).

Results

Pretreatment with Reference Example RE1 was associated with a significant increase in seizure threshold at both doses tested: At the dose of 30 mg/kg p.o., Reference Example RE1 produced a 91% increase in seizure threshold, whereas at the dose of 60 mg/kg p.o., the increase in seizure threshold was +218%. The increase produced by the higher dose of Reference Example RE1 was similar to the increase produced by the positive control, sodium valproate at 300 mg/kg p.o. (+258%).

Blood concentrations of Reference Example RE1 measured in satellite animals 2 hours after dosing were 5.3 and 9.1 µg/mL following the doses of 30 and 60 mg/kg p.o., respectively. These concentrations are equivalent to unbound concentrations in blood of 1.3 and 2.2 µM, respectively, and thus are consistent with concentrations of Reference Example RE1 that produce a significant increase in Kv3-mediated currents observed in the in vitro recombinant human Kv3 electrophysiology assay, described above.

Conclusions

These results suggest that Reference Example RE1 has anticonvulsant efficacy, and that this effect is likely to be mediated by the positive modulation of Kv3 potassium channels. Consequently, compounds which have activity in the assays of Biological Example 1 can have anticonvulsant efficacy.

Biological Example 5

Psychostimulant-Induced Hyperactivity in Mice
Experimental Preparation

Male CD-1 mice (25-35 g) were supplied by Charles River, Italy. Animals were group housed with free access to food (Standard rodent chow) and water under a 12 h light/dark cycle (lights on at 0600 h). A period of at least 5 days between arrival at GSK and the study was allowed in all cases.

Experimental Protocol

Animals were administered a test compound at the appropriate dose, route and pre-treatment time, and then returned to their home cage. Testing occurred in a separate room from that used for housing. Mice were treated orally (p.o.) with the test compound and placed individually into a Perspex box (length 20.5 cm, width 20.5 cm, height 34 cm) covered with a perforated lid. Infrared monitoring sensors were located around the perimeter walls (horizontal sensors). Two additional sensors were located 2.5 cm above the floor on opposite sides (vertical sensors). Data were collected and analysed using a VersaMax System (Accuscan Instruments Inc., Columbus, Ohio) which in turn transferred information to a computer. After 30 minutes of habituation, mice were treated with amphetamine dosed intraperitoneally (i.p.) at 2 mg/kg at 10 mL/kg, and subsequent locomotor activity in the test arena was assessed over a further 60 minutes. Locomotor activity was determined as the total distance (cm) travelled by each mouse in the test arena over the 60 minute test period.

Drugs and Materials

All doses were calculated as base. Clozapine was dissolved in distilled water and dosed at 3 mg/kg intraperitoneum (i.p.) at 10 mL/kg. Reference Example RE1 (10, 30 or 60 mg/kg) or vehicle (HPMC 0.5% w/v, Tween800.1% v/v in water) was administered p.o. at 10 mL/kg. Both clozapine and Reference Example RE1 were dosed immediately before placing the animal in the test arena (30 minutes before amphetamine administration).

Results

Amphetamine alone produced a large and significant increase in total distance travelled. A dose of 30 mg/kg p.o. of Reference Example RE1 significantly reduced the increase in total distance travelled produced by amphetamine. A higher dose of 60 mg/kg p.o. of Reference Example RE1 further reduced the increase in locomotor activity induced by amphetamine in a manner similar to the positive control, clozapine (3 mg/kg i.p.). Data are summarised in Table 1.

TABLE 1

Effects of Reference Example RE1 on amphetamine induced hyperlocomotion in the mouse. Reference Example RE1 was administered p.o. 30 minutes before amphetamine (2 mg/kg i.p.). Clozapine was administered i.p. 30 minutes before amphetamine (2 mg/kg i.p.). Total distance was assessed over 60 minutes starting immediately after amphetamine administration. Data are expressed as mean ± sem. Data were subjected to one-way analysis of variance (ANOVA) followed by Dunnett's test (** = $p < 0.01$ vs amphetamine treatment alone).

| Treatment | Total Distance Travelled (cm) |
| --- | --- |
| Vehicle | 1049 ± 522** |
| Amphetamine (AMPH) 2.0 mg/kg | 16304 ± 3309 |
| AMPH 2 mg/kg + Reference Example RE1 10 mg/kg | 15267 ± 3166 |
| AMPH 2 mg/kg + Reference Example RE1 30 mg/kg | 5790 ± 1436** |
| AMPH 2 mg/kg + Reference Example RE1 60 mg/kg | 1494 ± 378** |
| AMPH 2 mg/kg + Clozapine 3 mg/kg | 932 ± 362** |

Conclusions

These results show that Reference Example RE1, at doses similar to those that show anticonvulsant efficacy, is able to prevent hyperactivity induced by the psychostimulant, amphetamine. Thus, reference Example RE1 and other compounds that positively modulate Kv3.1 and/or Kv3.2 channels, as can be observed from the assay described in Biological Example 1, may be useful in the treatment of disorders associated with hyperactivity, such as bipolar mania, or disruption of the dopamine system, such that may occur in drug dependence, attention deficit hyperactivity disorder (ADHD), or schizophrenia.

Biological Example 6

Pharmaco-Electroencephalography (phEEG) in the Common Marmoset
Animals and Surgery Laboratory bred male (vasectomised) and female common marmosets (*Callithrix jacchus*) over 2 years of age, weighing 250-500 g were used in this study. The animals were caged in couples, in a housing room maintained at 25±1° C., 60% humidity and a 12 hour light/dark cycle (lights on at 0600, with 30 min simulated dawn and twilight). Animals received a standard diet and drinking water ad libitum. Only one animal of each pair was involved in the test, which was carried out with the animal situated in the home cage.

The effect of compounds of the disclosure was assessed using telemetric recording of cortical EEG (ECoG). A multichannel telemetric transmitter (DSI model TL11M2-F40-EET) is implanted intraperitoneally using standard surgical techniques in anaesthetised marmosets. Recording electrodes were permanently fixed, with dental cement, to the skull directly in contact with the dura mater through two drilled holes in the fronto-parietal region. Following surgery, animals were housed in pairs (one implanted, one unoperated partner) in their home cage with access to food and water ad libitum. Animals demonstrated a normal behavioural repertoire immediately after recovery from surgery; however, phEEG was assessed at least 3 weeks later. All in vivo studies were conducted in accordance with the Italian laws and conformed to GlaxoSmithkline ethical standards.

Experimental Procedure

The animals were placed in the nest-boxes in their room cages and EEG traces were recorded using Dataquest ART software for a 5-min period for each time-point and analyzed using Spike2 software (CED, UK). The spectral power in each frequency band was determined for each 2 sec epoch during the pre-treatment period and averaged; similarly spectral power in each band was determined for successive 2 sec epochs of each 5-min period of recording following vehicle or drug treatment. Change in the absolute spectral power, for each of the different bands (delta, theta, alpha and beta) was calculated offline.

Drug treatments were assigned according to a complete crossover design: All treatments were randomly distributed between animals, in separate experimental sessions, each animal received vehicle and each dose of drug, after an appropriate wash-out period.

Six animals were treated orally with Reference Example RE2 at the doses of 0.3, 1 and 3 mg/kg (1 ml/kg) and the EEG traces were recorded at +15, 30, 60, 90, 120 and 180 minutes following treatment. Reference Example RE2 was suspended in 12.5% (w/v) aqueous captisol containing 0.1% (w/v) Tween80 and 0.5% (w/v) HPMC.

Data Analysis

Four different frequency bands were considered: delta (1.50-6.00 Hz), theta (6.00-8.00 Hz), alpha (8.00-12.00 Hz) and beta (12.00-30.00 Hz). Values for spectral power in each band at each time point were first log transformed and then analysed with a mixed effect model with time as fixed effect, the baseline level as covariate, and animal as random term. Data are summarised as mean of the percentage changes from baseline and standard error.

Results

The pharmaco-EEG changes observed in these studies show that, compared to vehicle, Reference Example RE2 at the highest dose (3 mg/kg) induced a statistically significant increase of the absolute power in the delta band between 30 and 120 minutes ($p<0.05$) and a statistically significant increase in theta band power at 60 minutes ($p<0.05$). At the intermediate dose (1 mg/kg) Reference Example RE2 induced a marginally significant ($p<0.10$) increase in the absolute power in delta band at 30 minutes and a concomitant significant reduction in the beta band ($p<0.05$). No significant effects were observed in the alpha band at any dose of Reference Example RE2.

These results suggest that compounds which have activity in the assays of Biological Example 1 can modify the EEG of awake primates. Increases in delta-band EEG activity have previously been observed with antipsychotic compounds in humans.

Biological Example 7

Circadian Pattern of Expression of Kv3.1 and Kv3.2 Channels in the Superchiasmatic Nucleus of Mice Material & Methods Thirty adult male C57BL/6J mice (age: 4-5 weeks at the arrival; Charles River FR) were stored in six different cages (5 mice per cage) and maintained for 4 weeks in a dedicated room with 12 h light-12 h dark condition (lights on at 06:00, designated as Circadian time [CT] 6; lights off at 18:00, designated as CT 18. The room temperature was maintained at 21±2° C.; food and water were available ad libitum.

After this period, mice were sacrificed by cervical dislocation at different time points over a 24 hour period; 5 mice per time point. The animals were transferred from the storage room to the surgery room and then immediately sacrificed. During the dark phase, all these actions were performed under a dim red light.

Brains were removed from the skull and immediately immersed in isopentane maintained approximately at −30° C. and then stored at −70° C. prior to in situ hybridization analysis.

All the brains were cut by cryostat and a number of 14 µm-thick coronal sections were collected at the level in which the suprachiasmatic nucleus is present, approximately between −0.22 mm and −0.82 mm from Bregma (Paxinos and Franklin, "The mouse brain in stereotaxic coordinates"). The sections were then stored at −80° C. until usage. For each time point (CT12, 16, 20, 24, 4 and 8), five mice were collected and two non-consecutive sections for each mouse were selected and allowed to dry at room temperature, then immediately exposed to in situ hybridization protocol, as described in the previous experiments.

Results

A one-way ANOVA found no significant effect of time on Kv3.1 mRNA expression within the mouse suprachiasmatic nucleus (FIG. 6a). In contrast, one-way ANOVA indicated that there was a highly significant effect of the time on Kv3.2 mRNA expression within the mouse suprachiasmatic nucleus ($p<0.001$), with a significant peak of expression at ZT 10, the time point corresponding to 2 hours before the shift from the light to the dark phase, which is the active phase of the mice (FIG. 6b).

FIG. 6: (a) Expression of Kv3.1 mRNA in the suprachiasmatic nucleus of mice sacrificed during at different Circadian times over a 24-hour light-dark cycle. Kv3.b1 mRNA expression is expressed in nCi/g as mean±S.E.M. from n=5 mice per time point. (b) Expression of Kv3.2 mRNA in the superchiasmatic nucleus. Kv3.2 mRNA expression is expressed as mean±S.E.M. from n=5 mice per time point. ***$p<0.001$: Kv3.2 mRNA expression at CT 16 is significantly different from all the other timepoints. *$p<0.05$: the Kv3.2 mRNA expression at CT 20 is significantly different from the expression measured at CT 24 and 4.

These results indicate that Kv3.2 channel expression in the superchiasmatic nucleus varies over the 24-hour circadian cycle. Thus, given the central role of the superchiasmatic nucleus in setting the circadian clock in mammals, Kv3.2 channels are likely to be important to the function of this clock. Consequently, compounds that modulate Kv3.2 channels may have potential in the treatment of disorders associated with circadian dysfunction, including sleep and bipolar disorders.

Biological Example 9

Assessment of Physiological Sleep in the Rat

Methods:

Adult male CD rats (C. River, Italy) were implanted with telemetric probes and housed singly, under controlled condition (temperature 18-20° C.; relative humidity 45-50%; 12 hours light-dark cycle, lights on at 3 p.m., designated Circadian Time (CT) 0) with free access to food and water.

Reference Example RE1 was formulated in tween (0.1% v/v) and HPMC (0.5% v/v) and was administered orally at doses of 10, 30 and 60 mg/kg (vol. 2 ml/kg) at CT18 (6 hours before lights on). The electroencephalogram (EEG) and electromyogram (EMG) were recorded continuously, starting immediately after administration, using telemetric apparatus (DSI Dataquest® A.R.T. system). EEG and EMG recordings were analysed to evaluate sleep patterns using sleepSign® (Kissei Comtec Co.). Statistical analyses (1-way Anova followed by a Dunnett's test) was performed using Statistica-8 software.

Results:

Reference Example RE1 at 60 mg/kg significantly increased total sleep time (p<0.05, n=8) and time spent in non-REM sleep (p<0.05, n=8) over the 5 hour period immediately following dosing, but did not affect time spent in REM sleep.

These results suggest that compounds of the disclosure can increase physiological sleep in animals, which suggests that they may be useful in the treatment of sleep disorders in humans.

What is claimed is:

1. A compound of formula (II):

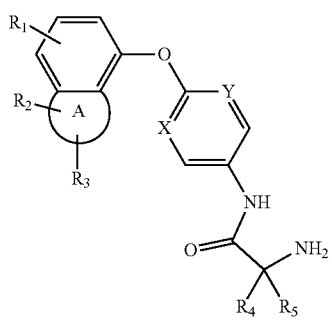

or a salt thereof;
wherein:
$R_1$ is H, $C_{1-4}$alkyl, halo, halo$C_{1-4}$alkyl, CN, $C_{1-4}$alkoxy, or halo$C_{1-4}$alkoxy;
$R_2$ is H, $C_{1-4}$alkyl, $C_{3-4}$ spiro carbocyclyl, halo$C_{1-4}$alkyl or halo;
$R_3$ is H, $C_{1-4}$alkyl, halo$C_{1-4}$alkyl or halo;
A is a 5 or 6 membered saturated or unsaturated heterocycle, with at least one O atom; which heterocycle is optionally fused with a cyclopropyl group to form a tricycle when considered together with the phenyl;
X is CH or N;
Y is CH or N;
$R_4$ is $C_{1-4}$alkyl;
$R_5$ is H, deuterium or $C_{1-4}$alkyl;
or $R_4$ and $R_5$ can be fused to form $C_{3-4}$ spiro carbocyclyl.

2. The process according to claim 1, wherein $R_1$ is methyl.

3. The compound according to claim 1, wherein A is a 5 membered saturated or unsaturated heterocycle, with at least one O atom; which heterocycle is optionally fused with a cyclopropyl group to form a tricycle when considered together with the phenyl.

4. The compound according to claim 1, wherein A is a 6 membered saturated or unsaturated heterocycle, with at least one O atom; which heterocycle is optionally fused with a cyclopropyl group to form a tricycle when considered together with the phenyl.

5. The compound according to claim 1, wherein the ring A contains one heteroatom.

6. The compound according to claim 1, wherein the ring A contains an oxygen in the meta position relative to the phenyl ring.

7. The compound according to claim 1, wherein the ring A is dihydrofuran or dihydropyran.

8. The compound according to claim 1 wherein $R_2$ is H, F, methyl, ethyl, isopropyl or a $C_3$ spiro group, such as $R_2$ is H, methyl or a $C_3$ spiro group.

9. The compound according to claim 1, wherein $R_3$ is H, $C_{1-4}$alkyl, halo$C_{1-4}$alkyl or halo, such as $R_3$ is H, F, methyl or ethyl.

10. The compound according to claim 9, wherein $R_3$ is H or methyl.

11. The compound according to claim 1, wherein X is CH.

12. The according to claim 1, wherein X is N.

13. The compound according to claim 1, wherein Y is CH.

14. The compound according to claim 1, wherein Y is N.

15. The compound according to claim 1, wherein $R_4$ is methyl.

16. The compound according to claim 1, wherein $R_4$ is ethyl.

17. The compound according to claim 1, wherein $R_5$ is H.

18. The compound according to claim 1, wherein $R_5$ is methyl.

* * * * *